United States Patent
Burke et al.

(10) Patent No.: US 11,639,483 B2
(45) Date of Patent: May 2, 2023

(54) MACROCYCLIC MUSK LACTONES AND USES THEREOF

(71) Applicant: PHYTO TECH CORP., Rancho Santa Margarita, CA (US)

(72) Inventors: Angélique Burke, Laguna Beach, CA (US); Noemi Montoya, Irvine, CA (US); Katherine Joyce Oglesby, Rancho Santa Margarita, CA (US)

(73) Assignee: PHYTO TECH CORP., Rancho Santa Margarita, CA (US)

( * ) Notice: Subject to any disclaimer, the term of this patent is extended or adjusted under 35 U.S.C. 154(b) by 0 days.

(21) Appl. No.: 17/690,872

(22) Filed: Mar. 9, 2022

(65) Prior Publication Data

US 2022/0298451 A1  Sep. 22, 2022

Related U.S. Application Data

(60) Provisional application No. 63/182,050, filed on Apr. 30, 2021, provisional application No. 63/158,847, filed on Mar. 9, 2021.

(51) Int. Cl.

| | |
|---|---|
| *A61K 31/35* | (2006.01) |
| *C11B 9/00* | (2006.01) |
| *A61Q 5/00* | (2006.01) |
| *A61Q 19/00* | (2006.01) |
| *A61K 8/49* | (2006.01) |
| *A61K 31/365* | (2006.01) |
| *C11D 3/50* | (2006.01) |

(52) U.S. Cl.
CPC .......... *C11B 9/0084* (2013.01); *A61K 8/4973* (2013.01); *A61K 31/365* (2013.01); *A61Q 5/00* (2013.01); *A61Q 19/00* (2013.01); *C11D 3/50* (2013.01)

(58) Field of Classification Search
CPC .. A61K 31/365; A61K 8/4973; C11B 9/0084; A61Q 5/00; A61Q 19/00
See application file for complete search history.

(56) References Cited

U.S. PATENT DOCUMENTS

| | | | | |
|---|---|---|---|---|
| 3,890,353 | A * | 6/1975 | Becker | 549/462 |
| 8,338,361 | B2 * | 12/2012 | Takahashi | C11B 9/0084 512/11 |
| 2015/0266847 | A1 | 9/2015 | Inaba et al. | |
| 2018/0134680 | A1 * | 5/2018 | Siegel | C07D 313/00 |

FOREIGN PATENT DOCUMENTS

| | | |
|---|---|---|
| CN | 106397384 A | 2/2017 |
| WO | WO-2010-082684 A1 | 7/2010 |
| WO | WO-2018-206297 A1 | 11/2018 |

OTHER PUBLICATIONS

Baker, GJ, et al. "Expression, Purification, and Biochemical Characterization of the Flavocytochrome P450 CYP505A30 from *Myceliophthora thermophile*," *ACS Omega* 2:4705-4724, American Chemical Society, Washington, DC (2017).

Miura, Y, et al. "Omega-1, Omega-2 and Omega-3 hydroxylation of long-chain fatty acids, amides and alcohols by a soluble enzyme system from *Bacillus megaterium*," *Biochim. Biophys. Acta*. 388:305-317, Elsevier Science Publishers, Amsterdam, the Netherlands (1975).

Wen, LP, et al. "Cloning of the gene encoding a catalytically self-sufficient cytochrome P-450 fatty acid monooxygenase induced by barbiturates in *Bacillus megaterium* and its functional expression and regulation in heterologous (*Escherichia coli*) and homologous (*Bacillus megaterium*) Hosts," *J. Biol. Chem.* 262: 6676-6682, Elsevier Science Publishers, Amsterdam, the Netherlands (1987).

Voloshina, Elena et al. "Conformational Analysis and CD Calculations of Methyl-Substituted 13-Tridecano-13-lactones," *Helvetica Chimica Acta* 88(2):194-209, John Wiley & Sons (Switzerland) (2005).

Bollbuck, B. et al. "Stereoselective Synthesis and Structural Variations of Ethyl Analogues of Galbanum Macrolides," *Tetrahedron* 55(23):7209-7220, Elsevier Science Publishers, Amsterdam, the Netherlands (1999).

Hotling, Susann et al. "Identification of a Grain Beetle Macrolide Pheromone and Its Synthesis by Ring-Closing Metathesis Using a Terminal Alkyne," *Organic Letters* 17(20):5004-5007, American Chemical Society, Washington, DC (2015).

International Search Report and Written Opinion for International Application No. PCT/US2022/019612, International Search Authority, European Patent Office, Rijswijk, the Netherlands, dated Jul. 6, 2022, 18 pages.

* cited by examiner

*Primary Examiner* — Marcos L Sznaidman
*Assistant Examiner* — Rayna Rodriguez
(74) *Attorney, Agent, or Firm* — Sterne, Kessler, Goldstein & Fox P.L.L.C.

(57) ABSTRACT

Provided herein are uses of lactones, such as macrocyclic lactones, for use in consumer products.

20 Claims, 16 Drawing Sheets

Specification includes a Sequence Listing.

17-Methyl-(9Z,12Z,15Z)-heptadecatrien-17-olide

MACROCYCLIC MUSK LACTONES AND USES THEREOF

INCORPORATION BY REFERENCE OF SEQUENCE LISTING

The content of the electronically submitted sequence listing (Name: 4733_0160002_Seqlisting_ST25; Size: 30,492 bytes; and Date of Creation: Mar. 9, 2022) is herein incorporated by reference in its entirety.

FIELD OF THE INVENTION

The field of the invention relates to lactone compounds (e.g., macrocyclic lactone compounds that may be flavor- or fragrance-bearing) and their uses (e.g., in fragrance materials).

BACKGROUND

Musk lactones are generally scarce and expensive. Currently, only a limited number of macrocyclic musk lactones are available and only with limited differentiated musky notes. Most of the existing musk lactones are chemically synthesized, and few are natural.

SUMMARY

Many macrolactones, particularly C14-C16 lactones are known in the art and many have been described as having to a greater or lesser extent a musk-like odor. However, these odors differ considerably in quality as well as musk intensity and only a few have so far found practical use in perfumery. Hexadecen-7-olide, also known as Ambrettolide, is a well-known fragrance material with a musky-floral odor (S. Arctander Perfume and Flavour Chemicals, monograph 105), is probably one of the most extensively used macrocyclic musk materials and is marked under many tradenames, while its isomers with the double bond in the 5 or 6 position only have a faint musky odor. Hexadecanolide (S. Arctander, monograph 923) is again a well-known musk fragrance material. There is a need in perfumery for novel musk fragrance materials with comparable or better odor properties than the ones which are presently used.

The present disclosure, in some aspects, provide lactones, such as macrocyclic lactones for use in consumer products. As described herein, the lactones are produced using biosynthetic methods from fatty acids. In some embodiments, the lactones have differentiated musky notes, can be used in consumer products comprising fragranced compositions, for boosting a second fragrance or overall fragrance performance, have mood enhancing and/or anti-inflammatory effects, and have increased substantivity (e.g., fiber substantivity) and biodegradability.

Accordingly, some aspects of the present disclosure provide fragrance compositions comprising a lactone comprising one or more compounds of the formula:

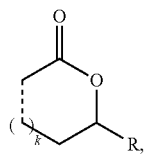

wherein:
R is methyl, ethyl, or n-propyl; each - - - is independently a single bond, E double bond, Z double bond, or triple bond, as valency permits; and
k is an integer between 6 and 30, inclusive.
In some embodiments, the lactone comprises one or more compounds of the formula:

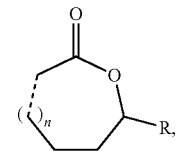

wherein:
R is methyl, ethyl, or n-propyl; each - - - is independently a single bond, E double bond, Z double bond, or triple bond, as valency permits; and
n is an integer between 6 and 20, inclusive.

Other aspects of the present disclosure provide consumer products comprising a fragrance composition comprising a lactone comprising one or more compounds of the formula:

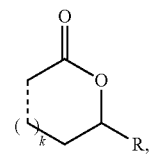

wherein:
R is methyl, ethyl, or n-propyl;
each - - - is independently a single bond, E double bond, Z double bond, or triple bond, as valency permits; and
k is an integer between 6 and 30, inclusive.
In some embodiments, the fragrance composition comprises a lactone comprising one or more compounds of the formula:

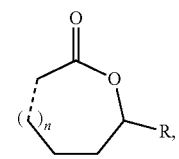

wherein:
R is methyl, ethyl, or n-propyl; each - - - is independently a single bond, E double bond, Z double bond, or triple bond, as valency permits; and
n is an integer between 6 and 20, inclusive.
In some embodiments, the lactone comprises one or more compounds of the formula:

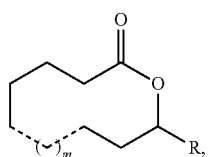

wherein:
R is methyl, ethyl, or n-propyl;
each - - - is independently a single bond or Z double bond, as valency permits, wherein 0, 1, 2, or 4 - - - are Z double bonds; and
m is an integer between 4 and 11, inclusive.
In some embodiments, the lactone comprises one or more compounds selected from:
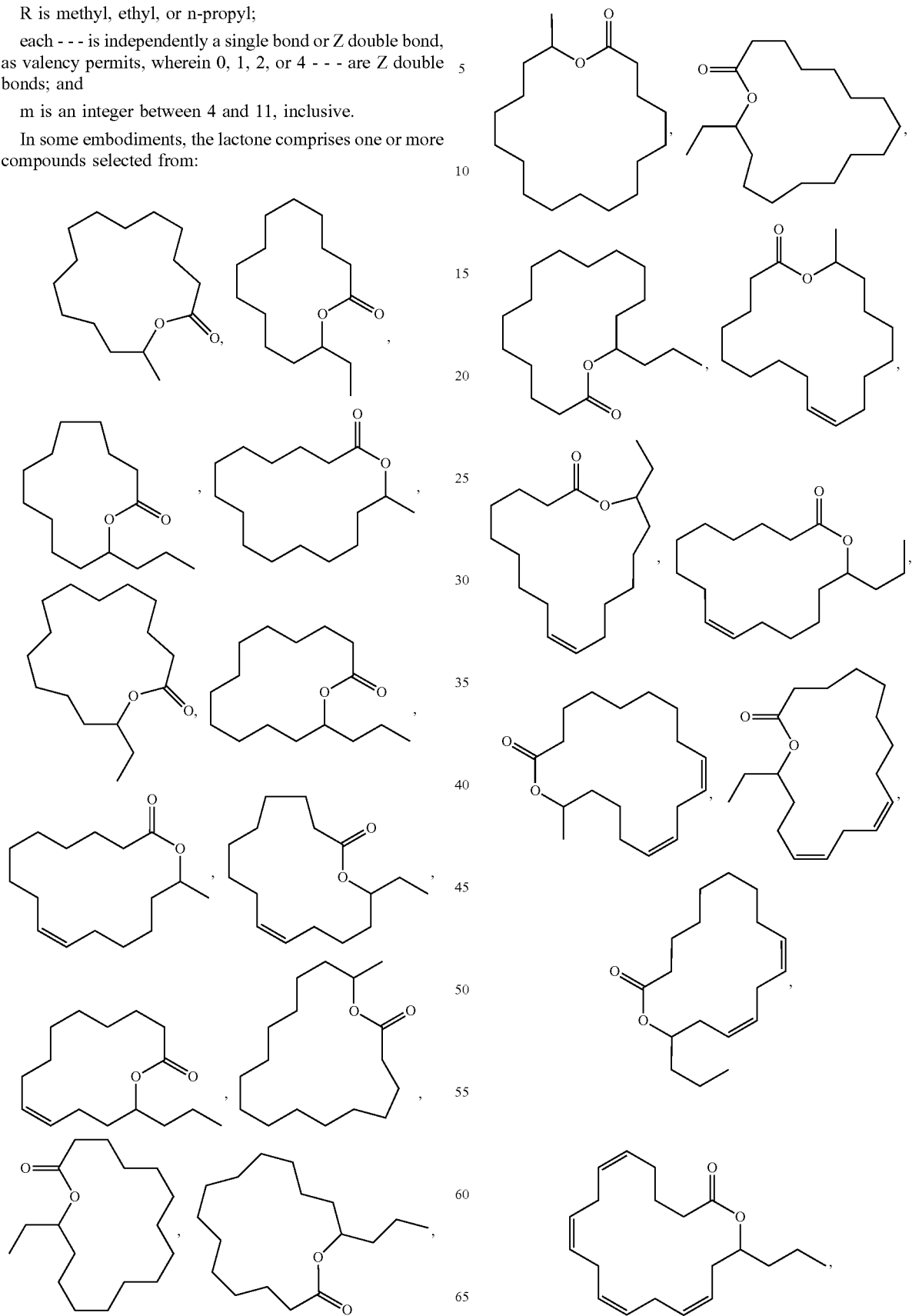

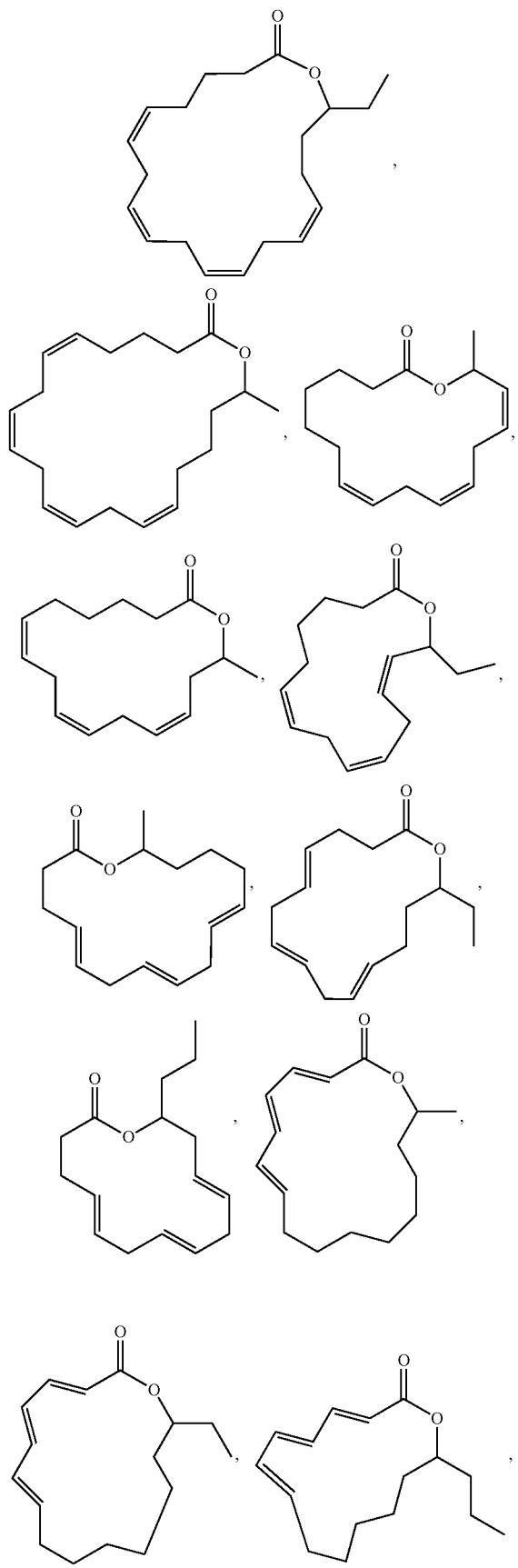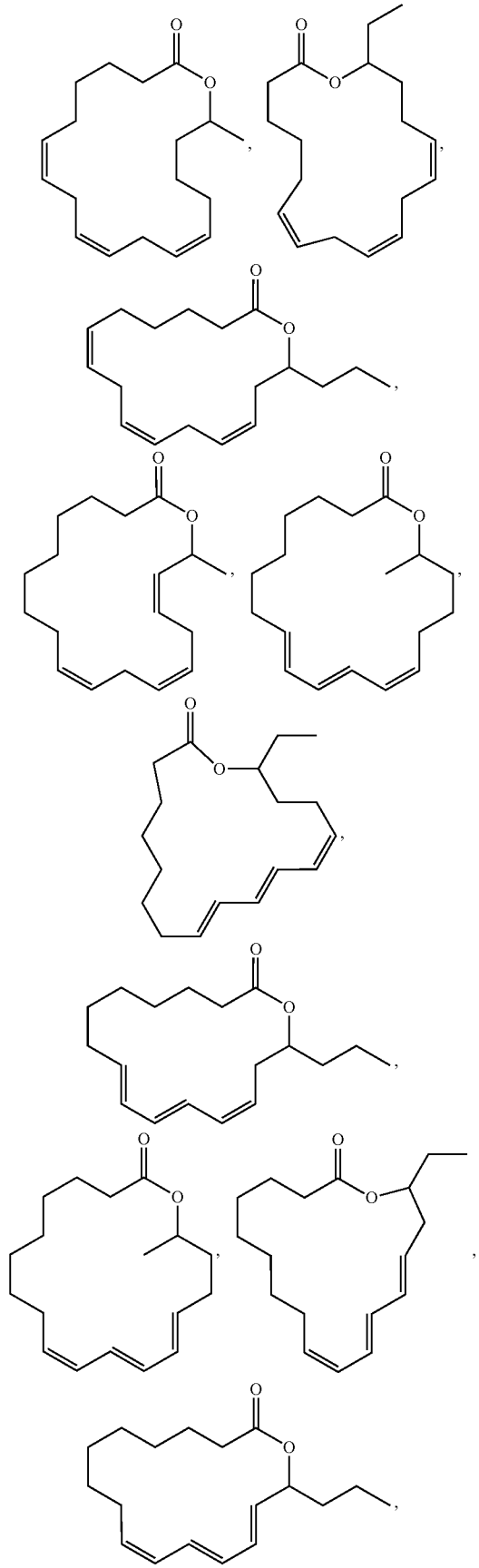

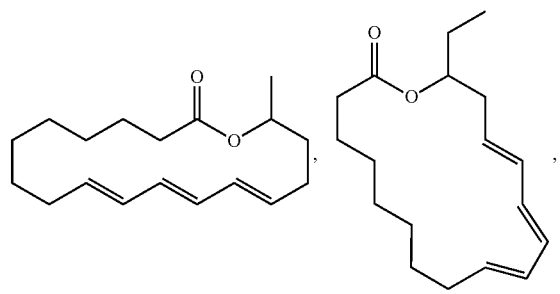
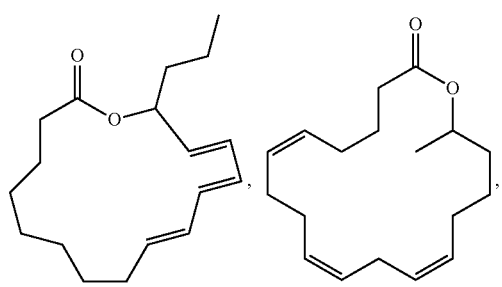
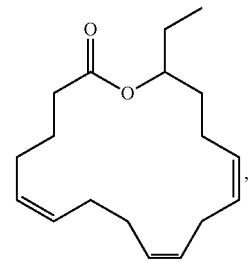
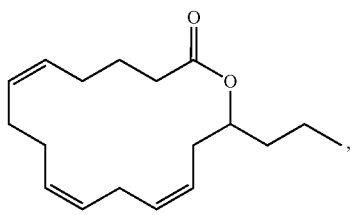
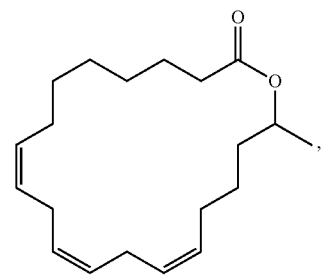
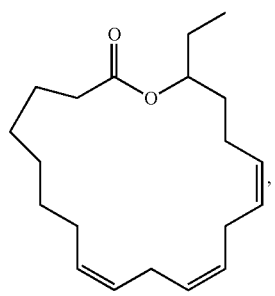
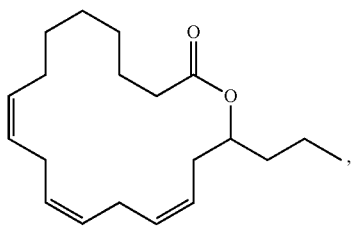
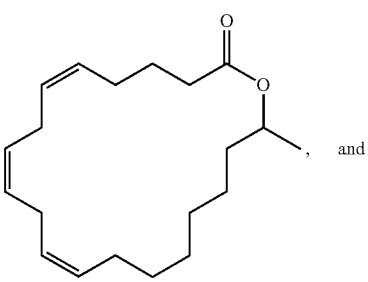
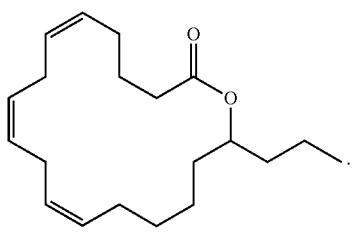
In some embodiments, the lactone comprises one or more compounds selected from:
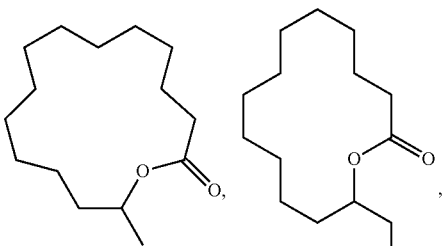
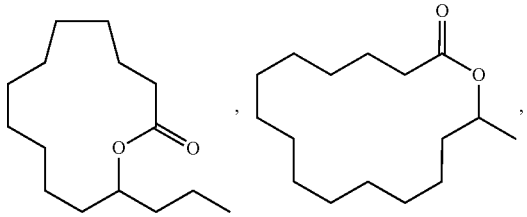
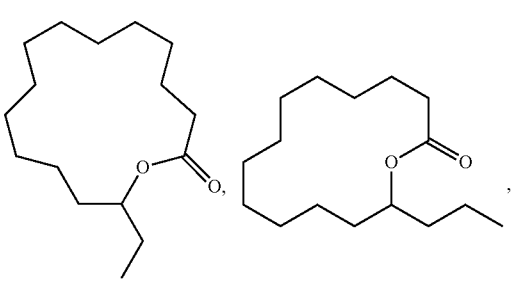

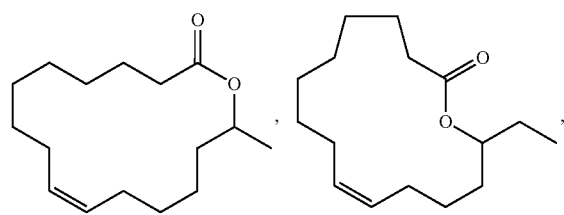
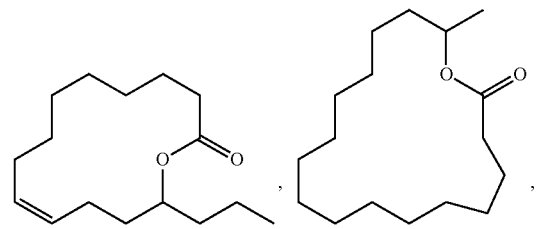
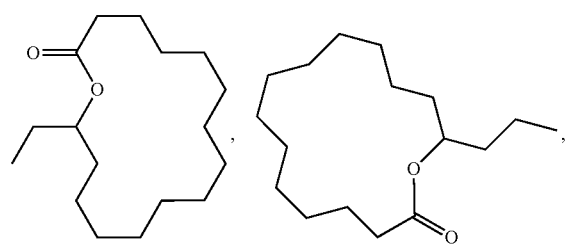
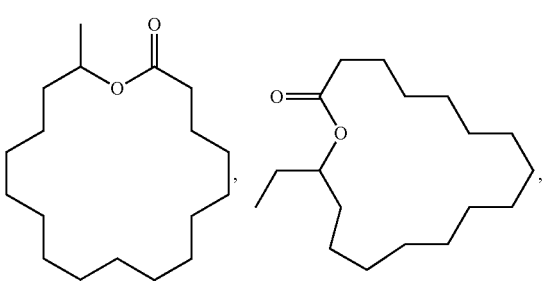
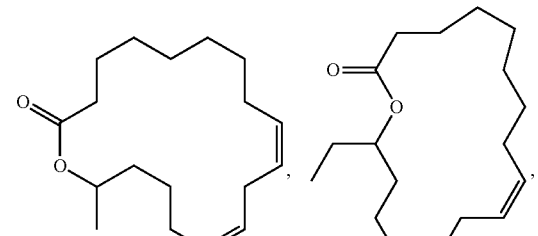
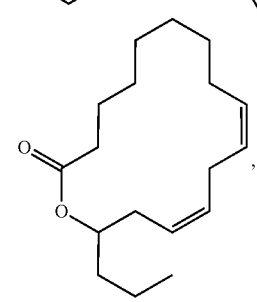
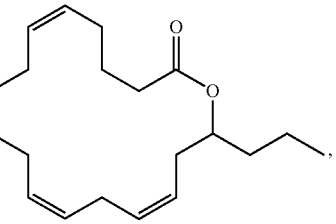
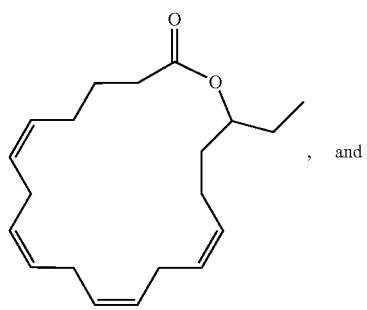
, and
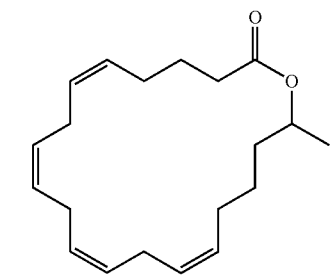
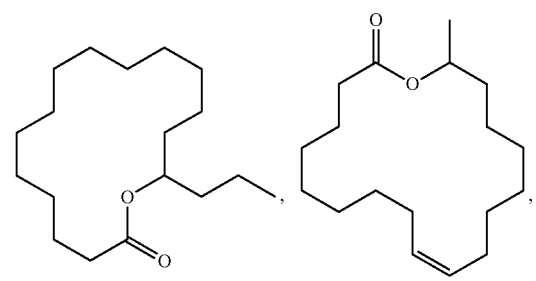
In some embodiments, the lactone comprises one or more compounds selected from:
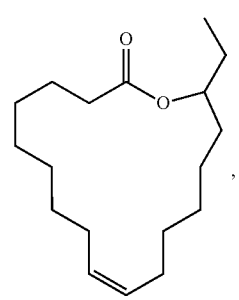 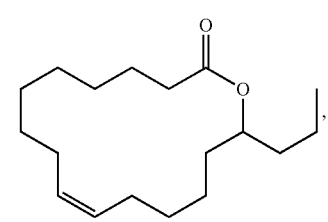 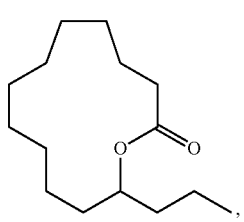 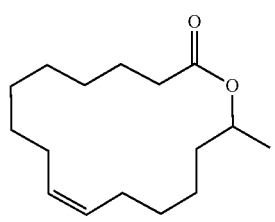

-continued
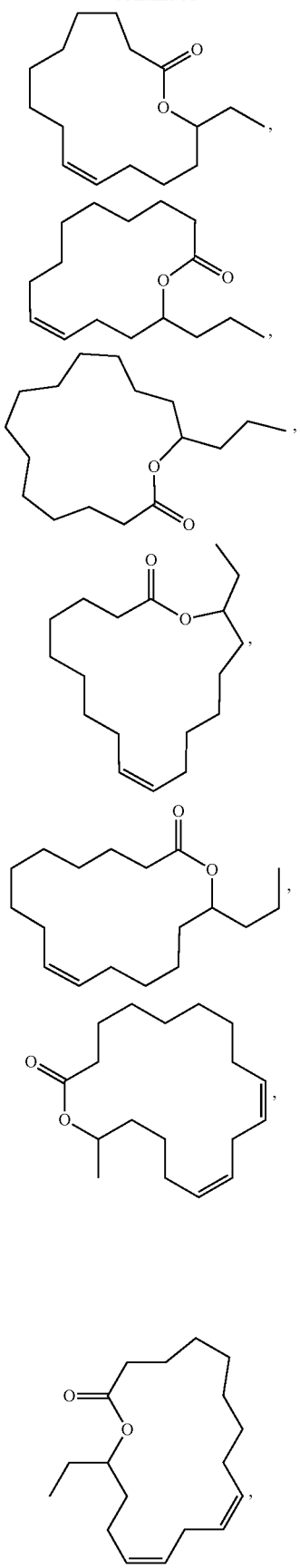
-continued
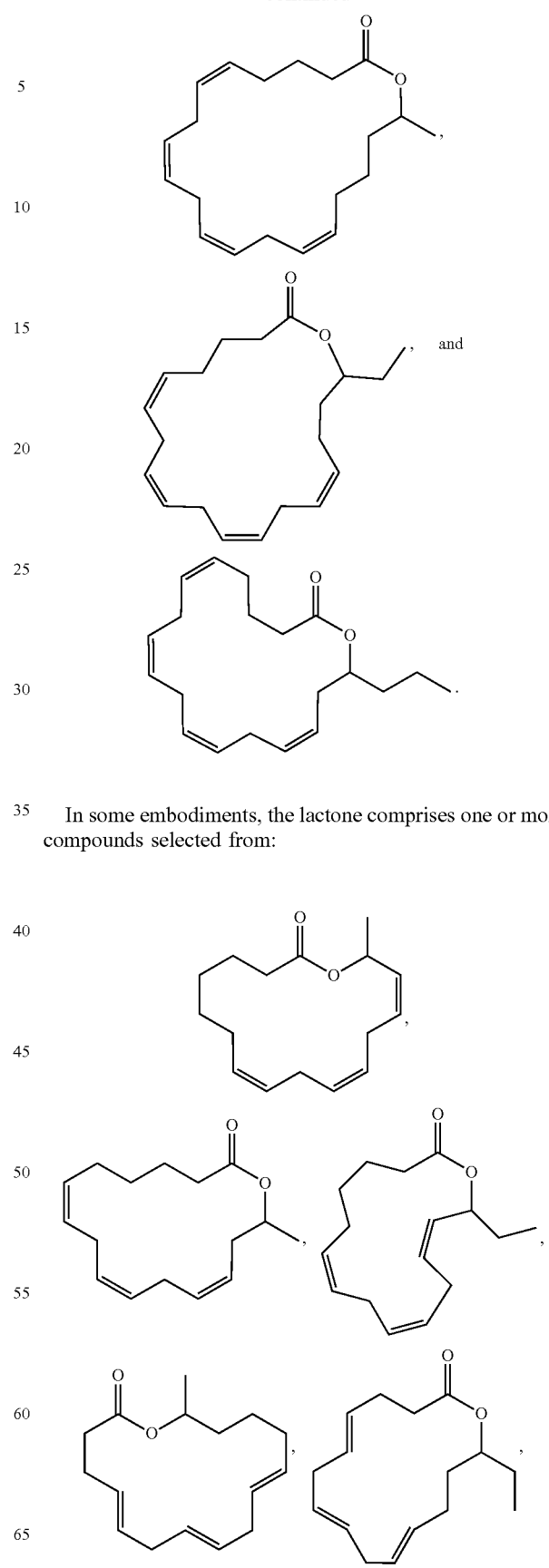
In some embodiments, the lactone comprises one or more compounds selected from:

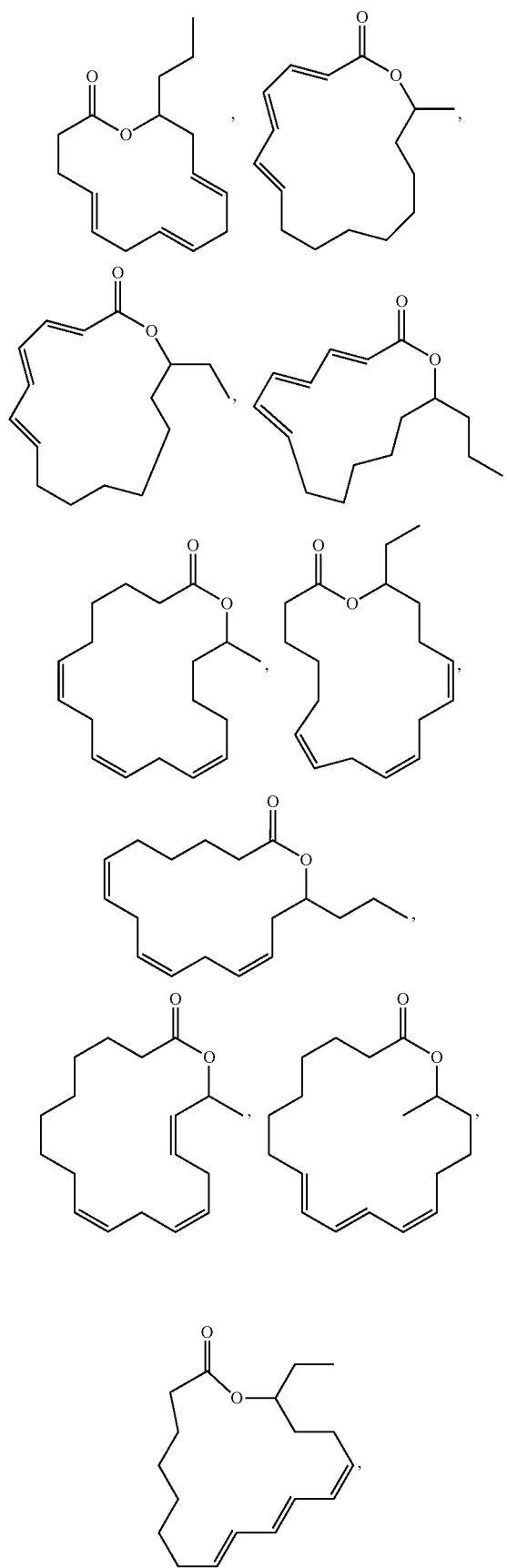
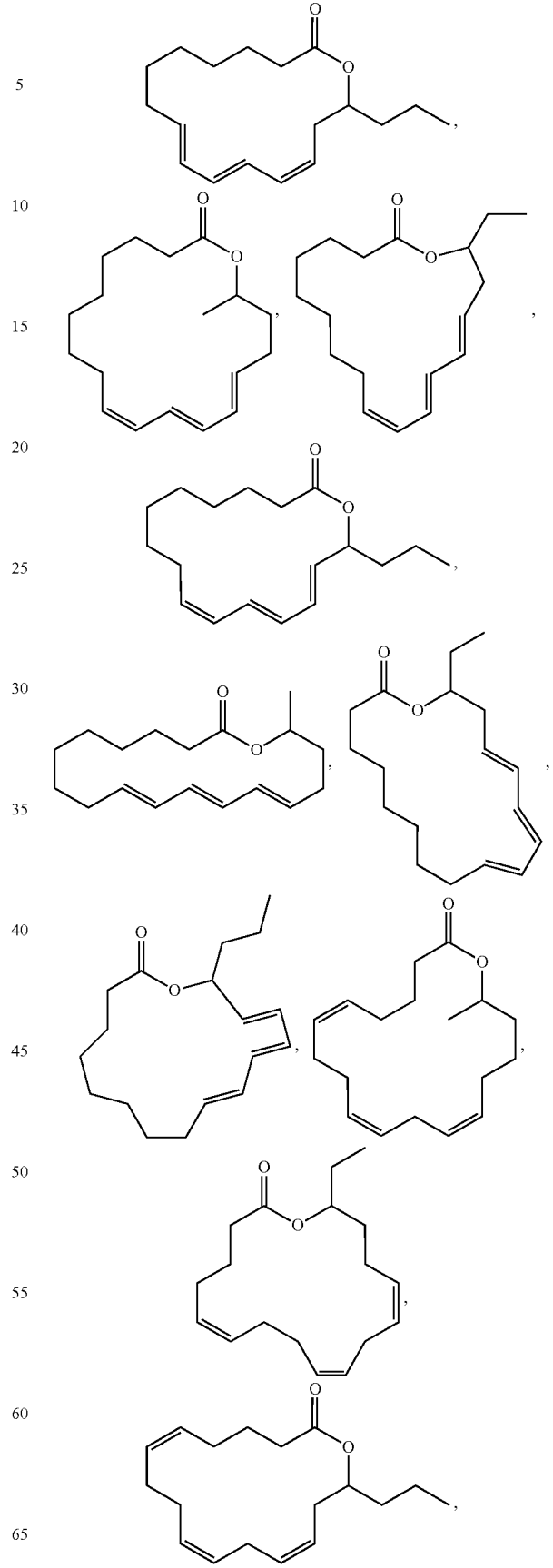

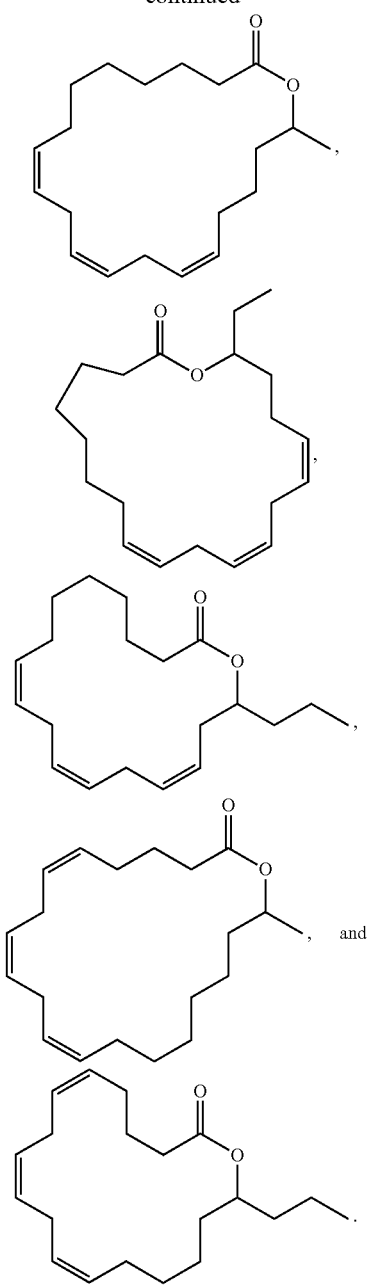

In some embodiments, the chiral carbon atom is of the S configuration. In some embodiments, the chiral carbon atom is of the R configuration.

In some embodiments, the consumer product is for skin application. In some embodiments, the consumer product is for non-skin application. In some embodiments, the consumer product is a perfume product. In some embodiments, the consumer product is a skin care product. In some embodiments, the consumer product is a hair care product. In some embodiments, the consumer product is a feminine hygiene product. In some embodiments, the consumer product is a fabric care product. In some embodiments, the consumer product is a cleaning product. In some embodiments, the consumer product further comprises a second fragrance. In some embodiments, the lactone is a booster for the second fragrance. In some embodiments, the lactone boosts overall fragrance performance. In some embodiments, the lactone improves the fragrance solubility, hence maximum fragrance load and impact in the consumer product. In some embodiments, the consumer product is for medicinal use, optionally wherein the medicinal use is anti-inflammatory. In some embodiments, the consumer product is for improving mood. In some embodiments, the lactone has increased substantivity. In some embodiments, the lactone has increased biodegradability. In some embodiments, the consumer product is selected from the group consisting of: fragrance, body wash, shampoo, after bath splash, eau de toilette, cologne, lotion, cream, liquid laundry detergent, compressed cleaning tablet, lip gloss, solid body moisturizer bar, hair care mousse, scented ink, gel hand sanitizer, candle, all-purpose cleaner, linen spray, fabric softener, dishwashing liquid, deodorant stick, soap, scented garbage bags, perfume bearing microcapsules, and eye patch.

In some embodiments, the lactone is produced by a method comprising:

(i) preparing a first reaction mixture comprising one or more fatty acids, a cytochrome P450 hydroxylase, and NADPH;

(ii) incubating the first reaction mixture of for a sufficient time to produce hydroxyl fatty acids selected from ω-1 hydroxyl fatty acids, ω-2 hydroxyl fatty acid, ω-3 hydroxyl fatty acid, and combinations thereof;

(iii) preparing a second reaction mixture comprising the hydroxyl fatty acids produced in step (ii) and a lipase; and (iv) incubating the second reaction mixture for a sufficient time to produce the lactone. 25. The method of claim 24, wherein step (ii) further comprises isolating the hydroxyl fatty acids from the first reaction mixture.

In some embodiments, the cytochrome P450 hydroxylase comprises an amino acid sequence that is at least 80% identical to the amino acid sequence of SEQ ID NO: 1 or SEQ ID NO: 3. In some embodiments, the cytochrome P450 hydroxylase comprises the amino acid sequence of SEQ ID NO: 1 or SEQ ID NO: 3. In some embodiments, the lipase is lipase B from *Candida antarctica*. In some embodiments, the lipase comprises an amino acid sequence that is at least 80% identical to the amino acid sequence of SEQ ID NO: 5. In some embodiments, the lipase comprises the amino acid sequence of SEQ ID NO: 5. In some embodiments, the lipase is immobilized on a solid support. In some embodiments, the second reaction mixture further comprises a solvent, optionally wherein the solvent is toluene or dichloroethane. In some embodiments, the hydroxyl fatty acids in the second reaction mixture are at a total concentration of 0.02-0.1 M, optionally wherein the hydroxyl fatty acids are at a total concentration of 0.025-0.5 M. In some embodiments, the lipase in the second reaction mixture is at a concentration of 20-150 g/L, optionally wherein the lipase is at a concentration of 50-100 g/L. In some embodiments, step (iv) further comprises isolating the lactone.

In some embodiments, the one or more fatty acids of step (i) comprise a linear fatty acid comprising 12-28 carbon atoms, optionally wherein the one or more fatty acids of step (i) comprise a linear fatty acid comprising 15, 16, 17, 18, or 20 carbon atoms. In some embodiments, the one or more fatty acids of step (i) comprise a saturated fatty acid. In some embodiments, the one or more fatty acids of step (i) comprise an unsaturated fatty acid, optionally wherein the unsaturated fatty acid comprises at least one double bond, optionally wherein the unsaturated fatty acid comprises at least one Z double bond.

In some embodiments, the one or more fatty acids of step (i) are selected from the group consisting of:
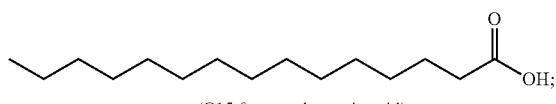
(C15:0, pentadecanoic acid)
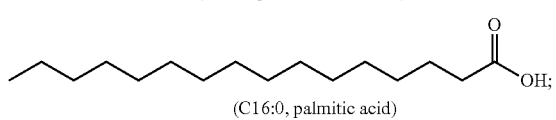
(C16:0, palmitic acid)
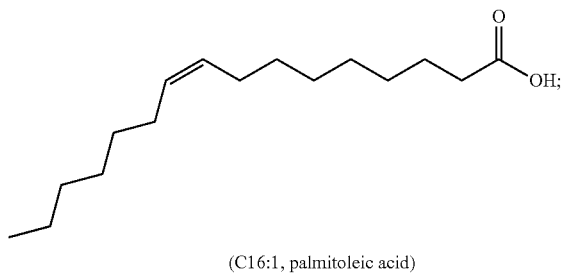
(C16:1, palmitoleic acid)
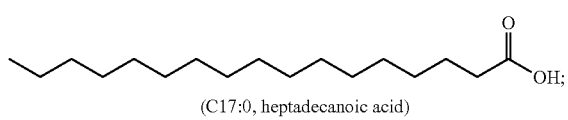
(C17:0, heptadecanoic acid)
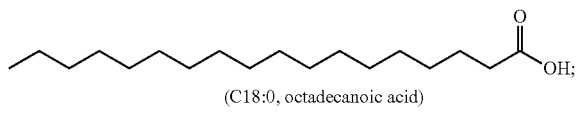
(C18:0, octadecanoic acid)
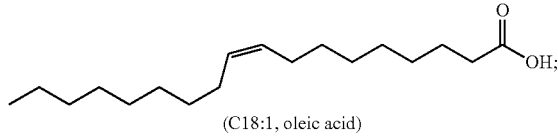
(C18:1, oleic acid)
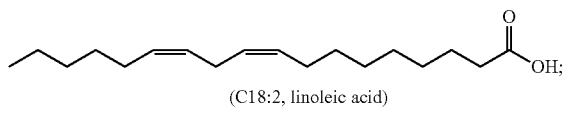
(C18:2, linoleic acid)
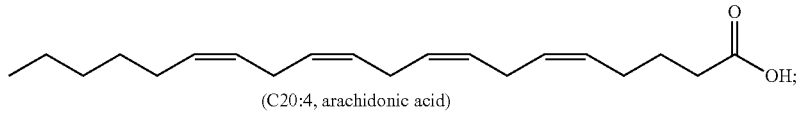
(C20:4, arachidonic acid)
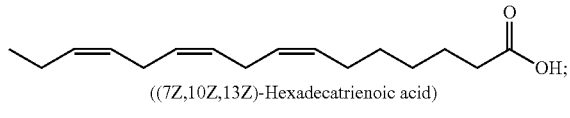
((7Z,10Z,13Z)-Hexadecatrienoic acid)
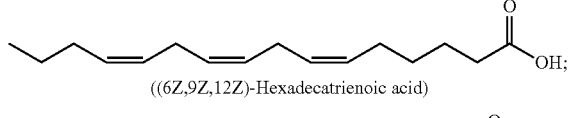
((6Z,9Z,12Z)-Hexadecatrienoic acid)
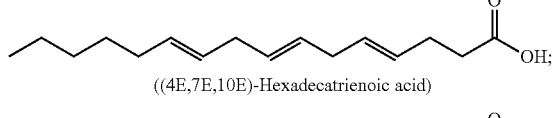
((4E,7E,10E)-Hexadecatrienoic acid)
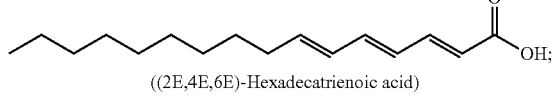
((2E,4E,6E)-Hexadecatrienoic acid)

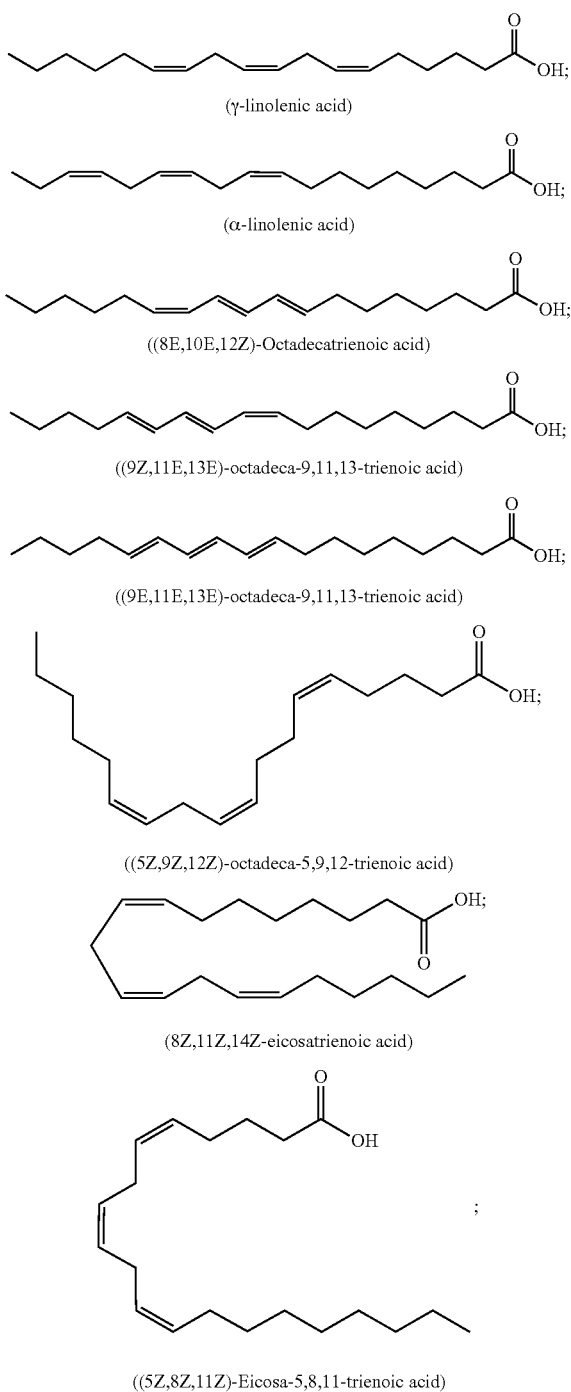
and combinations thereof.
In some embodiments, the one or more fatty acids of step (i) comprise
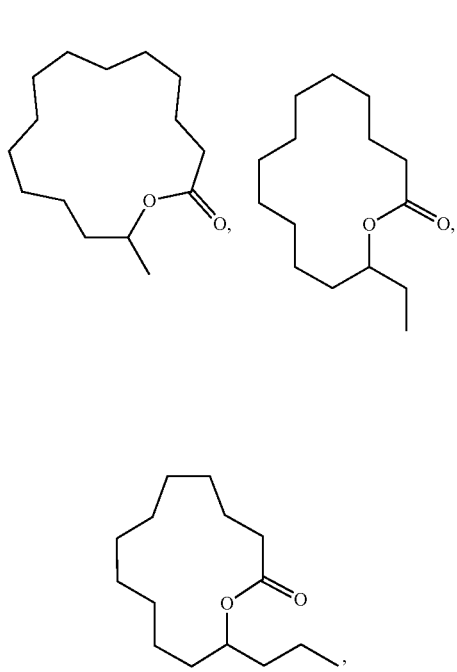
and the lactone produced in step (iv) comprises:
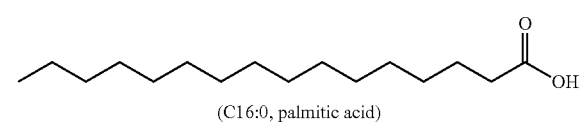 [SMILES: CCCCCCCCCCCCCCCC(=O)O]
(C16:0, palmitic acid)
and the lactone produced in step (iv) comprises:
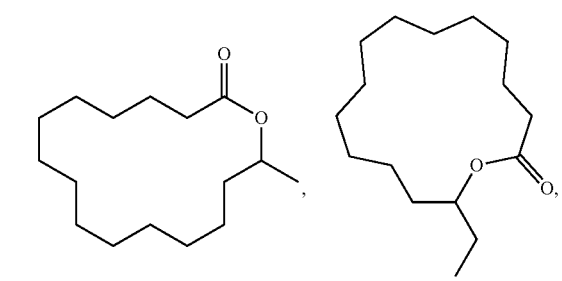
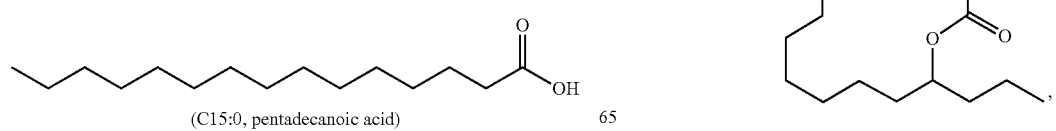
and combinations thereof.

In some embodiments, the one or more fatty acids of step (i) comprise

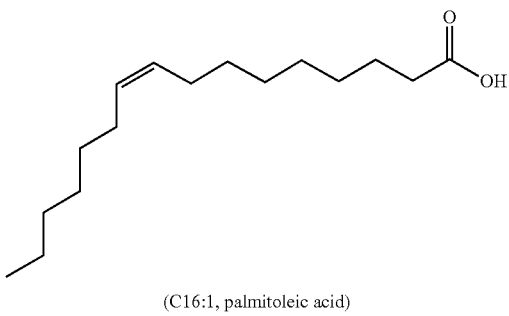 [SMILES: CCCCCC/C=C\CCCCCCCC(=O)O]

(C16:1, palmitoleic acid)

and the lactone produced in step (iv) comprises:

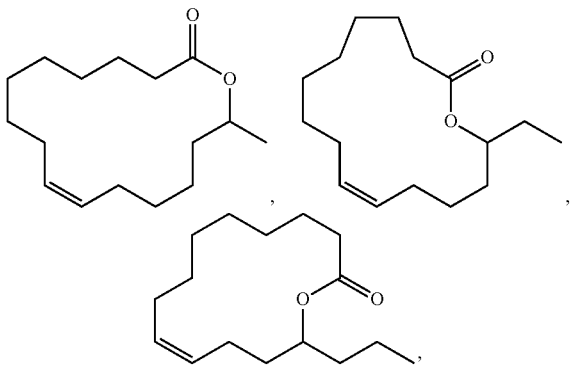

and combinations thereof.

In some embodiments, the one or more fatty acids of step (i) comprise

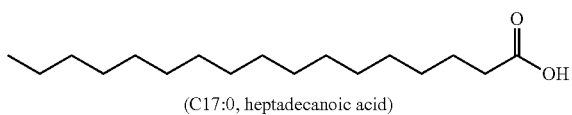 [SMILES: CCCCCCCCCCCCCCCCC(=O)O]

(C17:0, heptadecanoic acid)

and the lactone produced in step (iv) comprises:

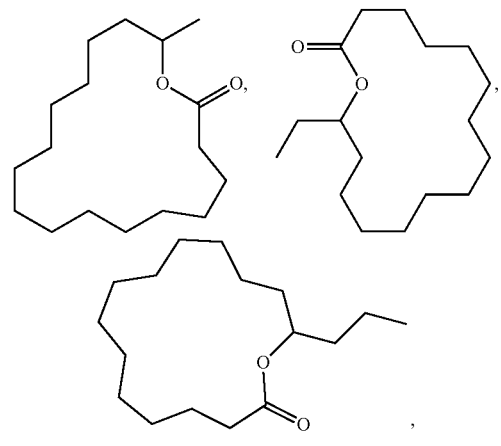

and combinations thereof.

In some embodiments, the one or more fatty acids of step (i) comprise

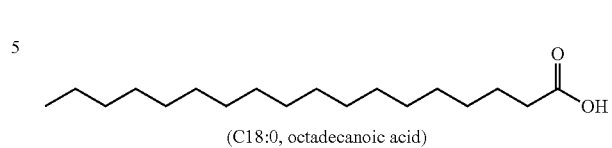

(C18:0, octadecanoic acid)

and the lactone produced in step (iv) comprises:

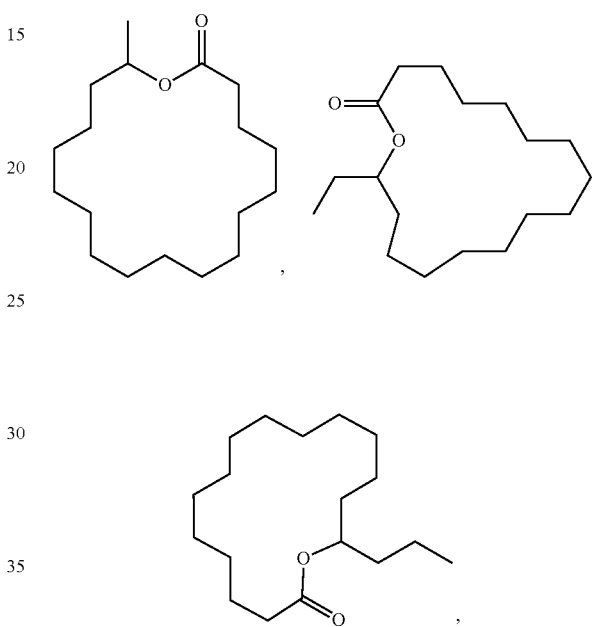

and combinations thereof.

In some embodiments, the one or more fatty acids of step (i) comprise

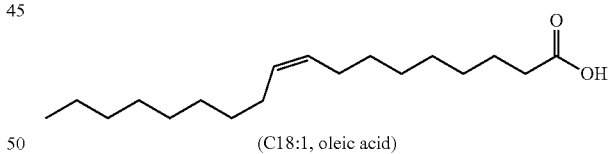

(C18:1, oleic acid)

and the lactone produced in step (iv) comprises:

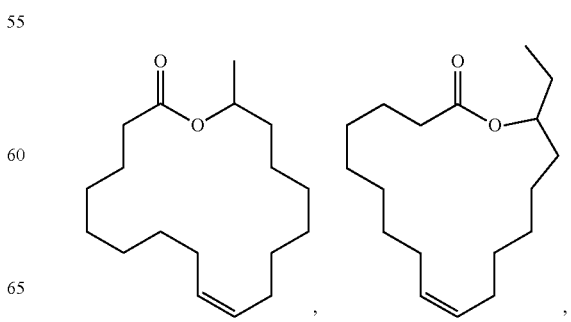

-continued

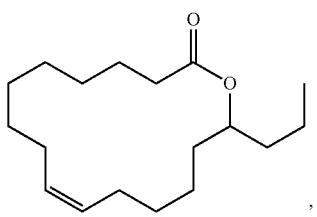

and combinations thereof.

In some embodiments, the one or more fatty acids of step (i) comprise

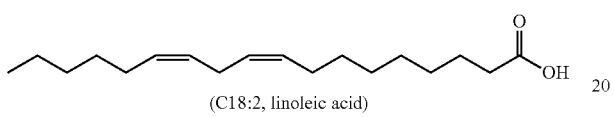
(C18:2, linoleic acid)

and the lactone produced in step (iv) comprises:

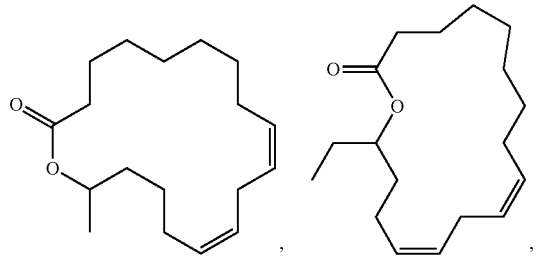

and combinations thereof.

In some embodiments, the one or more fatty acids of step (i) comprise

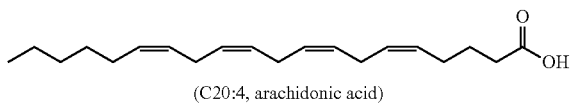 [SMILES: CCCCC/C=C\C/C=C\C/C=C\C/C=C\CCCC(=O)O]
(C20:4, arachidonic acid)

and the lactone produced in step (iv) comprises:

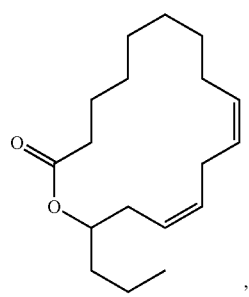

and combinations thereof.

In some embodiments, the one or more fatty acids used as substrates in the first reaction mixture in step (i) comprise

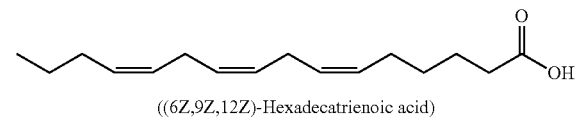 [SMILES: CCC/C=C\C/C=C\C/C=C\CCCCC(=O)O]
((7Z,10Z,13Z)-Hexadecatrienoic acid)

and the lactone produced in step (iv) comprises:

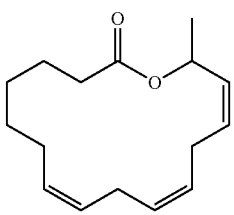

In some embodiments, the one or more fatty acids used as substrates in the first reaction mixture in step (i) comprise

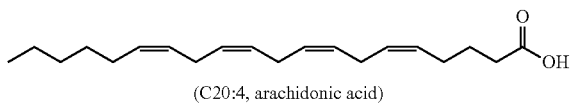 [SMILES: CCCCC/C=C\C/C=C\C/C=C\C/C=C\CCCC(=O)O]
((6Z,9Z,12Z)-Hexadecatrienoic acid)

and the lactone produced in step (iv) comprises:

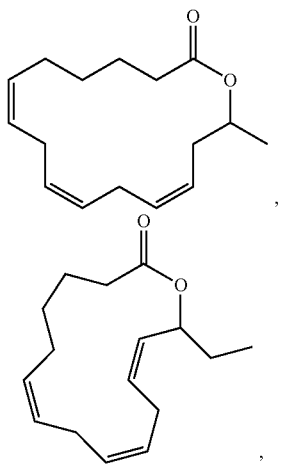

and combinations thereof.

In some embodiments, the one or more fatty acids used as substrates in the first reaction mixture in step (i) comprise

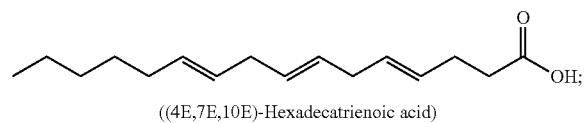 [SMILES: CCCCC/C=C/C/C=C/C/C=C/CCC(=O)O]

((4E,7E,10E)-Hexadecatrienoic acid)

and the lactone produced in step (iv) comprises:

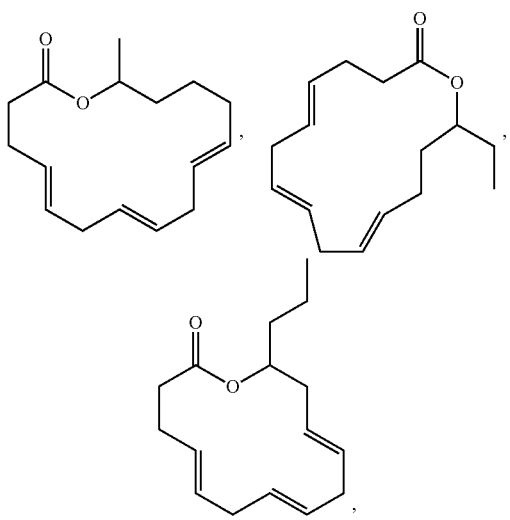

and combinations thereof.

In some embodiments, the one or more fatty acids used as substrates in the first reaction mixture in step (i) comprise

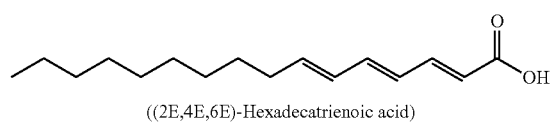 [SMILES: CCCCCCCCC/C=C/C=C/C=C/C(=O)O]

((2E,4E,6E)-Hexadecatrienoic acid)

and the lactone produced in step (iv) comprises:

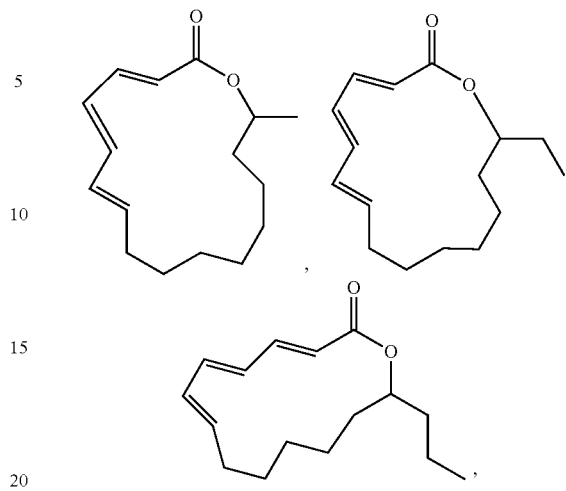

and combinations thereof.

In some embodiments, the one or more fatty acids used as substrates in the first reaction mixture in step (i) comprise and

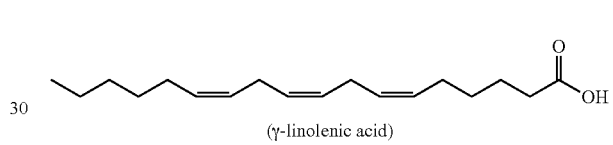

(γ-linolenic acid)

the lactone produced in step (iv) comprises:

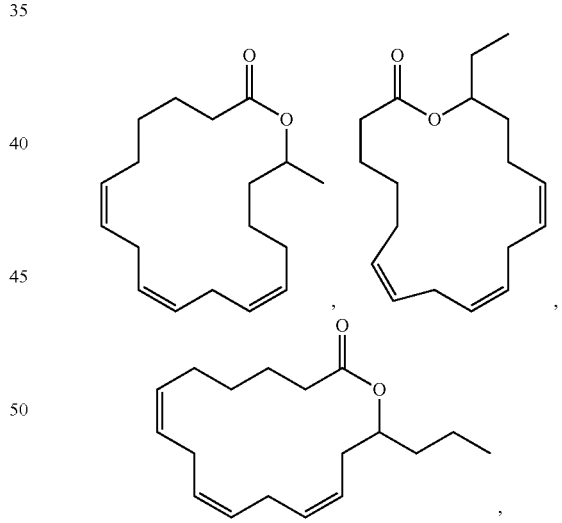

and combinations thereof.

In some embodiments, the one or more fatty acids used as substrates in the first reaction mixture in step (i) comprise and

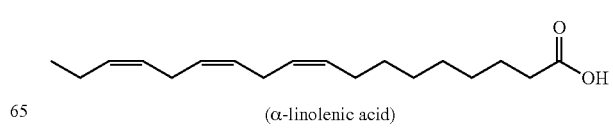

(α-linolenic acid)

the lactone produced in step (iv) comprises:

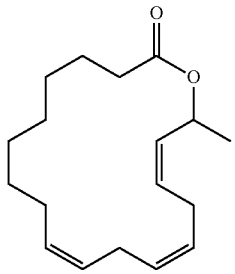

and the lactone produced in step (iv) comprises:

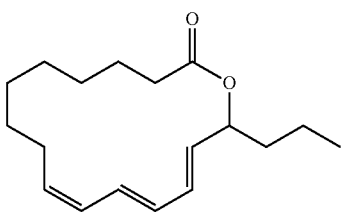

In some embodiments, the one or more fatty acids used as substrates in the first reaction mixture in step (i) comprise

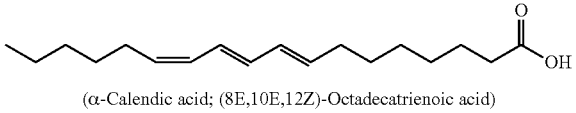 [SMILES: CCCCC\C=C/C=C/C=C/CCCCCCC(=O)O]

(α-Calendic acid; (8E,10E,12Z)-Octadecatrienoic acid)

and the lactone produced in step (iv) comprises:

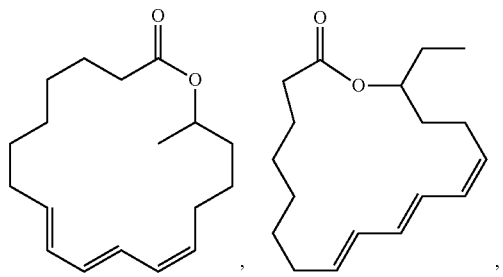

and combinations thereof.

In some embodiments, the one or more fatty acids used as substrates in the first reaction mixture in step (i) comprise

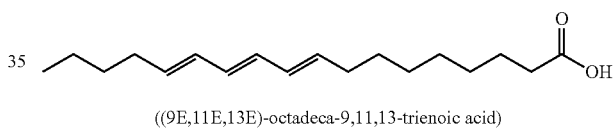

((9E,11E,13E)-octadeca-9,11,13-trienoic acid)

and the lactone produced in step (iv) comprises:

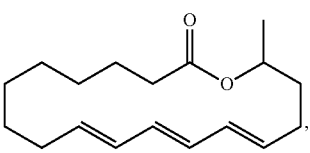

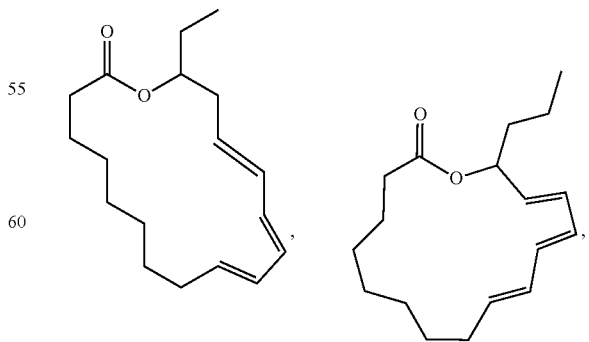

and combinations thereof.

In some embodiments, the one or more fatty acids used as substrates in the first reaction mixture in step (i) comprise

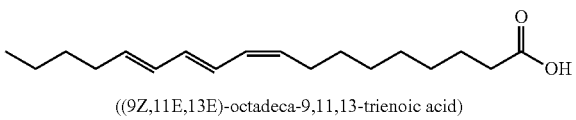 [SMILES: CCCC/C=C/C=C/C=C\CCCCCCCC(=O)O]

((9Z,11E,13E)-octadeca-9,11,13-trienoic acid)

In some embodiments, the one or more fatty acids used as substrates in the first reaction mixture in step (i) comprise

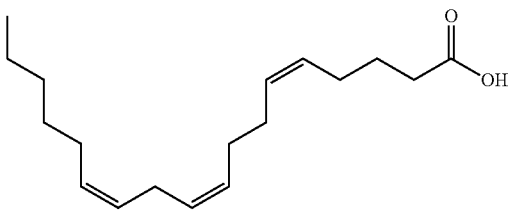

((5Z,9Z,12Z)-octadeca-5,9,12-trienoic acid)

and the lactone produced in step (iv) comprises:

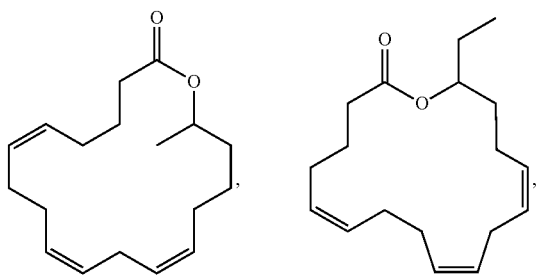

and combinations thereof.

In some embodiments, the one or more fatty acids used as substrates in the first reaction mixture in step (i) comprise

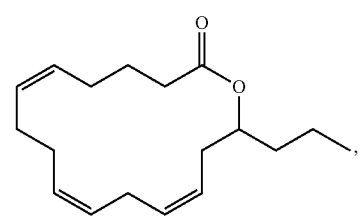

(8Z,11Z,14Z-eicosatrienoic acid)

and the lactone produced in step (iv) comprises:

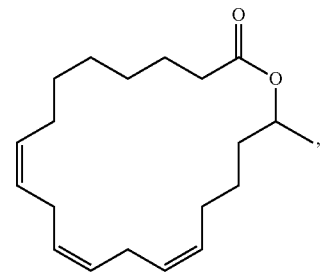

-continued

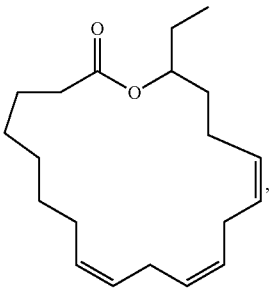

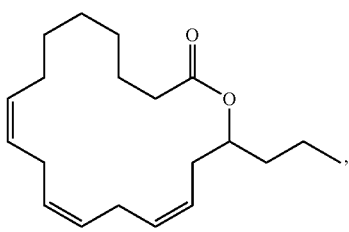

and combinations thereof.

In some embodiments, the one or more fatty acids used as substrates in the first reaction mixture in step (i) comprise

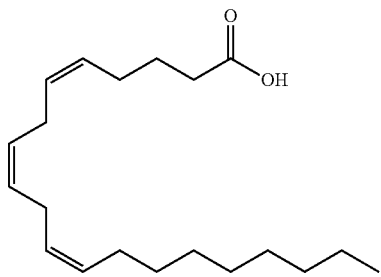

((5Z,8Z,11Z)-Eicosa-5,8,11-trienoic acid)

and the lactone produced in step (iv) comprises:

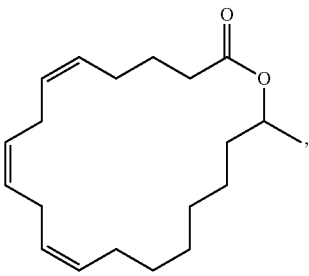

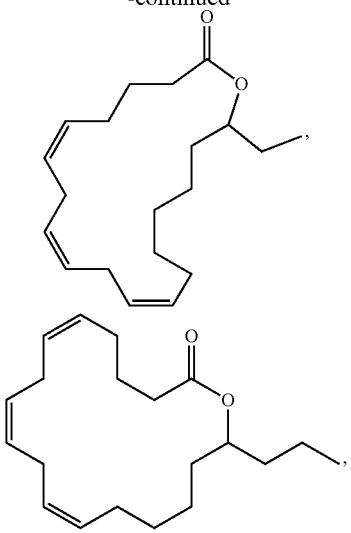

and combinations thereof.

In some embodiments, the first reaction mixture is in vitro. In some embodiments, the first reaction is a cell-based reaction mixture. In some embodiments, the cell-based reaction mixture comprises a cell selected from the group consisting of a yeast, a plant, an alga, a fungus, and a bacterium. In some embodiments, the cell-based reaction mixture comprises a bacterial cell of a genus selected from the group consisting of *Escherichia; Salmonella; Bacillus; Acinetobacter; Corynebacterium; Methylosinus; Methylomonas; Rhodococcus; Pseudomonas; Rhodobacter; Synechocystis; Brevibacteria; Microbacterium; Arthrobacter; Citrobacter; Escherichia; Klebsiella; Pantoea; Salmonella; Corynebacterium;* and *Clostridium,* optionally wherein the cell-based reaction mixture comprises an *E. coli* cell. In some embodiments, the cell-based reaction mixture comprises a fungus of a genus selected from the group consisting of *Saccharomyces; Zygosaccharomyces; Kluyveromyces; Candida; Streptomyces; Hansenula; Debaryomyces; Mucor; Pichia; Torulopsis; Aspergillus*; and *Arthrobotlys.*

In some embodiments, the lactone produced in step (iv) has a purity of at least 70%.

Other aspects of the present disclosure provide methods of producing a relaxed mood in a subject in need of same, the method comprising administering to the subject an effective amount of a fragrance composition described herein. Other aspects of the present disclosure provide method of reduce inflammation in a subject in need of same, the method comprising administering to the subject an effective amount of a fragrance composition described herein. In some embodiments, the subject is human.

Other aspects of the present disclosure provide methods of improving, enhancing, or modifying the fragrance of a fragrant composition, the method comprising adding a lactone comprising one or more compounds of the formula:

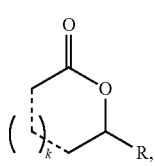

wherein:

R is methyl, ethyl, or n-propyl;

each - - - is independently a single bond, E double bond, Z double bond, or triple bond, as valency permits; and k is an integer between 6 and 30, inclusive;

In some embodiments, the method comprises adding a lactone comprising one or more compounds of the formula:

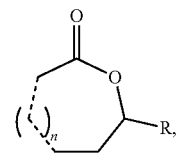

wherein:

R is methyl, ethyl, or n-propyl;

each - - - is independently a single bond, E double bond, Z double bond, or triple bond, as valency permits; and n is an integer between 6 and 20, inclusive.

In some embodiments, the lactone comprises one or more compounds selected from:

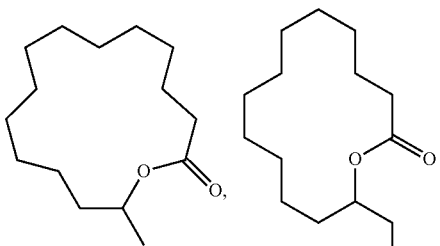

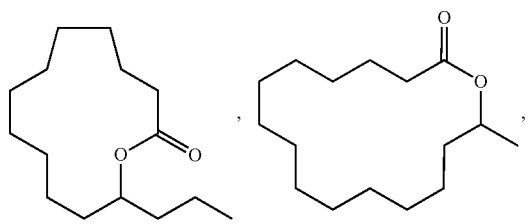

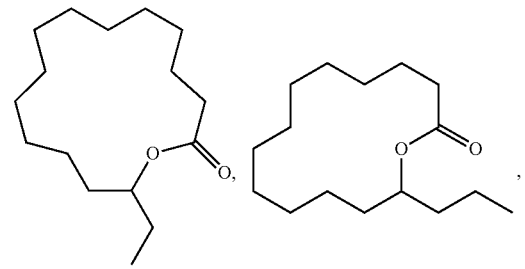

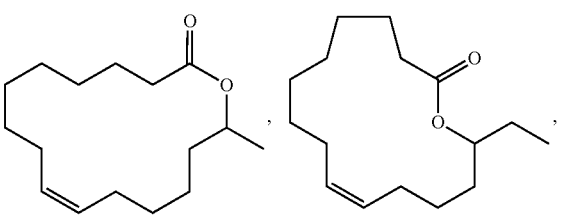

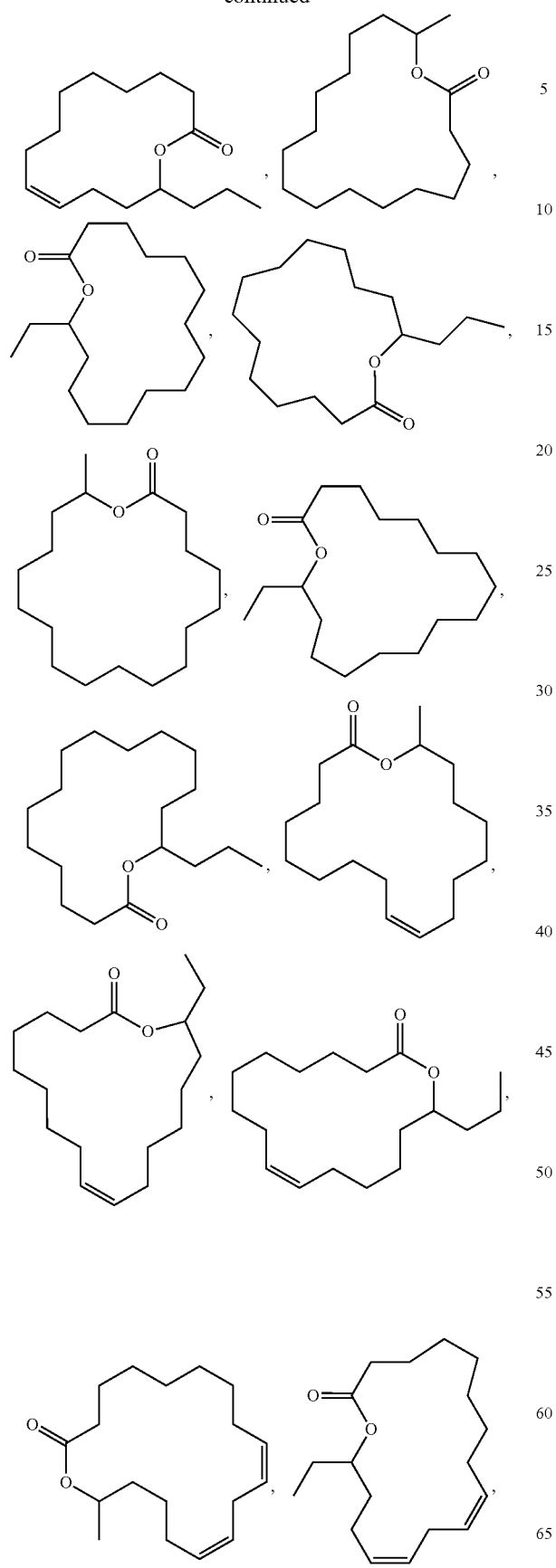
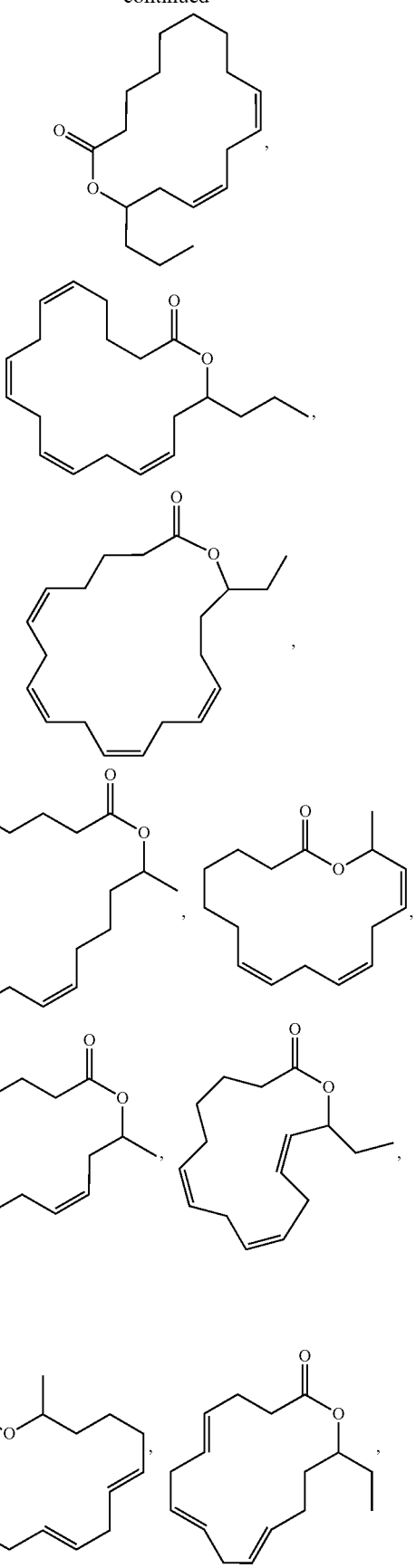

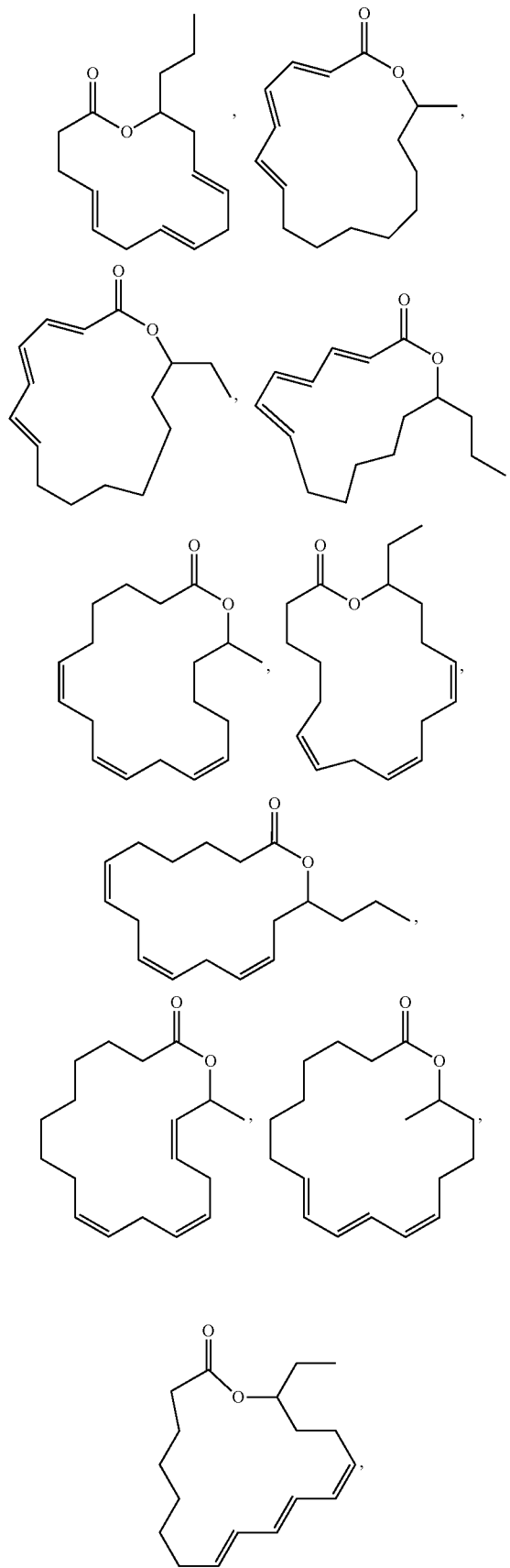
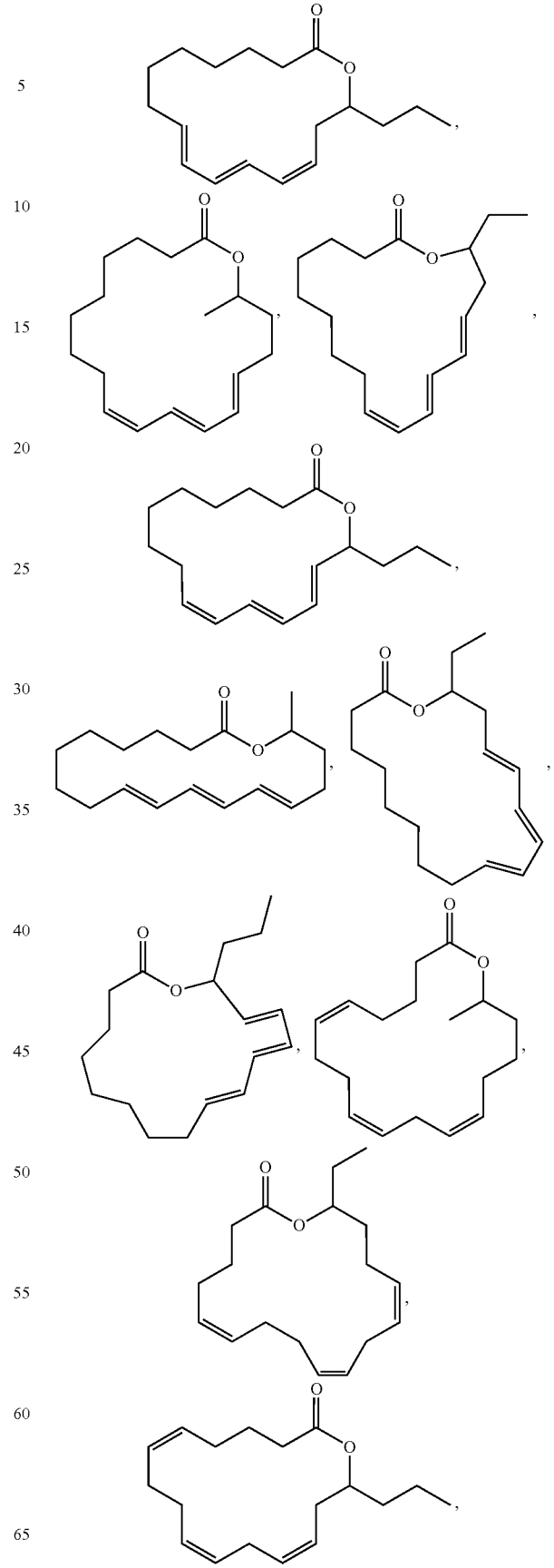

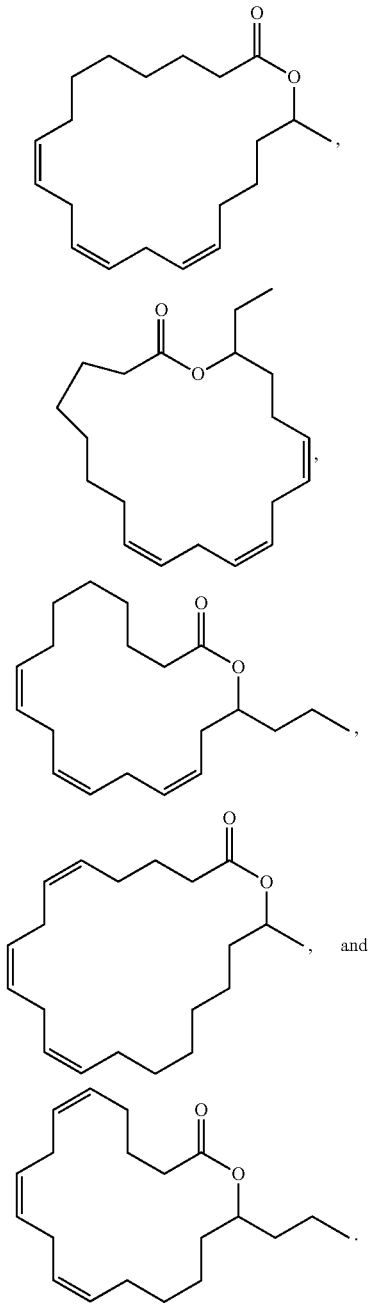
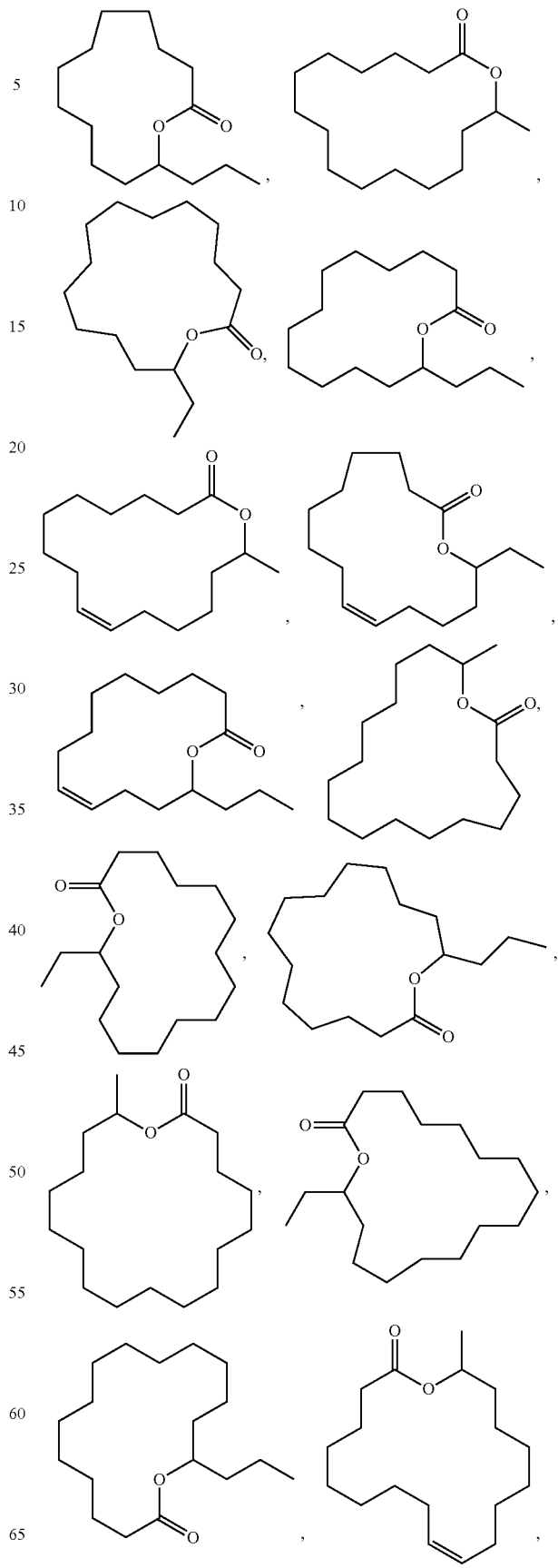
In some embodiments, the lactone comprises one or more compounds selected from:

-continued
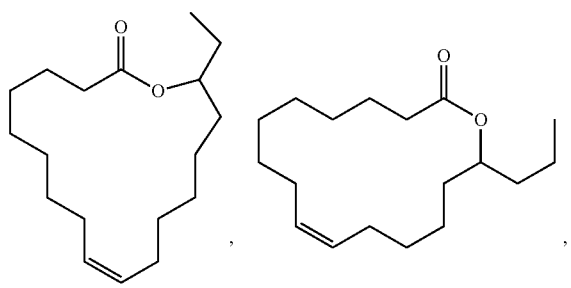
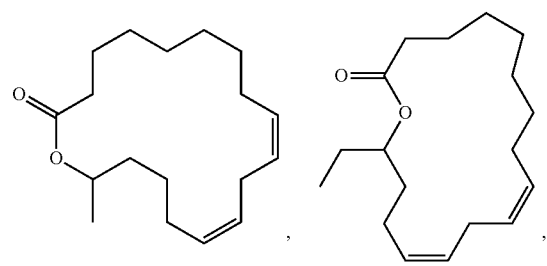
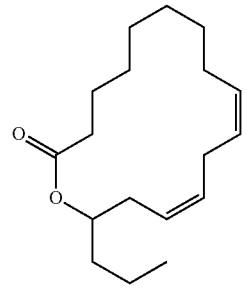
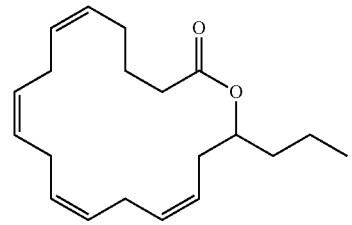
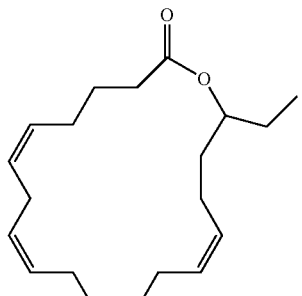
, and
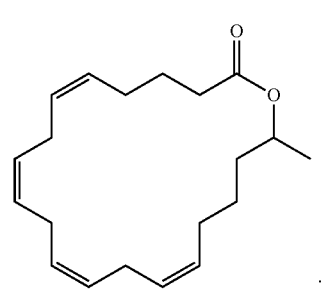
.
In some embodiments, the lactone comprises one or more compounds selected from:
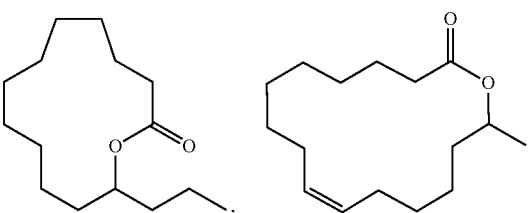
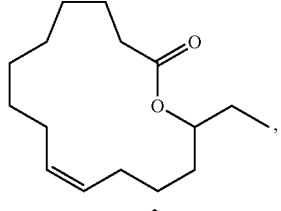
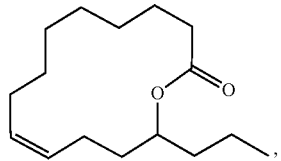
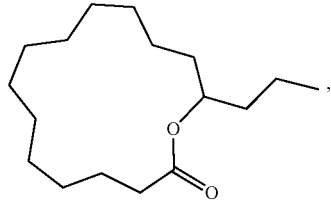
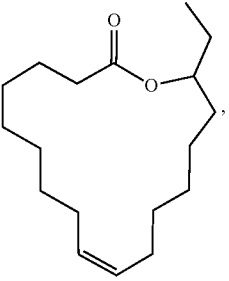
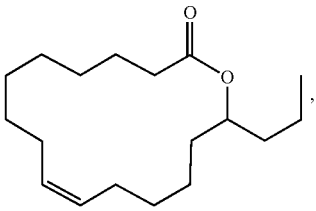
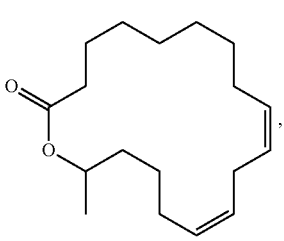

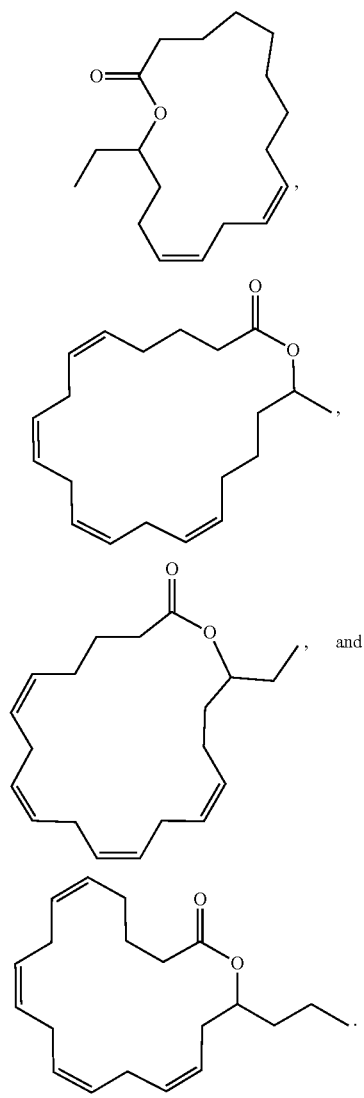
In some embodiments, the lactone comprises one or more compounds selected from:
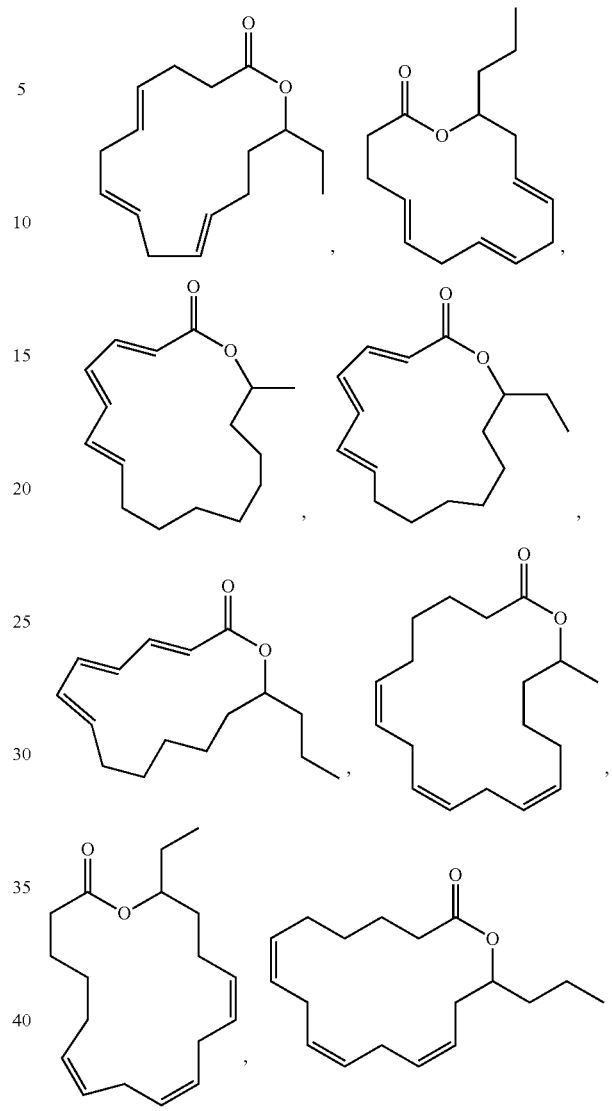
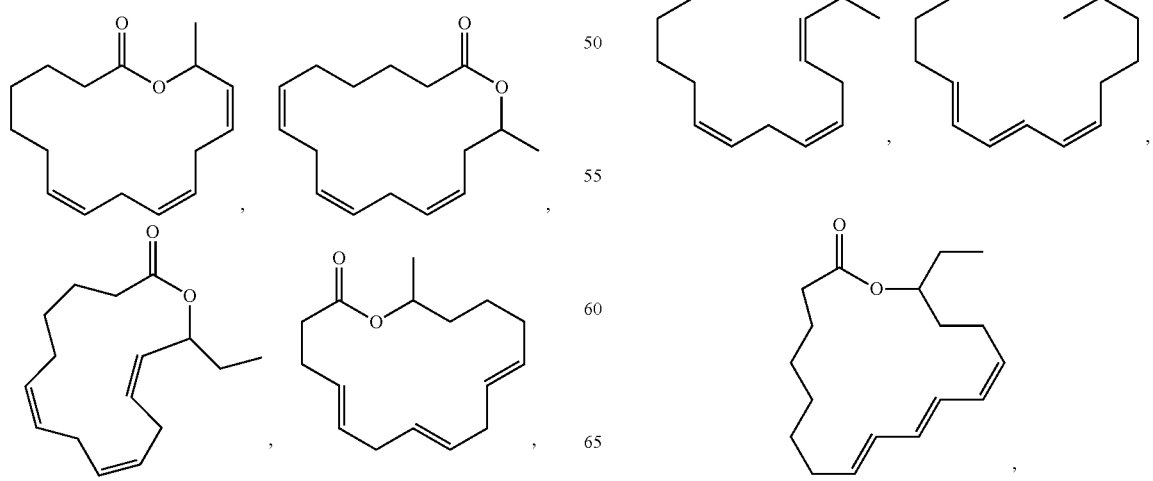

-continued

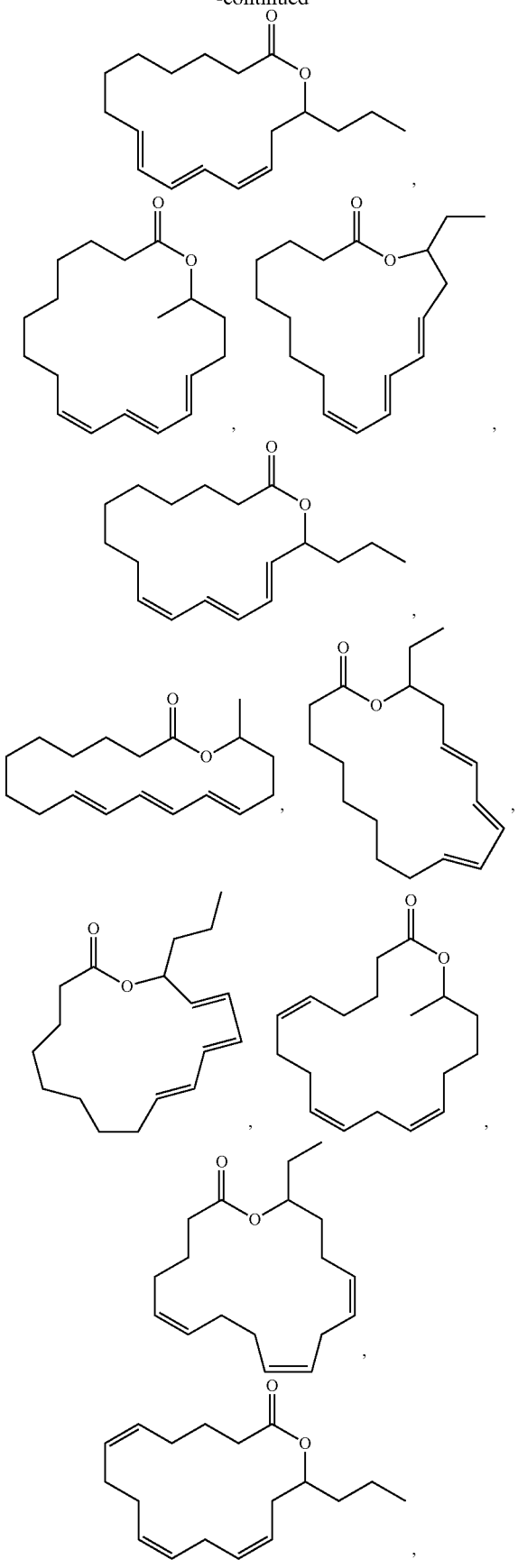

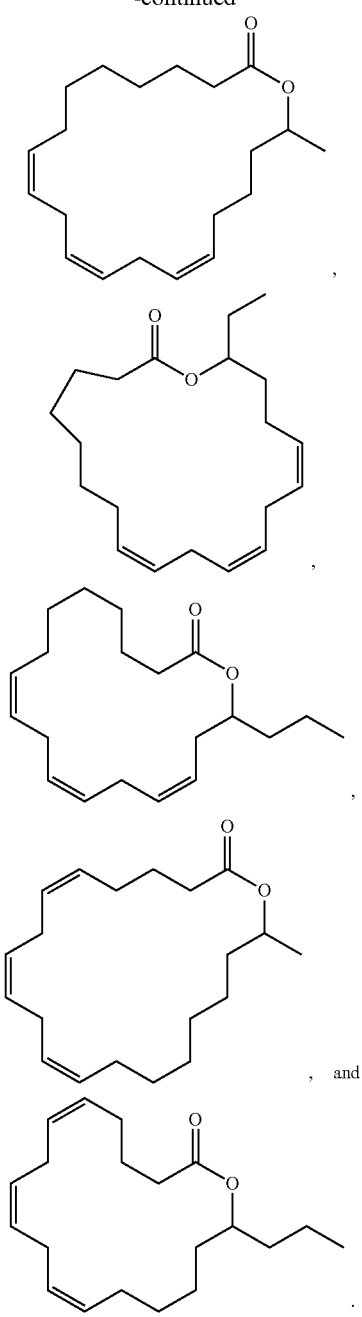

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiments disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DEFINITIONS

Figure 1:
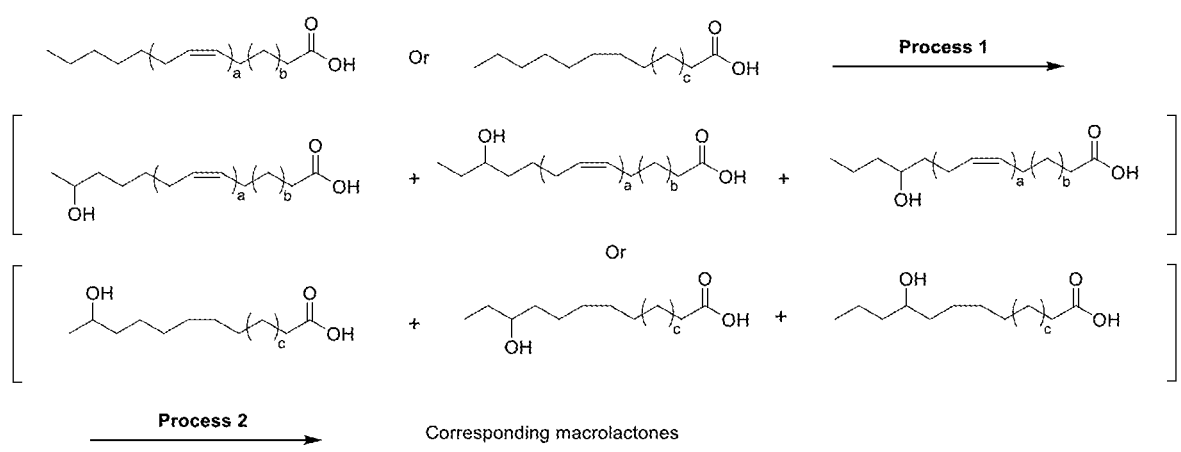
FIG. 1. Overall synthetic scheme showing fatty acid hydroxylation (Process 1) and a reaction of obtaining macrolactones (Process 2).

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "weight percent" or "wt-%" is meant to refer to the quantity by weight of a component in a material as a percentage of the total wet weight of the material (i.e., a fragrance formulation). Unless otherwise specified, all amounts expressed as a percentage herein represent the amount in weight percent.

The terms "fragrance composition", "fragrance", "fragrance formulation", "perfume" and "perfume composition" mean the same to refer to a perfumed composition that is a mixture of fragrance compounds including for example, alcohols, aldehydes, ketones, esters, ethers, acetates, nitriles, terpene hydrocarbons, nitrogenous or sulphurous heterocyclic compounds and essential oils of natural or synthetic origin, which are admixed so that the combined odors of the individual components produce a pleasant or desired fragrance. Many of these ingredients are listed in reference texts such as S. Arctander, Perfume and Flavor Chemicals, 1969, Montclair, N.J., USA (or any of its more recent versions), which is herein incorporated by reference in its entirety. As described herein, fragrance compositions can be a mixture of any number of fragrance compounds. For example, fragrance compositions include "simple accords", e.g., having fewer than 10 fragrance compounds, and "complex fragrances", e.g., having more than 30 fragrance compounds. In certain embodiments, the fragrance compositions of the present disclosure can be a combination of 2 or more accords.

As used herein, the term "improving" is understood to mean raising a fragrance composition to a more desirable character, the term "enhancing" is understood to mean making the fragrance composition greater in effectiveness, such as strength, and the term "modifying" is understood to mean providing the fragrance composition with a change in character.

As used herein, the term "isomers" refers to different compounds that have the same molecular formula but differ in arrangement and configuration of the atoms. Also as used herein, the term "stereoisomer" refers to any of the various stereo isomeric configurations which may exist for a given compound of the presently disclosed subject matter and includes geometric isomers. It is understood that a substituent may be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro or levorotatory) which they rotate plane polarized light at the wavelength of the sodium D line. The compounds of the presently disclosed subject matter contain one or more asymmetric centers and may thus give rise to enantiomers, diastereomers, and other stereoisomeric forms that may be defined, in terms of absolute stereochemistry, as (R)— or (S)—. The presently disclosed subject matter is meant to include all such possible isomers, including racemic mixtures, optically pure forms and intermediate mixtures. Optically active (R)— and (S)— isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

The term "alkyl" refers to a radical of a branched or unbranched, saturated acyclic hydrocarbon group. In certain embodiments, alkyl is $C_{3-36}$ alkyl. In certain embodiments, alkyl is $C_{10-36}$ alkyl. In certain embodiments, alkyl is $C_{11-27}$ alkyl. Unless otherwise provided, alkyl is $C_{3-29}$ alkyl.

The term "alkenyl" refers to a radical of a branched or unbranched, acyclic hydrocarbon group having one or more carbon-carbon double bonds (C═C bonds; e.g., 1, 2, 3, 4, 5, or 6 C═C bonds), as valency permits. In alkenyl groups,

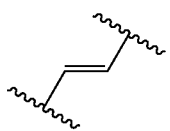

is an E double bond,

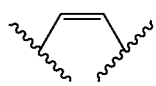 [SMILES: */C=C\*]

is an Z double bond. Other situations involving an E or Z double bond are as known in the art. In an alkenyl group, a C═C bond for which the stereochemistry is not specified (e.g., —CH═CH— or

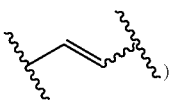

may be a E or Z double bond. In certain embodiments, alkenyl is $C_{3-36}$ alkenyl. In certain embodiments, alkenyl is $C_{10-36}$ alkenyl. In certain embodiments, alkenyl is $C_{11-27}$ alkenyl. Unless otherwise provided, alkenyl is $C_{3-29}$ alkenyl.

The term "alkynyl" refers to a radical of a branched or unbranched, acyclic hydrocarbon group having one or more carbon-carbon triple bonds (C≡C bonds; e.g., 1, 2, 3, or 4 triple bonds), as valency permits. In certain embodiments, alkynyl is $C_{3-36}$ alkynyl. In certain embodiments, alkynyl is $C_{10-36}$ alkynyl. In certain embodiments, alkynyl is $C_{11-27}$ alkynyl. Unless otherwise provided, alkynyl is $C_{3-29}$ alkynyl.

Affixing the suffix "ene" to a group indicates the group is a divalent moiety, e.g., alkylene is a divalent moiety of alkyl (e.g., $C_{3-36}$ alkyl, $C_{10-36}$ alkyl, $C_{11-27}$ alkyl, or $C_{3-29}$ alkyl), alkenylene is a divalent moiety of alkenyl (e.g., $C_{3-36}$ alkenyl, $C_{10-36}$ alkenyl, $C_{11-27}$ alkenyl, or $C_{3-29}$ alkenyl), and alkynylene is a divalent moiety of alkynyl (e.g., $C_{3-36}$ alkynyl, $C_{10-36}$ alkynyl, $C_{11-27}$ alkynyl, or $C_{3-29}$ alkynyl).

A "fatty acid" is a carboxylic acid of the formula: $R^4$—C(═O)OH, wherein $R^4$ is $C_{3-36}$ alkyl, $C_{3-36}$ alkenyl, or $C_{3-36}$ alkynyl (e.g., $C_{3-29}$ alkyl, $C_{3-29}$ alkenyl, or $C_{3-29}$ alkynyl). The carbon atom (e.g., C1) in $R^4$ that is farthest to the carboxyl moiety is labelled as ω (omega). The carbon atom (e.g., C2) next to C1 is labelled as ω-1. The carbon atom (e.g., C3) that is next to C2 and is not C1 is labelled as ω-2. The carbon atom (e.g., C4) that is next to C3 and is not C2 is labelled as ω-3. A 15:0 fatty acid is a fatty acid where the number of carbon atoms is 15, and the number of C═C and C≡C bonds is 0. A 16:0 fatty acid is a fatty acid where the number of carbon atoms is 16, and the number of C═C and C≡C bonds is 0. A 16:1 fatty acid is a fatty acid where the number of carbon atoms is 16, the number of C═C bonds is 1, and the number of C≡C bonds is 0. A 16:3 fatty acid is a fatty acid where the number of carbon atoms is 16, the number of C═C bonds is 3, and the number of C≡C bonds is 0. A 17:0 fatty acid is a fatty acid where the number of carbon atoms is 17, and the number of C═C and C≡C bonds is 0. An 18:0 fatty acid is a fatty acid where the number of carbon atoms is 18, and the number of C═C and C≡C bonds is 0. An 18:1 fatty acid is a fatty acid where the number of carbon atoms is 18, the number of C═C bonds is 1, and the number of C≡C bonds is 0. An 18:2 fatty acid is a fatty acid where the number of carbon atoms is 18, the number of C═C bonds is 2, and the number of C≡C bonds is 0. An 18:3 fatty acid is a fatty acid where the number of carbon atoms is 18, the number of C═C bonds is 3, and the number of C≡C bonds is 0. A 20:3 fatty acid is a fatty acid where the number of carbon atoms is 20, the number of C═C bonds is 3, and the number of C≡C bonds is 0. A 20:4 fatty acid is a fatty acid where the number of carbon atoms is 20, the number of C═C bonds is 4, and the number of C≡C bonds is 0. Other fatty acids can be named in this manner.

A "saturated fatty acid" is a fatty acid where $R^4$ is $C_{3-36}$ alkyl (e.g., $C_{3-29}$ alkyl).

An "unsaturated fatty acid" is a fatty acid where $R^4$ is $C_{3-36}$ alkenyl or $C_{3-36}$ alkynyl (e.g., $C_{3-29}$ alkenyl or $C_{3-29}$ alkynyl).

The term "hydroxyl" or "hydroxy" refers to the group —OH.

A "hydroxyl fatty acid," "hydroxy fatty acid," or "hydroxylated fatty acid" is a fatty acid where one or more hydrogen atom is replaced with hydroxyl. In some embodiments, the hydroxyl fatty acid is a fatty acid where one hydrogen atom is replaced with hydroxyl (mono-hydroxyl fatty acid). In some embodiments, the hydroxyl fatty acid is a fatty acid where more than one (e.g., 2, 3, or more) hydrogen atom is replaced with hydroxyl (poly-hydroxyl fatty acid).

A "lactone" is a monocyclic compound where the moiety —C(═O)O— is part of the monocyclic ring, and the remaining part of the monocyclic compound is alkylene, alkenylene, or alkynylene. When the alkylene, alkenylene, or alkynylene is branched, the lactone also includes the branch(es) of the alkylene, alkenylene, or alkynylene.

"Cellular system" is any cells that provide for the expression of ectopic proteins. It includes bacteria, yeast, plant cells and animal cells. It may include prokaryotic or eukaryotic host cells which are modified to express a recombinant protein and cultivated in an appropriate culture medium. It also includes the in vitro expression of proteins based on cellular components, such as ribosomes.

"Coding sequence" is to be given its ordinary and customary meaning to a person of ordinary skill in the art, and is used without limitation to refer to a DNA sequence that encodes for a specific amino acid sequence.

"Growing the Cellular System". Growing includes providing an appropriate medium that would allow cells to multiply and divide, to form a cell culture. It also includes providing resources so that cells or cellular components can translate and make recombinant proteins.

"Protein Expression". Protein production can occur after gene expression. It consists of the stages after DNA has been transcribed to messenger RNA (mRNA). The mRNA is then translated into polypeptide chains, which are ultimately folded into proteins. DNA or RNA may be present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

"Yeast". According to the current disclosure a yeast are eukaryotic, single-celled microorganisms classified as members of the fungus kingdom. Yeasts are unicellular organisms which are believed to have evolved from multicellular ancestors.

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art and is used without limitation to describe the relationship between nucleotide bases that are capable to hybridizing to one another. For example, with respect to DNA, adenosine is complementary to thymine and cytosine is complementary to guanine. Accordingly, the subject technology also includes isolated nucleic acid fragments that are complementary to the complete sequences as reported in the accompanying Sequence Listing as well as those substantially similar nucleic acid sequences.

The terms "nucleic acid" and "nucleotide" are to be given their respective ordinary and customary meanings to a person of ordinary skill in the art and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof. (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a lactone composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polyaminoacid product. Thus, exemplary polypeptides include polyaminoacid products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super-families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the field, and is used without limitation to refer to the transfer of a polynucleotide into a target cell for further expression by that cell. The transferred polynucleotide can be incorporated into the genome or chromosomal DNA of a target cell, resulting in genetically stable inheritance, or it can replicate independent of the host chromosomal DNA. Host organisms containing the transformed nucleic acid fragments are referred to as "transgenic" or "recombinant" or "transformed" organisms.

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

DETAILED DESCRIPTION

Novel compounds which have a musk-like odor are sought as replacements for rare and expensive musk or as scent components for fragrance compositions.

The present disclosure, in some aspects, provide lactones, such as macrocyclic lactones for use in consumer products. As described herein, the lactones are produced using biosynthetic methods from fatty acids. In some embodiments, the lactones have differentiated musky notes (also referred to herein as "musk lactones"), can be used in consumer products comprising fragranced compositions, for boosting a second fragrance or overall fragrance performance, have mood enhancing and/or anti-inflammatory effects, and have increased substantivity (e.g., fiber substantivity) and biodegradability.

The presently disclosed compounds can have fruity, musky, floral, aldehydic, and/or herbaceous odor notes; as well as a wide range of secondary odors, such as animalic, to woody notes. These compounds can be used alone or incorporated into a fragrance composition to modify or enhance the odor of existing fragrance compositions, solvents, media, consumer products, and the like.

The lactones described herein, such as macrocyclic lactones, may be used as such to impart, strengthen or improve the odor of a wide variety of products, or they may be used separately or in combinations with two or three other musk entities or with other commercially available musk compounds, of natural or synthetic origin, as a component of a perfume to contribute its odor character to the overall odor of such perfume. As used herein, a perfume is intended to mean a mixture of fragrance materials, if desired mixed with or dissolved in a suitable solvent or mixed with a solid substrate, which is used to impart a desired odor to the skin and/or to any other substract and/or any product for which an agreeable odor is indispensable or desirable.

The lactones are superior to other known lactone compounds further due to their enhanced fiber substantivity properties and biodegradability. The lactones are also able to reduce malodor, support positive mood, and have anti-inflammatory effects.

Lactones

In some embodiments, the lactones, such as macrocyclic lactones, produced herein comprise one or more compounds of the formula:

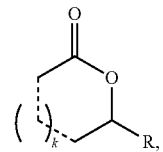

wherein:
R is methyl, ethyl, or n-propyl;
each - - - is independently a single bond, E double bond, Z double bond, or triple bond, as valency permits; and
k is an integer between 6 and 30, inclusive.

In some embodiments, the lactones (e.g., macrocyclic lactones) produced using the biosynthetic methods described herein comprise one or more compounds of the formula:

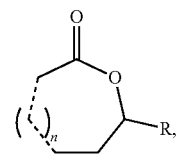

wherein:
R is methyl, ethyl, or n-propyl;
each - - - is independently a single bond, E double bond, Z double bond, or triple bond, as valency permits; and
n is an integer between 6 and 20, inclusive.

In certain embodiments, R is methyl. In certain embodiments, R is ethyl. In certain embodiments, R is n-propyl.

In certain embodiments, each - - - is a single bond. In certain embodiments, at least one (e.g., one, two, three, or four) - - - is an E or Z double bond. In certain embodiments, at least one (e.g., one, two, three, or four) - - - is an E double bond. In certain embodiments, at least one (e.g., one, two, three, or four) - - - is an Z double bond. In certain embodiments, each - - - is independently a single bond, E double bond, or Z double bond. In certain embodiments, each - - - is independently a single or Z double bond. In certain embodiments, one - - - is a Z double bond, and each remaining - - - is a single bond. In certain embodiments, two - - - are Z double bonds, and each remaining - - - is a single bond. In certain embodiments, three - - - are Z double bonds, and each remaining - - - is a single bond. In certain embodiments, four - - - are Z double bonds, and each remaining - - - is a single bond. In certain embodiments, at least one (e.g., one, two, or three) - - - is a triple bond. In certain embodiments, at least one of any two adjacent - - - is a single bond.

In certain embodiments, one - - - is an E or Z double bond, and the remining - - - are single bonds. In certain embodiments, two - - - are independently E or Z double bonds, and the remining - - - are single bonds. In certain embodiments, three - - - are independently E or Z double bonds, and the remining - - - are single bonds. In certain embodiments, four - - - are independently E or Z double bonds, and the remining - - - are single bonds. In certain embodiments, each double bond if present is a Z double bond. In certain embodiments, the lactone does not comprise any one of C=C=C, C=C≡C, and C≡C=C.

In certain embodiments, k is 6. In certain embodiments, k is 7. In certain embodiments, k is 8. In certain embodiments, k is 9. In certain embodiments, k is 10. In certain embodiments, k is 11. In certain embodiments, k is 12. In certain embodiments, k is 13. In certain embodiments, k is 14. In certain embodiments, k is 15. In certain embodiments, k is 16. In certain embodiments, k is 8, 9, 10, 11, 12, 13, or 15. In certain embodiments, k is an integer between 17 and 20, inclusive. In certain embodiments, k is an integer between 21 and 25, inclusive. In certain embodiments, k is an integer between 26 and 30, inclusive.

In certain embodiments, n is 6. In certain embodiments, n is 7. In certain embodiments, n is 8. In certain embodiments, n is 9. In certain embodiments, n is 10. In certain embodiments, n is 11. In certain embodiments, n is 12. In certain embodiments, n is 13. In certain embodiments, n is 14. In certain embodiments, n is 15, 16, 17, 18, 19, or 20. In certain embodiments, n is an integer between 7 and 14, inclusive.

In some embodiments, the lactones produced using the biosynthetic methods described herein include a chiral carbon atom, which is the carbon atom labelled with * in the formula:

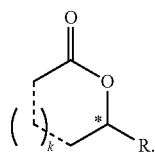

In certain embodiments, the lactones produced using the biosynthetic methods described herein include a chiral carbon atom, which is the carbon atom labelled with * in the formula:

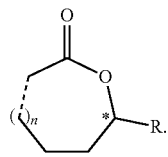

In certain embodiments, the chiral carbon atom is of the S configuration. In certain embodiments, the chiral carbon atom is of the R configuration.

In certain embodiments, the lactones produced using the biosynthetic methods described herein are a mixture of lactones. In certain embodiments, the lactones produced using the biosynthetic methods described herein are a mixture of (e.g., two or three) lactones having different n values and different R moieties when the difference in the RIS configurations if present is disregarded. In certain embodiments, the lactones produced using the biosynthetic methods described herein are a mixture of lactones having the same RIS configuration but different n values and different R moieties. In certain embodiments, the lactones produced using the biosynthetic methods described herein are a mixture of lactones having different RIS configurations but the same n values and the same R moieties. In certain embodiments, the lactones produced using the biosynthetic methods described herein are a mixture of lactones having different RIS configurations, different n values, and different R moieties. In certain embodiments, the lactones produced using the biosynthetic methods described herein are substantially (e.g., between 90% and 95%, between 95% and 97%, between 97% and 99%, or between 99% and 99.9%, inclusive, by mole) a racemic mixture of lactones.

In certain embodiments, the lactones produced using the biosynthetic methods described herein are substantially (e.g., between 90% and 95%, between 95% and 97%, between 97% and 99%, or between 99% and 99.9%, inclusive, by mole) one single type of lactone (e.g., substantially free of other types of lactones, including the opposite enantiomer of the one single type of lactone). In certain embodiments, the lactones produced using the biosynthetic methods described herein are substantially (between 90% and 95%, between 95% and 97%, between 97% and 99%, or between 99% and 99.9%, inclusive, by mole) two types of lactones, which are opposite enantiomers of each other (e.g., substantially free of other types of lactones).

In some embodiments, the one or more fatty acids used as substrates in the first reaction mixture in step (i) comprise

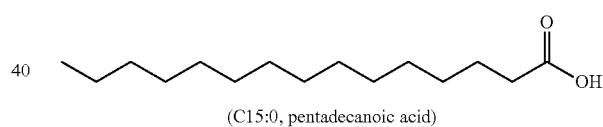

(C15:0, pentadecanoic acid)

and the lactone produced in step (iv) comprises:

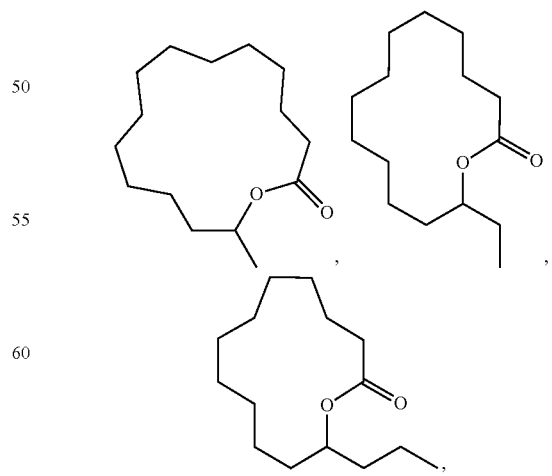

and combinations thereof.

In some embodiments, the one or more fatty acids used as substrates in the first reaction mixture in step (i) comprise

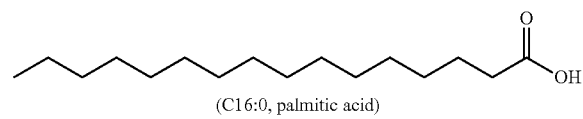 [SMILES: CCCCCCCCCCCCCCCC(=O)O]
(C16:0, palmitic acid)

and the lactone produced in step (iv) comprises:

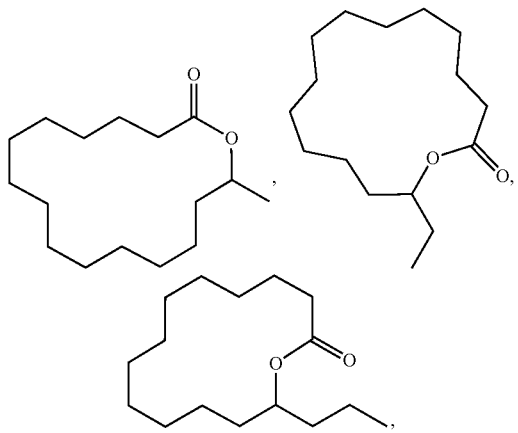

and combinations thereof.

In some embodiments, the one or more fatty acids used as substrates in the first reaction mixture in step (i) comprise

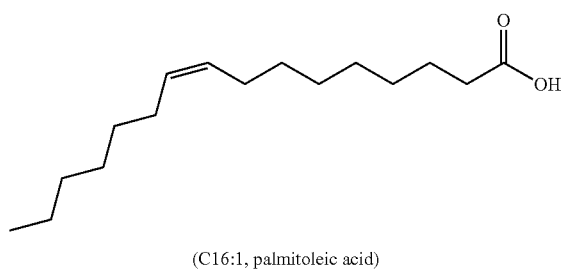 [SMILES: CCCCCC/C=C\CCCCCCCC(=O)O]
(C16:1, palmitoleic acid)

and the lactone produced in step (iv) comprises:

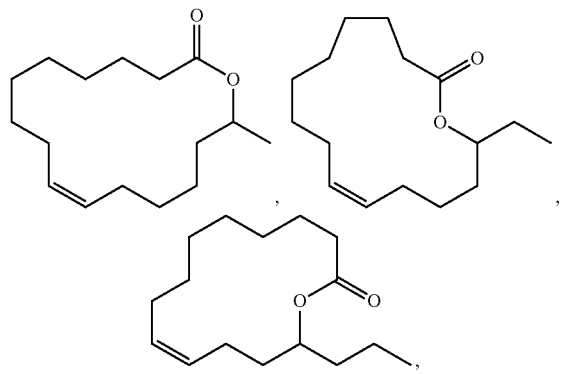

and combinations thereof.

In some embodiments, the one or more fatty acids used as substrates in the first reaction mixture in step (i) comprise

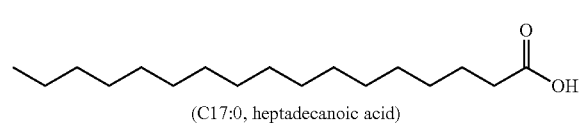 [SMILES: CCCCCCCCCCCCCCCCC(=O)O]
(C17:0, heptadecanoic acid)

and the lactone produced in step (iv) comprises:

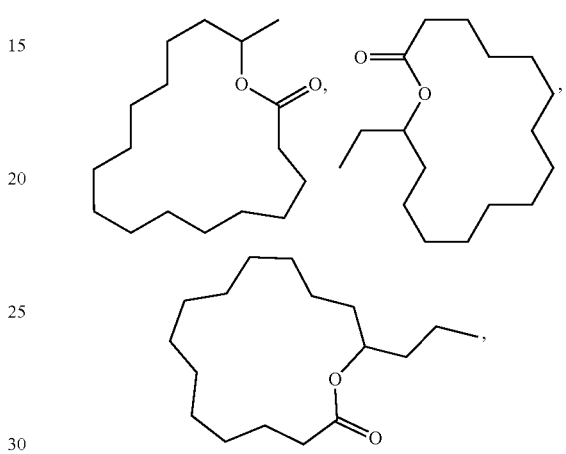

and combinations thereof.

In some embodiments, the one or more fatty acids used as substrates in the first reaction mixture in step (i) comprise

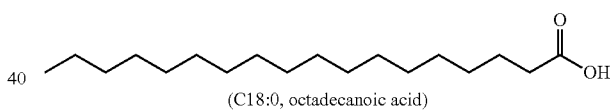
(C18:0, octadecanoic acid)

and the lactone produced in step (iv) comprises:

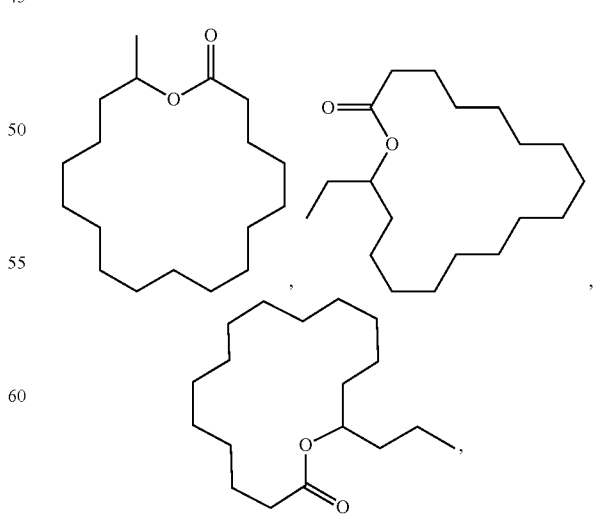

and combinations thereof.

In some embodiments, the one or more fatty acids used as substrates in the first reaction mixture in step (i) comprise

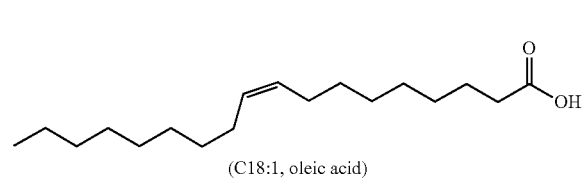 [SMILES: CCCCCCCC/C=C\CCCCCCCC(=O)O]

(C18:1, oleic acid)

and the lactone produced in step (iv) comprises:

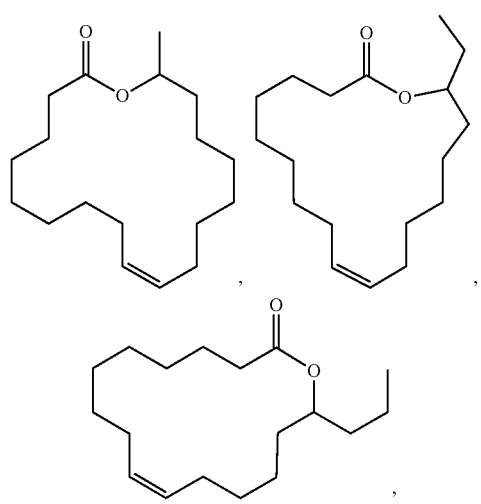

and combinations thereof.

In some embodiments, the one or more fatty acids used as substrates in the first reaction mixture in step (i) comprise

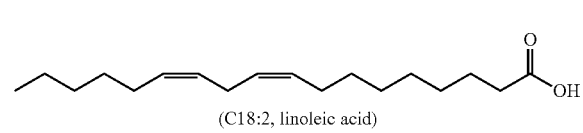 [SMILES: CCCCC/C=C\C/C=C\CCCCCCCC(=O)O]

(C18:2, linoleic acid)

and the lactone produced in step (iv) comprises:

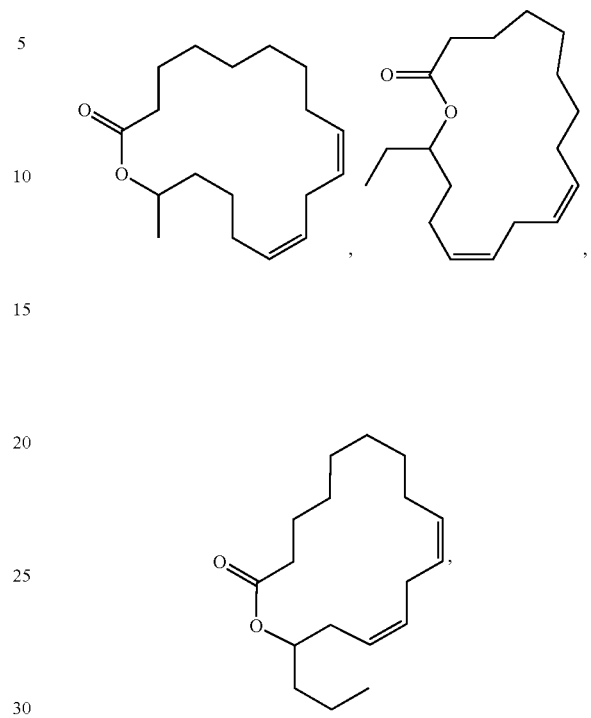

and combinations thereof.

In some embodiments, the one or more fatty acids used as substrates in the first reaction mixture in step (i) comprise

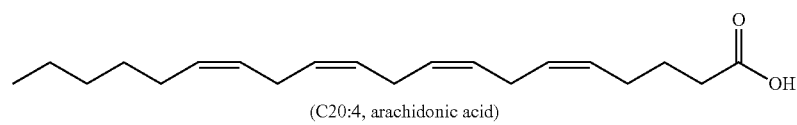

(C20:4, arachidonic acid)

and the lactone produced in step (iv) comprises:

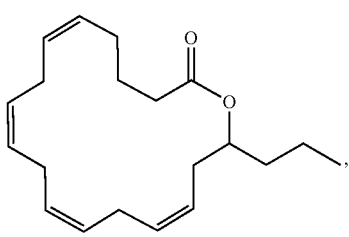

-continued

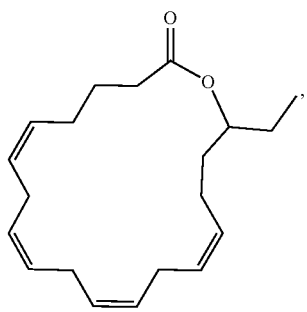

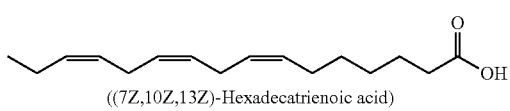 [SMILES: CC/C=C\C/C=C\C/C=C\CCCCCC(=O)O]
((7Z,10Z,13Z)-Hexadecatrienoic acid)

and combinations thereof.

In some embodiments, the one or more fatty acids used as substrates in the first reaction mixture in step (i) comprise and the lactone produced in step (iv) comprises:

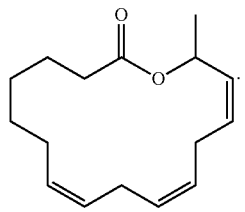

In some embodiments, the one or more fatty acids used as substrates in the first reaction mixture in step (i) comprise

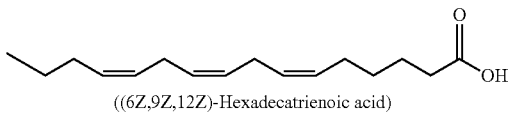 [SMILES: CCC/C=C\C/C=C\C/C=C\CCCCC(=O)O]
((6Z,9Z,12Z)-Hexadecatrienoic acid)

and the lactone produced in step (iv) comprises:

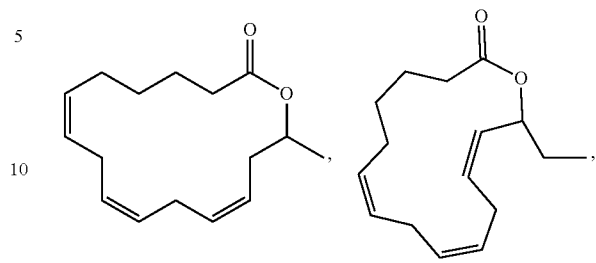

and combinations thereof.

In some embodiments, the one or more fatty acids used as substrates in the first reaction mixture in step (i) comprise

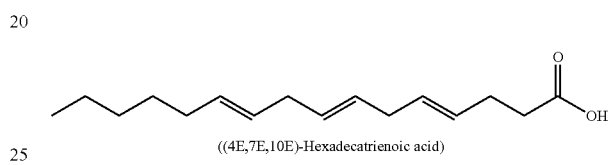
((4E,7E,10E)-Hexadecatrienoic acid)

and the lactone produced in step (iv) comprises:

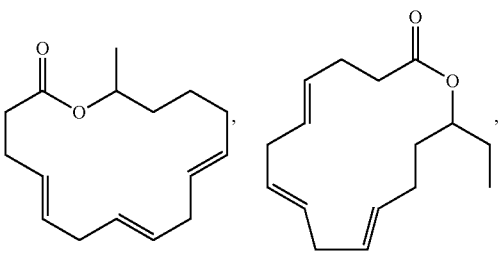

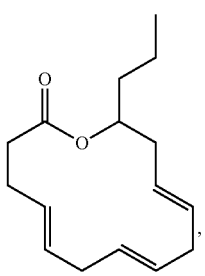

and combinations thereof.

In some embodiments, the one or more fatty acids used as substrates in the first reaction mixture in step (i) comprise

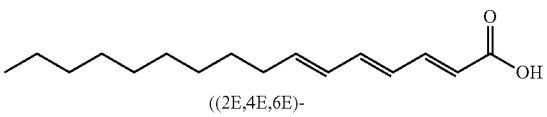 [SMILES: CCCCCCCCC/C=C/C=C/C=C/C(=O)O]
((2E,4E,6E)- and the lactone produced in step (iv) comprises:

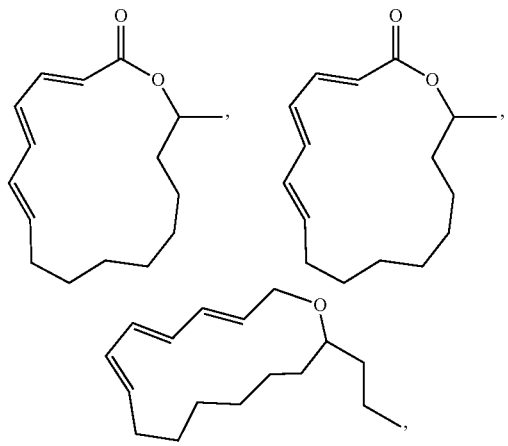

and combinations thereof.

In some embodiments, the one or more fatty acids used as substrates in the first reaction mixture in step (i) comprise and

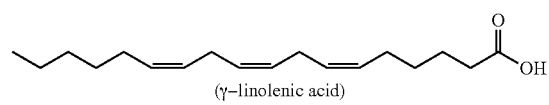
(γ-linolenic acid)

the lactone produced in step (iv) comprises:

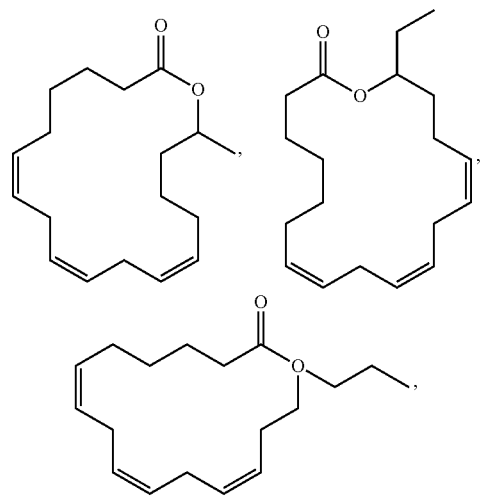

and combinations thereof.

In some embodiments, the one or more fatty acids used as substrates in the first reaction mixture in step (i) comprise and

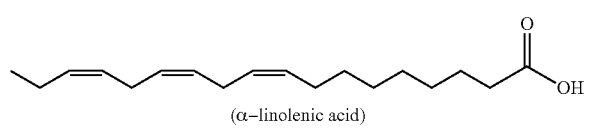 [SMILES: CC/C=C\C/C=C\C/C=C\CCCCCCCC(=O)O]
(α-linolenic acid)

the lactone produced in step (iv) comprises:

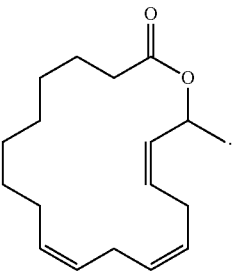 [SMILES: CC1/C=C\C/C=C\C/C=C\CCCCCCCC(=O)O1]

In some embodiments, the one or more fatty acids used as substrates in the first reaction mixture in step (i) comprise

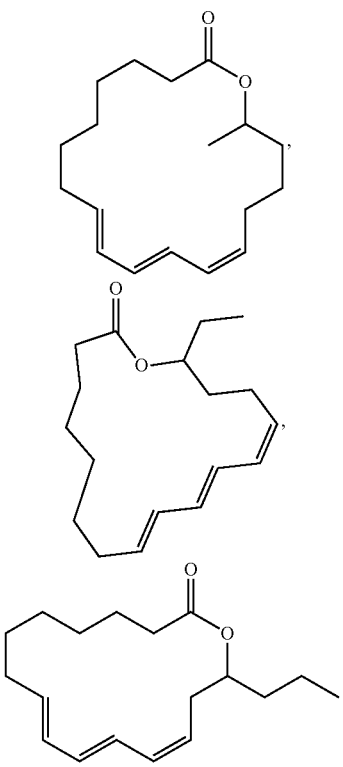

and the lactone produced in step (iv) comprises:

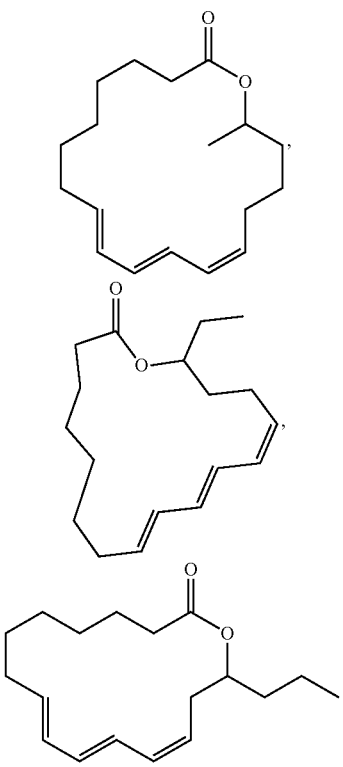

and combinations thereof.

In some embodiments, the one or more fatty acids used as substrates in the first reaction mixture in step (i) comprise

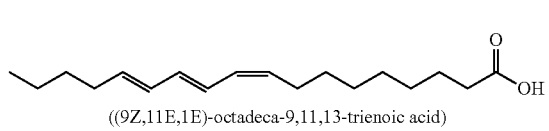 [SMILES: CCCC/C=C/C=C/C=C\CCCCCCCC(=O)O]
((9Z,11E,1E)-octadeca-9,11,13-trienoic acid)

and the lactone produced in step (iv) comprises:

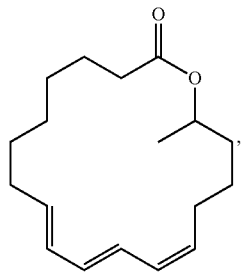

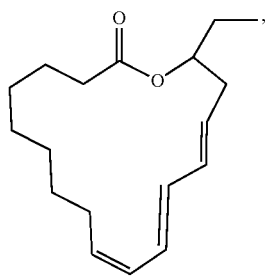

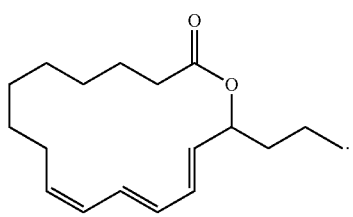

and combinations thereof.

In some embodiments, the one or more fatty acids used as substrates in the first reaction mixture in step (i) comprise

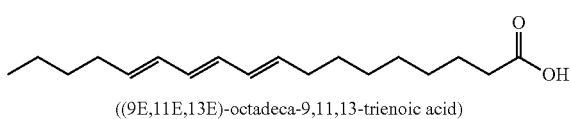 [SMILES: CCCC/C=C/C=C/C=C/CCCCCCCC(=O)O]

((9E,11E,13E)-octadeca-9,11,13-trienoic acid)

and the lactone produced in step (iv) comprises:

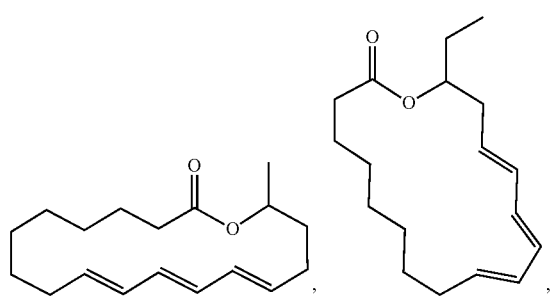

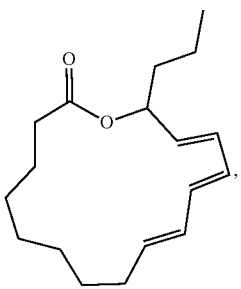

and combinations thereof.

In some embodiments, the one or more fatty acids used as substrates in the first reaction mixture in step (i) comprise

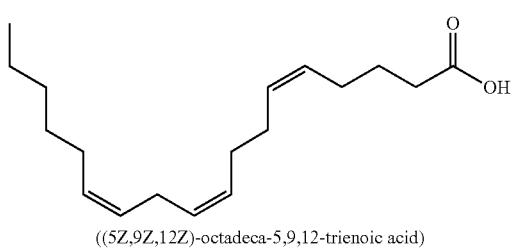 [SMILES: CCCCC/C=C\C/C=C\CC/C=C\CCCC(=O)O]

((5Z,9Z,12Z)-octadeca-5,9,12-trienoic acid)

and the lactone produced in step (iv) comprises:

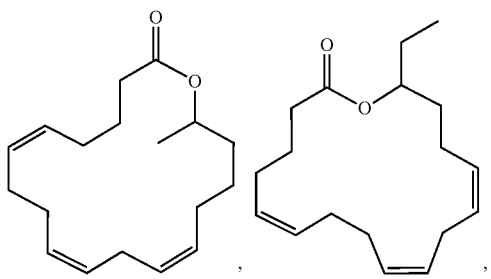

and combinations thereof.

In some embodiments, the one or more fatty acids used as substrates in the first reaction mixture in step (i) comprise

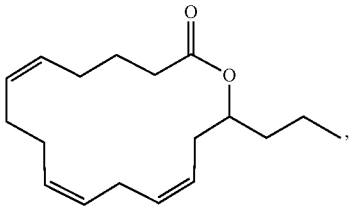

(8Z,11Z,14Z-eicosatrienoic acid)

and the lactone produced in step (iv) comprises:

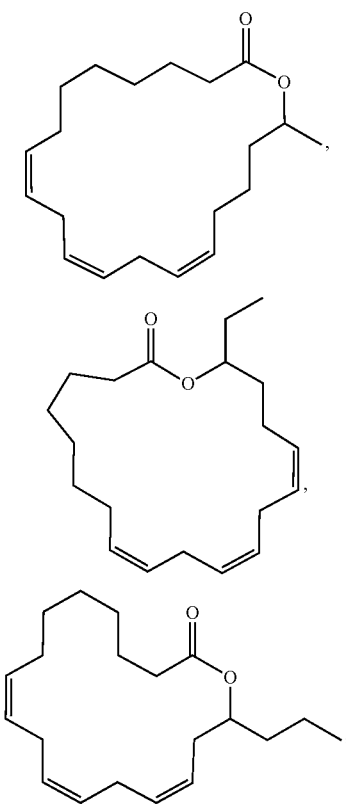

and combinations thereof.

In some embodiments, the one or more fatty acids used as substrates in the first reaction mixture in step (i) comprise

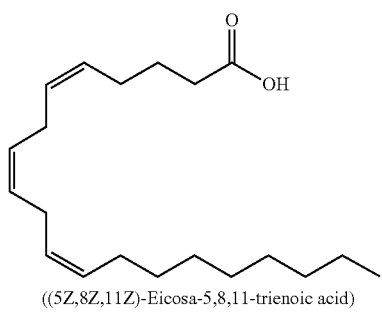 [SMILES: CCCCCCCC/C=C\C/C=C\C/C=C\CCCC(=O)O]

((5Z,8Z,11Z)-Eicosa-5,8,11-trienoic acid)

and the lactone produced in step (iv) comprises:

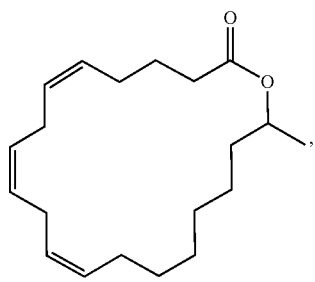

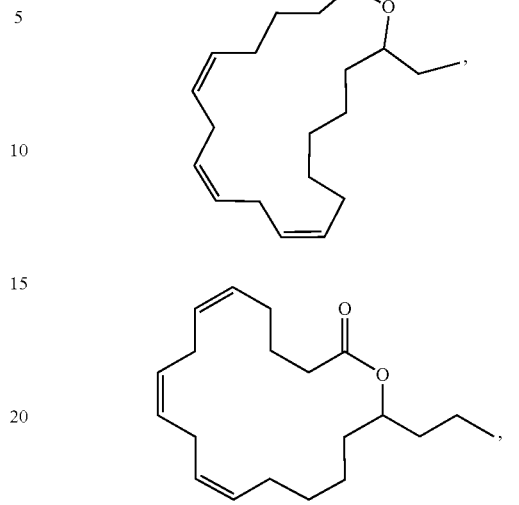

and combinations thereof.

In some embodiments, the lactone produced using the biosynthetic methods provided herein comprises any one or more (e.g., 1, 2, 3, 4, 5, 6, 7, 8, 9, 10, 11, 12, 13, 14, 15, 16, 17, 18, 19, 20, 21, 22, 23, or 24) of the lactones provided in Table 1. In some embodiments, the lactone produced using the biosynthetic methods provided herein comprises any one or more (e.g., 25, 26, 27, 28, 29, 30, or 31) of the lactones provided in Table 36.

Other aspects of the present disclosure provide novel lactones of the formula:

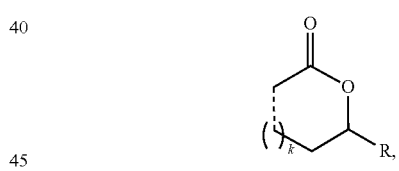

wherein:

R is methyl, ethyl, or n-propyl;

each - - - is independently a single bond, E double bond, Z double bond, or triple bond, as valency permits; and k is an integer between 6 and 30, inclusive;

provided that the lactone is not of the formula:

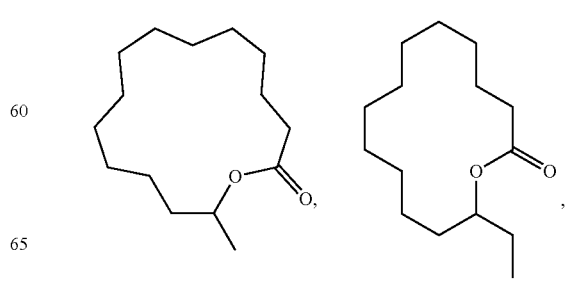

-continued
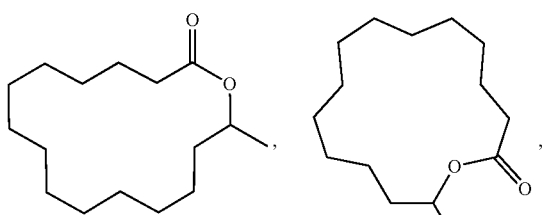
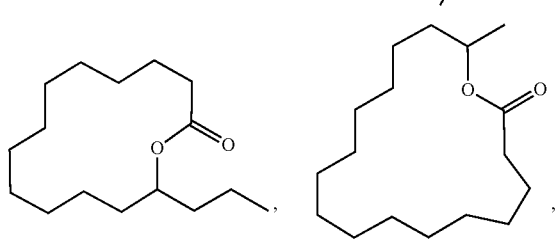
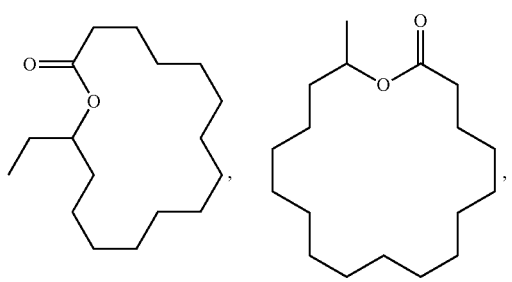
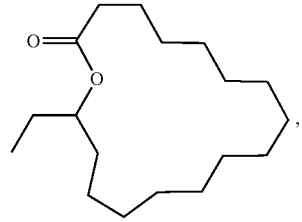
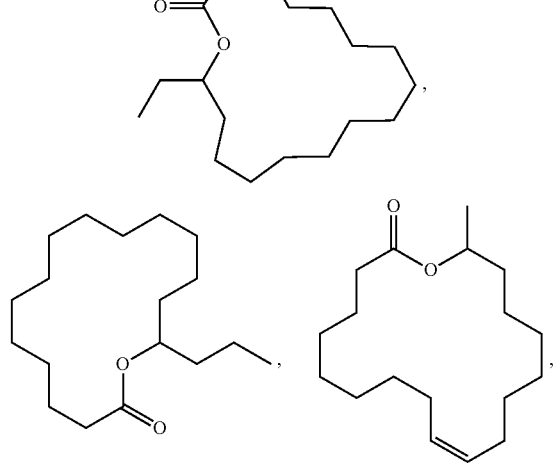
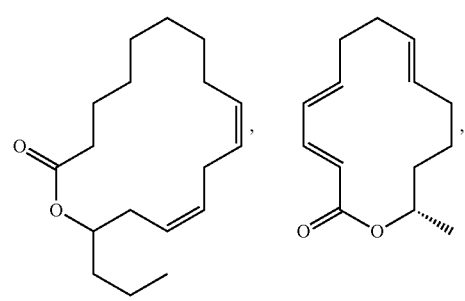
-continued
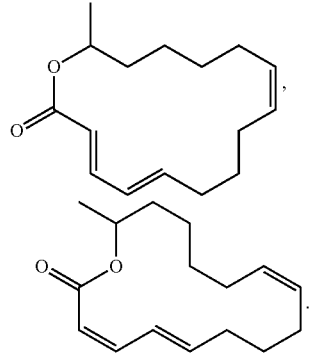
Other aspects of the present disclosure provide novel lactones of the formula:
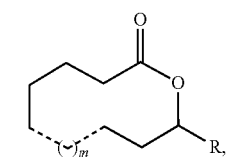
wherein:
R is methyl, ethyl, or n-propyl;
each - - - is independently a single bond or Z double bond, as valency permits, wherein 0, 1, 2, or 4 - - - are Z double bonds; and
m is an integer between 4 and 11, inclusive;
provided that the lactone is not of the formula:
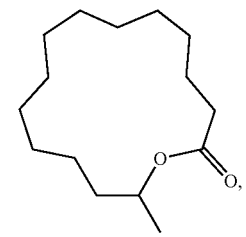 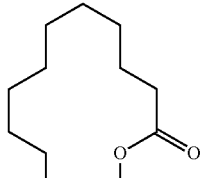
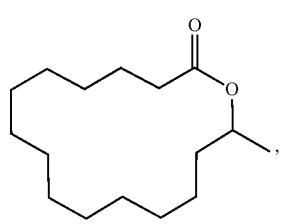 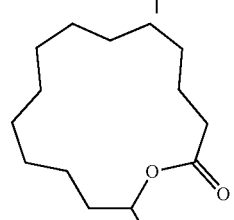
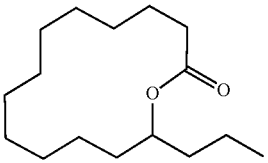 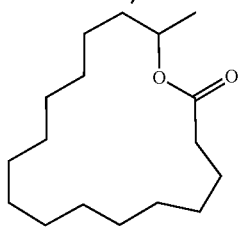

-continued
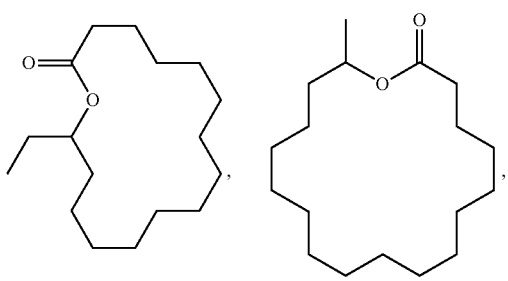
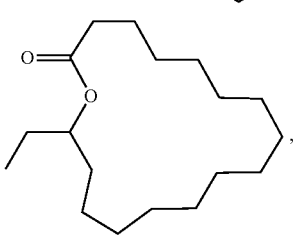
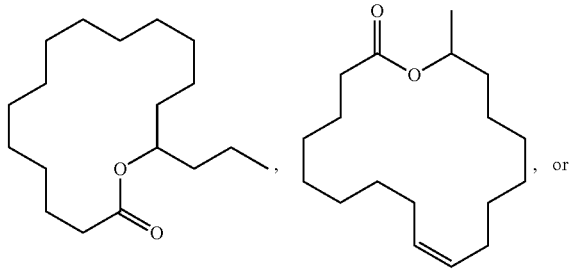, or
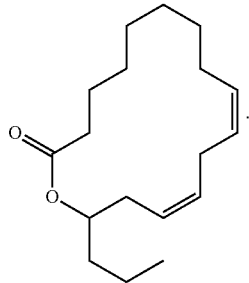 [SMILES: CCCC1C/C=C\C/C=C\CCCCCCCC(=O)O1]
In certain embodiments, the novel lactone is of the formula:
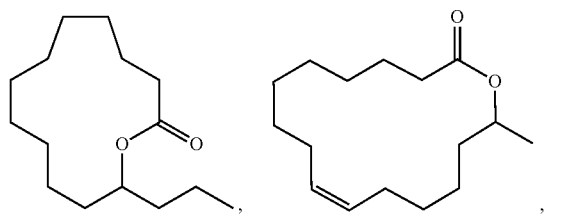,
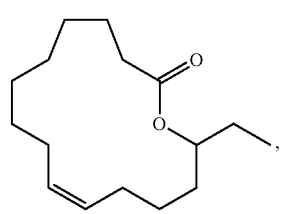,
-continued
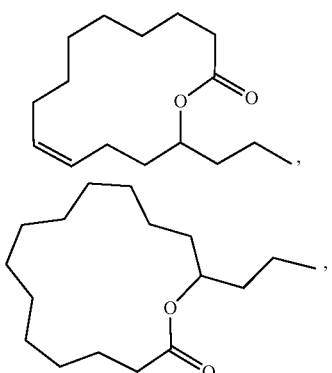,
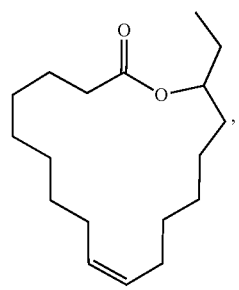,
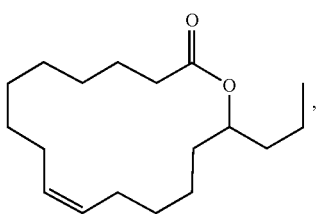,
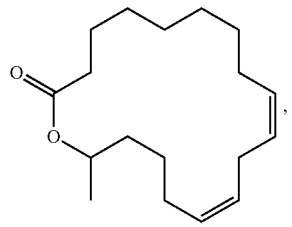,
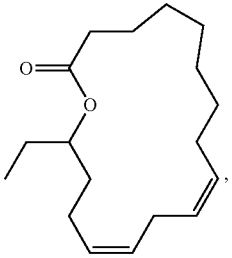,
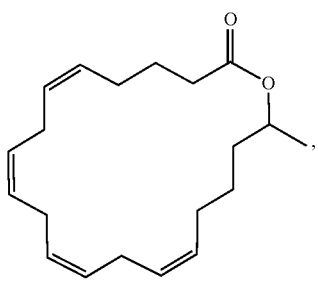,

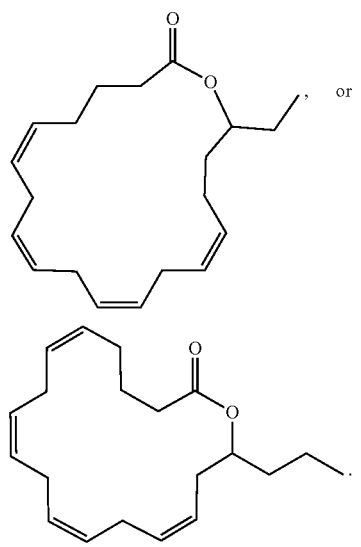
R is as described herein.
In certain embodiments, the novel lactone is of the formula:
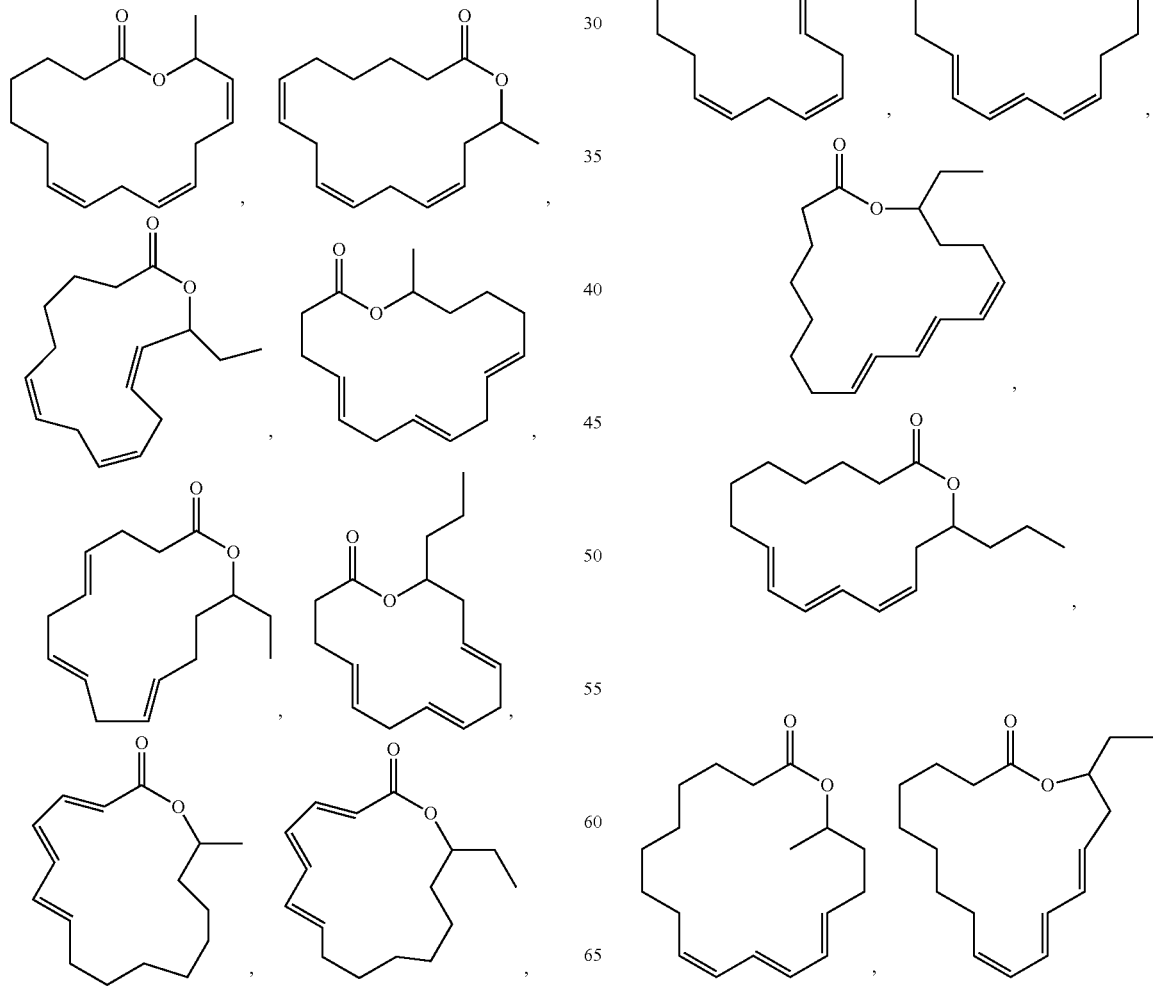
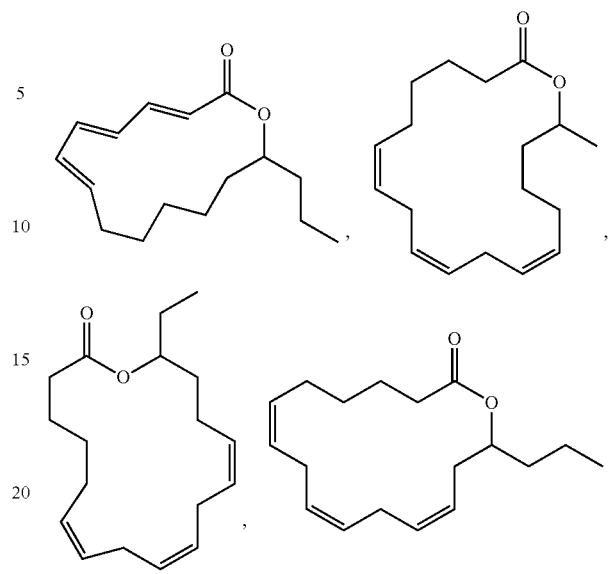

-continued

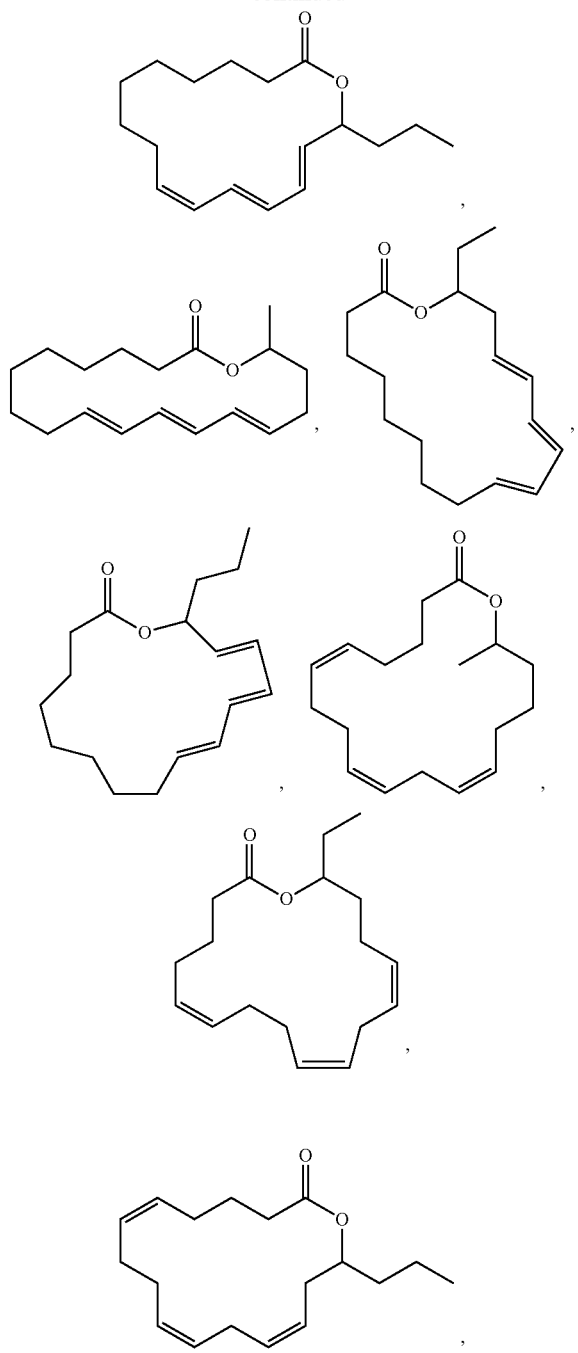

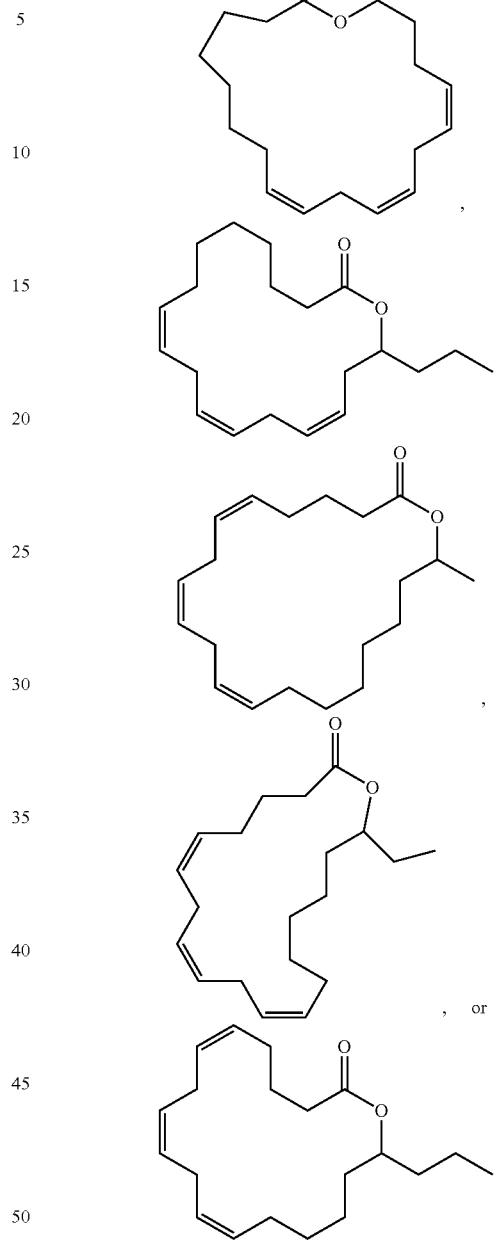

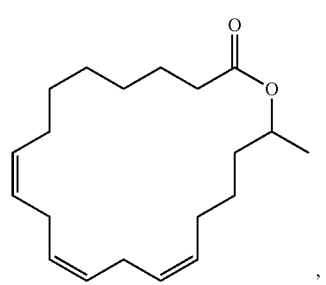

R is as described herein.

In certain embodiments, each - - - is a single bond. In certain embodiments, one - - - is a Z double bond, and the remining - - - are single bonds. In certain embodiments, two - - - are Z double bonds, and the remining - - - are single bonds. In certain embodiments, four - - - are Z double bonds, and the remining - - - are single bonds.

In certain embodiments, one - - - is an E or Z double bond, and the remining - - - are single bonds. In certain embodiments, two - - - are independently E or Z double bonds, and the remining - - - are single bonds. In certain embodiments, three - - - are independently E or Z double bonds, and the remining - - - are single bonds. In certain embodiments, four - - - are independently E or Z double bonds, and the remining - - - are single bonds. In certain embodiments, each double bond if present is a Z double bond. In certain embodiments, the lactone does not comprise any one of C=C=C, C=C≡C, and C≡C=C.

The variable k is as described herein.

In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10. In certain embodiments, m is 11.

In certain embodiments, the chiral carbon atom of the novel lactone is of the S configuration. In certain embodiments, the chiral carbon atom of the novel lactone is of the R configuration.

Another aspect of the present disclosure provides a mixture of two or more novel lactones. In certain embodiments, the mixture of two or more novel lactones is a mixture of the opposite enantiomers of

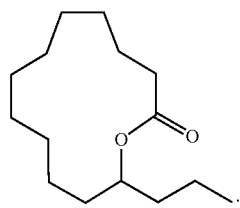 [SMILES: CCCC1CCCCCCCCCCC(=O)O1]

In certain embodiments, the mixture of two or more novel lactones is a mixture of the opposite enantiomers of

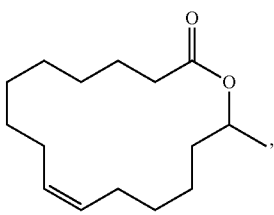 [SMILES: CC1CCCC/C=C\CCCCCCCC(=O)O1]

the opposite enantiomers of

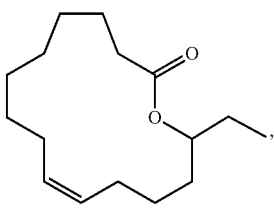 [SMILES: CCC1CCC/C=C\CCCCCCCC(=O)O1]

and the opposite enantiomers of

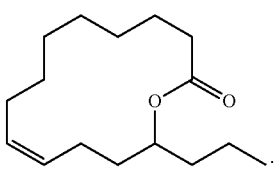 [SMILES: CCCC1CC/C=C\CCCCCCCC(=O)O1]

In certain embodiments, the mixture of two or more novel lactones is a mixture of the opposite enantiomers of

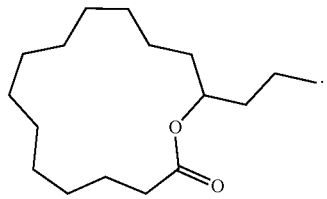 [SMILES: CCCC1CCCCCCCCCCCCC(=O)O1]

In certain embodiments, the mixture of two or more novel lactones is a mixture of the opposite enantiomers of

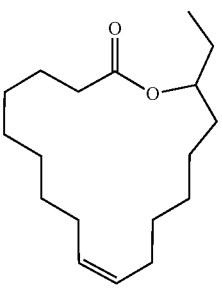 [SMILES: CCC1CCCCC/C=C\CCCCCCCC(=O)O1]

and the opposite enantiomers of

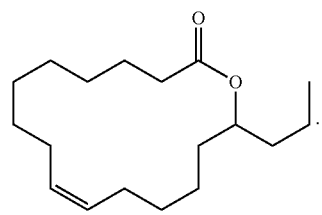

In certain embodiments, the mixture of two or more novel lactones is a mixture of the opposite enantiomers of

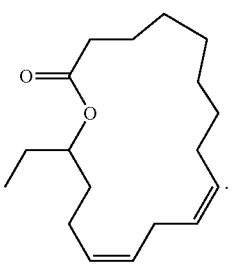 [SMILES: CCC1CC/C=C\C/C=C\CCCCCCCC(=O)O1]

and the opposite enantiomers of

In certain embodiments, the mixture of two or more novel lactones is a mixture of the opposite enantiomers of

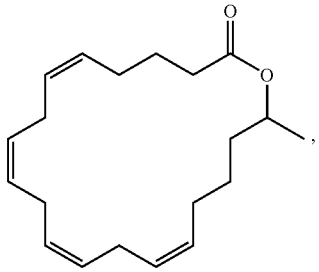 [SMILES: CC1CCC/C=C\C/C=C\C/C=C\C/C=C\CCCC(=O)O1]

the opposite enantiomers of

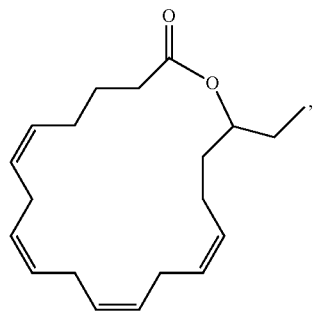 [SMILES: CCC1CC/C=C\C/C=C\C/C=C\C/C=C\CCCC(=O)O1]

and the opposite enantiomers of

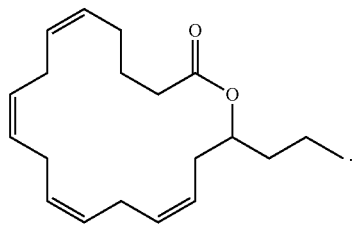 [SMILES: CCCC1C/C=C\C/C=C\C/C=C\C/C=C\CCCC(=O)O1]

In certain embodiments, the mixture of two or more novel lactones is a mixture of the opposite enantiomers of

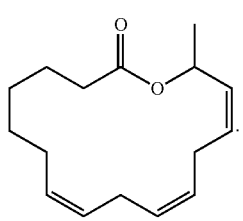 [SMILES: CC1/C=C\C/C=C\C/C=C\CCCCCC(=O)O1]

In certain embodiments, the mixture of two or more novel lactones is a mixture of the opposite enantiomers of

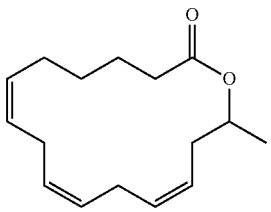 [SMILES: CC1C/C=C\C/C=C\C/C=C\CCCCC(=O)O1]

and the opposite enantiomers of

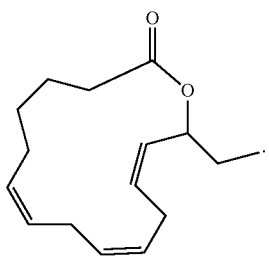 [SMILES: CCC1/C=C\C/C=C\C/C=C\CCCCC(=O)O1]

In certain embodiments, the mixture of two or more novel lactones is a mixture of the opposite enantiomers of

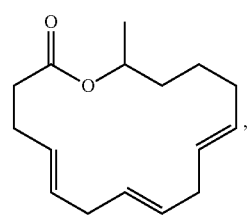 [SMILES: CC1CCC/C=C/C/C=C/C/C=C/CCC(=O)O1]

the opposite enantiomers of

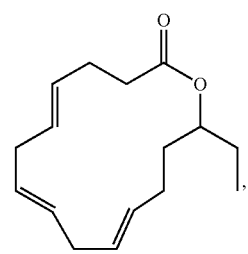 [SMILES: CCC1CC/C=C/C/C=C/C/C=C/CCC(=O)O1]

and the opposite enantiomers of

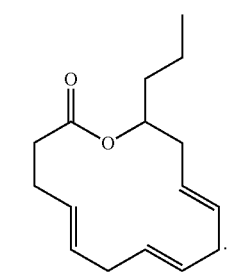 [SMILES: CCCC1C/C=C/C/C=C/C/C=C/CCC(=O)O1]

In certain embodiments, the mixture of two or more novel lactones is a mixture of the opposite enantiomers of

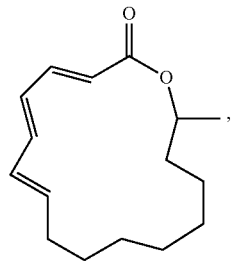 [SMILES: CC1CCCCCCC/C=C/C=C/C=C/C(=O)O1]

the opposite enantiomers of

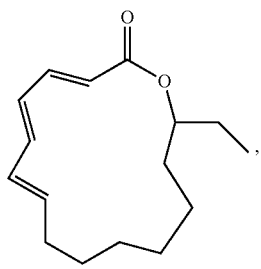 [SMILES: CCC1CCCCCC/C=C/C=C/C=C/C(=O)O1]

and the opposite enantiomers of

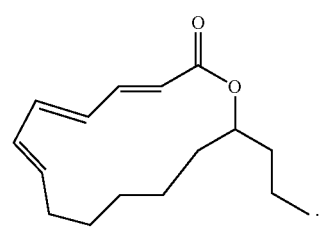 [SMILES: CCCC1CCCCC/C=C/C=C/C=C/C(=O)O1]

In certain embodiments, the mixture of two or more novel lactones is a mixture of the opposite enantiomers of

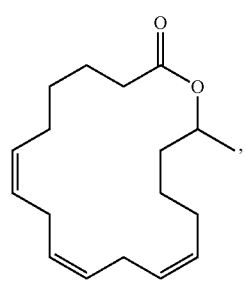 [SMILES: CC1CCC/C=C\C/C=C\C/C=C\CCCCC(=O)O1]

the opposite enantiomers of

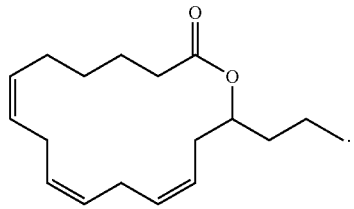 [SMILES: CCCC1C/C=C\C/C=C\C/C=C\CCCCC(=O)O1]

and the opposite enantiomers of

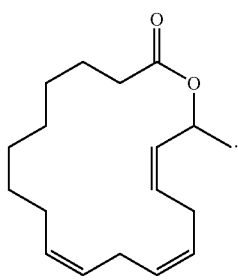 [SMILES: CC1/C=C\C/C=C\C/C=C\CCCCCCCC(=O)O1]

In certain embodiments, the mixture of two or more novel lactones is a mixture of the opposite enantiomers of In certain embodiments, the mixture of two or more novel lactones is a mixture of the opposite enantiomers of

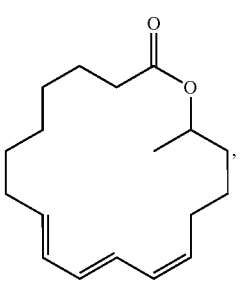 [SMILES: CC1CCC\C=C/C=C/C=C/CCCCCCC(=O)O1]

the opposite enantiomers of

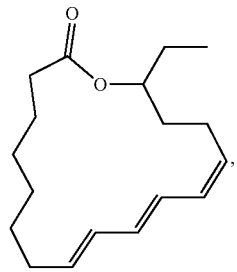 [SMILES: CCC1CC\C=C/C=C/C=C/CCCCCCC(=O)O1]

and the opposite enantiomers of

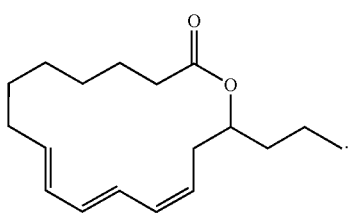 [SMILES: CCCC1C\C=C/C=C/C=C/CCCCCCC(=O)O1]

In certain embodiments, the mixture of two or more novel lactones is a mixture of the opposite enantiomers of

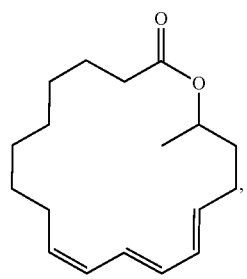 [SMILES: CC1CC/C=C/C=C/C=C\CCCCCCCC(=O)O1]

the opposite enantiomers of

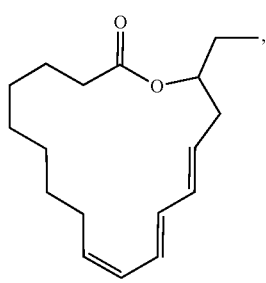 [SMILES: CCC1C/C=C/C=C/C=C\CCCCCCCC(=O)O1]

and the opposite enantiomers of

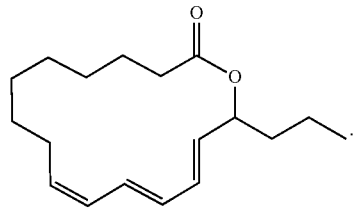 [SMILES: CCCC1/C=C/C=C/C=C\CCCCCCCC(=O)O1]

In certain embodiments, the mixture of two or more novel lactones is a mixture of the opposite enantiomers of

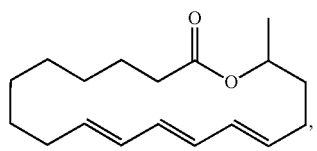 [SMILES: CC1CC/C=C/C=C/C=C/CCCCCCCC(=O)O1]

the opposite enantiomers of

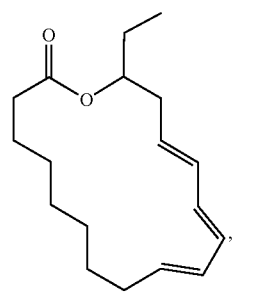 [SMILES: CCC1C/C=C/C=C/C=C/CCCCCCCC(=O)O1]

and the opposite enantiomers of

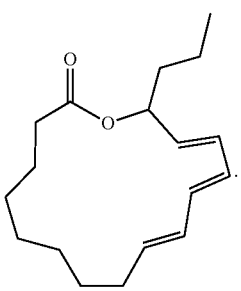 [SMILES: CCCC1/C=C/C=C/C=C/CCCCCCCC(=O)O1]

In certain embodiments, the mixture of two or more novel lactones is a mixture of the opposite enantiomers of

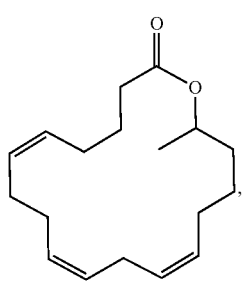 [SMILES: CC1CCC/C=C\C/C=C\CC/C=C\CCCC(=O)O1]

the opposite enantiomers of

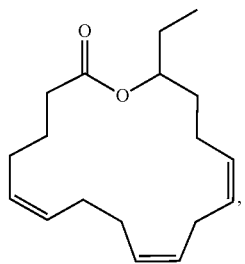 [SMILES: CCC1CC/C=C\C/C=C\CC/C=C\CCCC(=O)O1]

and the opposite enantiomers of

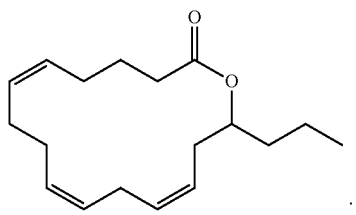 [SMILES: CCCC1C/C=C\C/C=C\CC/C=C\CCCC(=O)O1]

In certain embodiments, the mixture of two or more novel lactones is a mixture of the opposite enantiomers of

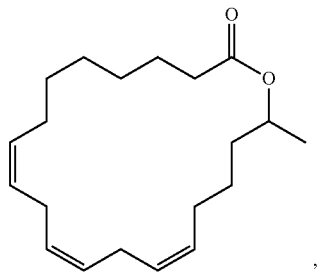 [SMILES: CC1CCC/C=C\C/C=C\C/C=C\CCCCCCC(=O)O1]

the opposite enantiomers of

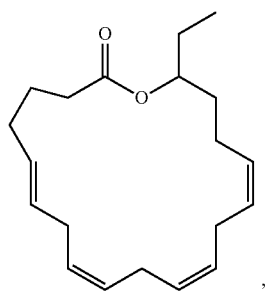 [SMILES: CCC1CC/C=C\C/C=C\C/C=C\C/C=C/CCCC(=O)O1]

and the opposite enantiomers of

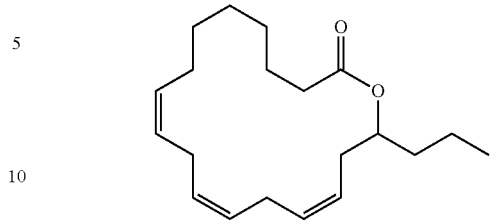

In certain embodiments, the mixture of two or more novel lactones is a mixture of the opposite enantiomers of

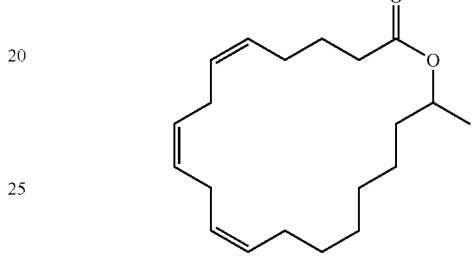

the opposite enantiomers of

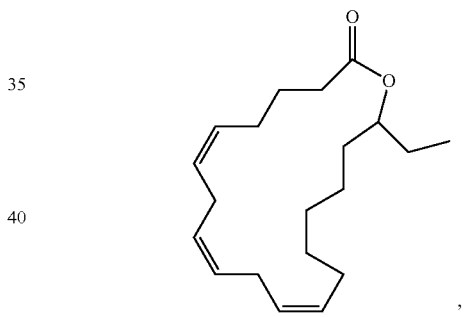

and the opposite enantiomers of

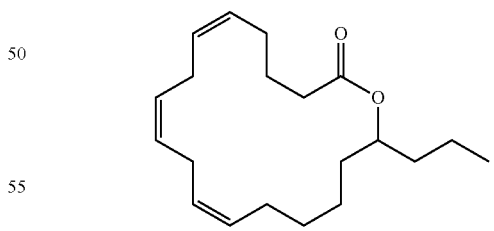

Uses of the Lactones

The presently disclosed compounds can have fruity, musky, floral, aldehydic, and/or herbaceous odor notes; as well as a wide range of secondary odors, such as animalic, to woody notes. The lactones can be used alone or incorporated into a fragrance composition to modify or enhance the odor of existing fragrance compositions, solvents, media, consumer products, and the like. In some embodiments, the lactones can be used in consumer products.

Fragrance Compositions

The lactones described herein can be formulated into different fragrance compositions. For example, a fragrance composition in accordance with the presently closure can include one or more, two or more, or three or more of the lactones described herein.

Formulations of fragrance compounds into fragrance compositions span the range from "simple accords" (<10 fragrance compounds) to "complex fragrances" (>30 fragrance compounds). For example, full bodied fragrance compositions generally do not comprise less than about 30 fragrance compounds. Such fragrance compositions can also contain or consist of at least one fragrance base, solvent, or combination thereof. Said fragrance bases or solvents may be a liquid or a solid and typically do not significantly alter the olfactory properties of the fragrance compounds.

Some non-limiting examples of fragrance bases include an emulsifying system, encapsulating materials, natural or modified starches, polymers, gums, pectins, gelatinous or porous cellular materials, and waxes.

Some non-limiting examples of solvents include dipropylene glycol, propylene glycol, diethyl phthalate (DEP), diisononyl phthalate (DINP), benzyl benzoate, benzyl alcohol, iso propyl myristate (IPM), isopropyl palmitate (IPP/Deltyl Prime), butyl stearate, dioctyl adipate, triethyl citrate, 5 methyl hydrogenated rosinate (CAS No. 8050-15-5), terpenes (e.g., GLIDSOL 100), paraffinic naphthenic solvent (e.g., LPA-170 SOLVENT), isoalkanes (e.g., SOLTROL 170 ISOPARAFFIN), isoparaffins, isooctadecanol, (e.g., TEGO ALKANOL 66), phe-noxyethanol, diethylene glycol monoethyl ether (CARBITOL 10 LOW GRAVITY), glycol ether (METHYL CARBITOL), Dipropylene Glycol Methyl Ether (e.g., DOWANOL DPM), Dipropylene Glycol Methyl Ether Acetate (e.g., DOWANOL DPMA), Propylene glycol methyl ether (e.g., DOWANOL PM GLYCOL ETHER), Tripropylene Glycol Methyl Ether, Diisoheptyl 15 Phthalate (e.g., JAYFLEX® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (+/−)-2,2-dimethyl-4-hydroxymethyl-1,3-20 dioxolane (e.g., AUGO CLEAN MULTI SOLVENT), ALCOHOL 40B ANHYDROUS 200 PROOF, ALCOHOL SDA 40B 190 PROOF, TRIACETIN, 3-Methoxy-3-methyl-1-butanol (Solfit), Benzyl Laurate, Tripropylene Glycol Methyl Ether (e.g., DOWANOL TPM), Dipropylene glycol n-butyl ether (e.g., DOWANOL DPNB), Dimethyl siloxane, trimethylsiloxy-terminated (e.g., DOWANOL CORNING 200 FLUID), Caprylic/Capric Triglycerides (e.g., NEOBEE M-5), propylene glycol and glyceryl oleate (e.g., ARLACEL 186), Uniceth-IC20L (e.g., ARLASOLVE 200 L), pro-panediol, 1,3, Butyl Cellosolve, Hexylene glycol, Glycerine, N Methyl Stearate, Isopropyl alcohol, 2-Methyl-1,3-propanediol (e.g., MP DIAL GLYCOL), Diethyl Citrate, Triethyl Acetyl Citrate, Isopentyldiacetate (IPD-AC, Dimethyl 2-methylpentanedioate (e.g., Rhodiasolv Iris), medium chain triglycerides (MCT), terpene hydrocarbons (e.g., DIPENTENE 5100, DL-LIMONENE (e.g., DIPENTENE 122), 3,5,5-trimethylhexyl acetate, Diethyl Malonate, Limonene (e.g., UNITENE D), cyclohexyl acetate, para-tertiary-butyl (e.g., VERTENEX), Ethyl Acetate, Diethyl Succinate, and natural solvents including, but not limited to, vegetable oils, such as sunflower oil.

The amount of the fragrance compound of the lactones present in a fragrance composition will depend on the formulation, but the compound of the present disclosure is typically present in an amount of from about 0.00001% to about 90.0% by weight of the total fragrance composition. Typically, a more preferred embodiment would contain between about 0.01% and about 20% by weight and a most preferred embodiment would contain between about 0.01% and about 10% by weight.

In certain embodiments, the one or more fragrance compounds of the present disclosure are formulated in a fragrance composition in amounts of from about 0.01% to about 99% by weight of the total fragrance composition, or from about 0.01% to about 90% by weight, or from about 0.01% to about 80% by weight, or from about 0.01% to about 70% by weight, or from about 0.01% to about 60% by weight, or from about 0.01% to about 50% by weight, or from about 0.01% to about 40% by weight, or from about 0.01% to about 30% by weight, or from about 0.01% to about 20% by weight, or from about 0.01% to about 10% by weight, or from about 0.02% to about 10% by weight, or from about 0.05% to about 10% by weight, or from about 0.1% to about 10% by weight, or from about 0.1% to about 5% by weight, or from about 0.5% to about 2% by weight, or about 1% of the total fragrance composition. In certain embodiments, the fragrance compositions of the present disclosure contain at least about 0.0001% by weight. For example, at a concentration of at least about 0.0001% by weight of the fragrance composition, some odor notes of the fragrance compounds can be detected. In certain embodiments, the fragrance compositions of the present disclosure contain at least about 0.1% by weight, or at least about 0.5% by weight. In more preferred embodiments, the fragrance compositions of the present disclosure contain at least about 1% by weight. For example, at a concentration of at least about 1% by weight of the fragrance composition, the full character of the fragrance compounds can be detected.

In certain embodiments, the fragrance compositions of the present disclosure contain at least about 98.5% by weight of a fragrance compound, e.g., lactones described herein. In one embodiment, the fragrance composition contains 100% by weight of a fragrance compound, e.g., one or more lactone described herein.

A fragrance composition can further include one or more additional fragrance accords or compounds. In certain embodiments, the additional fragrance accords or compounds can be but are not limited to, one or more aldehydic compound(s), one or more balsamic compound(s), one or more citrus compound(s), one or more floral compound(s), one or more fruity compound(s), one or more gourmand compound(s), one or more green compound(s), one or more marine compound(s), one or more mossy compound(s), one or more musk compound(s), one or more piney compound(s), one or more powdery compound(s), one or more spicy compound(s), and/or one or more woody compound(s), or combinations thereof.

For example, and not limitation, an aldehydic compound can be aldehyde C-12 MNA. A balsamic compound can be isopropoxy ethyl salicylate and/or benzy salicylate. A citrus compound can be citral, citronellal, L-citronellol, decanal, limonene, myrcenol, nootkatone, sinensal, bergamot oil, grapefruit oil, lemon oil, lime oil, and/or orange oil. A floral compound can be anisyl acetate, anisic aldehyde, benzyl acetate, bourgeonal, butyl acetate, cyclamen aldehyde, cyclohexyl lactone, δ-damascone, farnesal, L-farnesal, farnesol, florhydral, floralozone, geraniol, geranyl acetate, piperonal, hedione, heliobouquet, hexyl cinnamaldehyde, hexyl salicylate, indole, α-ionone, β-ionone, isopropoxy ethyl salicylate, hedione high cis, cis-jasmone, kovanol, laurinol, linalool, linalyl acetate, mayol, methyl dihydrojasmonate, γ-methyl ionone, methoxymelonal, nerol, nerolione, neryl acetate, 2-pentyl cyclopentanone, phenoxanol, phenoxy ethyl isobutyrate, phenylacetaldehyde, phenyl ethyl alcohol, rose oxide, suzaral, undecavertol, geranium oil, lavender oil, rose oil, and/or ylang oil. A fruity compound can be aldehyde C-16, allyl caproate, allyl cyclohexyl propionate, allyl heptanoate, amyl acetate, benzaldehyde, citronellyl acetate, citronellyl nitrile, cyclacet, damascenone, γ-decalactone, diethyl malonate, dimethyl phenyl ethyl carbinol, dimethyl sulfide, γ-dodecalactone, ethyl acetate, ethyl butyrate, ethyl caproate, ethyl decadienotate, ethyl-2-methylbutyrate, ethyl acetoacetate, ethyl propionate, floral, hexyl acetate, hexyl isobutyrate, isoamyl acetate, jasmolactone, manzanate, melonal, methyl heptyl ketone, γ-nonalactone, γ-octalactone, phenyl ethyl isobutyrate, raspberry ketone, ringonol, thesaron, tolyl aldehyde, γ-undecalactone, vanoris, and/or verdox. A gourmand compound can be caprylic acid, coumarin, ethyl fraison, ethyl vanillin, ethylmaltol (e.g., Veltol Plus), filbertone, furaneol, guaiacol, maple furanone, 2-acetyl pyrazine, 2,5-dimethyl pyrazine, and/or vanillin. A green compound can be dynascone, galbanolene, trans-2-hexenal, cis-3-hexenol, hexen-1-ol, cis-3-hexenyl acetate, cis-3-hexenyl butyrate, cis-3-hexenyl sali-cyclate, liffarome, methyl octine carbonate, 2,6-nonadienal, oxane, stemone, styrallyl acetate, triplal, undecavertol, violet methyl carbonate, Violiff, vionil, and/or violet leaf extract. A marine compound can be myrac aldehyde and/or Calone 1951. A mossy compound can be oakmoss #1. A musk compound can be ambrettolide, ambretone, ambroxan, exaltolide, galaxolide, habanolide, helvetolide, (1'R)-3-methyl-5-(2,2,3-rimethylcyclopentan-1-yl)-2-pentanone, muscenone, ethylene brassilate, muscone laevo, and/or tonalid. A piney compound can be β-pinene. A powdery compound can be heliotropine and/or whiskey lactone (methyl octalactone). A spicy compound can be β-caryophyllene, cinnamaldehyde, cuminaldehyde, eugenol, isoeugenol, perilla aldehyde, cardamom oil, clove oil, ginger extract and/or black pepper extract. A woody compound can be amber core, amber xtreme, ambroxan, cedramber, cedanol, ebanol, bacdanol, beta thujaplicin, javanol, norlimbanol dextro, osyrol, patchone, polyambrol, α-pinene, β-pinene, sandalmysore core, sandalore, isobornyl cyclo hexanol, orbitone, cedarwood oil, patchouli oil, sandalwood oil, and/or vetiver oil.

In certain embodiments, the additional fragrance compounds are formulated in a composition in an amount of from about 0.001% to about 99% by weight, or from about 0.01% to about 90% by weight, or from about 0.1% to about 80% by weight, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight.

In certain aspects, the present disclosure provides methods to modify, enhance, or improve the odor properties of a fragrance composition by adding an olfactory effective quantity of the compounds of the present disclosure, e.g., a compound of the lactones described herein, to the fragrance composition. As used herein, the term "olfactory effective quantity" means the amount of said compound in a fragrance composition in which the individual component will contribute its characteristic olfactory properties, for example an olfactory property found to be more hedonically appealing. A person of ordinary skill in the art may optimize the olfactory effect of the fragrance composition based on the incorporation of a fragrance compound of the present disclosure. The fragrance compound may be used individually, or a part of mixture such that the sum of the effects of all fragrance ingredients present in the mixture yields a higher hedonistic rating.

Therefore, the compound embodied in the present disclosure can be employed to modify the characteristics of existing fragrance composition via their own olfactory properties or through additively effecting the contributions of other ingredient(s) present within the said composition. The quantity will vary widely depending on the other ingredients present, their relative amounts, the desired effect and the nature of the product.

Consumer Products

In certain embodiments, the lactones and compositions of the present disclosure can be formulated as part of a consumer product. For example, and not limitation, the fragrance compounds and/or compositions can be used in perfumes, colognes, shampoos, rinses, skin cares, body shampoos, body rinses, body powders, air fresheners, deodorants, baths, foods, snacks, beverages, and the like, if necessary, in combination with auxiliary materials.

As embodied herein, the lactones described herein can be employed alone or incorporated into fragrance compositions, which can advantageously be used in a wide variety of consumer products. For example, the consumer products can be those intended to perfume a suitable substrate. As used herein, the term "substrate" means any surface to which the consumer product can be applied without causing any undue adverse effect. The substrate can be a wide range of materials including human or animal skin or hair, paper (e.g., fragranced paper), air in a room, fabric, furnishings, dishes, hard surfaces, and related materials. Thus, substrates can include body surfaces such as, for example, hair and skin. For example, the present disclosure provides a consumer product comprising: (a) at least one the lactones described herein; and (b) a consumer product base. As used herein, "consumer product base" means a composition for use as a consumer product to fulfill the specific purpose of the consumer product, such as cleaning, softening, and caring or the like. The present disclosure also provides a method for improving, enhancing, or modifying a consumer product base by adding thereto an olfactory effective amount of at least one compound of the lactones described herein.

The compound described herein may be employed in a consumer product base simply by directly mixing at least one compound of the lactones described herein, or a fragrance composition comprising at least one compound of the lactones described herein, with the consumer product base, or the compound described herein can, in an earlier step, be entrapped with an entrapment material, for example, fibrous materials including silk fibers, proteins including grain and legume sources, starches including rice starch, polymers, capsules, microcapsules and nanocapsules, liposomes, film formers, absorbents such as carbon or zeolites, cyclic oligosaccharides, steviol glycosides and mixtures thereof, or it can be chemically bonded to substrates, which are adapted to release the fragrance molecule upon application of an external stimulus such as light, enzymes, or the like, and then mixed with the consumer product base. Thus, the present disclosure additionally provides a method of manufacturing a perfumed consumer product, comprising incorporating a compound of the lactones described herein, as a fragrance ingredient, either by directly admixing the compound to the consumer product base or by admixing a fragrance composition comprising a compound of the lactones described herein with a consumer product base. Admixing can be performed using conventional techniques and methods. Through the addition of an olfactory effective amount of at least one compound of the present disclosure, the odor notes of a consumer product base can be improved, enhanced, or modified. For example, the consumer product base can be modified to improve or enhance a fruity, musky, floral, aldehydic, or herbaceous odor note.

In certain embodiments, the consumer products of the present disclosure can be, but are not limited to, air care products (e.g., candles, aerosols, air fresheners, liquid electric air fresheners, fragrance diffusers, gel air fresheners, plug-in air fresheners and oils, wax melts, etc.); baby care products (e.g., consumer products relating to disposable absorbent and/or non-absorbent articles, including adult incontinence garments, bibs, diapers, training pants, infant and toddler care wipes; and personal care products including hand soaps, shampoos, lotions, shower gels, and clothing); fabric and home care products (e.g., consumer products for fabric conditioning (including softening), laundry detergency, laundry and rinse additive and/or care, bleach, dryer sheets, perfume beads, air care, car care, dishwashing, hard surface cleaning and/or treatment, and other cleaning for consumer and or institutional use, etc.); personal care products (e.g., lotions, creams, moisturizers, body washes, hand soaps, shampoos, conditioners, soaps, etc.); family care products (e.g., wet or dry bath tissue, facial tissue, disposable handkerchiefs, disposable towels, and/or wipes, towels, toilet paper, tissue paper, wet towels, etc.); feminine care products (e.g., catamenial pads, incontinence pads, interlabial pads, panty liners, pessaries, sanitary napkins, tampons and tampon applicators, and/or wipes, etc.); sexual health care products (e.g., products relating to sexual aids or sexual health, including lubricants and condoms, etc.); pet care products (e.g., pet malodor cat litter, pet deodorizers, pet health and nutrition including pet foods, treats, other orally deliverable products, grooming aids, products for treating pet hair/fur including shampooing, styling, conditioning; deodorants and antiperspirants; products for cleansing or treating pet skin, including soaps, creams, lotions, and other topically applied products; training aids, toys and diagnostics techniques); fine fragrance (including hydro alcoholic solutions of perfume oil, such as parfum, extrait de parfum, eau de parfum, millesime, parfum de toilette, eau de toilette, eau de cologne, body splash, after shave, body mists, including baby colognes); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or antiaging cosmetics, sun protection products, massage oil, etc.); beauty care (e.g., products for treating human hair including shampooing, styling, conditioning; deodorants and antiperspirants; products for personal cleansing; products for treating human skin, including application of creams, lotions, and other topically applied products; products for shaving, rinse, rinse in shampoo; hair styling agents such as pomade, hair tonic, hair gel, hair cream and hair mousse; hair growing agents; hair coloring agents, etc.); and bath agents (e.g., powder bath additives, solid foaming bath additives, bath oils, bubble bath aroma generators, bath salts, etc.); hair removal products (e.g., products for hair removal including depilatory creams, sugar pastes or gels, waxes); writing products (e.g., pens, crayons, paints, pencils, paper, origami, seals, etc.); products for play (e.g., balls, beanbags, cards, tops, dolls, building blocks, etc.); flavored products (e.g., confections, beverages, snacks, prepared meals, over-the-counter medications, gum, etc.); pharmaceuticals (e.g., plasters, ointments, suppositories, tablets, liquid medicines, capsules, granules, pharmacologically active molecular and/or biological entities; their use in the treatment and/or prevention of diseases and/or alleviation of symptoms in humans and/or animals, and formulations, regimens, kits and/or routes of delivering such entities to subjects in need of treatment and/or prevention and/or alleviation, etc.); health care products (e.g., oral health care products, including any composition for use with any soft and/or hard tissue of the oral cavity or conditions associated therewith (e.g., anti-cavities compositions, anti-plaque chewing gum compositions, breath compositions, dentifrices, denture compositions, lozenges, rinses, and tooth whitening compositions), cleaning devices, floss and flossing devices and toothbrushes; over-the-counter health care including cough and cold remedies and treatments for other respiratory conditions, pain relievers whether topical, oral, or otherwise, gastrointestinal remedies including any composition suitable for the alleviation of gastrointestinal conditions such as heartburn, upset stomach, diarrhea, and irritable bowel syndrome, and nutrient supplementation such as calcium or fiber supplementation, etc. In certain embodiments, the disclosed subject matter provides for use of the fragrance compounds and compositions described herein in a consumer product as described herein.

A broad range of concentrations and/or amounts of the fragrance composition can be employed in a consumer product. In certain embodiments of the present disclosure, the fragrance composition is admixed with a consumer product wherein the composition is present in an amount from about 0.0001 to about 90% weight/weight (w/w), or from about 0.001 to about 75% w/w, or from about 1 to 25 about 50% w/w, or from about 5 to about 25% w/w, or from about 10 to about 15% w/w, and values in between.

In certain embodiments, the consumer product base additionally includes one or more bases, solvents, and combinations thereof.

For example, and not limitation, bases can include, but are not limited to, essential oils, lactones, aldehydes, alcohols, ketones, nitriles, esters, amides, oximes, molecules, or mixtures of plant or animal-derived molecules, prepared via fermentation biotechnology or bioconversion (enzymatic conversion of plant or animal materials). and other fragrant compounds and perfuming co-ingredients.

For further example and not limitation, the solvents can include, but are not limited to, dipropylene glycol, propylene glycol, diethphthalate (DEP), diisononyl phthalate (DINP), benzyl benzoate, benzyl alcohol, iso propyl myristate (IPM), isopropyl palmitate (IPP/Deltyl Prime), butyl stearate, dioctyl adipate, triethyl citrate, methyl hydrogenated rosinate (CAS No. 8050-15-5), terpenes (e.g., Glidsol 100), paraffinic naphthenic solvent (e.g., LPA-170 Solvent), isoalkanes (e.g., Soltrol 170 Isoparaffin), isoparaffins, isooctadecanol, (e.g., Tego Alkanol), phenoxyethanol, diethylene glycol monoethyl ether (Carbitol low gravity), glycol ether (Methyl Carbitol), Dipropylene Glycol Methyl Ether (e.g., Dowanol DPM), Dipropylene Glycol Methyl Ether Acetate (e.g., Dowanol DPMA), Propylene glycol methyl ether (e.g., Dowanol PM Glycol Ether), Tripropylene Glycol Methyl Ether, Diisoheptyl Phthalate (e.g., Jayflex® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (+/−)-2,2-dimethyl-4-hydroxymethyl-1,3-dioxolane (e.g., Augeo Clean Multi Solvent), Alcohol 40B Anhydrous 200 Proof, alcohol SDA 40B 190 Proof, Triacetin, 3-Methoxy-3-methyl-1-butanol (Solfit), Benzyl Laurate, Tripropylene Glycol Methyl Ether (e.g., Dowanol TPM), Dipropylene glycol n-butyl ether (e.g., Dowanol DPNB), Dimethyl siloxane, trimethylsiloxy-5 terminated (e.g., Dowanol Corning 200 Fluid), Caprylic/Capric Triglycerides (e.g., Neobee M-5), propylene glycol and glyceryl oleate (e.g., Arlacel 186), UnicethIC20L (e.g., Arlasolve 200 L), propanediol, 1,3, Butyl Cellosolve, Hexylene glycol, Glycerine, N Methyl Stearate, Isopropyl alcohol, 2-Methyl-1,3-propanediol (e.g., MP Dial Glycol), Diethyl Citrate, Triethyl Acetyl Citrate, Isopentyldiacetate (IPD-AC, Dimethyl 2-methylpentanedioate (e.g., Rhodiasolv Iris), medium chain triglycerides (MCT), terpene hydrocarbons (e.g., Dipentene 5100, DL-limonene (e.g., Dipentene 122), 3,5,5-trimethylhexyl acetate, Diethyl Malonate, Limonene (e.g., Unitene D), cyclohexyl acetate, paratertiarybutyl (e.g., Vertenex), Ethyl Acetate, Diethyl Succinate, and combinations thereof.

In some embodiments, the lactones described herein are used in consumer products comprising fragrance compositions. Non-limiting examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, pre-shave, aftershave, skin and other lotions, talcum powders, body deodorants and antiperspirants, etc.

The fragrances or cosmetics which can be scented using the mixture of lactone described herein or a fragrance composition comprising the lactones are not particularly limited, and for example, fragrance products, skin-care cosmetics, make-up cosmetics, hair cosmetics, anti-sunburn cosmetics, medicinal cosmetics, hair-care products, soap, body lotions, bath liquids, detergents, soft finishing agents, cleaners, kitchen detergents, bleaching agents, aerosol agents, deodorant-aromatics, sundries and the like can be cited.

Various forms thereof can be exemplified, such as perfumed water, Eau de Parfum, Eau de toilette, Eau de cologne and the like as the aforementioned fragrance products; face washing cream, vanishing cream, cleansing cream, cold cream, massage cream, milky lotion, toilette lotion, beauty wash, pack, make up remover and the like as the as the aforementioned skin-care cosmetics; foundation, face powder, pressed powder, talcum powder, rouge, lipstick, lip cream, cheek rouge, eye liner, mascara, eye shadow, eyebrow-color, eye pack, nail enamel, enamel remover and the like as the as the aforementioned make-up cosmetics; pomade, brilliantine, set lotion, hair stick, hair solid, hair oil, hair treatment, hair cream, hair tonic, hair liquid, hair spray, hair growth agent, hair dye and the like as the as the aforementioned hair cosmetics; suntan product, sun screen product and the like as the as the aforementioned anti-sunburn cosmetics; antiperspirant, after-shaving lotion and gel, permanent wave agent, medicinal soap, medicinal shampoo, medicinal skin cosmetics and the like as the as the aforementioned medicinal cosmetics; shampoo, rinse, rinse-in-shampoo, conditioner, treatment, hair pack and the like as the as the aforementioned hair-care products; toilet soap, bath soap, scented soap, transparent soap, synthetic soap and the like as the as the aforementioned soap; body soap, body shampoo, hand soap, face cream and the like as the as the aforementioned body lotions; bath agent (bath salt, bath tablet, bath liquid or the like), foam bath (bubble bath or the like), bath oil (bath perfume, bath capsule or the like), milk bath, bath jerry, bath cube and the like as the as the aforementioned bath liquids; heavy detergent for clothing, light detergent for clothing, liquid detergent, laundry soap, compact detergent, powder soap and the like as the as the aforementioned detergents; softener, furniture care and the like as the as the aforementioned soft finishing agents; cleanser, house cleaner, toilet cleaner, bath cleaner, glass cleaner, mold remover, waste pipe cleaner and the like as the as the aforementioned cleaners; kitchen soap, kitchen synthetic soap, tableware detergents and the like as the as the aforementioned kitchen detergents; oxidation type bleaching agent (a chlorine base bleaching agent, oxygen base bleaching agent or the like), reduction type bleaching agent (sulfur base bleaching agent or the like), optical bleaching agent and the like as the as the aforementioned bleaching agents; spray-type aerosols, powder spray and the like as the as the aforementioned aerosol agents; solid-type, gel-type, liquid-type (aqueous or oily) and the like counterparts as the aforementioned deodorant-aromatics; and tissue paper, toilet paper, dry shampoo, linen sprays, reeds stick air fresheners, gel beads air fresheners, all sort of depilatory product, fragranced paper (air freshener, toilet paper) and the like as the as the aforementioned sundries.

Product shape of the aforementioned lactones described herein may be the shape of the mixture itself, but as other shapes, optional shapes are selected and used, such as, for example, liquid shapes dissolved in alcohols, propylene glycol, glycerol, dipropylene glycol and the like polyhydric alcohols or triethyl citrate, benzyl benzoate, diethyl phthalate and the like esters; gum Arabic, tragacanth gum and the like natural gummy matters; emulsion shapes emulsified with glycerol fatty acid ester, sucrose fatty acid ester or the like emulsifier; powder shapes coated using gum Arabic and the like gummy matters, gelatin, dextrin and the like fillers; soluble or dispersion shapes solubilized or dispersed using a surfactant such as nonionic surfactant, anionic surfactant, cationic surfactant, ampholytic surfactant or the like; or microcapsules obtained by treating with an encapsulation agent.

In addition, the aforementioned fragrance composition may be used by stabilizing it and providing it with sustained release property, through its enclosure with cyclodextrin or the like inclusion agent. These may be used by optionally selecting suitable shape of the final product, such as liquid shape, solid shape, powder shape, gel shape, mist shape, aerosol shape or the like.

In this connection, amount of the aforementioned lactones, or a fragrance composition for fragrances or cosmetics, to be added to a fragrance product or the like final product is optionally changed according to the object to be used, conditions, expected effect and action and the like of each product and therefore cannot be determined, but is generally from about 0.00001 to about 20% by weight.

Other fragrance materials which can be advantageously combined with the lactones described herein in a perfume are, for example, natural products such as extracts, essential oils, absolutes, resinoids, resins, concretes, and molecules, or mixtures of plant or animal-derived molecules, prepared via fermentation biotechnology or bioconversion (enzymatic conversion of plant or animal materials) etc., but also synthetic materials such as hydrocarbons, alcohols, aldehydes, ketones, ethers, acids, esters, acetals, ketals, nitrites, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA Examples of fragrance materials which can be used in combination with the lactones described herein are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, other macrolactone musks, ethylene brassylate. Solvents which can be used for perfumes which contain the alcohol are, for example: ethanol, isopropanol, diethyleneglycol monoethyl ether, dipropylene glycol, diethyl phthalate, triethyl citrate, isopropyl myristate, etc.

The quantities in which the lactones described herein can be used in perfumes or in products to be perfumed may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the specialist in the art to be able to use the lactones described herein for his specific purpose. In perfumes an amount of 0.01% by weight or more of the lactones described herein will generally have a clearly perceptible olfactive effect. Preferably the amount is 0.1% or more, but generally not more than 40% by weight, more preferably at least 1%. The amount of the lactones described herein present in products will generally be at least 0.1 ppm by weight, preferably at least 1 ppm, more preferably at least 10 ppm. However, levels of up to about 99% by weight may be used in particular cases, depending on the product to be perfumed.

In some embodiments, the lactones described herein have superior biodegradability, which is an important characteristic of perfume ingredients. Good biodegradability of perfume ingredients prevents their undesirable accumulation in the environment. The lactones described herein are easily biodegradable and equal to polycyclic musk compounds in substantivity, they are able to partly or completely replace polycyclic musk in such perfumes. Therefore, perfumes containing the macrocyclic the lactones described herein, but which do not contain any polycyclic musk are specific embodiments of the disclosure. Other embodiments of the disclosure are perfumes containing the musk mixtures together with smaller amounts of polycyclic musk than would otherwise be used in such perfumes.

It is known that the perceived odor intensity of mixtures of perfume ingredients when evaluated as such is generally less than the sum of the perceived odors of the components. Thus, the perceived odor intensity of a 1:1 mixture of 2 of the components of the lactones described herein would be expected to be lower than the sum of the intensities of the separate components, i.e. in such mixtures odor suppression is generally found. The lactones described herein may be synergistic or antagonistic to the perceived intensity of the mixture prior to application to substrate. However, the lactones described herein, even if antagonistic when mixture is evaluated as such, may have synergistic performance in application.

As embodied herein, the fragrance composition can further include an additional fragrance compound selected from a citrus compound, a floral compound, a fruity compound, a gourmand compound, a green compound, a musk compound, a spicy compound, a woody compound, a marine compound, an aldehydic compound, a mossy compound, and combinations thereof. It can include molecules, or mixtures of plant or animal-derived molecules, prepared via fermentation biotechnology or bioconversion (enzymatic conversion of plant or animal materials). In certain embodiments, the fragrance composition can further include a solvent.

In certain aspects, the present disclosure also provides methods of modifying the odor properties of a fragrance composition by adding to the fragrance composition an olfactory effective quantity of a fragrance compound of the musky entity.

In certain other aspects, the present disclosure provides a consumer product comprising a consumer product base and a fragrance compound of the lactones described herein or an isomer thereof.

In certain embodiments, the consumer product is selected from a fine fragrance, a personal care product, a home care product or an air care product.

For example, the fine fragrance can be selected from parfum, extrait de parfum, eau de parfum, millesime, parfum de toilette, eau de toilette, eau de cologne, body splash, after shave, body mists, and baby colognes.

The personal care product can be selected from lotions, creams, moisturizers, body washes, hand soaps, shampoos, conditioners, and soaps. Furthermore, the personal care product can be selected from pet care products, including but not limited to pet shampoos.

The home care product can be selected from fabric conditioner, fabric softener, laundry detergent, laundry additive, rinse additive, bleach, dryer sheets, perfume beads, car care products, leather treating & fragrancing products, cat litter, dishwashing detergent, and hard surface cleaners. The air care product can be selected from a membrane, candle, aerosol, air freshener, liquid electric air freshener, fragrance diffuser, gel air freshener, plug-in air freshener, plug-in oil, wax melt and car air fresheners (membranes or hard plastic). Furthermore, the home care products can use encapsulated fragrances.

In some embodiments, the consumer product is selected from the group consisting of: fragrance, body wash, shampoo, after bath splash, eau de toilette, cologne, lotion (e.g., after shave lotion), cream (e.g., face, body and hand cream), liquid laundry detergent, compressed cleaning tablet lip gloss, solid body moisturizer bar, hair care mousse, scented ink, gel hand sanitizer, candle, all-purpose cleaner, linen spray, fabric softener, dishwashing liquid, deodorant stick, soap (e.g., bar soap), scented garbage bags, perfume bearing microcapsules, and eye patch.

Additional consumer products comprising the lactones described herein include, without limitation, effervescent dishwashing tablet, solid bars for shampoo, moisturizers, diapers & various hygiene pads.

The present disclosure also provides methods of modifying the odor properties of a consumer product by adding to a consumer product base an olfactory effective quantity of a fragrance compound of the lactones described herein, or an isomer thereof.

Biosynthetic Methods for Producing Lactones

The biosynthetic methods described herein utilize fatty acids (e.g., linear fatty acids) as substrates for enzymatic production of lactones, such as macrocyclic lactones (e.g., macrocyclic lactones having differentiated musky notes). The methods described herein comprise two enzymatic conversion steps. In the first step, the fatty acids are hydroxylated at ω-1, ω-2, or ω-3 positions by a cytochrome P450 enzyme having hydroxylase activity, or functional variants thereof to produce hydroxyl fatty acids (e.g., ω-1 hydroxyl fatty acids, ω-2 hydroxyl fatty acid, ω-3 hydroxyl fatty acid, and combinations thereof). In the second step, the hydroxyl fatty acids are subjected to macrocyclization by a lipase (e.g., Novozyme 435) to produce lactones, such as macrocyclic lactones, with methyl, ethyl, or propyl side chains. Without being bound to any particular theory, it is believed that either the macrocyclic rings, or the side chains, or both moieties impart the musky notes which are useful for industrial applications. The lactones, such as macrocyclic lactones, produced using the methods described herein that have musky notes are referred to as "musk lactones."

In some embodiments, the biosynthetic methods of producing lactones (e.g., macrocyclic lactones) comprises: (i) preparing a first reaction mixture comprising one or more fatty acids, a cytochrome P450 hydroxylase, and NADPH; (ii) incubating the first reaction mixture of for a sufficient time to produce hydroxyl fatty acids selected from ω-1 hydroxyl fatty acids, ω-2 hydroxyl fatty acids, ω-3 hydroxyl fatty acids, and combinations thereof. (iii) preparing a second reaction mixture comprising the hydroxyl fatty acids produced in step (ii) and a lipase; and (iv) incubating the second reaction mixture for a sufficient time to produce the musk lactone.

In the first reaction mixture, fatty acids are substrates that can be converted to a hydroxyl fatty acid by a cytochrome P450 hydroxylase in the presence of NADPH. In some embodiments, the one or more fatty acids in the first reaction mixture of step (i) comprise a linear fatty acid comprising at least 12 carbons (e.g., at least 12 carbons, at least 13 carbons, at least 14 carbons, at least 15 carbons, at least 16 carbons, at least 17 carbons, at least 18 carbons, at least 19 carbons, at least 20 carbons, or at least 25 carbons). In some embodiments, the one or more fatty acids in the first reaction mixture of step (i) comprise a linear fatty acid comprising 12-28 (e.g., 12-28, 12-25, 12-20, 12-15, 15-28, 15-25, 15-20, 20-28, 20-25, or 25-28) carbons. In some embodiments, the one or more fatty acids in the first reaction mixture of step (i) comprise a linear fatty acid comprising 12, 13, 14, 15, 16, 17, 18, 19, 20, 21, 22, 23, 24, 25, 26, 27, or 28 carbons, or any combinations thereof. In some embodiments, the one or more fatty acids in the first reaction mixture of step (i) comprise a linear fatty acid comprising 15, 16, 17, 18, 19, or 20 carbons, or any combinations thereof. In some embodiments, the one or more fatty acids in the first reaction mixture of step (i) comprises a mixture of linear fatty acid comprising different numbers of carbons, e.g., a mix of fatty acids comprising 15, 16, 17, 18, 19, or 20 carbons.

In some embodiments, the one or more fatty acids in the first reaction mixture of step (i) comprises a saturated fatty acid (i.e., no double bonds between any two carbons). In some embodiments, the one or more fatty acids in the first reaction mixture of step (i) comprises an unsaturated fatty acid. In some embodiments, the unsaturated fatty acid comprises at least one (e.g., 1, 2, 3, 4, 5, or more) double bond. In some embodiments, the unsaturated fatty acid comprises at least one (e.g., 1, 2, 3, 4, 5, or more) Z double bond.

In some embodiments, the one or more fatty acids in the first reaction mixture of step (i) are selected from the group consisting of:

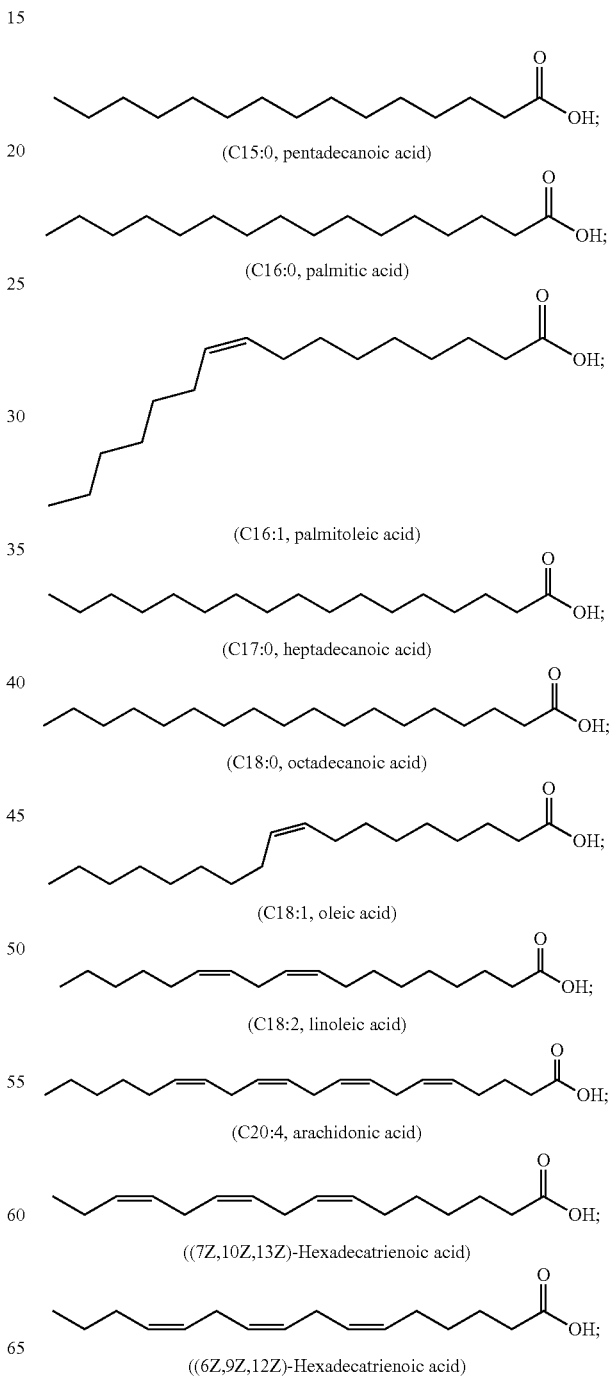

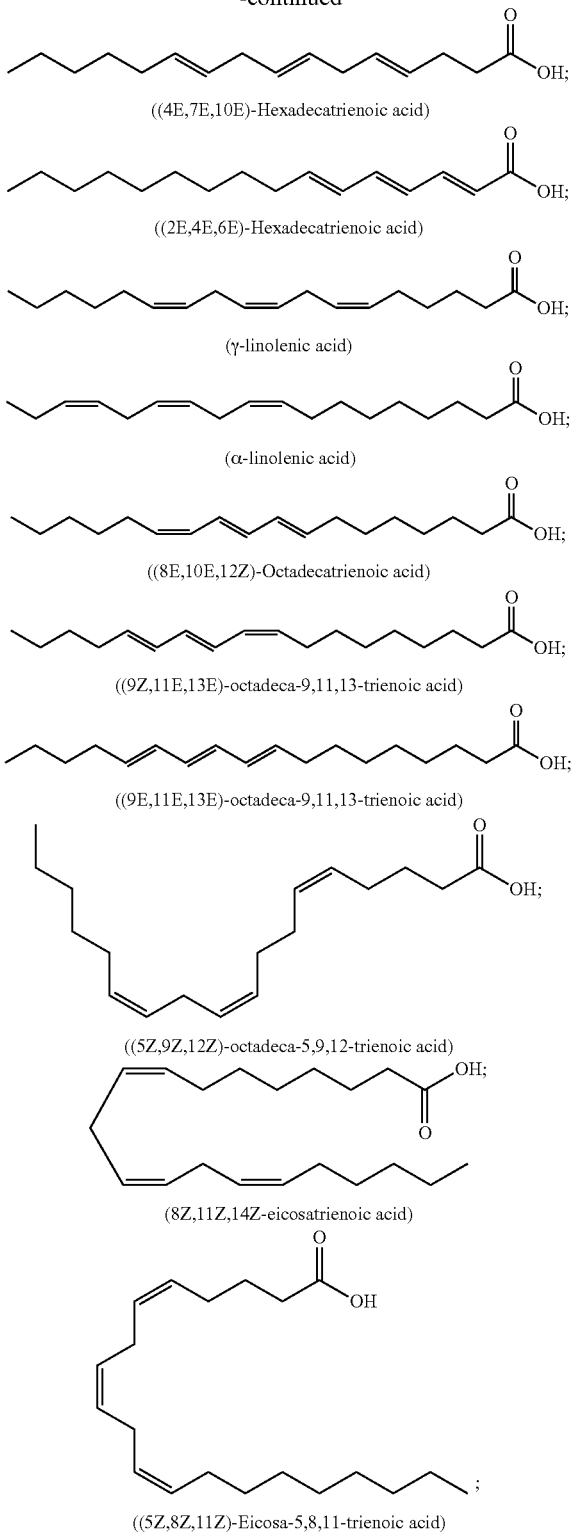

and any combinations thereof.

The enzyme that hydroxylates the fatty acid substrates in the first reaction mixture is a cytochrome P450 enzyme that has hydroxylase activity (referred to herein as "cytochrome P450 hydroxylase"), or a functional variant thereof. In some embodiments, the cytochrome P450 hydroxylase is a bacterial cytochrome P450 enzyme. Examples of Cytochrome P450 enzymes that may be used in accordance with the present disclosure include, without limitation, CYP102A1 from *Bacillus megaterium*; CYP106A1 from *Bacillus megaterium* DSM319; CYP106A2 from *B. megaterium* ATCC13368; CYP109B1 from *B. subtilis* 168; CYP109E1 from *B. megaterium* DSM19; CYP154C5 from *Nocardia farcinica* IFM 10152; CYP260A1 and CYP260B1 from *Sorangium cellulosum* Soce56; CYP154C3 from *Streptomyces griseus* SGR1085; CYP154C8 from *Streptomyces* sp. W2233-SM and CYP219A from *Novosphingobium aromaticivorans* DSM12444 (saro0307), CYP105A1 from *Streptomyces griseolus* ATCC 11796, CYP107E1 from *Micromonospora griseorubida*, CYP107D1 and CYP127A3 from *Mesorhizobium loti* MAFF303099 (mlr5876) CYP110A1, CYP110C1, CYP110D1 and CYP110E1 from *Nostoc* sp. PCC7120; CYP200A1 from *Bradyrhizobium japonicum* USDA110; CYP102A15 and CYP102A170 from polar *Bacillus* sp. PAMC 25034 and *Paenibacillus* sp. PAMC 22724, respectively; CYP709C1 from the wheat plant (*Triticum aestivum*); CYP147G1 from *Mycobacterium marinum*; CYP505D6 from White-Rot Fungus *Phanerochaete chrysosporium*; and the CYP102 family enzymes (bamf2522 and bamf0695) from *Bacillus amyloliquefaciens* DSM 7.

It was shown herein that a cytochrome P450 enzyme from *Bacillus megaterium* (CYP102A1, e.g., as described in Miura et al., Biochim. Biophys. Acta. 388: 305-317, 1975, incorporated herein by reference) and a cytochrome P450 enzyme from *Myceliophthora thermophile* (CYP505A30, UniProt Accession No.: G2QDZ3) were able to carry out the first step of the biosynthetic method described herein, i.e., converting fatty acids to mono-hydroxyl fatty acids that are hydroxylated at one of ω-1, ω-2, or ω-3 position, or combinations of the mono-hydroxyl fatty acids thereof. The amino acid sequence of CYP102A1 is provided as SEQ ID NO: 1. The amino acid sequence of CYP505A30 is provided as SEQ ID NO: 3.

In some embodiments, the cytochrome P450 hydroxylase used in the biosynthetic methods described herein comprises an amino acid sequence that is at least 70% (e.g., at least 70%, at least 75%, at least 80%, at least 85%, at least 90%, at least 95%, or at least 99%) identical to the amino acid sequence of SEQ ID NO: 1. In some embodiments, the cytochrome P450 hydroxylase used in the biosynthetic methods described herein comprises an amino acid sequence that is 70%, 75%, 80%, 85%, 90%, 95%, or 99% identical to the amino acid sequence of SEQ ID NO: 1. In some embodiments, the cytochrome P450 hydroxylase used in the biosynthetic methods described herein comprises the amino acid sequence of SEQ ID NO: 1.

In some embodiments, the cytochrome P450 hydroxylase used in the biosynthetic methods described herein comprises an amino acid sequence that is at least 70% (e.g., at least 70%, at least 75%, at least 80%, at least 85%, at least 90%, at least 95%, or at least 99%) identical to the amino acid sequence of SEQ ID NO: 3. In some embodiments, the cytochrome P450 hydroxylase used in the biosynthetic methods described herein comprises an amino acid sequence that is 70%, 75%, 80%, 85%, 90%, 95%, or 99% identical to the amino acid sequence of SEQ ID NO: 3. In some embodiments, the cytochrome P450 hydroxylase used in the biosynthetic methods described herein comprises the amino acid sequence of SEQ ID NO: 3.

In some embodiments, the first reaction mixture of step (i) is an in vitro reaction mixture, e.g., using an isolated recombinantly produced cytochrome P450 hydroxylase. In some embodiments, the first reaction mixture of step (i) is a cell-based reaction mixture. In some embodiments, the cell-based reaction mixture comprises a cell selected from the group consisting of a yeast, a plant, an alga, a fungus, and a bacterium. In some embodiments, the cell-based reaction mixture comprises a bacterial cell of a genus selected from the group consisting of *Escherichia; Salmonella; Bacillus; Acinetobacter; Corynebacterium; Methylosinus; Methylomonas; Rhodococcus; Pseudomonas; Rhodobacter; Synechocystis; Brevibacteria; Microbacterium; Arthrobacter; Citrobacter; Escherichia; Klebsiella; Pantoea; Salmonella; Corynebacterium*; and *Clostridium*. In some embodiments, the cell-based reaction mixture comprises an *E. coli* cell. In some embodiments, the cell-based reaction mixture comprises a fungus of a genus selected from the group consisting of *Saccharomyces; Zygosaccharomyces; Kluyveromyces; Candida; Streptomyces; Hansenula; Debaryomyces; Mucor; Pichia; Torulopsis; Aspergillus*; and *Arthrobotlys.*

In some embodiments, the cell used in the cell-based reaction mixture recombinantly express the cytochrome P450 hydroxylase. For example, the cell used in the cell-based reaction mixture may be transformed with a nucleic acid molecule (e.g., a vector such as an expression vector) comprising a nucleotide sequence encoding the cytochrome P450 hydroxylase. In some embodiments, the nucleotide sequence encoding the cytochrome P450 hydroxylase is operably linked to a promoter (e.g., an inducible promoter or a constitutive promoter). The transformed cells can be cultured under conditions that allow the expression of the cytochrome P450 hydroxylase. The cells contain the expressed cytochrome P450 hydroxylase can be collected and used in the cell-based reaction mixture. Nucleotide sequences encoding CYP102A1 (SEQ ID NO: 1) is provided as SEQ ID NO: 2. Nucleotide sequences encoding CYP505A30 (SEQ ID NO: 3) is provided as SEQ ID NO: 4.

In some embodiments, the cell (e.g., a bacterial cell such as an *E. coli* or *Bacillus* cell) used in the cell-based reaction mixture is transformed with a nucleic acid molecule comprising a nucleotide sequence that is at least 70% (e.g., at least 70%, at least 75%, at least 80%, at least 85%, at least 90%, at least 95%, or at least 99%) to the nucleotide sequence of SEQ ID NO: 2 or SEQ ID NO: 4. In some embodiments, the cell (e.g., a bacterial cell such as an *E. coli* or *Bacillus* cell) used in the cell-based reaction mixture is transformed with a nucleic acid molecule comprising a nucleotide sequence that is 70%, 75%, 80%, 85%, 90%, 95%, or 99% to the nucleotide sequence of SEQ ID NO: 2 or SEQ ID NO: 4. In some embodiments, the cell (e.g., a bacterial cell such as an *E. coli* or *Bacillus* cell) used in the cell-based reaction mixture is transformed with a nucleic acid molecule comprising a nucleotide the nucleotide sequence of SEQ ID NO: 2 or SEQ ID NO: 4.

In some embodiments, in step (ii) of the biosynthetic methods described herein, the first reaction mixture is incubated for a sufficient time to produce hydroxyl fatty acids. In some embodiments, the first reaction mixture is incubated for at least 1 hour (e.g., at least 1 hour, at least 2 hours, at least 5 hours, at least 10 hours, or longer). In some embodiments, the incubation is under 37° C. In some embodiments, the hydroxyl fatty acids produced in step (ii) of the biosynthetic methods described herein are mono-hydroxyl fatty acids that is hydroxylated at any one of positions ω-1, ω-2, or ω-3. In some embodiments, the hydroxyl fatty acids produced in step (ii) of the biosynthetic methods described herein comprises ω-1 hydroxyl fatty acids, ω-2 hydroxyl fatty acid, ω-3 hydroxyl fatty acid, and combinations thereof, and any combinations thereof.

In some embodiments, step (ii) of the biosynthetic method described herein further comprises isolating the hydroxyl fatty acids from the reaction mixture. Any suitable extraction methods may be used. F or example, the hydroxyl fatty acids may be extracted by liquid-liquid extraction using a mixture of hydrocarbon-based organic solvents (e.g., hexane) and a water-insoluble polar solvent (e.g., ethyl acetate).

The hydroxyl fatty acids produced in step (ii) can be further converted to lactones via macrolactonization catalyzed by a lipase. In some embodiments, as step (iii) of the biosynthetic methods described herein, a second reaction mixture is prepared, the second reaction mixture comprising the hydroxyl fatty acids produced in step (ii) and a lipase. One skilled in the art is able to identify suitable lipase for use in this reaction. In some embodiments, the lipase used in the second reaction mixture is lipase B from *Candida antarctica* (Uniprot Accession No.: P41365). The amino acid sequence of lipase B from *Candida antarctica* is provided as SEQ ID NO: 5. In this regard, Krishna et al. (Catalysis Reviews, Vol. 44, pp. 499-591, 2002) provides an overview of lipase-catalyzed esterifications in organic solvents. Each lipase can be tested with different solvents to identify the combination best suited to the lactonization of hydroxy fatty acids to yield musk lactones.

In some embodiments, the lipase used in the biosynthetic methods described herein comprises an amino acid sequence that is at least 70% (e.g., at least 70%, at least 75%, at least 80%, at least 85%, at least 90%, at least 95%, or at least 99%) identical to the amino acid sequence of SEQ ID NO: 5. In some embodiments, the lipase used in the biosynthetic methods described herein comprises an amino acid sequence that is 70%, 75%, 80%, 85%, 90%, 95%, or 99% identical to the amino acid sequence of SEQ ID NO: 5. In some embodiments, the lipase used in the biosynthetic methods described herein comprises the amino acid sequence of SEQ ID NO: 5.

In some embodiments, the lipase used in the second reaction mixture in step (iii) of the biosynthetic methods described herein is immobilized on a solid support (e.g., acrylic resin). In some embodiments, the lipase used in the second reaction mixture in step (iii) of the biosynthetic methods described herein is Novozyme 435 (lipase B from *Candida antarctica* immobilized on acrylic resin, available from Sigma, catalog #L4777). In some embodiments, wherein the second reaction mixture further comprises a solvent. Any suitable solvent may be used. In some embodiments, the solvent is toluene or dichloroethane.

In some embodiments, in the second reaction mixture, the hydroxyl fatty acids are at a total concentration of 0.02-0.1 M (e.g., 0.02 M, 0.03 M, 0.04 M, 0.05 M, 0.06 M, 0.07 M, 0.08 M, 0.09 M, or 0.1M). In some embodiments, in the second reaction mixture, the hydroxyl fatty acids are at a total concentration of 0.025-0.05 M (e.g., 0.025 M, 0.03 M, 0.035 M, 0.04 M, 0.045 M, or 0.05 M). In some embodiments, in the second reaction mixture, the lipase is at a concentration of 20-150 g/L (e.g., 20-150 g/L, 20-100 g/L, 20-50 g/L, 50-150 g/L, 50-100 g/L, or 100-150 g/L). In some embodiments, in the second reaction mixture, the lipase is at a concentration of 50-100 g/L (e.g., 50 g/L, 60 g/L, 70 g/L, 80 g/L, 90 g/L, or 100 g/L).

In some embodiments, as step (iv) of the biosynthetic methods described herein, the second reaction mixture is incubated for a sufficient time to produce hydroxyl fatty acids. In some embodiments, the second reaction mixture is incubated for at least 10 hours (e.g., at least 10 hours, at least 15 hours, at least 20 hours, at least 24 hours, or longer). In some embodiments, the second reaction mixture is incubated for 15-24 hours (e.g., 15, 16, 17, 18, 19, 20, 21, 22, 23, or 24 hours). In some embodiments, the incubation is under 40-60° C. (e.g., 40-60° C., 40-55° C., 40-50° C., 40-45° C., 45-60° C., 45-55° C., 45-50° C., 50-60° C., 50-55° C., or 55-60° C.). In some embodiments, the incubation is under 40° C., 45° C., 50° C., 55° C., or 60° C.

In some embodiments, following the incubation of the second reaction mixture, step (iv) further comprises isolating the lactone compounds from the reaction mixture. Known methods of isolating lactone compounds from reaction mixture can be used, including without limitation, filtration and/or chromatography methods. In some embodiments, the isolated lactone compounds are subjected to drying.

In some embodiments, the lactone compounds produced by the biosynthetic methods described herein have a purity of at least 50% w/w (e.g., at least 50%, at least 60%, at least 70%, at least 75%, at least 80%, at least 85%, at least 90%, at least 95%, or at least 99%) w/w. The purity relates to all the lactone compounds produced, which, in some embodiments, comprise lactone compounds of different structures. In some embodiments, the lactone compounds produced in step (iv) has musk notes.

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by GREENE PUBLISHING AND WILEY-INTERSCIENCE, 1987; (the entirety of each of which is incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Bacterial Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator. We only used one standard E. coli expression system for this proof-of-concept work. The further modification and optimization is in progress.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or E. coli DNA polymerase I, enzymes that remove protruding, 3'-single-stranded termini with their 3'-5'-exonucleolytic activities and fill-in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference to the extent it is consistent herewith).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared by the use of PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector.

In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

Microbial host cell expression systems and expression vectors containing regulatory sequences that direct high-level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in Saccharomyces); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (s) of the ribulose-1,5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

One with skill in the art will recognize that the lactone composition(s) produced by the methods described herein can be further purified and mixed with other lactones, flavors, or scents to obtain a desired composition for use in a variety of consumer products or foods.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the Blu1 and Cytochrome P450 genes of the current disclosure are capable of directing the production of a variety of lactones, such as macrocyclic lactones, and have a substantial percent sequence identity to the polynucleotide sequences provided herein and are encompassed within the scope of this disclosure.

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

EXAMPLES

Example 1: Lactone Production

In this process, a cytochrome P450 enzyme, e.g. P450 BM3 (Miura and Fulco, 1975) that has fatty acid subterminal hydroxylase activity, was used to make (0-1, (0-2 or (0-3 hydroxyl fatty acids or their mixtures (Process 1, Miura Y, Fulco A J. (1975) Omega-1, Omega-2 and Omega-3 hydroxylation of long-chain fatty acids, amides and alcohols by a soluble enzyme system from *Bacillus megaterium*. Biochim. Biophys. Acta. 388: 305-317).

The hydroxyl fatty acid products may be further processed by lipase-catalyzed ring closure reaction in organic solvents for the formation of branched-chain musky macrolactones (Process 2). The overall synthetic scheme is illustrated in FIG. 1.

Process 1 involves a fatty acid hydroxylation by subjecting the saturated or unsaturated fatty acid to the action of a biological catalyst (hydroxylase) present in a fermentation media. The hydroxyl fatty acid obtained from Process 1 may be isolated from the fermentation broth (for example by liquid-liquid extraction using a mixture of hydrocarbon-based organic solvents such as hexane and a water-insoluble polar solvent such as ethyl acetate).

Process 2 involves a reaction of obtaining macrolactones by subjecting the hydroxyl fatty acids to an intramolecular macrolactonization reaction catalyzed by a lipase enzyme. The lipase enzyme may be immobilized on a solid support and used for the macrolacronization process. The immobilized lipase can be easily recovered and recycled repeatedly for a long term.

Process 2 can be carried out in the presence of immobilized lipase catalyst such as Novozyme 435 in a solvent such as toluene of dichloroethane. The concentration of hydroxyl fatty acid is adjusted at 0.05 to 0.025 molar. The concentration of immobilized lipase enzyme may be appropriately selected to amounts that do not decrease the reaction rate. In the case of using Novozyme 435, it is preferable to adjust the concentration at 50 to 100 grams per liter. The reaction is usually shaken and stirred for about 15 to 24 hours at 40 to 60° C.

The target macrolactones can be isolated from the reaction mixture using a proper combination of conventional purification techniques such as filtration, chromatography, and drying.

Next, a total number of eight fatty acids were used for musk lactone production.

Figure 2:
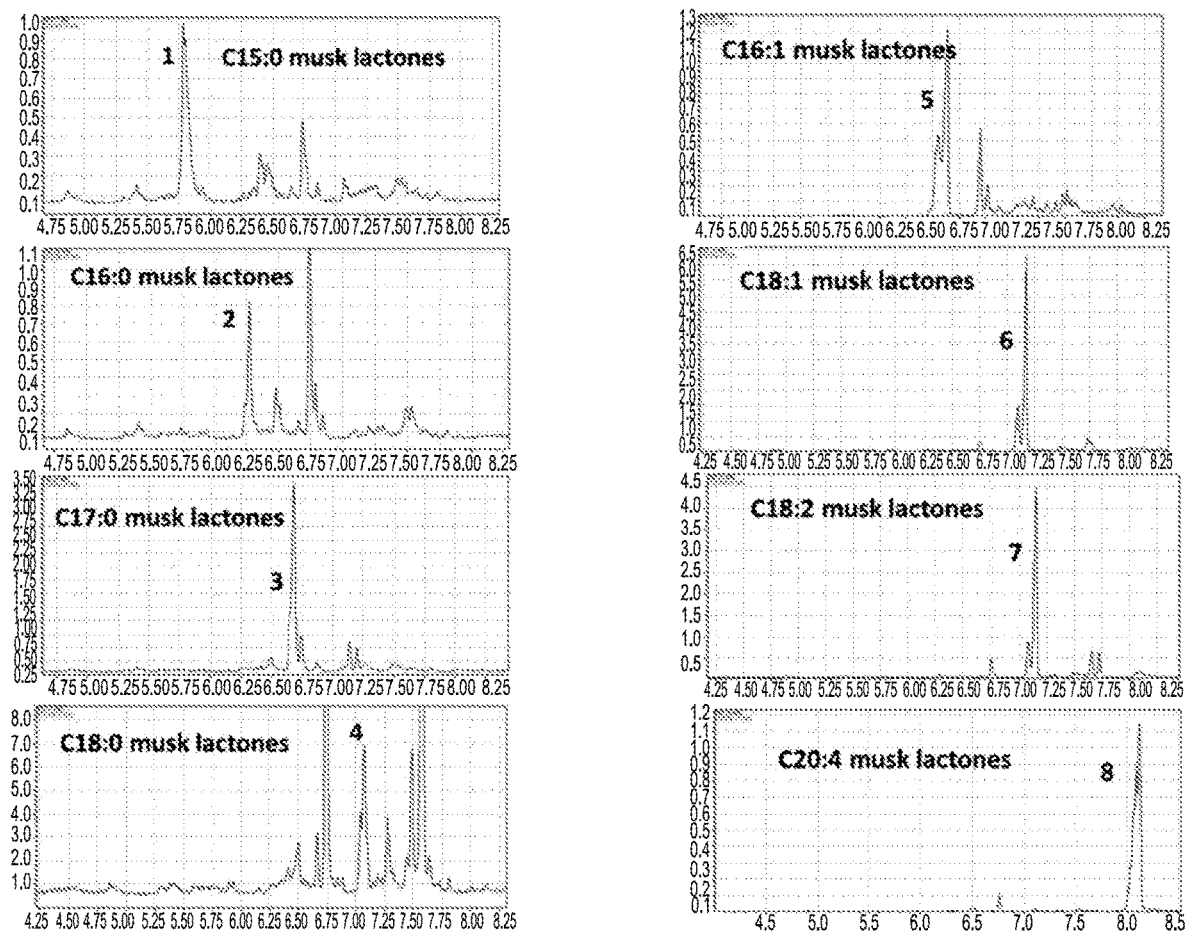
FIG. 2. GC/MS analysis of reaction products catalyzed by lipase. The numbers indicate the musk lactone peaks from different fatty acids. The molecular weights of these musky lactones match their calculated molecular weights.
Figure 3A:
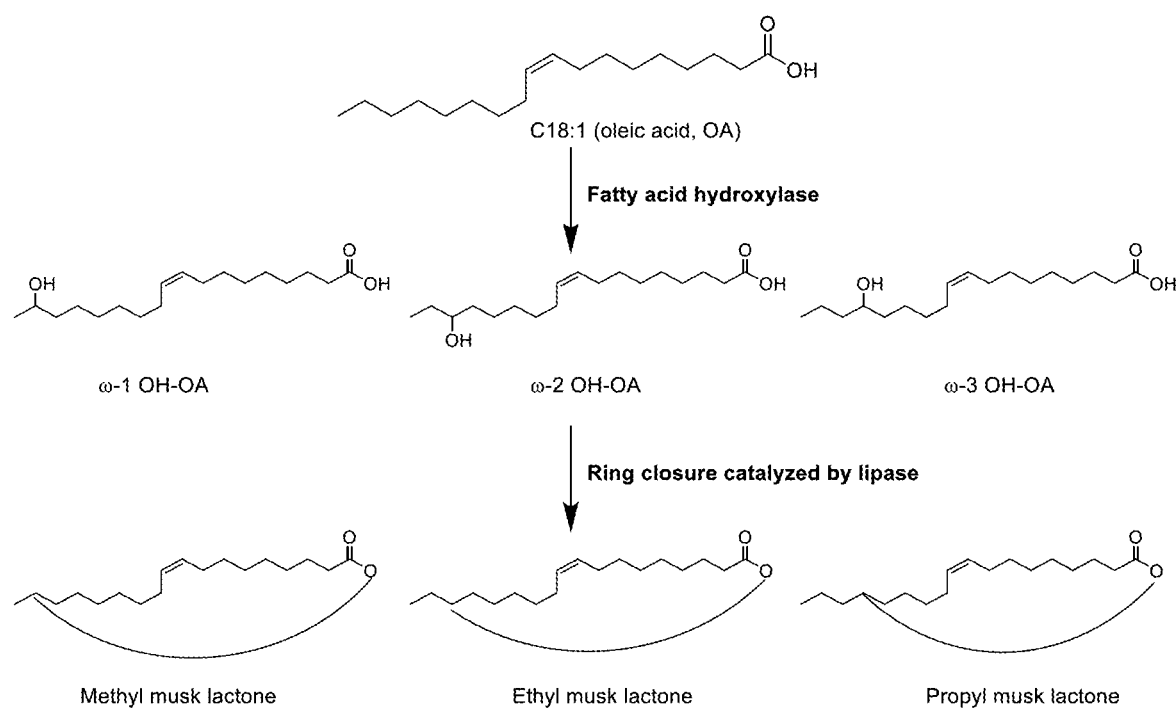
FIGS. 3A-3F. Reaction schemes showing fatty acid hydroxylation and ring closure for oleic acid (FIG. 3A), linoleic acid (FIG. 3B), arachidonic acid (FIG. 3C), palmitic acid (FIG. 3D), heptadecanoic acid (FIG. 3E), and octadecanoic acid (FIG. 3F).
Figure 3B:
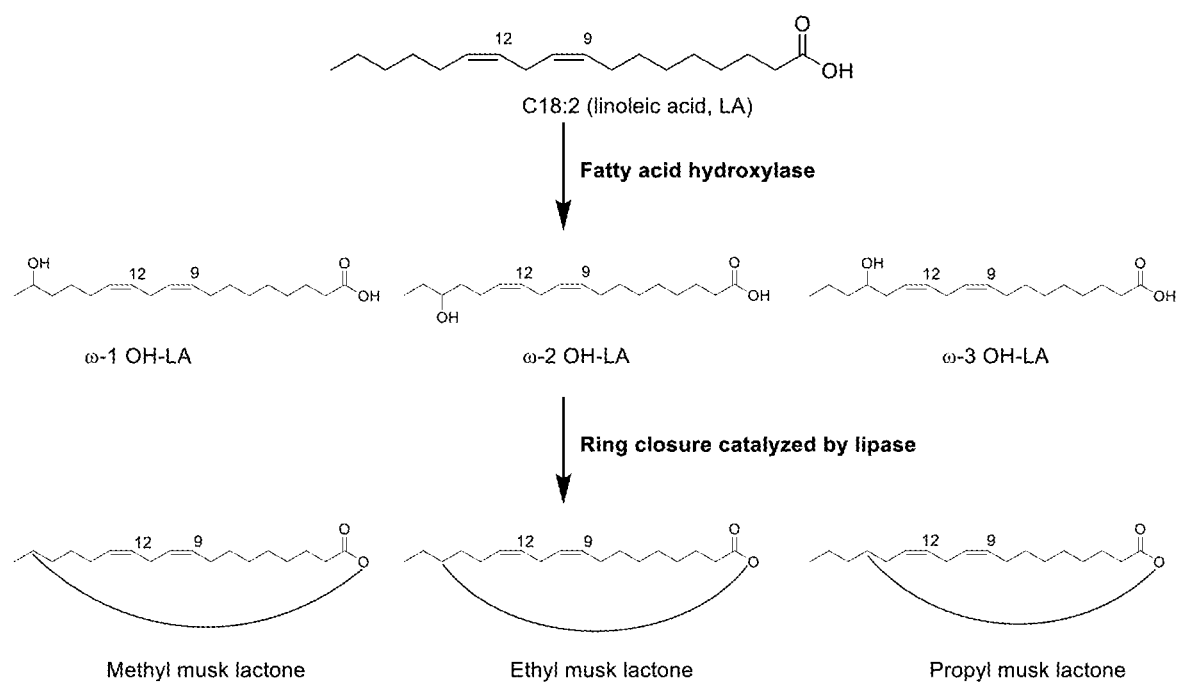
Figure 3C:
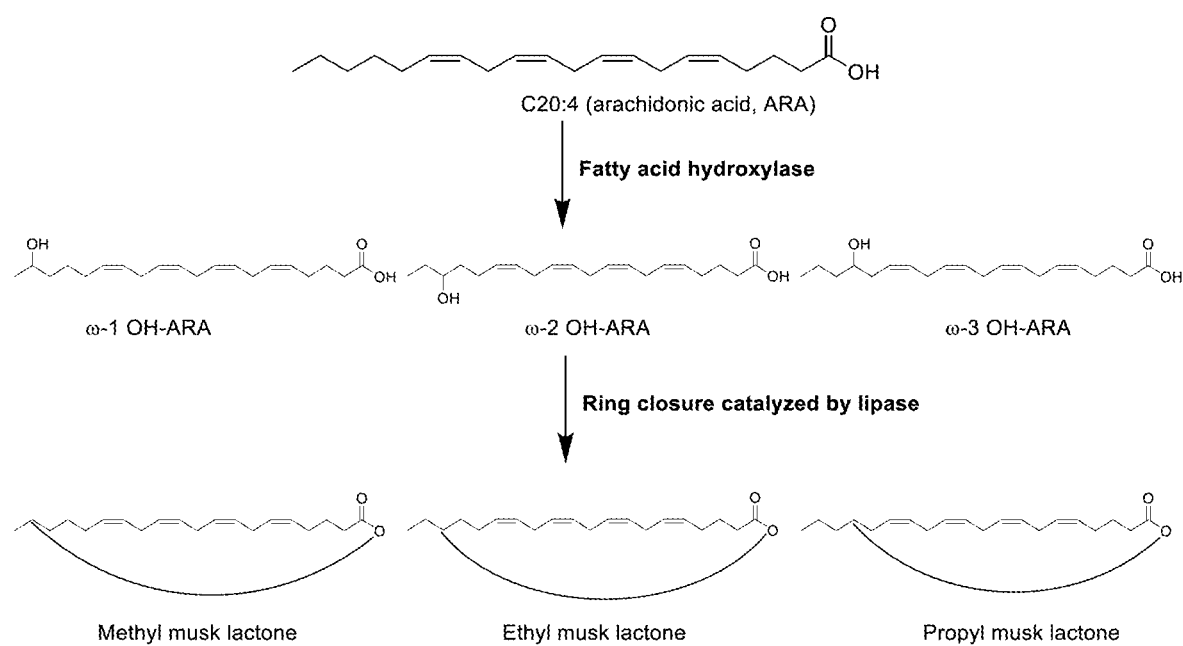
Figure 3D:
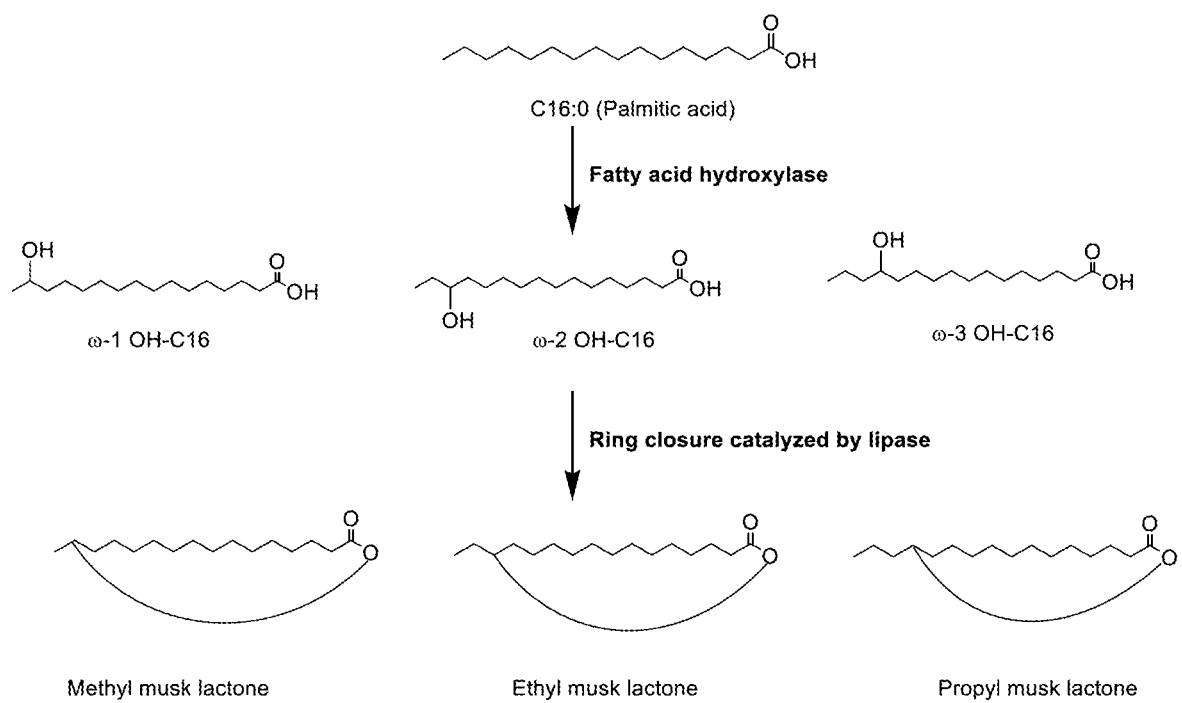
Figure 3E:
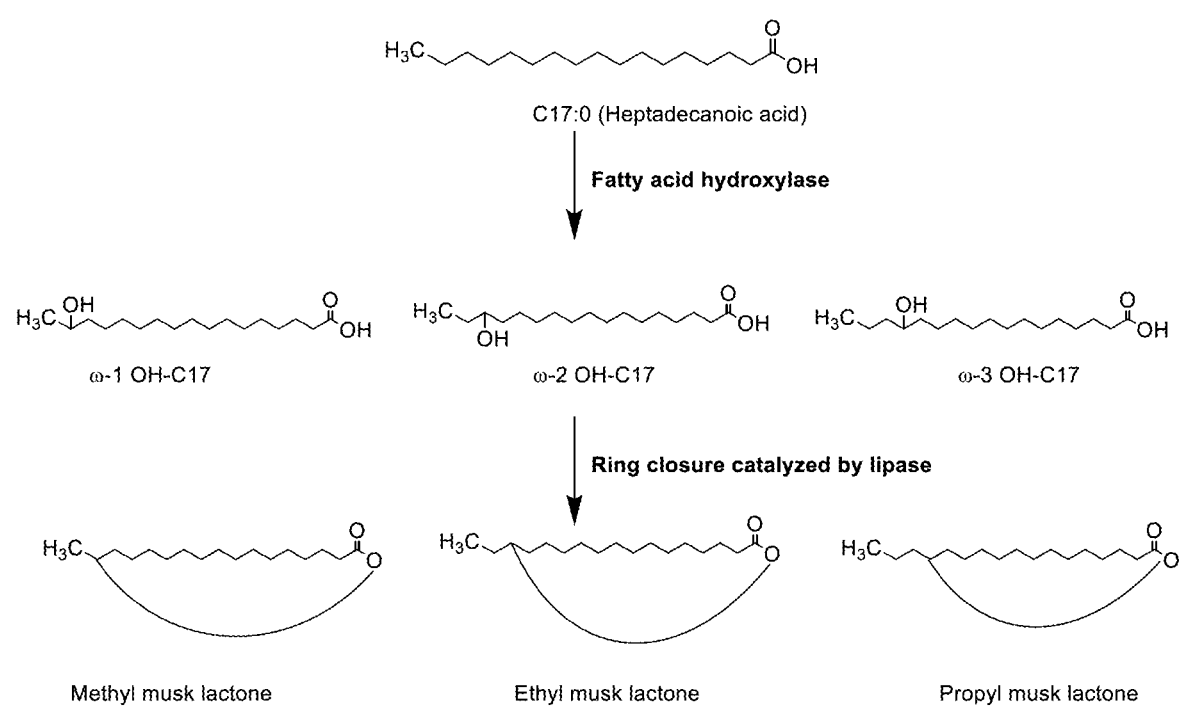
Figure 3F:
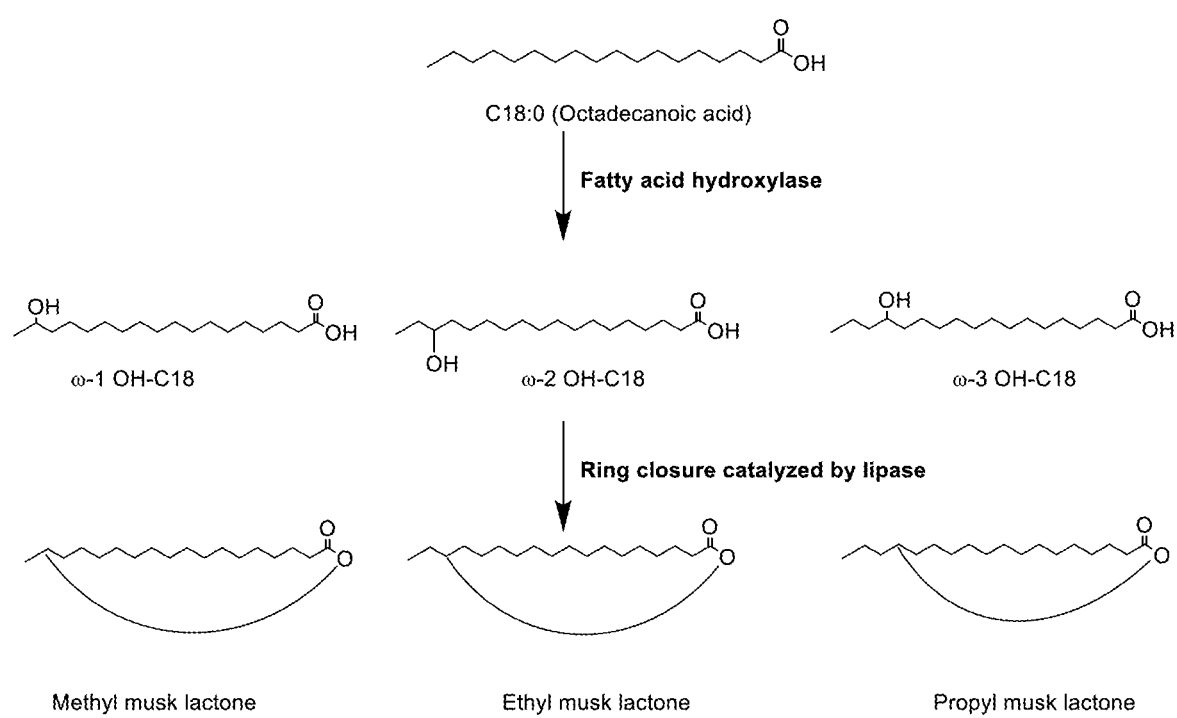

After hydroxylation and ring closure, eight different musk lactone mixtures were produced from these eight fatty acids, respectively as shown in FIG. 2. The eight fatty acids and corresponding musk lactone products is shown in Table 36. Reaction schemes showing fatty acid hydroxylation and ring closure are illustrated for oleic acid, linoleic acid, arachidonic acid, palmitic acid, heptadecanoic acid, and octadecanoic acid in FIGS. 3A-3F, respectively.

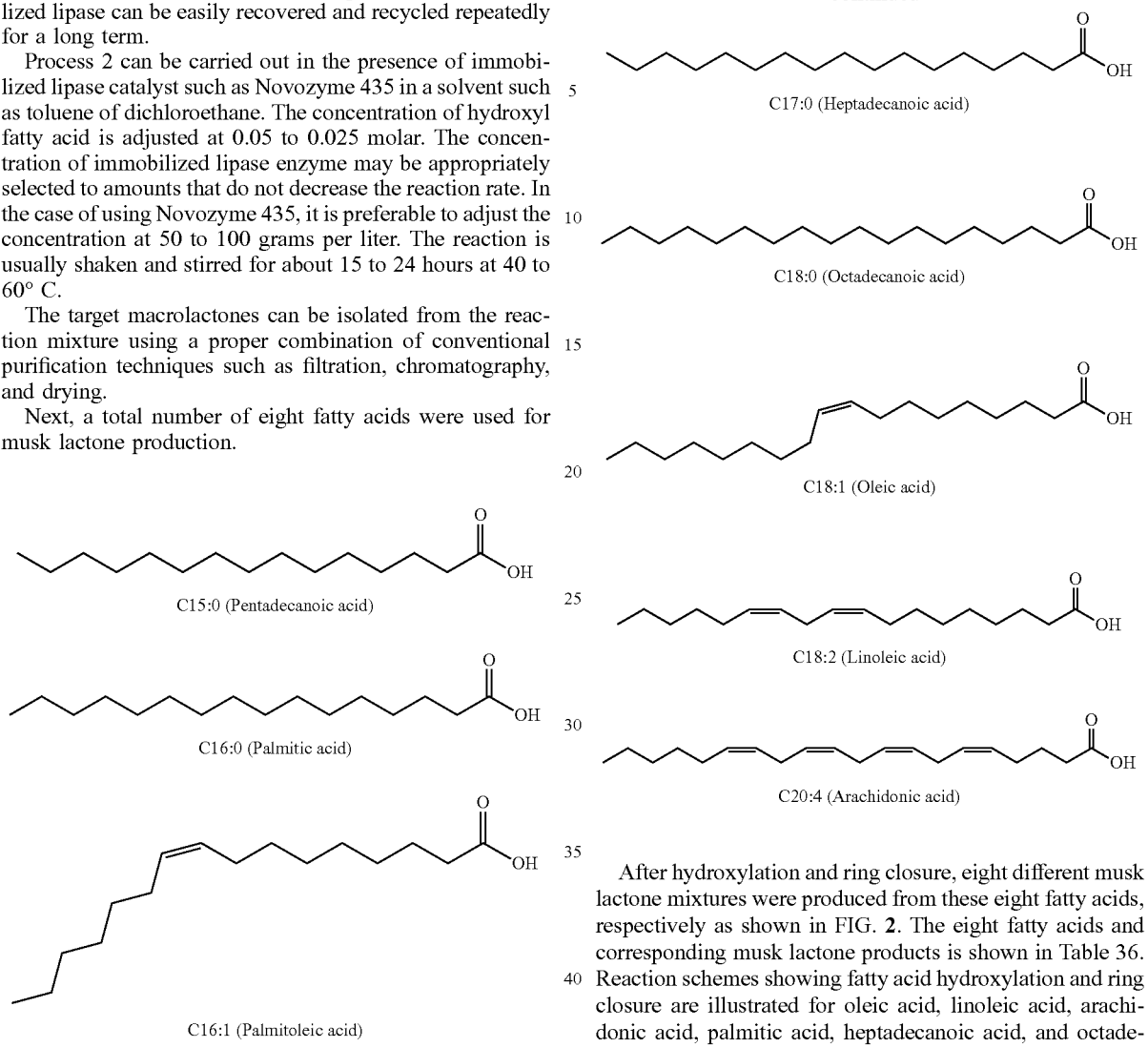

TABLE 36

| # | Parent Fatty Acid | MuL lactone product 1 | MuL lactone product 2 | MuL lactone product 3 |
|---|---|---|---|---|
| 1 | C18:1, Oleic Acid (OA) | (Z)-18-methyloxacyclooctadec-10-en-2-one racemic, CAS 2055033-69-5 (18R), CAS 2055033-71-9 (18S), CAS 2055033-70-8 | (Z)-17-ethyloxacycloheptadec-10-en-2-one | (Z)-16-propyloxacyclohexadec-10-en-2-one |

TABLE 36-continued

| Lactones | | | | |
|---|---|---|---|---|
| # | Parent Fatty Acid | MuL lactone product 1 | MuL lactone product 2 | MuL lactone product 3 |
| 2 | 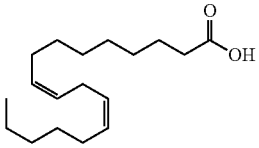 [SMILES: CCCCC/C=C\C/C=C\CCCCCCCC(=O)O]<br>C18:2, Linoleic acid (LA) | 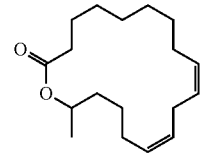 [SMILES: CC1CCC/C=C\C/C=C\CCCCCCCC(=O)O1]<br>(10Z, 13Z)-18-methyloxacyclooctadeca-10,13-dien-2-one | 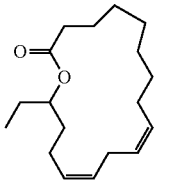 [SMILES: CCC1CC/C=C\C/C=C\CCCCCCCC(=O)O1]<br>(10Z, 13Z)-17-ethyloxacycloheptadeca-10,13-dien-2-one | 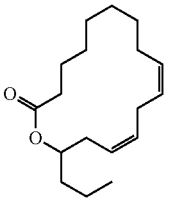 [SMILES: CCCC1C/C=C\C/C=C\CCCCCCCC(=O)O1]<br>(10Z, 13Z)-16-propyloxacyclohexadeca-10,13-dien-2-one (16R), CAS 1809795-94-5 (16S), CAS 1809894-22-1 |
| 3 | 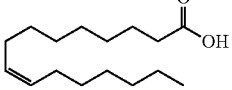<br>C16:1, Palmitoleic acid (A) | 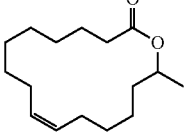<br>(Z)-16-methyloxacyclohexadec-10-en-2-one | 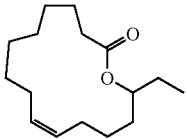 [SMILES: CCC1CCC/C=C\CCCCCCCC(=O)O1]<br>(Z)-15-ethyloxacyclopentadec-10-en-2-one | 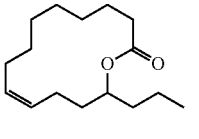 [SMILES: CCCC1CC/C=C\CCCCCCCC(=O)O1]<br>(Z)-14-propyloxacyclotetradec-10-en-2-one |
| 4 | 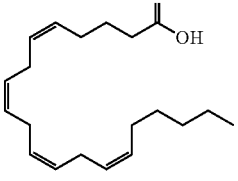<br>C20:4, Arachidonic acid (AA) | 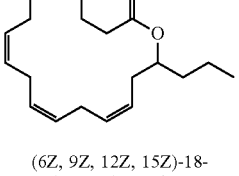<br>(6Z, 9Z, 12Z, 15Z)-18-propyloxacyclooctadeca-6, 9, 12, 15-tetraen-2-one | 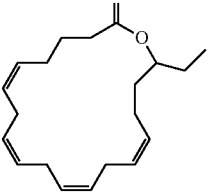<br>(6Z, 9Z, 12Z, 15Z)-19-ethyloxacyclononadeca-6, 9, 12, 15-tetraen-2-one | 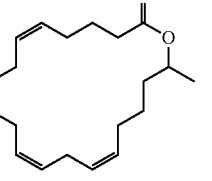<br>(6Z, 9Z, 12Z, 15Z)-20-methyloxacycloicosa-6, 9, 12, 15-tetraen-2-one |
| 5 | 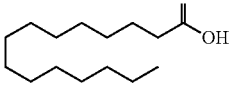<br>C15:0, pentadecanoic acid | 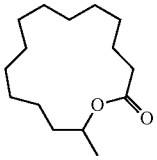 [SMILES: CC1CCCCCCCCCCCCC(=O)O1]<br>15-methyloxacyclopentadecan-2-one racemic, CAS 32539-85-8 (15R)-CAS 69297-55-8 (15S)-CAS 206124-09-6 | 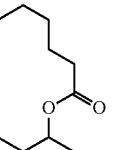<br>14-ethyloxacyclotetradecan-2-one racemic, CAS 4723-83-5 (14R)-CAS 239801-19-5 (14S)-CAS 239801-33-3 | 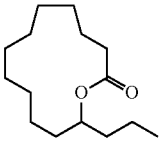 [SMILES: CCCC1CCCCCCCCCCC(=O)O1]<br>13-propyloxacyclotridecan-2-one CAS 89328-31-4 |
| 6 | 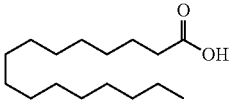 [SMILES: CCCCCCCCCCCCCCCC(=O)O]<br>C16:0, hexadecanoic acid (palmitic acid) | 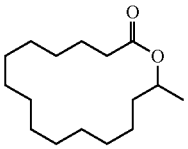 [SMILES: CC1CCCCCCCCCCCCCC(=O)O1]<br>16-methyloxacyclohexadecan-2-one, racemic, CAS 4459-57-8 (16R), CAS 69297-56-9 (16S), CAS 129214-002 | 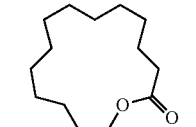<br>15-ethyloxacyclopentadecan-2-one racemic, CAS 140389-84-0 (15R), CAS 2260613-71-4 | 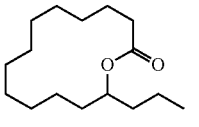<br>14-propyloxacyclotetradecan-2-one CAS 140390-02-9 |

TABLE 36-continued

Lactones

| # | Parent Fatty Acid | MuL lactone product 1 | MuL lactone product 2 | MuL lactone product 3 |
|---|---|---|---|---|
| 7 | 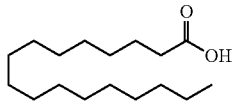 [SMILES: CCCCCCCCCCCCCCCCC(=O)O]<br>C17:0, heptadecanoic acid | 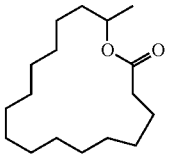 [SMILES: CC1CCCCCCCCCCCCCCC(=O)O1]<br>17-methyloxacycloheptadecan-2-one<br>CAS 111908-52-2 | 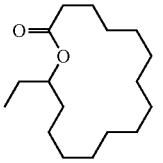 [SMILES: CCC1CCCCCCCCCCCCCC(=O)O1]<br>16-ethyloxacyclohexadecan-2-one<br>racemic, CAS 89426-66-4<br>(16R) CAS 239801-26-4<br>(16S) CAS 239801-36-6 | 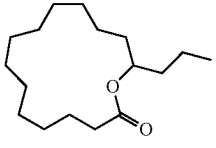 [SMILES: CCCC1CCCCCCCCCCCCC(=O)O1]<br>15-propyloxacyclopentadecan-2-one |
| 8 | 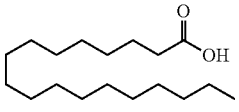 [SMILES: CCCCCCCCCCCCCCCCCC(=O)O]<br>C18:0, octadecanoic acid | 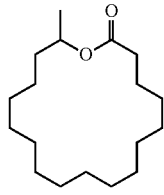 [SMILES: CC1CCCCCCCCCCCCCCCC(=O)O1]<br>18-methyloxacyclooctadecan-2-one<br>CAS 111879-77-7 | 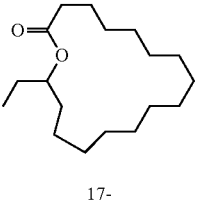<br>17-ethyloxacycloheptadecan-2-one<br>CAS 140389-85-1 | 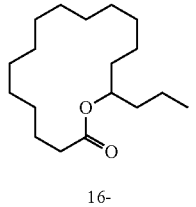<br>16-propyloxacyclohexadecan-2-one<br>CAS 140390-03-0 |

Fatty Acid Hydroxylation

The amino acid sequence of a BM3 homolog of *Myceliophthora thermophile* (CYP505A30) was obtained from UniProt (www.uniprot.org/uniprot/G2QDZ3.fasta) and the corresponding gene was codon optimized for expression in *Escherichia coli* and synthesized by GenScript (Piscataway, N.J.).

The resulting gene product was cloned into pETDuet-1 vector (AMP+, Novagen) through NdeI and XhoI sites. The construct was transformed into BL21(DE3) cells for expression.

In a typical experiment, an overnight culture was used to inoculate liquid LB medium (2%) containing 100 mg/L of carbenicillin and 0.4 mM 5-aminolevulinic acid. The culture was first grown at 37° C. to an OD600 of 0.6 and cooled down to 16° C. Then 1 mM IPTG was added to induce protein expression. After 16 hours of incubation at 16° C., cells were harvested by centrifugation.

Harvested cell pellets were re-suspended at a concentration of 100 g/L fresh weight in 100 mM potassium phosphate buffer (pH7.0) containing 0.1% Tween 40 and 10 mM NADPH. Then 1 g/L of fatty acid substrate was added. The mixture was shaken at 37° C. in a shaker.

Production of Branched-Chain Musky Macrolactones from Palmitic Acid

Figure 4:
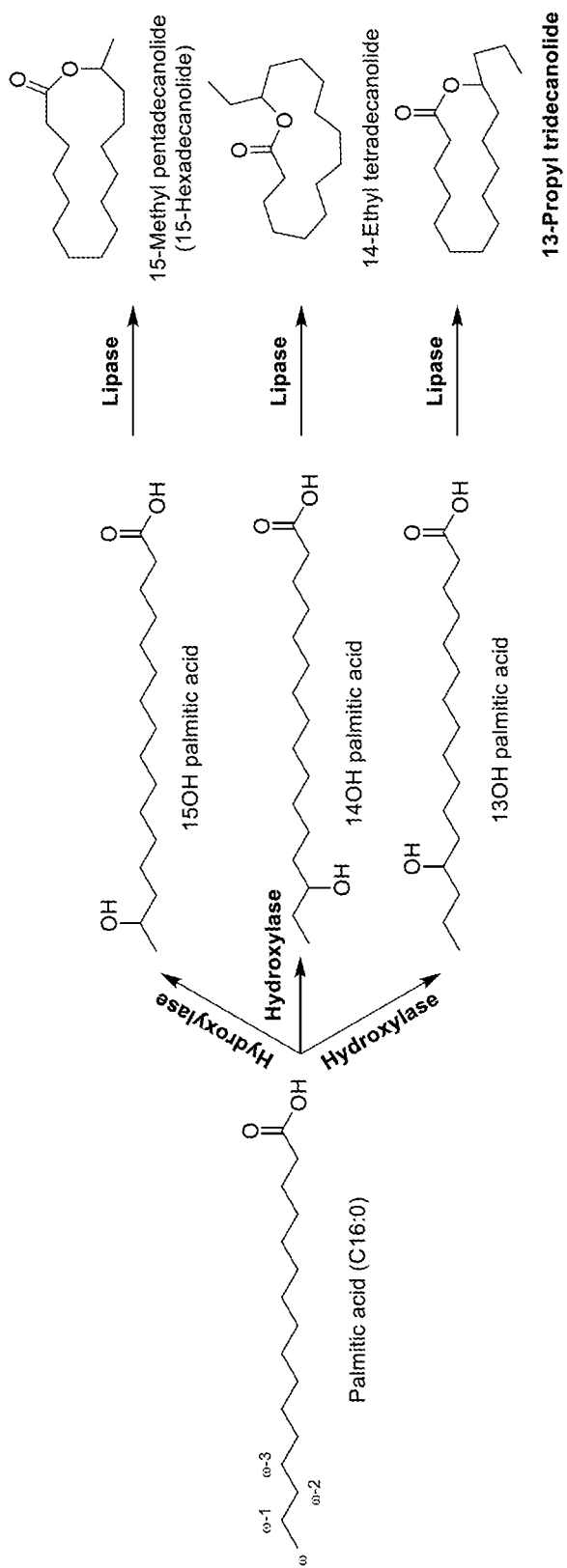
FIG. 4. Overall synthetic scheme showing palmitic acid hydroxylation (Process 1) and a reaction of obtaining corresponding musk lactone products (Process 2).

The overall synthetic scheme showing palmitic acid hydroxylation and a reaction of obtaining corresponding musk lactone products is illustrated in FIG. 4. Harvested cell pellets were re-suspended at a concentration of 100 g/L fresh weight in 100 mM potassium phosphate buffer (pH7.0) containing 0.1% Tween 40 and 10 mM NADPH. Then 1 g/L of palmitic acid (C16:0) was added. The mixture was shaken at 37° C. in a shaker.

Hydroxylated palmitic acids were extracted by ethyl acetate and ethyl acetate phase was dried in SpeedVac™ vacuum concentrator. Then Novozym 435 in the form of acrylic resin (Sigma) was added with toluene as solvent for ring closure reaction at 60° C. with shaking. The products from hydroxyl palmitic acids were analyzed by GC/MS.

GC/MS analysis was conducted on Shimadzu GC-2010 system coupled with GCMS-QP2010S detector. The analytical column is SHRXI-5MS (thickness 0.25 μm; length 30 m; diameter 0.25 mm) and the injection temperature is 265° C. under split mode. The temperature gradient is 0-3 min 150° C.; 3-6.7 min 150° C. to 260° C., a gradient of 30; 6.7-15.7 min, 260° C.

Production of Branched-Chain Musky Macrolactones from Oleic Acid

Figure 5:
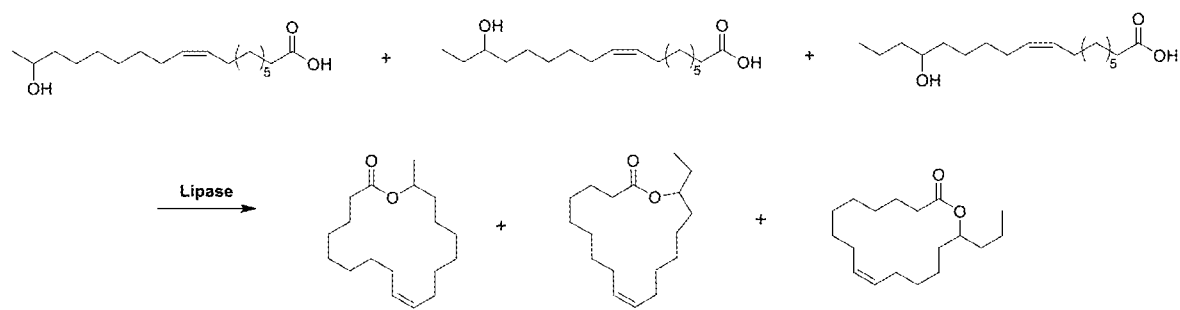
FIG. 5. Reaction showing hydroxyl oleic acid cyclized to obtain corresponding musk lactone products (Process 2).

First, oleic acid was hydroxylated to form hydroxyl fatty acid, as outlined in Process 1 in Example 1. Thereafter, the hydroxyl fatty acid were cyclized as illustrated in FIG. 5 (Process 2).

3 liters of fermentation broth containing hydroxyl oleic acid analogs were extracted with 11 liters of 50% ethyl acetate-hexane in 1-liter batches. The solvents were distilled off under reduced pressure to obtain 11.50 g of crude extract as a reddish oil. The crude extract was purified by column chromatography on silica gel eluting with 20 to 50% ethyl acetate-hexane to obtain 1.40 g of hydroxyl oleic acid isomers.

1.40 g (4.66 mmol) of hydroxyl oleic acid analogs was dissolved in 200 ml toluene. 20 g of Novozyme 435 was added to this solution. The reaction mixture was heated to 55° C. and stirred for 15 hours then cooled to room temperature. The immobilized lipase enzyme was separated by filtration and rinsed with dichloromethane. The volatiles were distilled off under reduced pressure to obtain 1.50 g of crude product as a yellow oil. The crude product was purified by column chromatography on silica gel eluting with 5% ethyl acetate-hexane to obtain 1.10 g (3.92 mmol, 62.7% isolated yield, 98% total purity of three isomers) of corresponding macrolactonization products.

It was confirmed by a sensory evaluation that the mixture of the three components has a "luxurious and novel musk fragrance . . . ".

Figure 6:
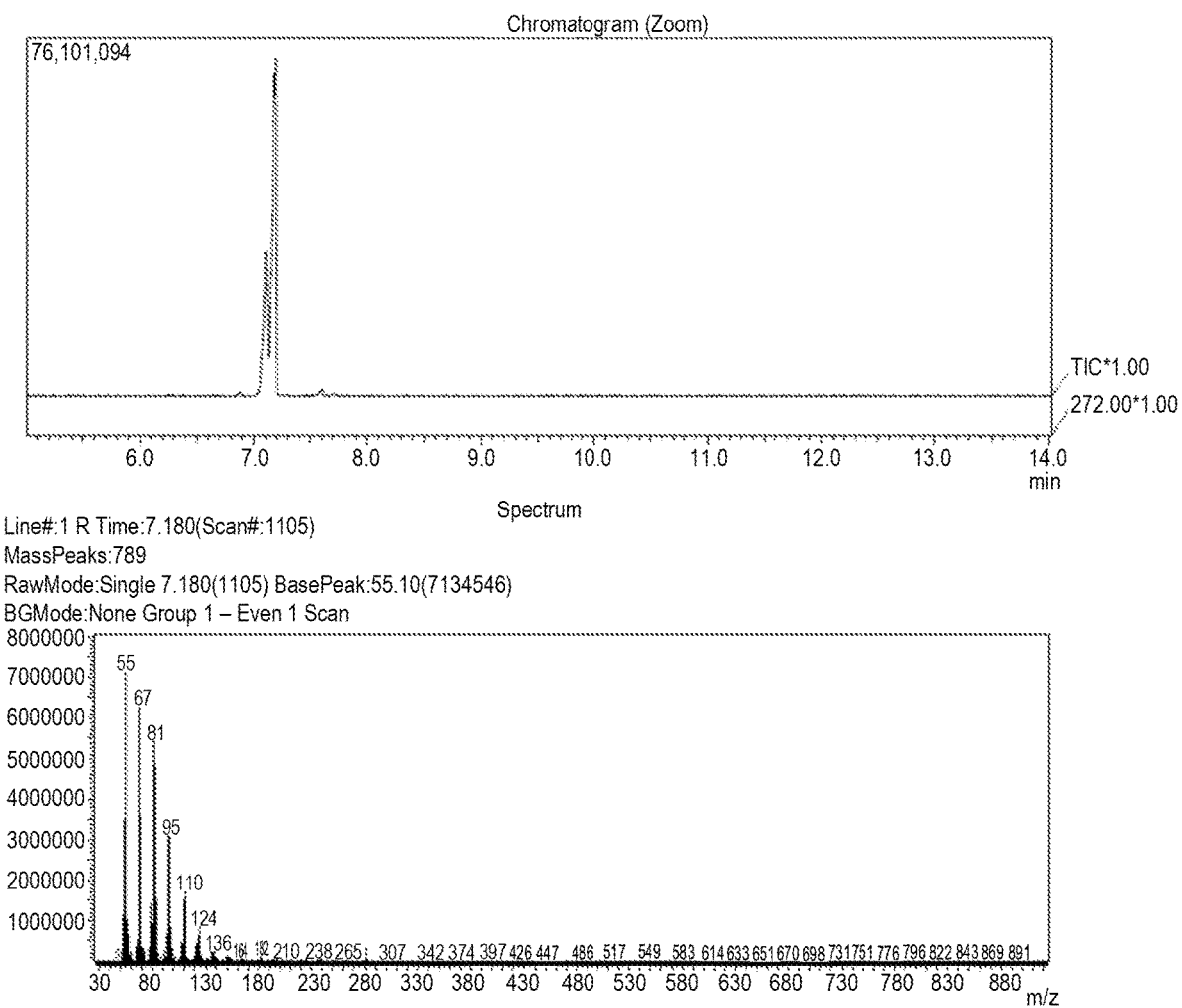
FIG. 6. Chromatogram and spectrum showing analysis of the oleic acid macrolactonization products.

A 1 mg/ml solution of the purified product in hexane was analyzed on a capillary gas chromatograph-mass spectrometer GCMS-QP2020 NX (manufactured by Shimadzu) using a 30 m×0.25 mm 0.25 μm Rtx-5MS (manufactured by Restek). The analysis was carried out using high purity helium for the mobile phase, at a flow rate of 1 mL/min. The temperature program used was 150° C. for 3 minutes, a temperature gradient of 50° C./minute to 260° C., and isothermic at 260° C. for 9 minutes. Results are shown in FIG. 6.

Production of Branched-Chain Musky Macrolactones from Linoleic Acid

Figure 7:
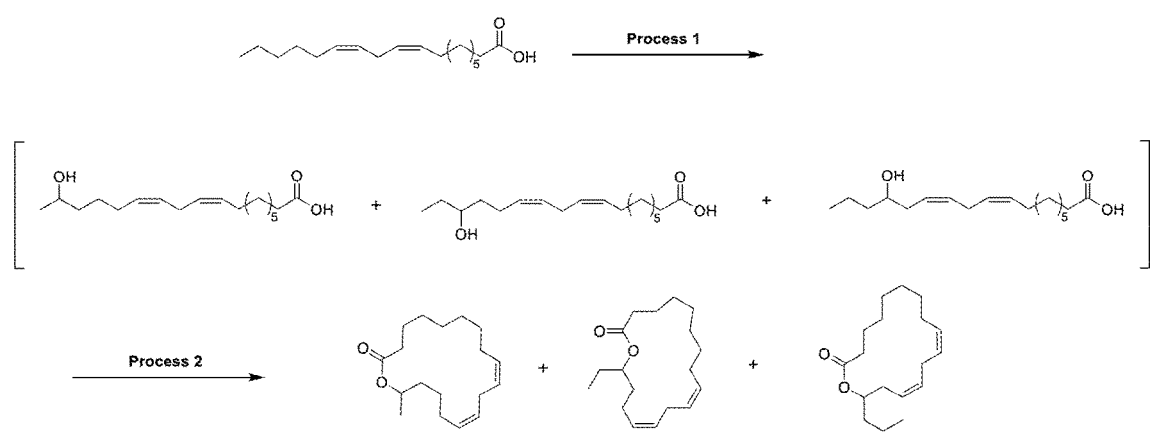
FIG. 7. Overall synthetic scheme showing linoleic acid hydroxylation (Process 1) and a reaction of obtaining corresponding musk lactone products (Process 2) is illustrated in FIG. 6.

The overall synthetic scheme showing linoleic acid hydroxylation (Process 1) and a reaction of obtaining corresponding musk lactone products (Process 2) is illustrated in FIG. 7. 2 liters of fermentation broth containing hydroxyl linoleic acid analogs was extracted with 7 liters of 50% ethyl acetate-hexane in 0.7-liter batches. The solvents were distilled off under reduced pressure to obtain 18.5 g of crude extract as a reddish oil. The crude extract was purified by column chromatography on silica gel eluting with 20 to 50% ethyl acetate-hexane to obtain 1.2 g of hydroxyl linoleic acid isomers.

1.2 g (4.05 mmol) of hydroxyl linoleic acid analogs was dissolved in 160 ml toluene. 16 g of Novozyme 435 (100 g/L) was added to this solution. The reaction mixture was heated to 50° C. and stirred for 17 hours then cooled to room temperature. The immobilized lipase enzyme was separated by filtration and rinsed with dichloromethane. The volatiles were distilled off under reduced pressure to obtain 1.10 g of crude product as a yellow oil.

The crude product was purified by column chromatography on silica gel eluting with 5% ethyl acetate-hexane to obtain 0.70 g (2.52 mmol, 62.2% isolated yield, 95% total purity of three isomers) of corresponding macrolactonization products.

Figure 8:
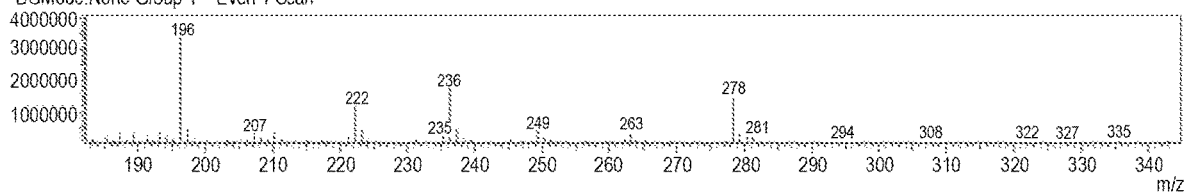
FIG. 8. GC/MS analysis of the linoleic acid macrolactonization products.

A 1 mg/ml solution of the purified product in hexane was analyzed on a capillary gas chromatograph-mass spectrometer GCMS-QP2020 NX (manufactured by Shimadzu) using a 30 m×0.25 mm 0.25 μm Rtx-5MS (manufactured by Restek). The analysis was carried out using high purity helium for the mobile phase, at a flow rate of 1 mL/min. The temperature program used was 150° C. for 3 minutes, a temperature gradient of 50° C./minute to 260° C., and isothermic at 260° C. for 9 minutes. Results are shown in FIG. 8.

Example 2: Use of the Lactones in Consumer Products

In Examples 2-9, panel studies were conducted to evaluate the characteristics and efficacy of musk lactones as a fragrance ingredient, particularly to determine whether the addition of musk lactones affected participants' preferences for fragrances or perfumed consumer products, as well as long-lastingness (persistence) of fragrancing of treated substrate after using a fragranced consumer product. Fragrance strength and duration is not easily measured quantitatively, so rather can be characterized based on huma evaluations. To qualitatively evaluate fragrance, panel studies were conducted as follows. In each of the panels, there were ten participants.

a) For non-skin applications, a blotting paper (perfume test strip, or mouillette) was dipped one third of its length into the fragrance composition and left in the open air. Panel participants were asked to evaluate the fragrance over a 48-hour period, with observations recorded at 2 hours, 4 hours, 6 hours, 12 hours, 24 hours, and 48 hours.

b) For skin applications, a single spray was applied from a distance of 6 inches to the participant's wrist and allowed to dry for 20 seconds. The panel participants were asked to evaluate the fragrance, with observations recorded every 2 hours for 8 hours. Participants indicated preference by indicating a preference for one scent over the other and ranked the strength of the scents by stronger, equal, or weaker.

c) For finished product assessment (e.g., a perfumed or aromatized product or article comprising a fragrance with sensorially active amounts of at least one of the compounds of the musk lactone; examples are formulae containing musk lactone), panel participants were asked to evaluate fragrance persistence and/or performance based on each product's usage (detailed in each example).

The lactones made using the methods described herein were evaluated by a 6-member panel study. Three examples of formulas containing a mixture of musk lactone compounds comprising (Z)-18-methyloxacyclooctadec-10-en-2-one, (Z)-17-ethyloxacycloheptadec-10-en-2-one, (Z)-16-propyloxacyclohexadec-10-en-2-one, (Z)-16-methyloxacyclohexadec-10-en-2-one, and (Z)-15-ethyloxacyclopentadec-10-en-2-one, hereinafter referred to as "musk lactone mixture A," are provided in Tables 1-3 (% are w/w).

TABLE 1

| Formula I | |
|---|---|
| Calone | 1.2% |
| Dipropylene glycol | 18.0% |
| Linalool | 20.0% |
| Musk lactone mixture A | 52.0% |
| Sandalwood oil | 8.0% |
| Vanillin | 0.8% |
| TOTAL | 100.0% |

TABLE 2

| Formula II | |
|---|---|
| Styrax Resinoid 1% Benzyl benzoate | 0.3% |
| Mate absolute | 0.5% |
| Anisyl alcohol Natural | 10.0% |
| Sandalwood | 0.5% |
| Musk lactone mixture A | 50.0% |
| Benzyl benzoate | 10.0% |
| Isopropyl myristate | 28.7% |
| TOTAL | 100.0% |

TABLE 3

| Formula III | |
|---|---|
| Aldehyde C-10 | 0.05% |
| Aldehyde C-12 lauric | 0.15% |
| Geraniol | 2.50% |
| Orris concrete | 0.10% |
| Lavender essential oil | 0.20% |

TABLE 3-continued

| Formula III | |
|---|---|
| Linalyl acetate | 3.00% |
| Musk lactone mixture A | 50.00% |
| Triethyl citrate natural | 43.60% |
| Vanillin | 0.40% |
| TOTAL | 100.00% |

A blotting paper (perfume test strip, or mouillette) was dipped one third of its length into the fragrance composition and left in the open air. Panel participants were asked to evaluate the fragrance over a 48-hour period, with observations recorded at 2 hours, 4 hours, 6 hours, 12 hours, 24 hours, and 48 hours. The odor of the mixture of musk lactones was described as musky, fruity, floral, aldehydic, and/or herbaceous. Some secondary odors were noted as well, such as animalic and woody.

Example 4: Consumer Products Containing the Lactones

Perfume Fine Fragrance

An exemplary fragrance composition comprising musk lactone mixture A and an additional fragrance compound was prepared and compared to a control composition comprising the same fragrance compound, but no musk lactone mixture. The formulas for exemplary fragrance composition with musk lactone mixture A and control fragrance composition without the musk lactone mixture are provided in Table 4.

TABLE 4

(% are w/w). FINE FRAGRANCE (20% LOAD)

| | FORMULA (with) | Control FORMULA (without) |
|---|---|---|
| Floral aldehydic perfume oil | 10% | 10% |
| Musk lactone mixture A | 10% | — |
| Triethyl citrate natural | — | 10% |
| Deionized water | 10% | 10% |
| Ethanol denatured | 70% | 70% |
| TOTAL | 100% | 100% |

A single spray was applied from a distance of 6 inches to the participant's wrist and allowed to dry for 20 seconds. The panel participants were asked to evaluate the fragrance, with observations recorded every 2 hours for 8 hours. Participants indicated preference by indicating a preference for one scent over the other and ranked the strength of the scents by stronger, equal, or weaker in periods ranging from 1 to 48 hours, 90% of the panelists observe longer lasting properties (e.g. about 36 hours) on skin in the exemplary formulation with 10% musk lactone mixture A compared to the control formulation without the musk lactone mixture. Perfume blotters were also tested over a period of 48 hours. In both cases, 90% of the panelists make the same observation and found that the exemplary formulation with musk lactone mixture A is preferred in overall liking and rated as more pleasant than the control formulation without the musk lactone mixture.

After Bath Splash

An after-bath splash product was prepared having an exemplary fragrance composition comprising a fragrance compound and musk lactone mixture A and compared to an after-bath splash product having a control composition comprising the same fragrance compound, but no musk lactone mixture. The formulas for exemplary bath-splash composition with musk lactone mixture A and control bath-splash composition without the musk lactone mixture are provided in Table 5.

TABLE 5

(% are w/w). AFTER BATH SPLASH (3% LOAD)

| | FORMULA (with) | Control FORMULA (without) |
|---|---|---|
| Citrus fougere perfume oil | 2% | 2% |
| Musk lactone mixture A | 1% | — |
| Triethyl citrate natural | — | 1% |
| Deionized water | 30% | 30% |
| Ethanol denatured | 67% | 67% |
| TOTAL | 100% | 100% |

In panel studies, after application of the compositions, the panel participants were asked to evaluate the fragrance, with observations recorded every 2 hours for 8 hours. Participants indicated preference by indicating a preference for one scent over the other and ranked the strength of the scents by stronger, equal, or weaker in periods ranging from 1 to 48 hours. 90% of the panelists observe longer lasting properties on skin in the exemplary formulation with musk lactone mixture A compared to the control formulation without the musk lactone mixture. The panelists observe that in the exemplary formulation with musk lactone mixture A, the fragrances last 48 hours longer. On tests on perfume blotters, 100% of the panelists make the same observation. Also, in both cases, the exemplary formulation with musk lactone mixture A is preferred in overall liking and rated as more pleasant than the control formulation without musk lactone mixture A.

Eau De Toilette

An exemplary fragrance composition comprising a fragrance compound and musk lactone mixture A was prepared and compared to a control composition comprising the same fragrance compound, but no musk lactone mixture. The formulas for exemplary composition and control fragrance composition are provided in Table 6.

TABLE 6

(% are w/w). EAU DE TOILETTE (8% LOAD)

| | FORMULA (with) | Control FORMULA (without) |
|---|---|---|
| Herbal woody perfume oil | 4% | 4% |
| Musk lactone mixture A | 4% | — |
| Triethyl citrate natural | — | 4% |
| Deionized water | 9% | 9% |
| Ethanol denatured | 83% | 83% |
| TOTAL | 100% | 100% |

In panel studies, a single spray was applied from a distance of 6 inches to the participant's wrist and allowed to dry for 20 seconds. The panel participants were asked to evaluate the fragrance, with observations recorded every 2 hours for 8 hours. Participants indicated preference by indicating a preference for one scent over the other and ranked the strength of the scents by stronger, equal, or weaker. 90% of the panelists prefer the fragrance of the exemplary formulation with musk lactone mixture A on skin to that of the control composition. On perfume blotters, 100% of the panelists prefer the fragrance of the exemplary formulation with musk lactone mixture A.

Cologne

An exemplary fragrance composition comprising a fragrance compound and musk lactone mixture A was prepared and compared to a control composition comprising the same fragrance compound, but no musk lactone mixture. The formulas for exemplary composition and control fragrance composition are provided in Table 7.

TABLE 7

(% are w/w). COLOGNE (5% LOAD)

|  | Formula (with) | Control Formula (without) |
| --- | --- | --- |
| Citrus floral perfume oil | 1% | 1% |
| Musk lactone mixture A | 4% | 0 |
| Triethyl citrate Natural | 0 | 4% |
| Ethanol denatured | 75% | 75% |
| Deionized water | 20% | 20% |
| TOTAL | 100% | 100% |

In panel studies, a single spray was applied from a distance of 6 inches to the participant's wrist and allowed to dry for 20 seconds. The panel participants were asked to evaluate the fragrance, with observations recorded every 2 hours for 8 hours. Participants indicated preference by indicating a preference for one scent over the other and ranked the strength of the scents by stronger, equal, or weaker. 90% of the panelists prefer the fragrance of the cologne including musk lactone mixture A on skin as compared to the comparative cologne that excluded the musk lactone mixture. On perfume blotters, 90% of the panelists prefer the fragrance of the exemplary cologne product with musk lactone mixture A.

After Shave Lotion

A shave lotion was prepared having an exemplary fragrance composition comprising a fragrance compound and musk lactone mixture A and compared to a shave lotion having a control composition comprising the same fragrance compound, but no musk lactone mixture. The formulas for exemplary shave lotion composition and control shave lotion fragrance composition are provided in Table 8.

TABLE 8

(% are w/w)-AFTER-SHAVE LOTION (0.6% load)

|  | FORMULA (with) | Control FORMULA (without) |
| --- | --- | --- |
| Leather perfume oil | 0.3% | 0.3% |
| Musk lactone mixture A | 0.3% | 0.0% |
| Triethyl citrate natural | 0.0% | 0.3% |
| Deionized water | 9.5% | 9.5% |
| Ethanol denatured | 89.9% | 89.9% |
| TOTAL | 100.0% | 100.0% |

In panel studies, after application, over periods ranging from one to twenty-four hours, 90% of the panelists determine longer lasting properties on skin for the product with musk lactone mixture A compared to the product without this musk lactone mixture. On perfume blotters, 80% of the panelists prefer the lasting quality of the product with the musk lactone mixture.

Face, Body and Hand Cream

A cream was prepared having an exemplary fragrance composition comprising a fragrance compound and musk lactone mixture A and compared to a cream having a control composition comprising the same fragrance compound, but no musk lactone mixture. The formulas for exemplary cream composition and control cream composition are provided in Table 9.

TABLE 9

(% are w/w). FACE, BODY AND HAND CREAM (0.5% load)

|  | Formula (with) | Control Formula (without) |
| --- | --- | --- |
| Deionized water | 90% | 90% |
| Floral bouquet perfume oil | 0.1% | 0.1% |
| Musk lactone mixture A | 0.4% | — |
| Triethyl citrate natural | — | 0.4% |
| Stearic acid | 2% | 2% |
| Palmitic acid | 2% | 2% |
| Palm glycerides | 5% | 5% |
| Squalene | 0.5% | 0.5% |
| TOTAL | 100% | 100% |

Over a period of one to four hours, panel participants were asked to evaluate fragrance persistence and/or performance. The body cream with exemplary fragrance containing musk lactone mixture A is judged by 80% of the panelists to exhibit a fragrance having greater intensity and longer lasting power than the fragrance of the comparative body cream without the musk lactone mixture.

Liquid Laundry Detergent

A liquid laundry detergent was prepared having an exemplary fragrance composition comprising a fragrance compound and musk lactone mixture A and compared to a liquid laundry detergent having a control composition comprising the same fragrance compound, but no musk lactone mixture. The formulas for exemplary liquid laundry detergent composition and control liquid laundry detergent composition are provided in Table 10.

TABLE 10

(% are w/w). LIQUID LAUNDRY DETERGENT (2% load)

|  | Formula (with) | Control Formula (without) |
| --- | --- | --- |
| Ternamyl Ultra | 0.002% | 0.002% |
| Mannanase | 0.004% | 0.004% |
| PEI ethoxylate dispersant | 5.900% | 5.900% |
| RV-base | 1.500% | 1.500% |
| DTPA | 0.600% | 0.600% |
| EDDS | 0.500% | 0.500% |
| Fluorescent Whitening | Agent 49 | 0.100% | 0.100% |
| 1,2 propylene diol | 15.300% | 15.300% |
| Glycerol | 4.900% | 4.900% |
| Monoethanolamine | 6.600% | 6.600% |
| NaOH | 0.100% | 0.100% |
| Sodium Bisulfite | 0.300% | 0.300% |
| Calcium Formate | 0.080% | 0.080% |
| Polyethylene Glycol (PEG) 4000 | 0.100% | 0.100% |

TABLE 10-continued (% are w/w). LIQUID LAUNDRY DETERGENT (2% load)

|  | Formula (with) | Control Formula (without) |
| --- | --- | --- |
| Dyes | 0.010% | 0.010% |
| Citrus aldehydic fragrance oil | 1.600% | 1.600% |
| Musk lactone mixture A | 0.400% | — |
| Triethyl citrate natural | — | 0.400% |
| Water | 62.004% | 62.004% |
| TOTAL | 100.000% | 100.000% |

In consumer panel studies, panel participants were asked to evaluate fragrance persistence and/or performance, using liquid laundry detergent, sample wash cloths are washed in a dilution in water of formula with or without musk lactone mixture A and subsequently dried. 100% of panelists prefer the wash cloths which had been treated with exemplary formula with the musk lactone mixture over those that had been washed with control.

Lip Gloss

An exemplary fragrance composition comprising a fragrance compound and musk lactone mixture A was prepared and compared to a control composition comprising the same fragrance compound, but no musk lactone mixture. The formulas for exemplary composition and control fragrance composition are provided in Table 11.

TABLE 11

(% are w/w)-LIP GLOSS (0.3% load)

|  | Formula (with) | Control Formula (without) |
| --- | --- | --- |
| Carnauba wax | 10% | 10% |
| Palm butter | 40% | 40% |
| Sweet almond oil | 9% | 9% |
| Benzoic acid | 0.5% | 0.5% |
| Vitamin E | 0.2% | 0.2% |
| Fruity fragrance oil | 0.2% | 0.2% |
| Musk lactone mixture A | 0.1% | 0% |
| Triethyl citrate natural | 0% | 0.1% |
| TOTAL | 100% | 100% |

In panel tests on lips, panel participants were asked to evaluate fragrance persistence and/or performance, 90% of the panelists judge exemplary formula containing the musk lactone mixture to have a stronger, longer-lasting fragrance than control formula.

Compressed Cleaning Tablet

A compressed form cleaning tablet was prepared having an exemplary cleaning tablet composition comprising a fragrance compound containing musk lactone mixture A and compared to a cleaning tablet having a control composition comprising the same cleaning tablet composition, comprising the same fragrance compound, but no musk lactone mixture. The formulas for exemplary cleaning tablet composition and control cleaning tablet composition are provided in Table 12.

TABLE 12

(% are w/w)-COMPRESSED CLEANING TABLET (20 g sample, 0.08% load)

|  | Formula (with) | Control Formula (without) |
| --- | --- | --- |
| Sodium bicarbonate | 68.59% | 68.59% |
| Citric acid | 22.86% | 22.86% |
| BTC 824 P-100 | 2.37% | 2.37% |
| Valfor 100 | 0.10% | 0.10% |
| Glucopon 50G | 2.00% | 2.00% |
| Arbocel TF 30 HG | 4.00% | 4.00% |
| Herbal citrus fragrance oil | 0.07% | 0.08% |
| Musk lactone mixture A | 0.01% | — |
| TOTAL | 100.00% | 100.00% |

When a kitchen counter is cleaned using the dissolved compressed cleaning tablet in water, panel participants were asked to evaluate fragrance persistence and/or performance. Panel results show that the area cleaned with exemplary formula containing musk lactone mixture A is olfactively preferred to the area cleaned with control formula after 30 minutes.

Solid Body Moisturizer Bar

A solid body moisturizer was prepared having an exemplary lotion bar composition comprising a fragrance with musk lactone mixture A and compared to a lotion bar having a control composition comprising the same compound, but without musk lactone mixture A. The formulas for exemplary lotion bar composition and control lotion bar composition are provided in Table 13.

TABLE 13

(% are w/w)-SOLID BODY MOISTURIZER (8% load)

|  | Formula (with) | Control Formula (without) |
| --- | --- | --- |
| Pure beeswax | 63.57% | 63.57% |
| Mango butter | 3.97% | 3.97% |
| Shea butter | 3.97% | 3.97% |
| Apricot kernel oil | 5.30% | 5.30% |
| Jojoba oil | 3.97% | 3.97% |
| Grape seed oil | 3.97% | 3.97% |
| Rosehips oil | 1.32% | 1.32% |
| Vitamin E oil | 1.32% | 1.32% |
| Evening primrose oil | 2.96% | 2.96% |
| Rosemary extract oil | 1.32% | 1.32% |
| Grapefruit seed extract | 0.33% | 0.33% |
| Floral aldehydic fragrance oil | 5.00% | 5.00% |
| Musk lactone mixture A | 3.00% | — |
| Triethyl citrate natural | — | 3.00% |
| TOTAL | 100.00% | 100.00% |

The lotion bar was applied on to the surface of clean skin of the participating panelists and panel participants were asked to evaluate fragrance persistence and/or performance. Panel results show that after 1 hour, the area where formula containing musk lactone mixture A is applied is olfactively preferred to the area applied with formula without musk lactone mixture A.

Hair Care Mousse

A hair mousse was prepared—having an exemplary mousse hair composition comprising a fragrance containing musk lactone mixture A and compared to a hair mousse with a control composition comprising the same fragrance compound, but without musk lactone mixture A. The formulas for exemplary hair mousse composition and comparative hair mousse composition are provided in Table 14.

TABLE 14

(% are w/w)-HAIR CARE MOUSSE (0.3% load)

| | Formula (with) | Control Formula (without) |
|---|---|---|
| Deionized water | 84.35% | 84.35% |
| Polyvinylpyrrolidone K-30 | 3.25% | 3.25% |
| Sodium benzoate | 0.50% | 0.50% |
| Ethanol denatured | 9.18% | 9.18% |
| Buyl ester polycarboxylic / Vinyl methyl ether / Maleic anhyride | 0.10% | 0.10% |
| Diethylene glycol dioctanoate / Diisononanoate | 1.42% | 1.42% |
| Polyoxyethylene 10-oleyl ether | 0.90% | 0.90% |
| Floriental fruity fragrance oil | 0.20% | 0.20% |
| Musk lactone mixture A | 0.10% | — |
| Triethyl citrate natural | — | 0.10% |
| TOTAL | 100.00% | 100.00% |

The hair mousse was applied on to the hair of the participating panelists and panel participants were asked to evaluate fragrance persistence and/or performance. The panel results show that 3 hours after application, panelists whose hair is applied with the exemplary formula containing musk lactone mixture A prefer their overall experience than panelists whose hair is applied with control formula.

Scented Ink (Applied to Substrate by Conventional Means Utilizing Water Flexographic Printing Presses)

A scented ink was prepared having an exemplary ink composition comprising a fragrance with musk lactone mixture A and compared to ink having a control composition comprising the same fragrance compound, but no musk lactone mixture. The formulas for exemplary ink composition and comparative ink composition are provided in Table 15.

TABLE 15

(% are w/w)-SCENTED INK (5% load)

| | Formula (with) | Control Formula (without) |
|---|---|---|
| Acrylic varnish | 30.30% | 30.30% |
| Joncryl SCX-260 Johnson (polymer emulsion) | 6.00% | 6.00% |
| Black-BK7R162 Carbon Reitech (pigment dispersion) | 50.00% | 50.00% |
| Deionized water | 4.00% | 4.00% |
| Wax compound 8855B (08-15223) | 4.50% | 4.50% |
| Defoamer Foammaster WB Zimmerman | 0.20% | 0.20% |
| Fruity fragrance oil | 4.00% | 4.00% |
| Musk lactone mixture A | 1.00% | — |
| Triethyl citrate natural | — | 1.00% |
| TOTAL | 100.00% | 100.00% |

In test panels, the ink was printed on scratch-and-sniff samples which are then put to test. Panel participants were asked to evaluate fragrance persistence and/or performance. 93% of panelists prefer the samples prepared with the ink of formula containing musk lactone mixture A and feel that these are longer-lasting than the samples prepared with the ink of control formula, one week after printing. Such fragranced ink could also be used for fountain pens or to print T-shirts.

Gel Hand Sanitizer

A gel hand sanitizer was prepared having an exemplary gel hand sanitizer composition comprising a fragrance containing musk lactone mixture A and compared to a gel hand sanitizer having a control composition comprising the same fragrance compound, but no musk lactone mixture. The formulas for exemplary gel hand sanitizer composition and comparative gel hand sanitizer composition are provided in Table 16.

TABLE 16

(% are w/w)-GEL HAND SANITIZER (0.15% load)

| | Formula (with) | Control Formula (without) |
|---|---|---|
| Alcohol denatured (SDA 40B 190) | 62.00% | 62.00% |
| Acrylates/C10-30 alkyl acrylate crosspolymer | 0.50% | 0.50% |
| Ethoxylated (15) cocoa alkylamine | 0.30% | 0.30% |
| Isopropyl alcohol | 9.30% | 9.30% |
| Octyl isononanoate | 1.00% | 1.00% |
| Glycerin | 6.75% | 6.75% |
| Deionized water | 20.00% | 20.00% |
| Citrus tea fragrance oil | 0.10% | 0.10% |
| Musk lactone mixture A | 0.05% | — |
| Triethyl citrate natural | — | 0.05% |
| TOTAL | 100.00% | 100.00% |

Participating panelists disinfect their hands using either exemplary formula containing musk lactone mixture A or control formula. Panel participants were asked to evaluate fragrance persistence and/or performance. Ten minutes after application, 100% of panelists who use the exemplary formula containing the musk lactone mixture feel that the sanitizing gel has good protection, is preferred and perceived as longer-lasting compared to 65% of panelists using control formula.

Candle

A candle was prepared having an exemplary candle composition comprising a fragrance containing musk lactone mixture A and compared to a candle having a control composition comprising the same fragrance compound, but no musk lactone mixture. The formulas for exemplary candle composition and comparative candle composition are provided in Table 17.

TABLE 17

( % are w/w)-CANDLE

| | Formula (with) | Control Formula (without) |
|---|---|---|
| Soy wax | 55% | 55% |
| Paraffin wax | 30% | 30% |
| Gourmand fragrance oil | 10% | 10% |
| Musk lactone mixture A | 5% | — |
| Benzyl benzoate | — | 5% |
| TOTAL | 100% | 100% |

Participating panelists evaluate booths where either exemplary candle according to formula containing musk lactone mixture A or control candle after the candles have been burning for one hour. 99% of panelists prefer the level of fragrance in the booth with exemplary formulation containing the musk lactone mixture, as well as 89% found the strength of the scent appropriate.

All-Purpose Cleaner

A ready-to-use (RTU) all-purpose cleaner (APC) was prepared having an exemplary fragrance composition comprising a fragrance compound and musk lactone mixture A and compared to a RTU APC having a control composition comprising the same fragrance compound, but no musk lactone mixture. The formulas for exemplary RTU APC composition and control RTU APC composition are provided in Table 18.

TABLE 18

(% are w/w)-ALL-PURPOSE CLEANER (0.03% load)

|  | Formula (with) | Control Formula (without) |
|---|---|---|
| Glucopon 425 UP | 6.00% | 6.00% |
| Mackam HPL 32 | 2.00% | 2.00% |
| Baking soda | 0.40% | 0.40% |
| Sodium citrate | 1.00% | 1.00% |
| Integra44 | 0.35% | 0.35% |
| Herbal fragrance oil | 0.02% | 0.02% |
| Musk lactone mixture A | 0.01% | — |
| Triethyl citrate natural | — | 0.01% |
| Water | 90.22% | 90.22% |
| TOTAL | 100% | 100% |

Over a period of one to four hours, the RTU APC with exemplary fragrance containing musk lactone mixture A is judged by 80% of the panelists to exhibit a fragrance having greater intensity and longer lasting power than the fragrance of the comparative RTU APC without the musk lactone mixture.

Example 3: Sustainability of the Lactones

In this example, alternative natural musk includes Musk Tonquin or Angelica root or seeds were compared with the lactones described herein (e.g., produced using the methods described herein). When compared on sustainability profile, in terms of renewability due to being plant-based, reduced environmental footprint, in consideration of ethical aspects and other environmental factors, Table 19 shows clear sustainability advantage for the musk lactone described herein (e.g., produced using the methods described herein).

TABLE 19

| COMPOUND | ORIGIN | PROCESS TECHNOLOGY | ETHICAL, SAFETY AND ENVIRONMENTAL CONSIDERATIONS |
|---|---|---|---|
| musk lactones described herein | Fatty acids | Bioconversion | Negligible carbon, water and land footprint |
| Musk Tonquin | Endangered species of musk deer | Musk sac harvest Prepare tincture | Animal species near extinction; limited ranching / animal cruelty |
| Ambrette (Musk mallow) | Musk mallow root and seed | Extraction with ethanol | Rare plant grown in limited areas on the Mediterranean coast; cultivation not sustainable |
| Synthetic nitromusk | Petroleum | Synthesis | Nonrenewable source; strong producer of greenhouse gases, bioaccumulation and human safety concerns |
| Synthetic macrocyclic ketones | Petroleum | Synthesis | Nonrenewable source; strong producer of greenhouse gases |
| Synthetic polycyclic musk | Petroleum | Synthesis | Nonrenewable source; strong producer of greenhouse gases |
| Synthetic linear musk | Petroleum | Synthesis | Nonrenewable source; strong producer of greenhouse gases |

Example 4: Biodegradability of the Lactones

A paper published in Green Chemistry issue number 12 in 2011: "Incorporating environmental attributes into musk design", by Boethling et al. introduces summarized existing information regarding biodegradation and aquatic toxicity data for musk compounds. Bioaccumulation potential is then estimated using EPA's BCFBAF© (a component of EPI Suite©), KOAWIN© and ECOSAR© programs, and the results are used to compare musks across the various structural classes and make inferences about their environmental attributes.

The biodegradability capability of the musk lactone produced using the methods described herein, relevant information is gathered from the referenced article in Table 20 below.

TABLE 20

| NAME | TYPE | % DEG IN READY TEST OECD 301B |
|---|---|---|
| GALAXOLIDE | PCM | 0 |
| MUSK XYLENE | NM | 2 |
| MUSCONE | MCM | 80 |
| Various types | MCM | 43 to 100 |

The musk lactone produced using the methods described herein is of the macrocyclic type (MCM); Table 20 shows clearly that when it comes to biodegradability, this type of musk is of more interest for any environmentally responsible flavor and fragrance company.

Example 5: Use of the Lactones on Fabrics

Linen Spray

An exemplary linen spray aerosol composition comprising a fragrance compound and musk lactone mixture A was prepared and compared to a control linen spray aerosol composition comprising the same fragrance compound, but no musk lactone mixture. The formulas for exemplary composition containing the musk lactone and control fragrance composition are provided in Table 21.

TABLE 21

(% are w/w)-LINEN SPRAY (2% load)

| | Formula (with) | Control Formula (without) |
|---|---|---|
| Floral aldehydic perfume oil | 1.5% | 1.5% |
| Musk lactone mixture A | 0.5% | 0.0% |
| Triethyl citrate natural | 0.0% | 0.5% |
| Ethanol denatured | 23.0% | 23.0% |
| Deionized water | 75.0% | 75.0% |
| TOTAL | 100.0% | 100.0% |

After having sprayed fabric swatches with linen spray aerosols of formulas with or without musk lactone mixture A, 93% of panelists prefer the fabric sprayed with the musk lactone mixture; moreover, 87% feel this fragrance is lasting longer with the musk lactone mixture.

Fabric Softener

An exemplary fabric softener composition comprising a fragrance compound and musk lactone mixture A was prepared and compared to a control fabric softener composition comprising the same fragrance compound, but no musk lactone mixture. The formulas for exemplary composition containing the musk lactone mixture and control fragrance composition are provided in Table 22.

TABLE 22

( % are w/w)-FABRIC SOFTENER (1% load)

| | Formula (with) | Control Formula (without) |
|---|---|---|
| Part A | | |
| Rewoquat® WE 18 (Goldschmidt) (di-(tallow carboxyethyl) hydroxy-ethyl methylammonium methosulfate) | 10.00% | 10.00% |
| Deionised water | 74.45% | 74.45% |
| Calcium chloride | 0.50% | 0.50% |
| Myacide® BT330 (Boots) 2-bromo-2-nitrohropane-1,3-diol | 0.05% | 0.05% |
| Part B | | |
| Isopropyl myristate | 11.50% | 11.40% |
| Isopar (ID M (Exxon) | 2.50% | 2.50% |
| Floral aldehydic fragrance oil | 0.90% | 0.90% |
| Musk lactone mixture A | 0.10% | — |
| Triethyl citrate natural | — | 0.10% |
| TOTAL | 100.00% | 100.00% |

One hour after washing and drying cotton wash cloths with diluted fabric softener compositions, 87% of panelists feel the fragrance from the formula containing musk lactone mixture A is stronger, more pleasant and longer lasting than the fragrance on wash cloths treated with formula without the musk lactone mixture.

Additionally, substantivity is evaluated olfactively by a panel after treating samples of substrate with a perfumed product, such as a fabric softener for cotton fabric or a shampoo for hair, containing the lactones described herein or other musk fragrances for comparison, according to standard procedures described below. Thus, the evaluation is essentially a relative odor intensity measurement. It is known that the perceived odor intensity of mixtures of perfume ingredients when evaluated as such is generally less than the sum of the perceived odors of the components. Thus, the perceived odor intensity of a 1:1 mixture of 2 of the components of the lactones described herein would be expected to be lower than the sum of the intensities of the separate components, i.e. in such mixtures odor suppression is generally found. On the contrary, the perceived odor intensity on substrate treated with the lactones described herein is at least equal to, but in most cases greater than the perceived intensity of substrate treated with equal amounts of the separate components.

Comparison of the fiber substantivity of single polycyclic musks and macrocyclic musks with musk mixtures is described herein. 70% Solutions in isopropyl myristate of the musks and musk mixtures to be tested are dosed at 0.25% w/w in a single Arquad fabric softener (GT 117B). The test is carried out by rinsing "6"×6" (weight: 16 g) cotton terry towel pieces at ambient temperature in a tergotometer according to the procedure below:

3 g of fabric softener containing the test musk is added to 1 liter of water and agitated for one minute to disperse. The fabric piece is added and washed for 10 minutes with constant agitation at 100 rpm. On completion of the wash cycle, the pieces are hand wringed and line dried for 20 hours.

The cloths are assessed olfactively by a 14 member-panel. A 10-point scale is used running from 9 (very good) to 0 (very poor).

The results are presented below in Table 23a and Table 23b:

TABLE 23a

ODOR STRENGTH ON FABRIC TREATED WITH SOFTENER

| | Rating (10-point scale) | Standard deviation |
|---|---|---|
| Musk mixture 1 * | 6.9 | 1.5 |
| Hexadecanolide | 4.8 | 2.1 |
| Musk lactone mixture A | 5.9 | 2.9 |
| Tonalid | 7.2 | 1.5 |
| Galaxolide | 3.8 | 2.3 |

TABLE 23b

ODOR STRENGTH ON BLOTTER

| | Rating (10-point scale) | Standard deviation |
|---|---|---|
| Musk mixture 1 * | 2.9 | 1.5 |
| Hexadecanolide | 5.8 | 2.1 |
| Musk lactone mixture A | 6.9 | 2.9 |
| Tonalid | 8.2 | 1.5 |
| Galaxolide | 5.8 | 2.3 |

*The musk mixture mixture A consisted of 50% Hexadecanolide (MCM) and 50% musk lactone (MCM).
**Trademark for a polycyclic musk marketed by PFW.
***Trademark for a polycyclic musk marketed by IFF.

Example 6: Uses of the Lactones for Masking Malodor

Dishwashing Liquid

An exemplary dishwashing composition comprising a fragrance compound and musk lactone mixture A was prepared and compared to a control composition comprising the same fragrance compound, but no musk lactone mixture. The formulas for exemplary composition containing the musk lactone mixture and control fragrance composition are provided in Table 24.

TABLE 24

( % are w/w)-DISHWASHING LIQUID (0.3% load)

| | Formula (with) | Control Formula (without) |
|---|---|---|
| Neodol™ 91-8 | 16.00% | 16.00% |
| Ammonium lauryl sulfate | 4.00% | 4.00% |
| Cocoamidopropyl betaine | 3.00% | 3.00% |
| Lauric/myristic monoethanolamide | 4.00% | 4.00% |
| Beeswax (yellow) | 1.00% | 1.00% |
| Petrolatum | 1.00% | 1.00% |
| Citrus blend perfume oil | 0.25% | 0.25% |
| Musk lactone mixture A | 0.05% | — |
| Triethyl citrate natural | — | 0.05% |
| Colorant | 0.20% | 0.20% |
| Deionized water | 70.50% | 70.50% |
| TOTAL | 100.00% | 100.00% |

In panel studies, 90% of the panelists find that food malodor is efficiently suppressed when dishes are cleaned then dried using exemplary formulation including musk lactone mixture A.

Deodorant Stick

In this example, an exemplary deodorant stick composition comprising a fragrance compound and musk lactone mixture A was prepared and compared to a control composition comprising the same fragrance compound, but no musk lactone mixture. The formulas for exemplary composition containing the musk lactone mixture and control composition are provided in Table 25.

TABLE 25

( % are w/w)-DEODORANT STICK (1% load)

| | Formula (with) | Control Formula (without) |
|---|---|---|
| Citrus woody fragrance oil | 0.5% | 0.5% |
| Musk lactone mixture A | 0.5% | — |
| Triethyl citrate natural | — | 0.5% |
| Water | 15.0% | 15.0% |
| Cyclomethicone | 30.0% | 30.0% |
| Aluminum chlorohydrate | 20.0% | 20.0% |
| Zinc gluconate | 4.0% | 4.0% |
| Stearyl alcohol | 15.0% | 15.0% |
| Cetearyl isononanoate | 15.0% | 15.0% |
| TOTAL | 100.0% | 100.0% |

In panel studies, 96% of the panelists found that underarm body malodor was efficiently suppressed when armpits had been applied with deodorant stick of exemplary formulation including musk lactone mixture A.

Bar Soap

In this example, an exemplary bar soap composition comprising a fragrance compound and musk lactone mixture A was prepared and compared to a control composition comprising the same fragrance compound, but no musk lactone mixture. The formulas for exemplary composition containing the musk lactone mixture and control fragrance composition are provided in Table 26.

TABLE 26

( % are w/w)-BAR SOAP (1% load)

| | Formula (with) | Control Formula (without) |
|---|---|---|
| Propylene glycol | 25.0% | 25.0% |
| Castor oil | 5.0% | 5.0% |
| Coconut oil | 8.5% | 8.5% |
| Tallow | 8.5% | 8.5% |
| Caustic soda | 8.5% | 8.5% |
| Deionized water | 5.0% | 5.0% |
| Oleic acid | 5.0% | 5.0% |
| Stearic acid | 15.0% | 15.0% |
| Glycerine | 8.5% | 8.5% |
| Quadrol | 10.0% | 10.0% |
| Shea butter fragrance oil | 0.5% | 0.5% |
| Musk lactone mixture A | 0.5% | — |
| Triethyl citrate natural | — | 0.5% |
| TOTAL | 100.0% | 100.0% |

In panel studies, 91% of the panelists found that cooking malodor on hands was efficiently suppressed when hands were washed with bar soap of exemplary formulation including musk lactone mixture A. On perfume blotters, 90% of the panelists preferred the fragrance of the exemplary bar soap formula fragrance with the musk lactone mixture.

Scented Garbage Bags

An exemplary scented garbage bag composition comprising a fragrance compound and musk lactone mixture A was prepared and compared to a control composition comprising the same fragrance compound, but no musk lactone mixture. The formulas for exemplary composition containing the musk lactone mixture and control fragrance composition are provided in Table 27.

TABLE 27

( % are w/w)-SCENTED GARBAGE BAGS (2% load)

| | Formula (with) | Control Formula (without) |
|---|---|---|
| Polyethylene pellets | 98.0% | 98.0% |
| Floral fragrance oil | 1.8% | 1.8% |
| Musk lactone mixture A | 0.2% | — |
| Isopropyl myristate nat | — | 0.2% |
| TOTAL | | |

In panel studies, 91% of the panelists found that garbage malodor was more efficiently reduced when garbage was contained in a bag of exemplary formulation including musk lactone mixture A. On perfume blotters, 90% of the panelists preferred the fragrance of the exemplary formula fragrance containing the musk lactone mixture.

Perfume Bearing Microcapsules

An exemplary perfume bearing microcapsules composition comprising a fragrance compound and musk lactone mixture A was prepared and compared to a control composition comprising the same fragrance compound, but no musk lactone mixture. The formulas for exemplary composition containing the musk lactone mixture and control fragrance composition are provided in Table 28. Furthermore, this composition could be applied to a cotton substrate which can be used for feminine hygiene.

TABLE 28

( % are w/w)-PERFUME-BEARING MICROCAPSULES (1% load) LOTION TO BE APPLIED TO A COTTON SUBSTRATE SUCH AS FEMININE HYGIENE PAD

|  | Formula (with) | Control Formula (without) |
| --- | --- | --- |
| Methyl-betacyclodextrin | 1.00% | 1.00% |
| Hydroxyethyl-betacyclodextrin | 1.00% | 1.00% |
| Activated carbon | 1.50% | 1.50% |
| Kieselguhr | 0.50% | 0.50% |
| VALFOR 300-63 | 0.13% | 0.13% |
| Cetyl pyridinium chloride | 0.15% | 0.15% |
| Zinc chloride | 0.10% | 0.10% |
| Chlorohexidine | 0.45% | 0.45% |
| Preservatives | 0.10% | 0.10% |
| Fruity fragrance oil | 0.90% | 0.90% |
| Musk lactone mixture A | 0.10% | — |
| Triethyl citrate natural | — | 0.10% |
| Ethanol | 5.00% | 5.00% |
| Water | 89.07% | 89.07% |
| TOTAL | 100.00% | 100.00% |

In panel studies, 100% of the panelists found that intimate malodor was more efficiently reduced when using a pad treated with exemplary formulation including musk lactone mixture A. On perfume blotters, 90% of the panelists preferred the fragrance of the exemplary formula fragrance including the musk lactone mixture.

Example 7: Use of the Lactones for Improving Health

A composition of a fragrance or a finished product described herein may be useful for maintaining, enhancing, and/or improving health, and/or another condition of a subject, anxiety, mood (e.g., as described in U.S. Pat. No. 7,824,715, incorporated herein by reference).

The moods elicited by different fragrances were investigated using naive consumers. Each subject assessed each of the test fragrances, presented blind and in a balance randomised order. The method used was line-scaling. In this method a mark is placed on a line at a point between the two ends which represents the relative similarity/difference between the properties of the sample and the adjectives associated with each end of the line. The instructions given were "Please put a mark on each line listed to indicate how you feel about the odor". This was followed by a list of the attributes, shown below, each with a line scale as illustrated. The data were analyzed using standard statistical methods, see below.

The characteristics assessed include: trendy, calming, nostalgic, relaxing, warm, comforting, stimulating, happy, modern, irritating, sensual, depressing, stressful, invigorating, soothing, cooling, refreshing, sexy, safe, reassuring, caring, liking on a scale from extremely to not at all. The data was analysed by Analysis of Variance (ANOVA) to generate mean scores which were used for further analysis.

No other natural substance compared to musks has such a complex aroma associated with so many different and personal descriptions. Musks in general can be described as sweet, warm, enveloping, sexy, sensual, nude skin-like, baby skin-like. Furthermore, the musk lactone has been described by experts as musky, fruity, floral, aldehydic, and/or herbaceous. Some secondary odors were noted as well, such as animalic and woody.

Example 8: Use of the Lactones as Boosters

Booster in Shampoo

An exemplary fragrance composition comprising a fragrance compound and musk lactone mixture A was prepared and compared to a control composition comprising more of the same fragrance compound, but no musk lactone mixture. The formulas for exemplary composition containing the musk lactone mixture and control fragrance composition are provided in Table 29.

TABLE 29

( % are w/w)-SHAMPOO (0.8% load)

|  | Formula (with) | Control Formula (without) |
| --- | --- | --- |
| Fruity floral fragrance oil | 0.2% | 0.5% |
| Musk lactone mixture A | 0.3% | — |
| Ammonium lauryl sulfate | 35.0% | 35.0% |
| Citric acid | 0.4% | 0.4% |
| Cocamidopropyl betaine | 7.0% | 7.0% |
| Dimeticone | 1.0% | 1.0% |
| Disodium EDTA | 0.1% | 0.1% |
| Polyquaternium 10 | 0.2% | 0.2% |
| Sodium laureth sulfate | 5.5% | 5.5% |
| Water | 50.0% | 50.0% |
| TOTAL | 100.0% | 100.0% |

In panel tests on hair swatches and in use (washing one's own hair), 85% of the panelists judge exemplary formula containing musk lactone mixture A to have a stronger fragrance than control formula. Therefore, using the musk lactone mixture allows formulators to use less fragrance oil while still achieving comparable overall olfactive strength.

Additionally, musk lactone mixture A has a booster effect in fragrances of different of log P used in products such as body wash, shampoo, bar soap, fabric conditioner and laundry detergent. The examples below refer to shampoo and fabric softener. See Tables 30, 31, 32 below.

Log P is a well-established measure of a compound's polarity, which informs its preferred affinity for water or oil phases. It is defined as the logarithm of the compound partition coefficient between n-octanol and water. This ratio is measured by dividing the amount of the material that dissolves in the octanol to that which dissolves in the water. It is also possible to estimate the log P values by calculation, which are known as c Log P values. The lower the log P value, the more a material will favor water; the higher the log P, the more it will favor oil. Perfume molecules are mostly non-polar and have log P values in the range of 3 to 7. In product applications such as laundry detergent or shampoo, substantivity implies the ability of a fragrance or a fragrance ingredient to deposit onto the substrate after use. In these cases, we deal with partition of the material between an aqueous phase (the water in the washing machine or shower) and a solid, non-aqueous phase (the fabric or hair). The most important factor is therefore the log P of the material. The less a perfume ingredient favors the water phase, the higher its log P is, the more it will stick to the cloth, hair, skin, or whatever solid substrate presents itself as an alternative.

Another characteristic which is very helpful in formulating fragrances is the boiling point. The boiling point informs on a material's volatility—the more volatile an ingredient is, the more easily noticeable it will be by nose. The blooming of a fragrance is directly related to its boiling point. Bloom is the ability of a fragrance to perfume a room when the fragrance is introduced, not directly as an oil or aerosol, but in a product such as soap.

Wet bloom is the fragrance effect in the room when the soap is in use, when it is wet. Bloom requires the properties of volatility (to reach the nose for detection) and low odor threshold.

The more volatile (lower boiling) a substance is, the more easily it will evaporate. Two main factors determine volatility:
- molecular weight
- ability to form non-bonded interactions between each other and to any surface or medium on which they are placed.

Musk lactone mixture A has a boosting effect on overall fragrance performance (increases fragrance bloom and/or substantivity) over any type of fragrance oils classified by their c Log P:
a. Fragrance with ingredients with a c Log P<3
b. Fragrance with ingredients with a 3<c Log P<5
c. Fragrance with ingredients with a 5<c Log P The more polar a molecule is, the more easily it forms electrostatic bonds, such as hydrogen bonds, to other molecules around it, whether they are other fragrance molecules, cellulose (such as cotton fibers) or proteins (such as hair). (See, e.g., Fundamentals of Fragrance Chemistry, Charles S. Sell, Wiley-VCH, 2019, incorporated by reference).

TABLE 30

( % are w/w)-BOOSTING EFFECT IN SHAMPOO

| | Formula (with) | Control Formula (without) |
|---|---|---|
| Fragrance logP < 3 | 80 | 80 |
| Musk lactone mixture A | 20 | 0 |
| Triethyl citrate natural | 0 | 20 |
| TOTAL | 100 | 100 |

In this example, an un-fragranced shampoo base (such as the one described in Table 29) was prepared. The exemplary sample was made by adding 0.8% of the formula containing musk lactone mixture A shown in Table 30, while the control sample was prepared by adding 0.8% of the control formula to the shampoo. Panelists evaluated the blooming in controlled size plastic containers. 86% of panelists found exemplary formula containing the musk lactone mixture to be stronger and more filling of the container space than control formula.

TABLE 31a ( % are w/w)-BOOSTING EFFECT IN SHAMPOO

| | Formula (with) | Control Formula (without) |
|---|---|---|
| 3 < Fragrance logP < 5 | 80 | 80 |
| Musk lactone mixture A | 20 | 0 |
| Triethyl citrate natural | 0 | 20 |
| TOTAL | 100 | 100 |

In this example, an un-fragranced shampoo base (such as the one described in Table 29) was prepared. The exemplary sample was made by adding 0.8% of the formula containing musk lactone mixture A shown in Table 31a, while the control sample was prepared by adding 0.8% of the control formula to the shampoo. Panelists evaluated the blooming in controlled size plastic containers. 92% of panelists found exemplary formula containing the musk lactone mixture to be stronger and more filling of the container space than control formula.

TABLE 31b ( % are w/w)-BOOSTING EFFECT IN FABRIC SOFTENER

| | Control Formula (with) | Formula (without) |
|---|---|---|
| 3 < Fragrance logP < 5 | 80 | 80 |
| Musk lactone mixture A | 20 | 0 |
| Triethyl citrate natural | 0 | 20 |
| TOTAL | 100 | 100 |

In this example, using evaluation method c), an un-fragranced fabric softener base (such as the one described in Table 22) was prepared. The exemplary sample was made by adding 1% of the formula containing musk lactone mixture A shown in Table 31b, while the control sample was prepared by adding 1% of the control formula to the fabric softener. One hour after washing and drying cotton wash cloths with diluted fabric softener compositions, 91% of panelists felt the fragrance from softener fragranced with exemplary formula containing the musk lactone mixture was stronger, more pleasant and longer lasting than the fragrance on wash cloths treated with the control formula.

TABLE 32

( % are w/w)-BOOSTING EFFECT IN FABRIC SOFTENER

| | Formula (with) | Control Formula (without) |
|---|---|---|
| 5 < Fragrance logP | 80 | 80 |
| Musk lactone mixture A | 20 | 0 |
| Triethyl citrate natural | 0 | 20 |
| TOTAL | 100 | 100 |

In this example, an un-fragranced fabric softener base (such as the one described in Table 22) was prepared. The exemplary sample was made by adding 1% of the formula containing musk lactone mixture A shown in Table 33, while the control sample was prepared by adding 1% of the control formula to the fabric softener. One hour after washing and drying cotton wash cloths with diluted fabric softener compositions, 89% of panelists felt the fragrance from softener fragranced with exemplary formula containing the musk lactone mixture was stronger, more pleasant and longer lasting than the fragrance on wash cloths treated with the control formula.

Example 9: Use of the Lactones as Anti-Inflammatory Agent

Musks are part of Traditional Chinese Medicine, as they stimulate the brain and blood circulation to increase arousal, relieve fatigue and enhance human vitality. Muscone is reported to be a potent anti-inflammatory agent that reduces the levels of anti-inflammatory cytokines in vitro and in vivo. 4-Methylcyclopentadecanone (4-MCPC) is the isomer of muscone and a by-product of muscone synthesis that was discarded in the past. Experimental studies have shown that 4-MCPC has similar pharmacological effects as muscone in some aspects.

In this example, an exemplary anti-inflammatory cream composition comprising musk lactone mixture A was prepared and compared to a control composition comprising no musk lactone mixture. The formulas for exemplary composition containing the musk lactone mixture and control cream composition are provided in Table 34. The formula for a secondary control cream composition comprising thyme oil as the anti-inflammatory active agent (instead of the musk lactone), as it is traditionally used as a natural anti-inflammatory active agent, was also included as control.

TABLE 34

( % are w/w)-ANTI-INFLAMMATORY CREAM

|  | Formula (with) | Control Formula (without) | Control Formula (with Thyme oil) |
|---|---|---|---|
| Almond oil | 5 | 5 | 5 |
| Stearic acid | 10 | 10 | 10 |
| Glycerol | 3 | 3 | 3 |
| Cetostearyl alcohol | 10 | 10 | 10 |
| Tween 80 | 8 | 8 | 8 |
| Sodium benzoate | 0.1 | 0.1 | 0.1 |
| Sorbitol solution | 6 | 6 | 6 |
| Sodium hydroxide | 1.5 | 1.5 | 1.5 |
| Deionized water | 60 | 60 | 60 |
| Musk lactone mixture A | 10 | 0 | 0 |
| Triethyl citrate natural | 0 | 10 | 0 |
| Thyme oil | 0 | 0 | 10 |
| TOTAL | 100 | 100 | 100 |

The panel tests show that both creams made with formula containing musk lactone mixture A or thyme oil help in reducing inflammation; and formula containing the musk lactone mixture is preferred olfactively by 100% of panelists over the formula containing the thyme oil.

Eye Patches

In this example, an exemplary anti-inflammatory eye patches composition comprising musk lactone mixture A was prepared and compared to a control composition comprising no musk lactone mixture. The formulas for exemplary composition containing the musk lactone mixture and control cream composition are provided in Table 35. The formula for a secondary control eye patches composition comprising Curcuma extract as the anti-inflammatory active agent (instead of the musk lactone mixture), as it is traditionally used as a natural anti-inflammatory active agent, was also included as control.

TABLE 35

( % are w/w)-ANTI-INFLAMMATORY EYE PATCHES

|  | Formula (with) | Control Formula (without) | Control Formula (with Curcuma extract) |
|---|---|---|---|
| Deionized water | 65 | 65 | 65 |
| Glycerin | 15 | 15 | 15 |
| Dipropylene glycol | 10 | 10 | 10 |

TABLE 35-continued ( % are w/w)-ANTI-INFLAMMATORY EYE PATCHES

|  | Formula (with) | Control Formula (without) | Control Formula (with Curcuma extract) |
|---|---|---|---|
| Musk lactone mixture A | 10 | 0 | 0 |
| Triethyl citrate natural | 0 | 10 | 0 |
| Curcuma extract | 0 | 0 | 10 |
| TOTAL | 100 | 100 | 100 |

In the panel tests, both eye patches made with formula containing musk lactone mixture A or the Curcuma extract help in reducing the appearance of dark circles under the eyes, after 2 weeks of daily use. The formula containing the musk lactone mixture is preferred olfactively by 95% of panelists over the formula containing the Curcuma extract for daily skin care usage.

Example 10

Figure 9:
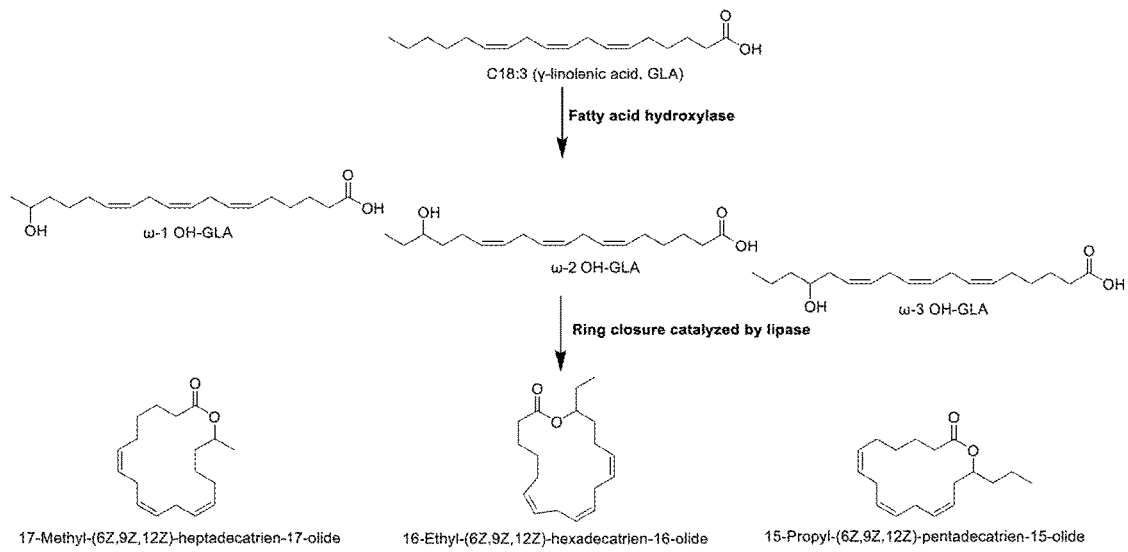
FIG. 9. Production of musk lactones from hydroxy γ-linolenic acid (GLA, C18:3).

In this process, a cytochrome P450 enzyme e.g. P450 BM3 (Miura and Fulco, 1975; Wen and Fulco, 1987) or its homologs (Baker et. al, 2017) that have fatty acid subterminal hydroxylase activity to make ω-1, ω-2 or ω-3 hydroxy fatty acids or their mixtures was used. After extraction and purification, hydroxy fatty acid were subject to lipase-catalyzed ring closure reaction in organic solvents for the formation of branched-chain musky macrolactones (FIG. 9).

The amino acid sequence of a BM3 homolog of *Myceliophthora thermophile* (CYP505A30) was obtained from UniProt (www.uniprot.org/uniprot/G2QDZ3.fasta) and the corresponding gene was codon optimized for expression in *Escherichia coli* and synthesized by GenScript (Piscataway, N.J.).

The resulting gene product was cloned into pETDuet-1 vector (AMP+, Novagen) through NdeI and XhoI sites. The construct was transformed into BL21(DE3) cells for expression.

In a typical experiment, an overnight culture was used to inoculate liquid LB medium (2%) containing 100 mg/L of carbenicillin and 0.4 mM 5-aminolevulinic acid. The culture was first grown at 37° C. to an OD600 of 0.6 and cooled down to 16° C. Then 1 mM IPTG was added to induce protein expression. After 16 h of incubation at 16° C., cells were harvested by centrifugation.

Figure 10:
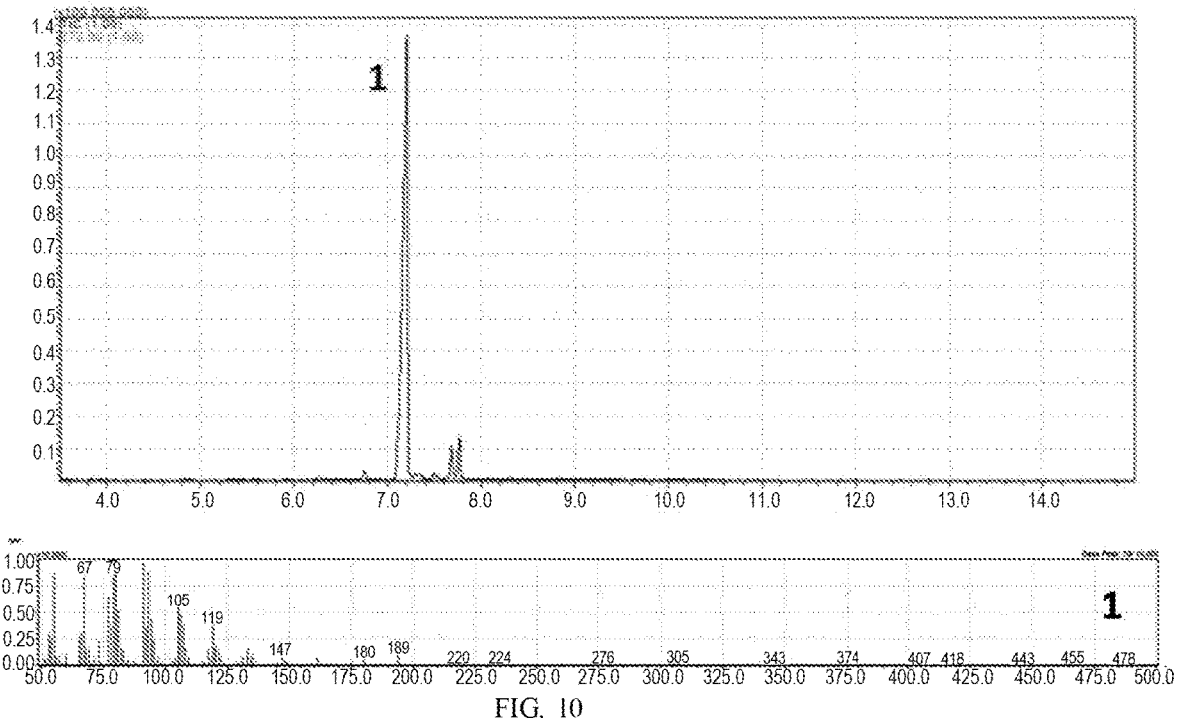
FIG. 10. GC/MS analysis of musk lactones derived from hydroxy GLA (molecular weight: 276).

Harvested cell pellets were re-suspended at a concentration of 100 g/L fresh weight in 100 mM potassium phosphate buffer (pH7.0) containing 0.1% Tween 40 and 10 mM NADPH. Then 1 g/L of γ-linolenic acid (GLA, C18:3) was added. The mixture was shaken at 37° C. in a shaker. Results of GC/MS analysis of musky lactones derived from hydroxy GLA (molecular weight: 276) are shown in FIG. 10.

Additional fatty acid substrates that may be used and the lactone products are provided below and shown in Table 36.

Production of Branched-Chain Musky Macrolactones from α-Linolenic Acid (ALA)

Harvested cell pellets were re-suspended at a concentration of 100 g/L fresh weight in 100 mM potassium phosphate buffer (pH7.0) containing 0.1% Tween 40 and 10 mM NADPH. Then 1 g/L of α-linolenic acid (ALA, C18:3) was added. The mixture was shaken at 37° C. in a shaker for 5 hours.

Figure 11:
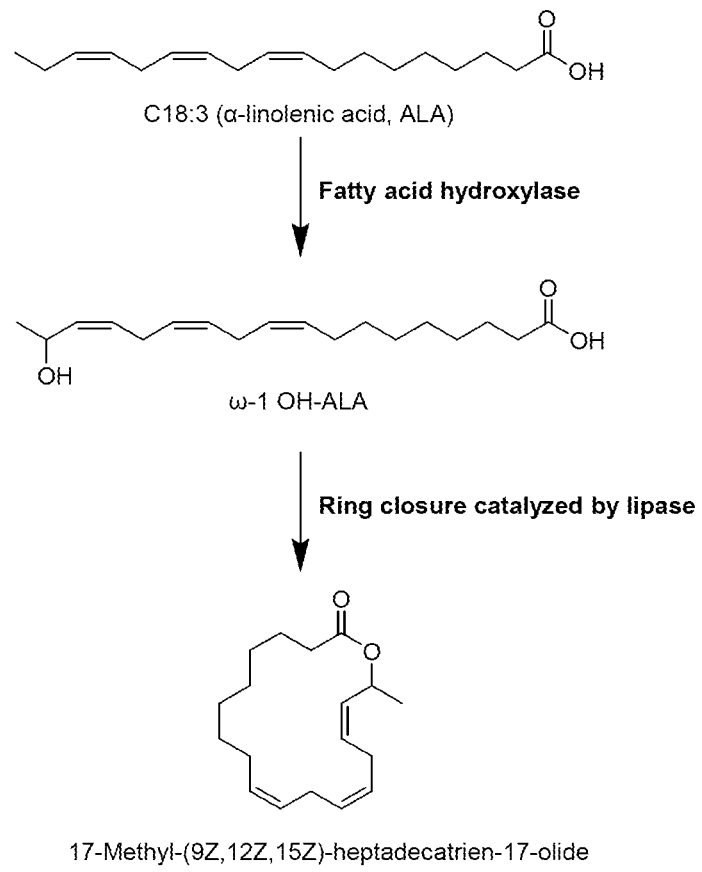
FIG. 11. Production of musky lactone from α-linolenic acid (ALA, C18:3).
Figure 12:
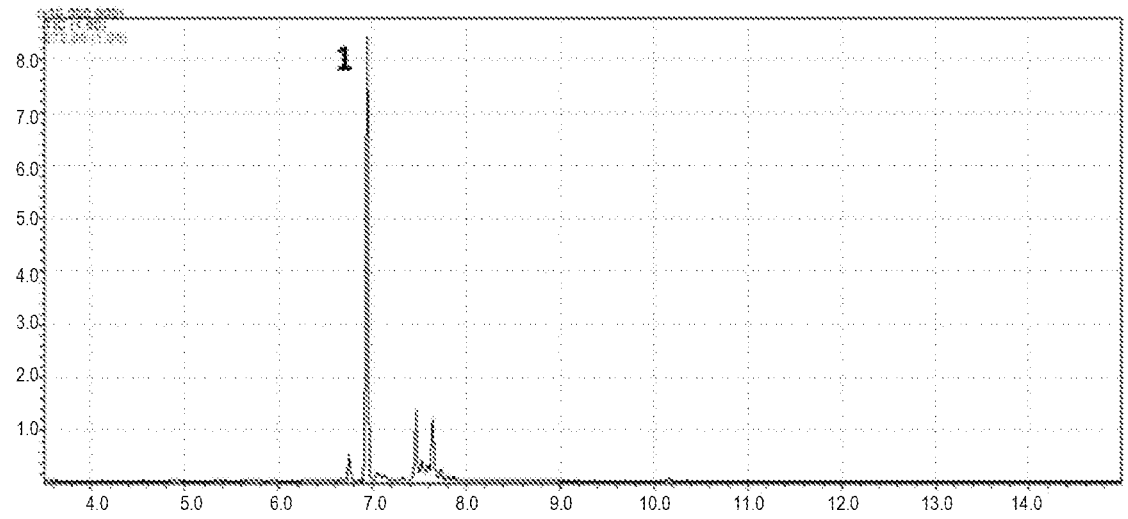
FIG. 12. GC/MS analysis of musk lactone from hydroxy ALA (molecular weight: 276).
Figure 12:
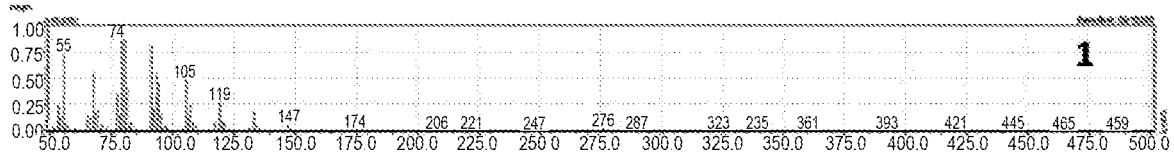

Hydroxylated α-linolenic acid was extracted by ethyl acetate and ethyl acetate phase was dried in SpeedVac™ vacuum concentrator. Then Novozym 435 in the form of acrylic resin (Sigma) was added with toluene as solvent for ring closure reaction at 60° C. with shaking. The products from hydroxy α-linolenic acid were analyzed by GC/MS. See FIGS. 11 and 12.

Production of Branched-Chain Musky Macrolactones from C20:3 (8Z,11Z,14Z-Eicosatrienoic Acid, Dihomo-γ-Linolenic Acid, DGLA)

Harvested cell pellets were re-suspended at a concentration of 100 g/L fresh weight in 100 mM potassium phosphate buffer (pH7.0) containing 0.1% Tween 40 and 10 mM NADPH. Then 1 g/L of dihomo-γ-linolenic acid (DGLA, C20:3) was added. The mixture was shaken at 37° C. in a shaker for 5 hours.

Figure 13:
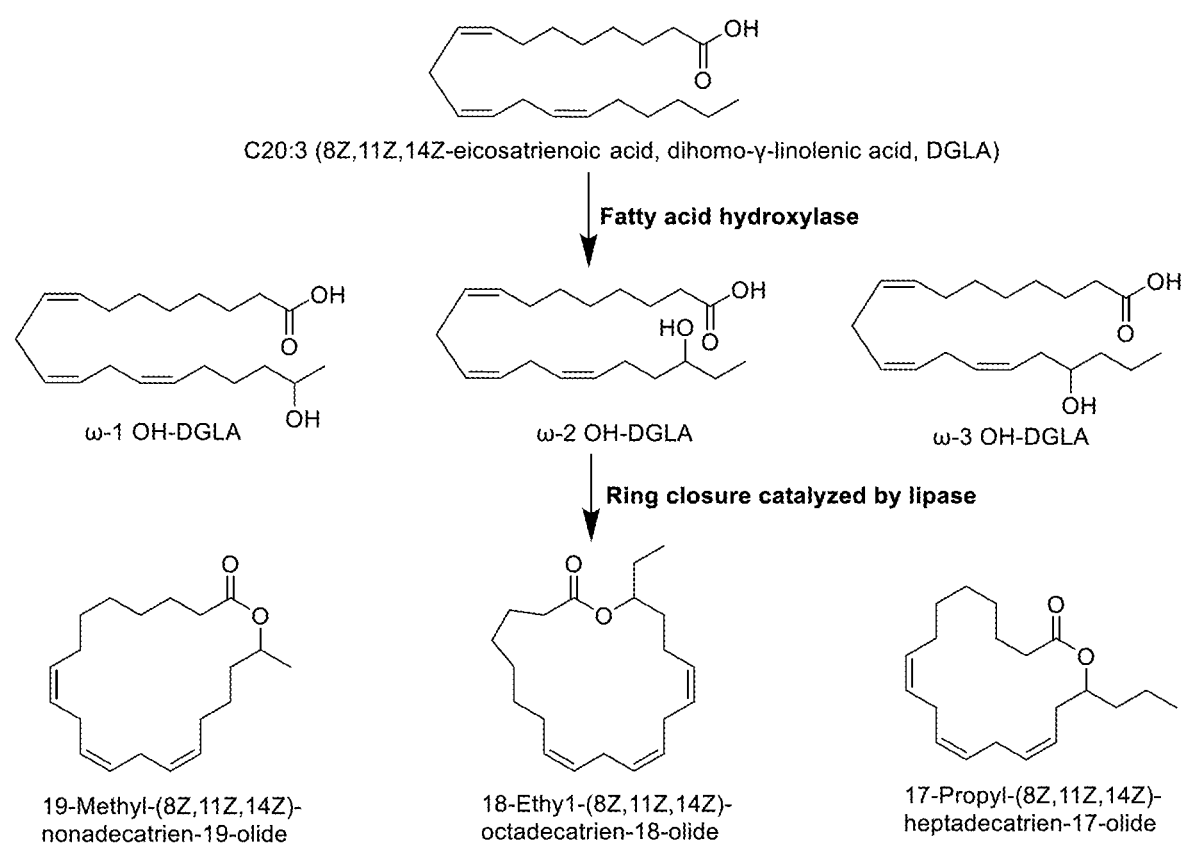
FIG. 13. Production of musk lactone from 8Z,11Z,14Z-eicosatrienoic acid, dihomo-γ-linolenic acid (DGLA, C20:3).
Figure 14:
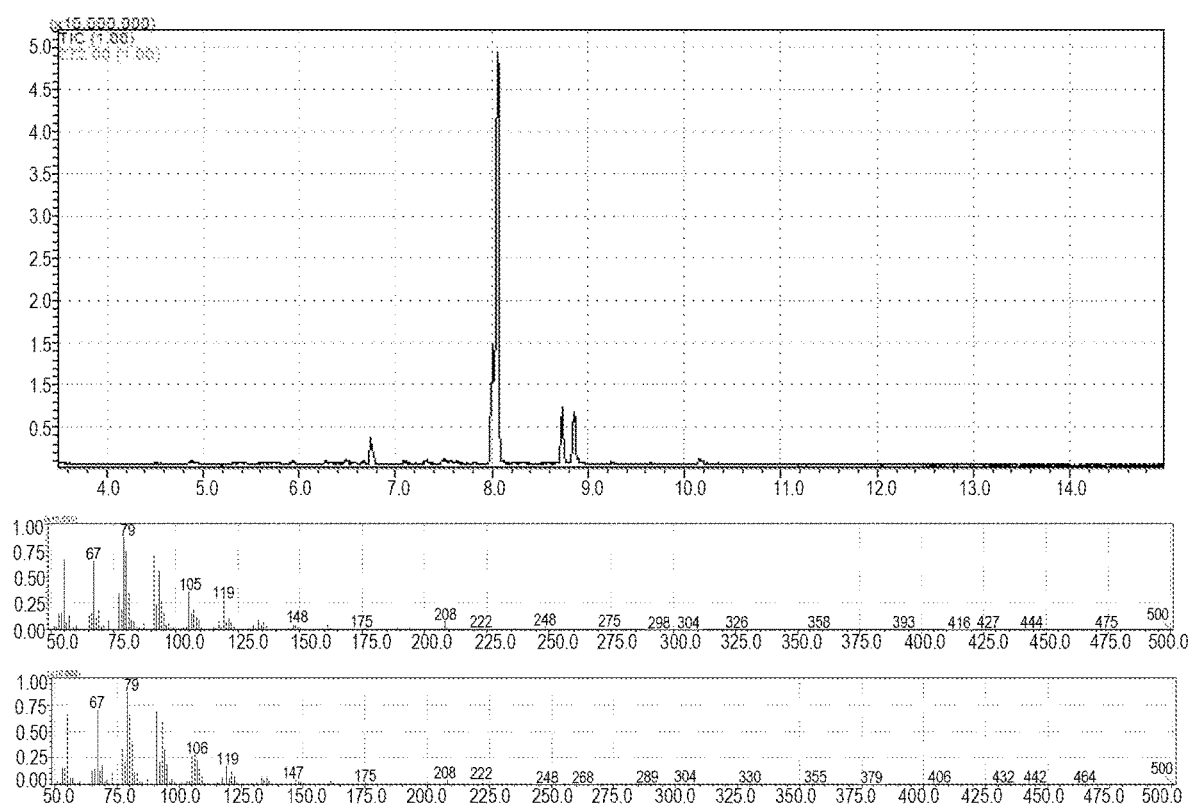
FIG. 14. GC/MS analysis of musk lactone from hydroxy DGLA (molecular weight: 304).

Hydroxylated DGLA was extracted by ethyl acetate and ethyl acetate phase was dried in SpeedVac™ vacuum concentrator. Then Novozym 435 in the form of acrylic resin (Sigma) was added with toluene as solvent for ring closure reaction at 60° C. with shaking. The products from hydroxy DGLA acids were analyzed by GC/MS. See FIGS. 13 and 14.

TABLE 36

Additional fatty acid substrates and lactones

| # | Parent Fatty Acid | MuL lactone product 1 | MuL lactone product 2 | MuL lactone product 3 |
|---|---|---|---|---|
| 1 | (Roughanic acid; (7Z, 10Z, 13Z)-Hexadecatrienoic acid) | [structure] | | |
| 2 | (Hexadecatrienoic acid; (6Z,9Z,12Z)-Hexadecatrienoic acid) | [structure] | [structure] | |
| 3 | ((4E,7E, 10E)-Hexadecatrienoic acid) | [structure] | [structure] | [structure] |
| 4 | ((2E,4E,6E)-Hexadecatrienoic acid) | [structure] | [structure] | [structure] |
| 5 | (γ-linolenic acid; GLA) | [structure] | [structure] | [structure] |
| 6 | (α-linolenic acid; ALA) | [structure] | | |

TABLE 36-continued

Additional fatty acid substrates and lactones

| # | Parent Fatty Acid | MuL lactone product 1 | MuL lactone product 2 | MuL lactone product 3 |
|---|---|---|---|---|
| 7 | 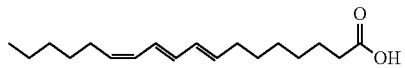 [SMILES: CCCCC\C=C/C=C/C=C/CCCCCCC(=O)O] (α-Calendic acid; (8E, 10E,12Z)-Octadecatrienoic acid) | 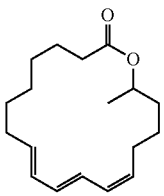 [SMILES: CC1CCC\C=C/C=C/C=C/CCCCCCC(=O)O1] | 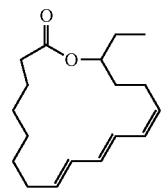 [SMILES: CCC1CC\C=C/C=C/C=C/CCCCCCC(=O)O1] | 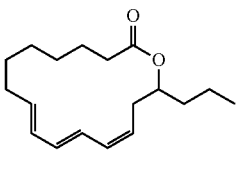 [SMILES: CCCC1C\C=C/C=C/C=C/CCCCCCC(=O)O1] |
| 8 | 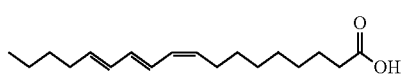 [SMILES: CCCC/C=C/C=C/C=C\CCCCCCCC(=O)O] (α-Eleostearic acid; (9Z,11E,13E)-octadeca-9,11,13-trienoic acid) | 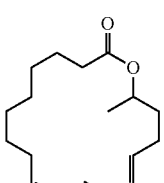 | 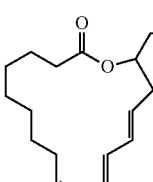 | 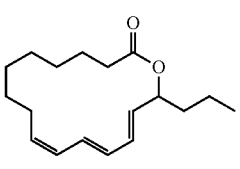 [SMILES: CCCC1/C=C/C=C/C=C\CCCCCCCC(=O)O1] |
| 9 | 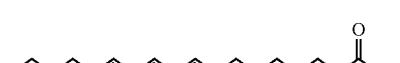 (β-Eleostearic acid; (9E,11E,13E)-octadeca-9,11,13-trienoic acid) | 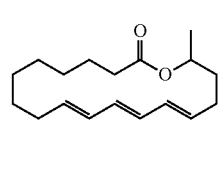 [SMILES: CC1CC/C=C/C=C/C=C/CCCCCCCC(=O)O1] | 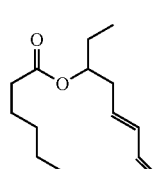 | 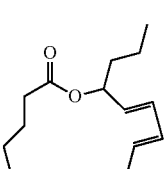 |
| 10 | 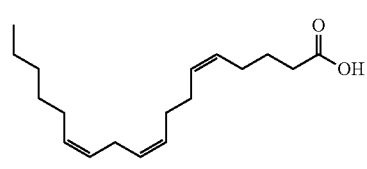 [SMILES: CCCCC/C=C\C/C=C\CC/C=C\CCCC(=O)O] (Pinolenic acid; (5Z,9Z,12Z)-octadeca-5,9,12-trienoic acid) | 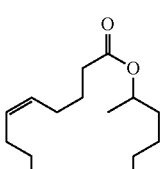 | 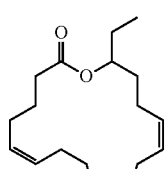 | 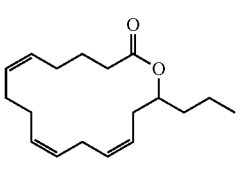 [SMILES: CCCC1C/C=C\C/C=C\CC/C=C\CCCC(=O)O1] |
| 11 | 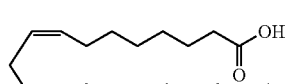 (8Z,11Z,14Z-eicosatrienoic acid; dihomo-γ-linolenic acid; DGLA) | 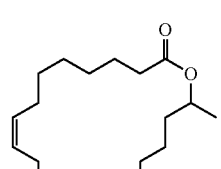 | 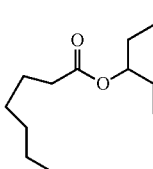 | 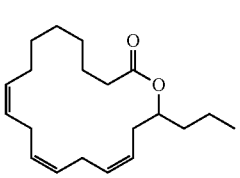 [SMILES: CCCC1C/C=C\C/C=C\C/C=C\CCCCCCC(=O)O1] |
| 12 | 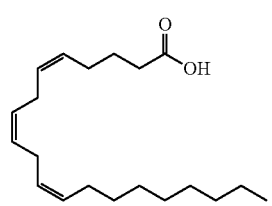 [SMILES: CCCCCCCC/C=C\C/C=C\C/C=C\CCCC(=O)O] (Mead acid; (5Z,8Z,11Z)-Eicosa-5,8,11-trienoic acid) | 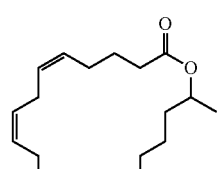 | 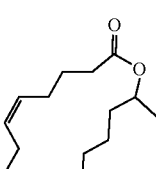 | 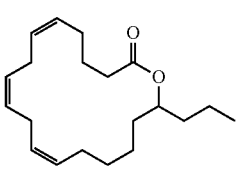 [SMILES: CCCC1CCCC/C=C\C/C=C\C/C=C\CCCC(=O)O1] |

Example 11: Use of the Lactones to Increase Maximum Load Potential

Increased Load in Shampoo

An exemplary fragrance composition comprising a fragrance compound and musk lactone mixture A was prepared and compared to a control without the musk lactone mixture and a composition comprising more of the same fragrance compound, and ambrettolide instead. The formulas for exemplary composition containing the musk lactone mixture and ambrettolide containing fragrance composition are provided in Table 37.

TABLE 37

(% are w/w) - SHAMPOO (0.8% load)

| | Formula (with musk lactone mixture A) - clear appearance | Formula (without) - clear appearance | Formula (with Ambrettolide) -cloudy appearance |
|---|---|---|---|
| Fruity floral fragrance oil | 0.2% | 0.2% | 0.2% |
| Musk lactone mixture A | 0.3% | — | — |
| Ambrettolide | — | 0.2% | 0.3% |
| Ammonium lauryl sulfate | 35.0% | 35.0% | 35.0% |
| Citric acid | 0.4% | 0.4% | 0.4% |
| Cocamidopropyl betaine | 7.0% | 7.0% | 7.0% |
| Dimethicone | 1.0% | 1.0% | 1.0% |
| Disodium EDTA | 0.1% | 0.1% | 0.1% |
| Polyquaternium 10 | 0.2% | 0.2% | 0.2% |
| Sodium laurel sulfate | 5.5% | 5.5% | 5.5% |
| Water | 50.0% | 50.1% | 50.0% |
| TOTAL | 100.0% | 100.0% | 100.0% |

The shampoo formula with musk lactone mixture A remained clear and the fragrance impact was much stronger than both the clear shampoo formula with a lower level of ambrettolide remaining clear. This may be due to the increased solubility of the fragrance materials in the musk lactone mixture containing fragrance. Fragrance strength was judged using a 20 member QDA (quantitative descriptive analysis) sensory panel. Shampoo formulae with ambrettolide at the same loading as musk lactone mixture was cloudy, indicating poor solubility. Similar results were found with other musks, including dihydroambrettolide, l-muscone, velvione, musk ambrette, tonalide/fixolide, galaxolide and, to a slightly lesser extent, ethylene brassylate.

Furthermore, musk lactone mixture A and other musks were also evaluated at two different loadings in laundry detergent base, as shown in Tables 38 and 39. In each case, the musk lactone mixture A showed significantly better solubility enabling clear performance delivery or at least higher loading in laundry detergent.

TABLE 38

| 0.04% Musk in laundry detergent base | Appearance |
|---|---|
| Musk lactone mixture A | Clear |
| Dihydroambrettolide, | Very cloudy |
| 1-Muscone, | Very cloudy |
| Velvione, | Very cloudy |
| Tonalide/Fixolide, | Very cloudy |
| Galaxolide | Very cloudy |
| Ethylene Brassylate. | Very cloudy |
| Ambrettolide | Very cloudy |

TABLE 39

| 0.08% Musk in laundry detergent base | Appearance |
|---|---|
| Musk lactone mixture A | Cloudy |
| Dihydroambrettolide | Phase separation |
| 1-Muscone | Phase separation |
| Velvione | Phase separation |
| Tonalide/Fixolide | Phase separation |
| Galaxolide | Phase separation |
| Ethylene Brassylate | Phase separation |
| Ambrettolide | Phase separation |

Example 12: Use of Musk Lactone Mixture a to Increase Substantivity and Olfactive Performance in Liquid Detergent Use Olfactive evaluations in use were performed by an expert panel. The range of materials evaluated was comprehensive, including musk products commercially available: Nitromusk, Polycyclic and Macrocyclic categories (Ambrettolide, Dihydro Ambrettolide, Scentolide, Muscone, Muscenone, Velvione, Musk Ambrette, Edenolide, Ethylene Brassylate, Galaxolide, Tonalide, Habanolide, Globanone, Macrolide, Oxalide T and others).

Evaluation samples were prepared using unperfumed laundry detergent (formulation example in Example 4, Table 10) at two different dosages: 10% Solution @ 0.8% (yielding 0.08% musk lactone mixture A) or 1.5% (yielding 0.15% musk lactone mixture A) driven by relative product performance in formulas and practical laboratory practices to execute the comparisons. The concentration of musk lactone mixture A in each evaluation was at the same concentration as the commercial musk.

The evaluations were performed in use stages: Jar (POP—Point of purchase), damp towel, Dry towel (1 day) and Storage Dry towel (7 days and 15 days). A five points scale was utilized, rating both strength and hedonic character:

Strength (STR) is rated as the overall scent power coming up from the substrate, due to physicochemical properties and commonly described as a combination of diffusion, bloom, body and or volume perceptions. Scale used: (++) significantly superior, (+) directionally superior, (0) comparable, (−) directionally inferior, (−−) Significantly inferior.

Hedonic (HED) character is rated as the overall perception of the odor quality expected from the material (standard reference in blotter evaluation of the material per se. Scale used:
(++) significantly superior
(+) directionally superior
comparable
(−) directionally inferior
(−−) Significantly inferior The comparison results of musk lactone mixture A against each musk product are shown in Table 40. The results provide a strong indication of a superior substantivity in dry towel (1 day, 7 days and 15 days) as well as olfactive performance of musk lactone mixture A in all evaluation stages.

TABLE 40

MUSK LACTONE MIXTURE A
IN USE COMPARISON WITH
COMMERCIAL MUSKS @ TWO DIFFERENT
DOSAGES IN LAUNDRY DETERGENT
UNPERFUMED BASE

| NAME | JAR STR / HED | DAMP STR / HED | DRY TWL 1 DAY STR / HED | DRY TWL 7 DAYS STR / HED | DRY TWL 15 DAYS STR / HED |
|---|---|---|---|---|---|
| AMBRETTOLIDE [10% IPM @0.8%] | --/-- | --/+ | --/-- | --/-- | --/-- |
| DIHYDRO AMBRETTOLIDE [10% IPM @0.8%] | 0/-- | 0/+ | 0/+ | 0/+ | 0/+ |
| SCENTOLIDE [10% IPM @0.8%] | 0/0 | 0/0 | --/-- | --/-- | --/-- |
| MUSCONE [10% IPM @0.8%] | ++/++ | ++/+ | +/++ | +/++ | +/++ |
| MUSCENONE [10% IPM @0.8%] | +/++ | +/++ | ++/++ | ++/++ | ++/++ |
| VELVIONE [10% IPM @0.8%] | +/0 | +/+ | ++/++ | ++/++ | ++/++ |
| MUSK AMBRETTE [10% IPM @0.8%] | ++/-- | ++/-- | +/0 | +/0 | +/0 |
| EDENOLIDE [10% IPM @0.8%] | 0/0 | --/-- | 0/0 | 0/0 | 0/0 |
| OXALIDE T [10% IPM @0.8%] | 0/-- | 0/0 | 0/0 | 0/0 | 0/0 |
| ETHYLENE BRASSYLATE [10% IPM @1.5%] | --/-- | --/-- | --/-- | --/-- | --/-- |
| GALAXOLIDE [10% IPM @1.5%] | --/-- | --/-- | --/-- | --/-- | --/-- |

Musk lactone mixture A performs well at a spectrum of dosages that represent the standard use levels for musk raw materials. The results were excellent on Strength and Hedonic character in all evaluation stages. Musk lactone mixture A demonstrated to have a unique space in between the commercially available options, due to its intrinsic origin and exceptional performance.

The performance vs polycyclic musks was significantly superior in all the use stages and directionally vs macrocyclic musks. More notably, when compared to macrocyclic musks (similar chemical structure), musk lactone mixture A performed significantly better in both attributes.

Furthermore, the performance in use in formulation corroborated the initial results of monadic evaluations, as presented in the Example 2, Table 10.

REFERENCES

Baker G J, Girvan H M, Matthews S, McLean K J, Golovanova M, Waltham T N, Rigby S E J, Nelson D R, Blankley R T, Munro A W. (2017) Expression, Purification, and Biochemical Characterization of the Flavocytochrome P450 CYP505A30 from *Myceliophthora thermophile*. ACS Omega 2: 4705-4724.

Miura Y, Fulco A J. (1975) Omega-1, Omega-2 and Omega-3 hydroxylation of long-chain fatty acids, amides and alcohols by a soluble enzyme system from *Bacillus megaterium*. Biochim. Biophys. Acta. 388: 305-317.

Wen L P, Fulco A J. (1987) Cloning of the gene encoding a catalytically self-sufficient cytochrome P-450 fatty acid monooxygenase induced by barbiturates in *Bacillus megaterium* and its functional expression and regulation in heterologous (*Escherichia coli*) and homologous (*Bacillus megaterium*) hosts. J. Biol. Chem. 262: 6676-6682.

Example 13: Amino Acid and Nucleotide Sequences

Amino acid sequence of cytochrome
P450 CYP102A1 from
Bacillus megaterium
                                    SEQ ID NO: 1
MTIKEMPQPKTFGELKNLPLLNTDKPVQALMKIAD

ELGEIFKFEAPGRVTRYLSSQRLIKEACDESRFDK

NLSQALKFVRDFAGDGLFTSWTHEKNWKKAHNILL

PSFSQQAMKGYHAMMVDIAVQLVQKWERLNADEHI

EVPEDMTRLTLDTIGLCGFNYRFNSFYRDQPHPFI

TSMVRALDEAMNKLQRANPDDPAYDENKRQFQEDI

KVMNDLVDKIIADRKASGEQSDDLLTHMLNGKDPE

TGEPLDDENIRYQIITFLIAGHETTSGLLSFALYF

LVKNPHVLQKAAEEAARVLVDPVPSYKQVKQLKYV

GMVLNEALRLWPTAPAFSLYAKEDTVLGGEYPLEK

GDELMVLIPQLHRDKTIWGDDVEEFRPERFENPSA

IPQHAFKPFGNGQRACIGQQFALHEATLVLGMMLK

HFDFEDHTNYELDIKETLTLKPEGFVVKAKSKKIP

LGGIPSPSTEQSAKKVRKKAENAHNTPLLVLYGSN

```
MGTAEGTARDLADIAMSKGFAPQVATLDSHAGNLP
REGAVLIVTASYNGHPPDNAKQFVDWLDQASADEV
KGVRYSVFGCGDKNWATTYQKVPAFIDETLAAKGA
ENIADRGEADASDDFEGTYEEWREHMWSDVAAYFN
LDIENSEDNKSTLSLQFVDSAADMPLAKMHGAFST
NVVASKELQQPGSARSTRHLEIELPKEASYQEGDH
LGVIPRNYEGIVNRVTARFGLDASQQIRLEAEEEK
LAHLPLAKTVSVEELLQYVELQDPVTRTQLRAMAA
KTVCPPHKVELEALLEKQAYKEQVLAKRLTMLELL
EKYPACEMKFSEFIALLPSIRPRYYSISSSPRVDE
KQASITVSVVSGEAWSGYGEYKGIASNYLAELQEG
DTITCFISTPQSEFTLPKDPETPLIMVGPGTGVAP
FRGFVQARKQLKEQGQSLGEAHLYFGCRSPHEDYL
YQEELENAQSEGIITLHTAFSRMPNQPKTYVQHVM
EQDGKKLIELLDQGAHFYICGDSQMAPAVEATLM
KSYADVHQVSEADARLWLQQLEEKGRYAKDVWAG
Nucleotide sequence of cytochrome
P450 CYP102A1 from Bacillus megaterium
                              SEQ ID NO: 2
ATGACAATTAAAGAAATGCCTCAGCCAAAAACGTT
TGGAGAGCTTAAAAATTTACCGTTATTAAACACAG
ATAAACCGGTTCAAGCTTTGATGAAAATTGCGGAT
GAATTAGGAGAAATCTTTAAATTCGAGGCGCCTGG
TCGTGTAACGCGCTACTTATCAAGTCAGCGTCTAA
TTAAAGAAGCATGCGATGAATCACGCTTTGATAAA
AACTTAAGTCAAGCGCTTAAATTTGTACGTGATTT
TGCAGGAGACGGGTTATTTACAAGCTGGACGCATG
AAAAAAATTGGAAAAAAGCGCATAATATCTTACTT
CCAAGCTTCAGTCAGCAGGCAATGAAAGGCTATCA
TGCGATGATGGTCGATATCGCCGTGCAGCTTGTTC
AAAAGTGGGAGCGTCTAAATGCAGATGAGCATATT
GAAGTACCGGAAGACATGACACGTTTAACGCTTGA
TACAATTGGTCTTTGCGGCTTTAACTATCGCTTTA
ACAGCTTTTACCGAGATCAGCCTCATCCATTTATT
ACAAGTATGGTCCGTGCACTGGATGAAGCAATGAA
CAAGCTGCAGCGAGCAAATCCAGACGACCCAGCTT
ATGATGAAAACAAGCGCCAGTTTCAAGAAGATATC
AAGGTGATGAACGACCTAGTAGATAAAATTATTGC
AGATCGCAAAGCAAGCGGTGAACAAAGCGATGATT
TATTAACGCATATGCTAAACGGAAAAGATCCAGAA
ACGGGTGAGCCGCTTGATGACGAGAACATTCGCTA
TCAAATTATTACATTCTTAATTGCGGGACACGAAA
```

```
CAACAAGTGGTCTTTTATCATTTGCGCTGTATTTC
TTAGTGAAAAATCCACATGTATTACAAAAAGCAGC
AGAAGAAGCAGCACGAGTTCTAGTAGATCCTGTTC
CAAGCTACAAACAAGTCAAACAGCTTAAATATGTC
GGCATGGTCTTAAACGAAGCGCTGCGCTTATGGCC
AACTGCTCCTGCGTTTTCCCTATATGCAAAAGAAG
ATACGGTGCTTGGAGGAGAATATCCTTTAGAAAAA
GGCGACGAACTAATGGTTCTGATTCCTCAGCTTCA
CCGTGATAAAACAATTTGGGGAGACGATGTGGAAG
AGTTCCGTCCAGAGCGTTTTGAAAATCCAAGTGCG
ATTCCGCAGCATGCGTTTAAACCGTTTGGAAACGG
TCAGCGTGCGTGTATCGGTCAGCAGTTCGCTCTTC
ATGAAGCAACGCTGGTACTTGGTATGATGCTAAAA
CACTTTGACTTTGAAGATCATACAAACTACGAGCT
GGATATTAAAGAAACTTTAACGTTAAAACCTGAAG
GCTTTGTGGTAAAAGCAAATCGAAAAAAATTCCG
CTTGGCGGTATTCCTTCACCTAGCACTGAACAGTC
TGCTAAAAAAGTACGCAAAAGGCAGAAAACGCTC
ATAATACGCCGCTGCTTGTGCTATACGGTTCAAAT
ATGGGAACAGCTGAAGGAACGGCGCGTGATTTAGC
AGATATTGCAATGAGCAAAGGATTTGCACCGCAGG
TCGCAACGCTTGATTCACACGCCGGAAATCTTCCG
CGCGAAGGAGCTGTATTAATTGTAACGGCGTCTTA
TAACGGTCATCCGCCTGATAACGCAAAGCAATTTG
TCGACTGGTTAGACCAAGCGTCTGCTGATGAAGTA
AAAGGCGTTCGCTACTCCGTATTTGGATGCGGCGA
TAAAAACTGGGCTACTACGTATCAAAAAGTGCCTG
CTTTTATCGATGAAACGCTTGCCGCTAAGGGGCA
GAAAACATCGCTGACCGCGGTGAAGCAGATGCAAG
CGACGACTTTGAAGGCACATATGAAGAATGGCGTG
AACATATGTGGAGTGACGTAGCAGCCTACTTTAAC
CTCGACATTGAAAACAGTGAAGATAATAAATCTAC
TCTTTCACTTCAATTTGTCGACAGCGCCGCGGATA
TGCCGCTTGCGAAAATGCACGGTGCGTTTTCAACG
AACGTCGTAGCAAGCAAAGAACTTCAACAGCCAGG
CAGTGCACGAAGCACGCGACATCTTGAAATTGAAC
TTCCAAAAGAAGCTTCTTATCAAGAAGGAGATCAT
TTAGGTGTTATTCCTCGCAACTATGAAGGAATAGT
AAACCGTGTAACAGCAAGGTTCGGCCTAGATGCAT
CACAGCAAATCCGTCTGGAAGCAGAAGAAGAAAAA
TTAGCTCATTTGCCACTCGCTAAAACAGTATCCGT
```

```
AGAAGAGCTTCTGCAATACGTGGAGCTTCAAGATC
CTGTTACGCGCACGCAGCTTCGCGCAATGGCTGCT
AAAACGGTCTGCCCGCCGCATAAAGTAGAGCTTGA
AGCCTTGCTTGAAAAGCAAGCCTACAAAGAACAAG
TGCTGGCAAAACGTTTAACAATGCTTGAACTGCTT
GAAAAATACCCGGCGTGTGAAATGAAATTCAGCGA
ATTTATCGCCCTTCTGCCAAGCATACGCCCGCGCT
ATTACTCGATTTCTTCATCACCTCGTGTCGATGAA
AAACAAGCAAGCATCACGGTCAGCGTTGTCTCAGG
AGAAGCGTGGAGCGGATATGGAGAATATAAAGGAA
TTGCGTCGAACTATCTTGCCGAGCTGCAAGAAGGA
GATACGATTACGTGCTTTATTTCCACACCGCAGTC
AGAATTTACGCTGCCAAAAGACCCTGAAACGCCGC
TTATCATGGTCGGACCGGGAACAGGCGTCGCGCCG
TTTAGAGGCTTTGTGCAGGCGCGCAAACAGCTAAA
AGAACAAGGACAGTCACTTGGAGAAGCACATTTAT
ACTTCGGCTGCCGTTCACCTCATGAAGACTATCTG
TATCAAGAAGAGCTTGAAAACGCCCAAAGCGAAGG
CATCATTACGCTTCATACCGCTTTTTCTCGCATGC
CAAATCAGCCGAAAACATACGTTCAGCACGTAATG
GAACAAGACGGCAAGAAATTGATTGAACTTCTTGA
TCAAGGAGCGCACTTCTATATTTGCGGAGACGGAA
GCCAAATGGCACCTGCCGTTGAAGCAACGCTTATG
AAAAGCTATGCTGACGTTCACCAAGTGAGTGAAGC
AGACGCTCGCTTATGGCTGCAGCAGCTAGAAGAAA
AAGGCCGATACGCAAAAGACGTGTGGGCTGGGTAA
```

Amino acid sequence of cytochrome P450
CYP505A30 from Mycehophthora
thermophile
                              SEQ ID NO: 3
```
MADKTTETVPIPGPPGLPLVGNALAFDSELPLRTF
QEFAEEYGEIYRLTLPTGTTLVVSSQALVHELCDD
KRFKKPVAAALAEVRNGVNDGLFTAREEEPNWGIA
HRILMPAFGPASIQGMFTEMHEIASQLALKWARHG
PDTPIFVTDDFTRLTLDTLALCTMNFRFNSYYHDE
LHPFINAMGNFLTESGARAMRPAITSIFHQAANRK
YWEDIEVLRKTAQGVLDTRRKUPTNRKDLLSAMLD
GVDAKTGQKLSDSSIIDNLITFLIAGHETTSGLLS
FAFYLLIKHQDAYRKAQEEVDRVIGKGPIKVEHIK
KLPYIAAVLRETLRLCPTIPIINRAAKQDEVIGGK
YAVAKDQRLALLLAQSHLDPAVYGETAKQFIPERI
VILDENFERLNREYPDCWKPFGTMRACIGRPFAW
QEAVLVMAMLLQNFDFVLHDPYYELHYKQTLTTKP
KDFYMRAILRDGLTATELEHRLAGNAASVARSGGG
GGGPSKPTAQKTSPAEAKPMSIFYGSNTGTCESLA
QRLATDAASHGYAAAAVEPLDTATEKLPTDRPVVI
ITASFEGQPPDNAAKFCGWLKNLEGDELKNVSYAV
FGCGHHDWSQTFHRIPKLVHQTMKAHGASPICDEG
LTDVAEGNIVIFTDFEQWEDDVFWPAVRARYGAAG
AVAETEDAPGSDGLNIHFSSPRSSTLRQDVREATV
VGEALLTAPDAPPKKHIEVQLPDGATYKVGDYLAV
LPVNSKESIGRVMRKFQLSWDSHVTIASDRWTALP
TGTPVPAYDVLGSYVELSQPATKRGILRLADAAED
EATKAELQKLAGDLYTSEISLKRASVLDLLDRFPS
ISLPFGTFLSLLPPIRPRQYSISSSPLNDPSRATL
TYSLLDSPSLANPSRRFVGVATSYLSSLVRGDKLL
VSVRPTHTAFRLPDEDKMGETAIICVGAGSGLAPF
RGFIQERAALLAKGTQLAAALLFYGCRSPEKDDLY
RDEFDKWQESGAVDVRRAFSRVDSDDTEARGCRHV
QDRLWHDREEVKALWDRGARVYVCGSRQVGEGVKT
AMGRIVLGEEDAEDAISKWYETVRNDRYATDVFD
```

Codon optimized nucleotide sequence
of cytochrome P450 CYP505A30 from
Mycehophthora thermophile
                              SEQ ID NO: 4
```
ATGGCGGATAAGACCACCGAAACCGTGCCGATTCC
GGGTCCGCCGGGCCTGCCGCTGGTTGGTAATGCGC
TGGCGTTTGATAGCGAACTGCCGCTGCGTACCTTC
CAGGAATTTGCGGAGGAATACGGCGAGATCTATCG
TCTGACCCTGCCGACCGGTACCACCCTGGTGGTTA
GCAGCCAAGCGCTGGTTCACGAACTGTGCGACGAT
AAGCGTTTCAAGAAGCCGGTTGCTGCGGCGCTGGC
GGAAGTGCGTAACGGCGTTAACGACGGTCTGTTTA
CCGCGCGTGAAGAGGAGCCGAACTGGGGCATCGCG
CACCGTATTCTGATGCCGGCGTTTGGTCCGGCGAG
CATTCAGGGCATGTTTACCGAAATGCACGAGATCG
CGAGCCAACTGGCGCTGAAATGGGCGCGTCACGGT
CCGGACACCCCGATTTTCGTTACCGACGATTTTAC
CCGTCTGACCCTGGATACCCTGGCGCTGTGCACCA
TGAACTTCCGTTTTAACAGCTACTATCACGACGAA
CTGCACCCGTTCATCAACGCGATGGGCAACTTTCT
GACCGAGAGCGGTGCGCGTGCGATGCGTCCGGCGA
TCACCAGCATTTTCCACCAGGCGGCGAACCGTAAG
TACTGGGAAGATATTGAGGTTCTGCGTAAAACCGC
```

```
GCAAGGTGTGCTGGACACCCGTCGTAAGCACCCGA
CCAACCGTAAAGATCTGCTGAGCGCGATGCTGGAC
GGCGTGGATGCGAAAACCGGTCAGAAACTGAGCGA
CAGCAGCATCATTGATAACCTGATCACCTTTCTGA
TTGCGGGCCACGAAACCACCAGCGGTCTGCTGAGC
TTCGCGTTTTACCTGCTGATTAAGCACCAGGACGC
GTATCGTAAAGCGCAAGAAGAGGTGGATCGTGTTA
TCGGCAAGGGCCCGATTAAAGTTGAACACATCAAG
AAACTGCCGTACATCGCGGCGGTGCTGCGTGAAAC
CCTGCGTCTGTGCCCGACCATTCCGATCATTAACC
GTGCGGCGAAGCAGGACGAAGTTATCGGTGGCAAG
TACGCGGTGGCGAAAGATCAGCGTCTGGCGCTGCT
GCTGGCGCAAAGCCACCTGGACCCGGCGGTTTATG
GCGAAACCGCGAAGCAATTCATTCCGGAGCGTATG
CTGGACGAAAACTTTGAGCGTCTGAACCGTGAGTA
TCCGGATTGCTGGAAACCGTTCGGTACCGGCATGC
GTGCGTGCATCGGTCGTCCGTTTGCGTGGCAGGAA
GCGGTGCTGGTTATGGCGATGCTGCTGCAAAACTT
CGACTTTGTTCTGCACGATCCGTACTATGAGCTGC
ACTACAAGCAGACCCTGACCACCAAGCCGAAAGAC
TTCTATATGCGTGCGATCCTGCGTGATGGCCTGAC
CGCGACCGAACTGGAGCACCGTCTGGCGGGTAACG
CGGCGAGCGTGGCGCGTAGCGGTGGCGGTGGCGGT
GGCCCGAGCAAACCGACCGCGCAGAAAACCAGCCC
GGCGGAAGCGAAACCGATGAGCATCTTCTACGGCA
GCAACACCGGTACCTGCGAGAGCCTGGCGCAACGT
CTGGCGACCGATGCGGCGAGCCACGGTTATGCTGC
GGCGGCGGTGGAACCGCTGGACACCGCGACCGAGA
AGCTGCCGACCGATCGTCCGGTGGTTATCATTACC
GCGAGCTTCGAGGGTCAGCCGCCGGACAACGCGGC
GAAGTTTGCGGCTGCTGAAAAACCTGGAAGGTG
ATGAGCTGAAAAACGTGAGCTACGCGGTTTTCGGT
TGCGGCCACCACGACTGGAGCCAGACCTTTCACCG
TATTCCGAAGCTGGTTCACCAAACCATGAAAGCGC
ACGGTGCGAGCCCGATCTGCGACGAAGGCCTGACC
GATGTGGCGGAGGGTAACATGTTCACCGATTTTGA
ACAATGGAGGACGATGTGTTCTGGCCGGCGGTTC
GTGCGCGTTATGGCGCGGCGGGTGCGGTTGCGGAA
ACCGAGGACGCGCCGGGTAGCGATGGTCTGAACAT
CCACTTTAGCAGCCCGCGTAGCAGCACCCTGCGTC
AGGACGTGCGTGAAGCGACCGTGGTTGGTGAAGCG
```

```
CTGCTGACCGCGCCGGATGCGCCGCCGAAGAAACA
CATTGAAGTTCAACTGCCGGACGGCGCGACCTACA
AAGTGGGTGATTATCTGGCGGTGCTGCCGGTTAAC
AGCAAGGAGAGCATTGGTCGTGTTATGCGTAAATT
CCAGCTGAGCTGGGACAGCCACGTGACCATCGCGA
GCGATCGTTGGACCGCGCTGCCGACCGGTACCCCG
GTGCCGGCGTACGACGTTCTGGGTAGCTATGTGGA
GCTGAGCCAACCGGCGACCAAACGTGGTATCCTGC
GTCTGGCGGATGCGGCGGAAGATGAGGCGACCAAG
GCGGAACTGCAAAAACTGGCGGGTGATCTGTACAC
CAGCGAGATTAGCCTGAAACGTGCGAGCGTTCTGG
ACCTGCTGGATCGTTTCCCGAGCATCAGCCTGCCG
TTCGGTACCTTTCTGAGCCTGCTGCCGCCGATTCG
TCCGCGTCAATACAGCATCAGCAGCAGCCCGCTGA
ACGACCCGAGCCGTGCGACCCTGACCTATAGCCTG
CTGGATAGCCCGAGCCTGGCGAACCCGAGCCGTCG
TTTCGTGGGCGTTGCGACCAGCTACCTGAGCAGCC
TGGTTCGTGGTGACAAGCTGCTGGTGAGCGTTCGT
CCGACCCACACCGCGTTTCGTCTGCCGGACGAAGA
TAAAATGGGTGAAACCGCGATCATTTGCGTGGGTG
CGGGTAGCGGTCTGGCGCCGTTCCGTGGTTTTATC
CAGGAACGTGCGGCGCTGCTGGCGAAAGGTACCCA
ACTGGCGGCGGCGCTGCTGTTCTACGGTTGCCGTA
GCCCGGAGAAGGACGATCTGTATCGTGACGAATTC
GATAAATGGCAAGAGCGGTGCGGTGGATGTTCG
TCGTGCGTTTAGCCGTGTTGATAGCGACGATACCG
AGGCGCGTGGTTGCCGTCACGTTCAGGACCGTCTG
TGGCACGATCGTGAAGAGGTGAAGGCGCTGTGGGA
CCGTGGCGCGCGTGTGTACGTTTGCGGTAGCCGTC
AAGTGGGCGAAGGTGTTAAAACCGCGATGGGCCGT
ATCGTGCTGGGTGAAGAGGACGCGGAGGATGCGAT
CAGCAAGTGGTATGAAACCGTGCGTAATGACCGTT
ATGCGACCGATGTGTTCGACTAA
```

Amino acid sequence of Lipase B
from *Candida antarctica*
SEQ ID NO: 5
MKLLSLTGVAGVLATCVAATPLVKRLPSGSDPAFS
QPKSVLDAGLTCQGASPSSVSKPILLVPGTGTTGP
QSFDSNWIPLSTQLGYTPCWISPPPFMLNDTQVNT
EYMVNAITALYAGSGNNKLPVLTWSQGGLVAQWGL
TFFPSIRSKVDRLMAFAPDYKGTVLAGPLDALAVS
APSVWQQTTGSALTTALRNAGGLTQIVPTTNLYSA -continued

TDEIVQPQVSNSPLDSSYLFNGKNVQAQAVCGPLF

VIDHAGSLTSQFSYVVGRSALRSTTGQARSADYGI

-continued

TDCNPLPANDLTPEQKVAAAALLAPAAAAIVAGPK

QNCEPDLMPYARPFAVGKRTCSGIVTP

---

What is claimed is:

1. A fragrance composition comprising compounds of the formula:

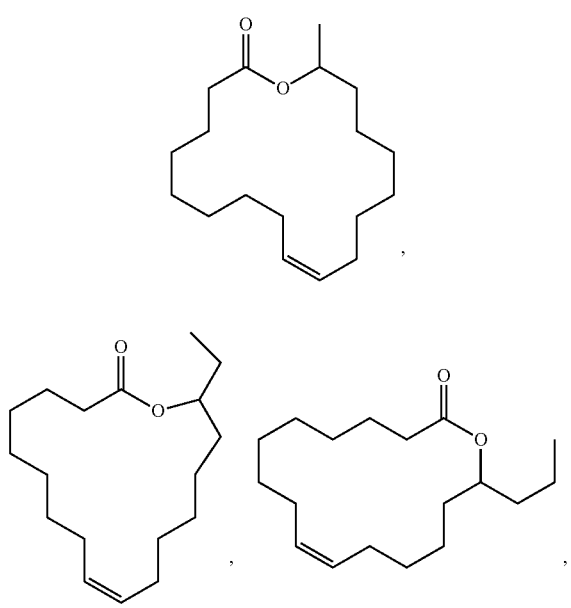

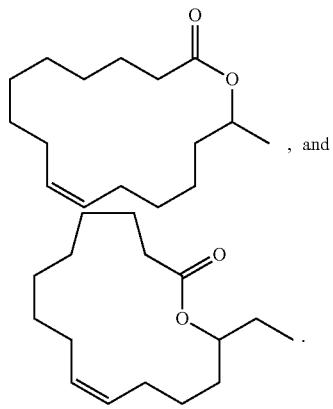

, and

2. A consumer product comprising the fragrance composition of claim 1.

3. The consumer product of claim 2, wherein the consumer product is a perfume product, a skin care product, a hair care product, a feminine hygiene product, a fabric care product, or a cleaning product.

4. The consumer product of claim 2, wherein the consumer product further comprises a second fragrance.

5. The consumer product of claim 2, wherein the consumer product is selected from the group consisting of: fragrance, body wash, shampoo, after bath splash, eau de toilette, cologne, lotion, cream, liquid laundry detergent, compressed cleaning tablet, lip gloss, solid body moisturizer bar, hair care mousse, scented ink, gel hand sanitizer, candle, all-purpose cleaner, linen spray, fabric softener, dishwashing liquid, deodorant stick, soap, scented garbage bags, perfume bearing microcapsules, and eye patch.

6. A method of improving, enhancing, or modifying the fragrance of a fragrant composition, the method comprising adding the composition of claim 1 to the fragrant composition.

7. The composition of claim 1, wherein the total concentration of the compounds is from about 0.01% and about 20% by weight.

8. The composition of claim 7, wherein the total concentration of the compounds is from about 0.01% and about 10% by weight.

9. The composition of claim 1, further comprising a solvent.

10. The composition of claim 9, wherein the solvent is propylene glycol, dipropylene glycol, water, or ethanol.

11. The composition of claim 1, further comprising one or more additional fragrance accords or compounds.

12. The composition of claim 11, wherein the one or more additional fragrance accords or compounds is an aldehydic compound, a balsamic compound, a citrus compound, a floral compound, a fruity compound, a gourmand compound, a green compound, a marine compound, a mossy compound, a musk compound, a piney compound, a powdery compound, a spicy compound, a woody compound, or a combination thereof.

13. The composition of claim 12, wherein the one or more additional fragrance accords or compounds is an aldehydic compound.

14. The composition of claim 12, wherein the one or more additional fragrance accords or compounds is a citrus compound.

15. The composition of claim 12, wherein the one or more additional fragrance accords or compounds is a floral compound.

16. The composition of claim 12, wherein the one or more additional fragrance accords or compounds is a fruity compound.

17. The composition of claim 12, wherein the one or more additional fragrance accords or compounds is a gourmand compound.

18. The composition of claim 12, wherein the one or more additional fragrance accords or compounds is a musk compound.

19. The composition of claim 12, wherein the one or more additional fragrance accords or compounds is a piney compound.

20. The composition of claim 12, wherein the one or more additional fragrance accords or compounds is a spicy compound.

* * * * *

SEQUENCE LISTING

<160> NUMBER OF SEQ ID NOS: 5

<210> SEQ ID NO 1
<211> LENGTH: 1049
<212> TYPE: PRT
<213> ORGANISM: Artificial Sequence
<220> FEATURE:
<223> OTHER INFORMATION: Cytochrome P450 CYP102A1 from Bacillus
      megaterium

<400> SEQUENCE: 1

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
```

```
                305                 310                 315                 320
        Glu Ala Leu Arg Leu Trp Pro Thr Ala Pro Ala Phe Ser Leu Tyr Ala
                        325                 330                 335

Lys Glu Asp Thr Val Leu Gly Gly Glu Tyr Pro Leu Glu Lys Gly Asp
                        340                 345                 350

Glu Leu Met Val Leu Ile Pro Gln Leu His Arg Asp Lys Thr Ile Trp
                        355                 360                 365

Gly Asp Asp Val Glu Glu Phe Arg Pro Glu Arg Phe Glu Asn Pro Ser
                        370                 375                 380

Ala Ile Pro Gln His Ala Phe Lys Pro Phe Gly Asn Gly Gln Arg Ala
        385                 390                 395                 400

Cys Ile Gly Gln Gln Phe Ala Leu His Glu Ala Thr Leu Val Leu Gly
                        405                 410                 415

Met Met Leu Lys His Phe Asp Phe Glu Asp His Thr Asn Tyr Glu Leu
                        420                 425                 430

Asp Ile Lys Glu Thr Leu Thr Leu Lys Pro Glu Gly Phe Val Val Lys
                        435                 440                 445

Ala Lys Ser Lys Lys Ile Pro Leu Gly Gly Ile Pro Ser Pro Ser Thr
                        450                 455                 460

Glu Gln Ser Ala Lys Lys Val Arg Lys Lys Ala Glu Asn Ala His Asn
        465                 470                 475                 480

Thr Pro Leu Leu Val Leu Tyr Gly Ser Asn Met Gly Thr Ala Glu Gly
                        485                 490                 495

Thr Ala Arg Asp Leu Ala Asp Ile Ala Met Ser Lys Gly Phe Ala Pro
                        500                 505                 510

Gln Val Ala Thr Leu Asp Ser His Ala Gly Asn Leu Pro Arg Glu Gly
                        515                 520                 525

Ala Val Leu Ile Val Thr Ala Ser Tyr Asn Gly His Pro Pro Asp Asn
                        530                 535                 540

Ala Lys Gln Phe Val Asp Trp Leu Asp Gln Ala Ser Ala Asp Glu Val
        545                 550                 555                 560

Lys Gly Val Arg Tyr Ser Val Phe Gly Cys Gly Asp Lys Asn Trp Ala
                        565                 570                 575

Thr Thr Tyr Gln Lys Val Pro Ala Phe Ile Asp Glu Thr Leu Ala Ala
                        580                 585                 590

Lys Gly Ala Glu Asn Ile Ala Asp Arg Gly Glu Ala Asp Ala Ser Asp
                        595                 600                 605

Asp Phe Glu Gly Thr Tyr Glu Glu Trp Arg Glu His Met Trp Ser Asp
                        610                 615                 620

Val Ala Ala Tyr Phe Asn Leu Asp Ile Glu Asn Ser Glu Asp Asn Lys
        625                 630                 635                 640

Ser Thr Leu Ser Leu Gln Phe Val Asp Ser Ala Ala Asp Met Pro Leu
                        645                 650                 655

Ala Lys Met His Gly Ala Phe Ser Thr Asn Val Val Ala Ser Lys Glu
                        660                 665                 670

Leu Gln Gln Pro Gly Ser Ala Arg Ser Thr Arg His Leu Glu Ile Glu
                        675                 680                 685

Leu Pro Lys Glu Ala Ser Tyr Gln Glu Gly Asp His Leu Gly Val Ile
                        690                 695                 700

Pro Arg Asn Tyr Glu Gly Ile Val Asn Arg Val Thr Ala Arg Phe Gly
        705                 710                 715                 720

Leu Asp Ala Ser Gln Gln Ile Arg Leu Glu Ala Glu Glu Lys Leu
                        725                 730                 735
```

Ala His Leu Pro Leu Ala Lys Thr Val Ser Val Glu Leu Leu Gln
        740                 745                 750

Tyr Val Glu Leu Gln Asp Pro Val Thr Arg Thr Gln Leu Arg Ala Met
        755                 760                 765

Ala Ala Lys Thr Val Cys Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 2
<211> LENGTH: 3150
<212> TYPE: DNA
<213> ORGANISM: Artificial Sequence
<220> FEATURE:
<223> OTHER INFORMATION: Cytochrome P450 CYP102A1 from Bacillus
      megaterium

<400> SEQUENCE: 2
atgacaatta agaaatgcc tcagccaaaa acgtttggag agcttaaaaa tttaccgtta        60
ttaaacacag ataaaccggt tcaagctttg atgaaaattg cggatgaatt aggagaaatc       120
tttaaattcg aggcgcctgg tcgtgtaacg cgctacttat caagtcagcg tctaattaaa      180
gaagcatgcg atgaatcacg ctttgataaa aacttaagtc aagcgcttaa atttgtacgt      240

```
gattttgcag gagacgggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga cgacctagt agataaaatt     660 attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtcgattcc gcagcatgcg tttaaaccgt ttggaaacgg tcagcgtgcg    1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca attttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
```

-continued

```
tataaaggaa ttgcgtcgaa ctatcttgcc gagctgcaag aaggagatac gattacgtgc      2640
tttatttcca caccgcagtc agaatttacg ctgccaaaag accctgaaac gccgcttatc      2700
atggtcggac cgggaacagg cgtcgcgccg tttagaggct ttgtgcaggc gcgcaaacag      2760
ctaaaagaac aaggacagtc acttggagaa gcacatttat acttcggctg ccgttcacct      2820
catgaagact atctgtatca agaagagctt gaaaacgccc aaagcgaagg catcattacg      2880
cttcataccg cttttctcg catgccaaat cagccgaaaa catacgttca gcacgtaatg      2940
gaacaagacg gcaagaaatt gattgaactt cttgatcaag gagcgcactt ctatatttgc      3000
ggagacggaa gccaaatggc acctgccgtt gaagcaacgc ttatgaaaag ctatgctgac      3060
gttcaccaag tgagtgaagc agacgctcgc ttatggctgc agcagctaga agaaaaaggc      3120
cgatacgcaa aagacgtgtg ggctgggtaa                                       3150
```

<210> SEQ ID NO 3
<211> LENGTH: 1080
<212> TYPE: PRT
<213> ORGANISM: Artificial Sequence
<220> FEATURE:
<223> OTHER INFORMATION: Cytochrome P450 CYP505A30 from Myceliophthora thermophile

<400> SEQUENCE: 3

```
Met Ala Asp Lys Thr Thr Glu Thr Val Pro Ile Pro Gly Pro Pro Gly
1               5                   10                  15

Leu Pro Leu Val Gly Asn Ala Leu Ala Phe Asp Ser Glu Leu Pro Leu
            20                  25                  30

Arg Thr Phe Gln Glu Phe Ala Glu Tyr Gly Glu Ile Tyr Arg Leu
        35                  40                  45

Thr Leu Pro Thr Gly Thr Thr Leu Val Val Ser Ser Gln Ala Leu Val
    50                  55                  60

His Glu Leu Cys Asp Asp Lys Arg Phe Lys Lys Pro Val Ala Ala Ala
65                  70                  75                  80

Leu Ala Glu Val Arg Asn Gly Val Asn Asp Gly Leu Phe Thr Ala Arg
                85                  90                  95

Glu Glu Glu Pro Asn Trp Gly Ile Ala His Arg Ile Leu Met Pro Ala
            100                 105                 110

Phe Gly Pro Ala Ser Ile Gln Gly Met Phe Thr Glu Met His Glu Ile
        115                 120                 125

Ala Ser Gln Leu Ala Leu Lys Trp Ala Arg His Gly Pro Asp Thr Pro
    130                 135                 140

Ile Phe Val Thr Asp Asp Phe Thr Arg Leu Thr Leu Asp Thr Leu Ala
145                 150                 155                 160

Leu Cys Thr Met Asn Phe Arg Phe Asn Ser Tyr Tyr His Asp Glu Leu
                165                 170                 175

His Pro Phe Ile Asn Ala Met Gly Asn Phe Leu Thr Glu Ser Gly Ala
            180                 185                 190

Arg Ala Met Arg Pro Ala Ile Thr Ser Ile Phe His Gln Ala Ala Asn
        195                 200                 205

Arg Lys Tyr Trp Glu Asp Ile Glu Val Leu Arg Lys Thr Ala Gln Gly
    210                 215                 220

Val Leu Asp Thr Arg Arg Lys His Pro Thr Asn Arg Lys Asp Leu Leu
225                 230                 235                 240

Ser Ala Met Leu Asp Gly Val Asp Ala Lys Thr Gly Gln Lys Leu Ser
                245                 250                 255
```

-continued

Asp Ser Ser Ile Ile Asp Asn Leu Ile Thr Phe Leu Ile Ala Gly His
            260                 265                 270

Glu Thr Thr Ser Gly Leu Leu Ser Phe Ala Phe Tyr Leu Leu Ile Lys
        275                 280                 285

His Gln Asp Ala Tyr Arg Lys Ala Gln Glu Glu Val Asp Arg Val Ile
    290                 295                 300

Gly Lys Gly Pro Ile Lys Val Glu His Ile Lys Lys Leu Pro Tyr Ile
305                 310                 315                 320

Ala Ala Val Leu Arg Glu Thr Leu Arg Leu Cys Pro Thr Ile Pro Ile
                325                 330                 335

Ile Asn Arg Ala Ala Lys Gln Asp Glu Val Ile Gly Gly Lys Tyr Ala
            340                 345                 350

Val Ala Lys Asp Gln Arg Leu Ala Leu Leu Leu Ala Gln Ser His Leu
        355                 360                 365

Asp Pro Ala Val Tyr Gly Glu Thr Ala Lys Gln Phe Ile Pro Glu Arg
    370                 375                 380

Met Leu Asp Glu Asn Phe Glu Arg Leu Asn Arg Glu Tyr Pro Asp Cys
385                 390                 395                 400

Trp Lys Pro Phe Gly Thr Gly Met Arg Ala Cys Ile Gly Arg Pro Phe
                405                 410                 415

Ala Trp Gln Glu Ala Val Leu Val Met Ala Met Leu Leu Gln Asn Phe
            420                 425                 430

Asp Phe Val Leu His Asp Pro Tyr Tyr Glu Leu His Tyr Lys Gln Thr
        435                 440                 445

Leu Thr Thr Lys Pro Lys Asp Phe Tyr Met Arg Ala Ile Leu Arg Asp
    450                 455                 460

Gly Leu Thr Ala Thr Glu Leu Glu His Arg Leu Ala Gly Asn Ala Ala
465                 470                 475                 480

Ser Val Ala Arg Ser Gly Gly Gly Gly Pro Ser Lys Pro Thr
                485                 490                 495

Ala Gln Lys Thr Ser Pro Ala Glu Ala Lys Pro Met Ser Ile Phe Tyr
            500                 505                 510

Gly Ser Asn Thr Gly Thr Cys Glu Ser Leu Ala Gln Arg Leu Ala Thr
        515                 520                 525

Asp Ala Ala Ser His Gly Tyr Ala Ala Ala Val Glu Pro Leu Asp
    530                 535                 540

Thr Ala Thr Glu Lys Leu Pro Thr Asp Arg Pro Val Val Ile Ile Thr
545                 550                 555                 560

Ala Ser Phe Glu Gly Gln Pro Pro Asp Asn Ala Ala Lys Phe Cys Gly
                565                 570                 575

Trp Leu Lys Asn Leu Glu Gly Asp Leu Lys Asn Val Ser Tyr Ala
            580                 585                 590

Val Phe Gly Cys Gly His His Asp Trp Ser Gln Thr Phe His Arg Ile
        595                 600                 605

Pro Lys Leu Val His Gln Thr Met Lys Ala His Gly Ala Ser Pro Ile
    610                 615                 620

Cys Asp Glu Gly Leu Thr Asp Val Ala Glu Gly Asn Met Phe Thr Asp
625                 630                 635                 640

Phe Glu Gln Trp Glu Asp Val Phe Trp Pro Ala Val Arg Ala Arg
                645                 650                 655

Tyr Gly Ala Ala Gly Ala Val Ala Glu Thr Glu Asp Ala Pro Gly Ser
            660                 665                 670

Asp Gly Leu Asn Ile His Phe Ser Ser Pro Arg Ser Ser Thr Leu Arg

```
              675                 680                 685
Gln Asp Val Arg Glu Ala Thr Val Gly Glu Ala Leu Leu Thr Ala
    690                 695                 700
Pro Asp Ala Pro Pro Lys Lys His Ile Glu Val Gln Leu Pro Asp Gly
705                 710                 715                 720
Ala Thr Tyr Lys Val Gly Asp Tyr Leu Ala Val Leu Pro Val Asn Ser
                725                 730                 735
Lys Glu Ser Ile Gly Arg Val Met Arg Lys Phe Gln Leu Ser Trp Asp
                740                 745                 750
Ser His Val Thr Ile Ala Ser Asp Arg Trp Thr Ala Leu Pro Thr Gly
                755                 760                 765
Thr Pro Val Pro Ala Tyr Asp Val Leu Gly Ser Tyr Val Glu Leu Ser
770                 775                 780
Gln Pro Ala Thr Lys Arg Gly Ile Leu Arg Leu Ala Asp Ala Ala Glu
785                 790                 795                 800
Asp Glu Ala Thr Lys Ala Glu Leu Gln Lys Leu Ala Gly Asp Leu Tyr
                805                 810                 815
Thr Ser Glu Ile Ser Leu Lys Arg Ala Ser Val Leu Asp Leu Leu Asp
                820                 825                 830
Arg Phe Pro Ser Ile Ser Leu Pro Phe Gly Thr Phe Leu Ser Leu Leu
                835                 840                 845
Pro Pro Ile Arg Pro Arg Gln Tyr Ser Ile Ser Ser Pro Leu Asn
850                 855                 860
Asp Pro Ser Arg Ala Thr Leu Thr Tyr Ser Leu Leu Asp Ser Pro Ser
865                 870                 875                 880
Leu Ala Asn Pro Ser Arg Arg Phe Val Gly Val Ala Thr Ser Tyr Leu
                885                 890                 895
Ser Ser Leu Val Arg Gly Asp Lys Leu Leu Val Ser Val Arg Pro Thr
                900                 905                 910
His Thr Ala Phe Arg Leu Pro Asp Glu Asp Lys Met Gly Glu Thr Ala
                915                 920                 925
Ile Ile Cys Val Gly Ala Gly Ser Gly Leu Ala Pro Phe Arg Gly Phe
                930                 935                 940
Ile Gln Glu Arg Ala Ala Leu Leu Ala Lys Gly Thr Gln Leu Ala Ala
945                 950                 955                 960
Ala Leu Leu Phe Tyr Gly Cys Arg Ser Pro Glu Lys Asp Asp Leu Tyr
                965                 970                 975
Arg Asp Glu Phe Asp Lys Trp Gln Glu Ser Gly Ala Val Asp Val Arg
                980                 985                 990
Arg Ala Phe Ser Arg Val Asp Ser Asp Asp Thr Glu Ala Arg Gly Cys
            995                 1000                1005
Arg His Val Gln Asp Arg Leu Trp His Asp Arg Glu Glu Val Lys
        1010                1015                1020
Ala Leu Trp Asp Arg Gly Ala Arg Val Tyr Val Cys Gly Ser Arg
        1025                1030                1035
Gln Val Gly Glu Gly Val Lys Thr Ala Met Gly Arg Ile Val Leu
        1040                1045                1050
Gly Glu Glu Asp Ala Glu Asp Ala Ile Ser Lys Trp Tyr Glu Thr
        1055                1060                1065
Val Arg Asn Asp Arg Tyr Ala Thr Asp Val Phe Asp
        1070                1075                1080

<210> SEQ ID NO 4
```

<211> LENGTH: 3243
<212> TYPE: DNA
<213> ORGANISM: Artificial Sequence
<220> FEATURE:
<223> OTHER INFORMATION: Cytochrome P450 CYP505A30 from Myceliophthora thermophile

<400> SEQUENCE: 4

| | | | | | |
|---|---|---|---|---|---|
| atggcggata | agaccaccga | aaccgtgccg | attccgggtc | cgccgggcct | gccgctggtt | 60 |
| ggtaatgcgc | tggcgtttga | tagcgaactg | ccgctgcgta | ccttccagga | atttgcggag | 120 |
| gaatacggcg | agatctatcg | tctgaccctg | ccgaccggta | ccaccctggt | ggttagcagc | 180 |
| caagcgctgg | ttcacgaact | gtgcgacgat | aagcgtttca | agaagccggt | tgctgcggcg | 240 |
| ctggcggaag | tgcgtaacgg | cgttaacgac | ggtctgttta | ccgcgcgtga | agaggagccg | 300 |
| aactggggca | tcgcgcaccg | tattctgatg | ccggcgtttg | gtccggcgag | cattcagggc | 360 |
| atgtttaccg | aaatgcacga | gatcgcgagc | caactggcgc | tgaaatgggc | gcgtcacggt | 420 |
| ccggacaccc | cgattttcgt | taccgacgat | tttacccgtc | tgaccctgga | taccctggcg | 480 |
| ctgtgcacca | tgaacttccg | ttttaacagc | tactatcacg | acgaactgca | cccgttcatc | 540 |
| aacgcgatgg | gcaactttct | gaccgagagc | ggtgcgcgtg | cgatgcgtcc | ggcgatcacc | 600 |
| agcattttcc | accaggcggc | gaaccgtaag | tactgggaag | atattgaggt | tctgcgtaaa | 660 |
| accgcgcaag | gtgtgctgga | cacccgtcgt | aagcacccga | ccaaccgtaa | agatctgctg | 720 |
| agcgcgatgc | tggacggcgt | ggatgcgaaa | accggtcaga | aactgagcga | cagcagcatc | 780 |
| attgataacc | tgatcacctt | tctgattgcg | ggccacgaaa | ccaccagcgg | tctgctgagc | 840 |
| ttcgcgtttt | acctgctgat | taagcaccag | gacgcgtatc | gtaaagcgca | agaagaggtg | 900 |
| gatcgtgtta | tcggcaaggg | cccgattaaa | gttgaacaca | tcaagaaact | gccgtacatc | 960 |
| gcggcggtgc | tgcgtgaaac | cctgcgtctg | tgcccgacca | ttccgatcat | taaccgtgcg | 1020 |
| gcgaagcagg | acgaagttat | cggtggcaag | tacgcggtgg | cgaaagatca | gcgtctggcg | 1080 |
| ctgctgctgg | cgcaaagcca | cctggacccg | gcggtttatg | cgaaaccgc | gaagcaattc | 1140 |
| attccggagc | gtatgctgga | cgaaaacttt | gagcgtctga | accgtgagta | tccggattgc | 1200 |
| tggaaaccgt | tcggtaccgg | catgcgtgcg | tgcatcggtc | gtccgtttgc | gtggcaggaa | 1260 |
| gcggtgctgg | ttatggcgat | gctgctgcaa | aacttcgact | tgttctgca | cgatccgtac | 1320 |
| tatgagctgc | actacaagca | gaccctgacc | accaagccga | agacttcta | tatgcgtgcg | 1380 |
| atcctgcgtg | atggcctgac | cgcgaccgaa | ctggagcacc | gtctggcggg | taacgcggcg | 1440 |
| agcgtggcgc | gtagcggtgg | cgtggcggt | ggcccgagca | aaccgaccgc | gcagaaaacc | 1500 |
| agcccggcgg | aagcgaaacc | gatgagcatc | ttctacggca | gcaacaccgg | tacctgcgag | 1560 |
| agcctggcgc | aacgtctggc | gaccgatgcg | gcgagccacg | ttatgctgc | ggcggcggtg | 1620 |
| gaaccgctgg | acaccgcgac | cgagaagctg | ccgaccgatc | gtccggtggt | tatcattacc | 1680 |
| gcgagcttcg | agggtcagcc | gccggacaac | cggcgaagt | tttgcggctg | gctgaaaaac | 1740 |
| ctggaaggtg | atgagctgaa | aaacgtgagc | tacgcggttt | tcggttgcgg | ccaccacgac | 1800 |
| tggagccaga | cctttcaccg | tattccgaag | ctggttcacc | aaaccatgaa | agcgcacggt | 1860 |
| gcgagcccga | tctgcgacga | aggcctgacc | gatgtggcgg | agggtaacat | gttcaccgat | 1920 |
| tttgaacaat | gggaggacga | tgtgttctgg | ccggcggttc | gtgcgcgtta | tggcgcggcg | 1980 |
| ggtgcggttg | cggaaaccga | ggacgcgccg | gtagcgatg | gtctgaacat | ccactttagc | 2040 |
| agcccgcgta | gcagcaccct | gcgtcaggac | gtgcgtgaag | cgaccgtggt | tggtgaagcg | 2100 |

```
ctgctgaccg cgccggatgc gccgccgaag aaacacattg aagttcaact gccggacggc    2160
gcgacctaca aagtgggtga ttatctggcg gtgctgccgg ttaacagcaa ggagagcatt    2220
ggtcgtgtta tgcgtaaatt ccagctgagc tgggacagcc acgtgaccat cgcgagcgat    2280
cgttggaccg cgctgccgac cggtaccccg gtgccggcgt acgacgttct gggtagctat    2340
gtggagctga gccaaccggc gaccaaacgt ggtatcctgc gtctggcgga tgcggcggaa    2400
gatgaggcga ccaaggcgga actgcaaaaa ctggcgggtg atctgtacac cagcgagatt    2460
agcctgaaac gtgcgagcgt tctggacctg ctggatcgtt tcccgagcat cagcctgccg    2520
ttcggtacct ttctgagcct gctgccgccg attcgtccgc gtcaatacag catcagcagc    2580
agcccgctga acgacccgag ccgtgcgacc ctgacctata gcctgctgga tagcccgagc    2640
ctggcgaacc cgagccgtcg tttcgtgggc gttgcgacca gctacctgag cagcctggtt    2700
cgtggtgaca agctgctggt gagcgttcgt ccgacccaca ccgcgtttcg tctgccggac    2760
gaagataaaa tgggtgaaac cgcgatcatt tgcgtgggtg cgggtagcgg tctggcgccg    2820
ttccgtggtt ttatccagga acgtgcgcg ctgctggcga aaggtaccca actgcgcgcg    2880
gcgctgctgt tctacggttg ccgtagcccg gagaaggacg atctgtatcg tgacgaattc    2940
gataaatggc aagagagcgg tgcggtggat gttcgtcgtg cgtttagccg tgttgatagc    3000
gacgataccg aggcgcgtgg ttgccgtcac gttcaggacc gtctgtggca cgatcgtgaa    3060
gaggtgaagg cgctgtggga ccgtggcgcg cgtgtgtacg tttgcggtag ccgtcaagtg    3120
ggcgaaggtg ttaaaaccgc gatgggccgt atcgtgctgg gtgaagagga cgcggaggat    3180
gcgatcagca gtggtatga aaccgtgcgt aatgaccgtt atgcgaccga tgtgttcgac    3240
taa                                                                 3243
```

<210> SEQ ID NO 5
<211> LENGTH: 342
<212> TYPE: PRT
<213> ORGANISM: Artificial Sequence
<220> FEATURE:
<223> OTHER INFORMATION: Lipase B from Candida antarctica

<400> SEQUENCE: 5

```
Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Ala Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160
```

```
Lys Gly Thr Val Leu Ala Gly Pro Leu Asp Ala Leu Ala Val Ser Ala
            165             170             175

Pro Ser Val Trp Gln Gln Thr Thr Gly Ser Ala Leu Thr Thr Ala Leu
            180             185             190

Arg Asn Ala Gly Gly Leu Thr Gln Ile Val Pro Thr Thr Asn Leu Tyr
            195             200             205

Ser Ala Thr Asp Glu Ile Val Gln Pro Gln Val Ser Asn Ser Pro Leu
            210             215             220

Asp Ser Ser Tyr Leu Phe Asn Gly Lys Asn Val Gln Ala Gln Ala Val
225             230             235             240

Cys Gly Pro Leu Phe Val Ile Asp His Ala Gly Ser Leu Thr Ser Gln
            245             250             255

Phe Ser Tyr Val Val Gly Arg Ser Ala Leu Arg Ser Thr Thr Gly Gln
            260             265             270

Ala Arg Ser Ala Asp Tyr Gly Ile Thr Asp Cys Asn Pro Leu Pro Ala
            275             280             285

Asn Asp Leu Thr Pro Glu Gln Lys Val Ala Ala Ala Leu Leu Ala
            290             295             300

Pro Ala Ala Ala Ile Val Ala Gly Pro Lys Gln Asn Cys Glu Pro
305             310             315             320

Asp Leu Met Pro Tyr Ala Arg Pro Phe Ala Val Gly Lys Arg Thr Cys
            325             330             335

Ser Gly Ile Val Thr Pro
            340
```